(12) United States Patent
Anticevic et al.

(10) Patent No.: US 12,154,677 B2
(45) Date of Patent: Nov. 26, 2024

(54) SYSTEMS AND METHODS FOR NEURO-BEHAVIORAL RELATIONSHIPS IN DIMENSIONAL GEOMETRIC EMBEDDING (N-BRIDGE)

(71) Applicant: Yale University, New Haven, CT (US)

(72) Inventors: Alan Anticevic, New Haven, CT (US); John Murray, New Haven, CT (US); Jie Lisa Ji, New Haven, CT (US)

(73) Assignee: Yale University, New Haven, CT (US)

(*) Notice: Subject to any disclaimer, the term of this patent is extended or adjusted under 35 U.S.C. 154(b) by 199 days.

(21) Appl. No.: 16/980,136

(22) PCT Filed: Mar. 13, 2019

(86) PCT No.: PCT/US2019/022110
§ 371 (c)(1),
(2) Date: Sep. 11, 2020

(87) PCT Pub. No.: WO2019/178271
PCT Pub. Date: Sep. 19, 2019

(65) Prior Publication Data
US 2021/0005306 A1    Jan. 7, 2021

Related U.S. Application Data

(60) Provisional application No. 62/642,900, filed on Mar. 14, 2018.

(51) Int. Cl.
*G16H 20/70* (2018.01)
*A61B 5/00* (2006.01)
(Continued)

(52) U.S. Cl.
CPC .............. *G16H 20/70* (2018.01); *A61B 5/055* (2013.01); *A61B 5/165* (2013.01); *A61B 5/7264* (2013.01); *G16H 40/63* (2018.01); *G16H 50/20* (2018.01)

(58) Field of Classification Search
CPC ........ G16H 20/70; G16H 40/63; G16H 50/20; A61B 5/165; A61B 5/7264
See application file for complete search history.

(56) References Cited

U.S. PATENT DOCUMENTS 4,862,359 A    8/1989   Trivedi et al.
9,504,415 B1   11/2016  Modarres
(Continued)

OTHER PUBLICATIONS

Bielczyk, Natalia Z et al. "Circuit to construct mapping: a mathematical tool for assisting the diagnosis and treatment in major depressive disorder." Frontiers in psychiatry vol. 6 29. Feb. 26, 2015 (Year: 2015).*

(Continued)

*Primary Examiner* — Sheetal R Paulson
(74) *Attorney, Agent, or Firm* — Sterne, Kessler, Goldstein & Fox P.L.L.C.

(57) ABSTRACT

Described herein are example methods and systems for neuro-behavioral relationships in dimensional geometric bedding (N-BRIDGE), which includes a comprehensive, data-driven analytic framework for mapping the multi-dimensional relationships between neural and behavioral features in humans N-BRIDGE allows mapping of variations along newly-defined data-driven behavioral dimensions that capture the geometry of behavioral/symptom variation to variation in specific neural features. A method for treating a patient based on neuro-behavioral mapping includes receiving, from a user interface of a computing device, behavioral data of a patient corresponding to mental health or cognitive status of the patient, predicting, by at least one processor of the computing device, a neural feature map for the patient representative of neural data based on the behavioral data, determining, by the at least one processor, a therapeutic associated with the neural feature map, and (Continued)

treating the patient with the therapeutic associated with the neural feature map.

13 Claims, 117 Drawing Sheets

(51) Int. Cl.
    *A61B 5/055*     (2006.01)
    *A61B 5/16*     (2006.01)
    *G16H 40/63*     (2018.01)
    *G16H 50/20*     (2018.01)

(56) References Cited

U.S. PATENT DOCUMENTS

| | | | |
|---|---|---|---|
| 2007/0112585 A1* | 5/2007 | Breiter | G16B 40/20 705/2 |
| 2010/0076274 A1* | 3/2010 | Severson | G06F 16/435 707/E17.127 |
| 2010/0311023 A1 | 12/2010 | Kan et al. | |
| 2013/0060125 A1 | 3/2013 | Zeman et al. | |
| 2015/0045688 A1 | 2/2015 | Nardi | |
| 2016/0019693 A1* | 1/2016 | Silbersweig | G06T 11/60 382/128 |
| 2017/0258389 A1* | 9/2017 | Howard | A61B 5/4082 |
| 2017/0364929 A1 | 12/2017 | Ferreira | |
| 2018/0236235 A1* | 8/2018 | Hettrick | A61N 1/36082 |
| 2019/0090749 A1* | 3/2019 | Leuthardt | G06T 7/0012 |
| 2019/0142338 A1* | 5/2019 | Fang | A61B 5/372 600/408 |
| 2022/0160287 A1* | 5/2022 | Nenadovic | A61B 5/384 |

OTHER PUBLICATIONS

Medaglia, John D., and Danielle S. Bassett. "Network analyses and nervous system disorders." arXiv preprint arXiv:1701.01101 (2017) (Year: 2017).*

European Extended Search Report mailed Dec. 16, 2021 for European Application No. EP 19 76 7121.7; 11 pages.

Seeman, P. & Lee, T. Antipsychotic drugs: direct correlation between clinical potency and presynaptic action on dopamine neurons. *Science* 188, 1217-1219 (1975).

Anticevic, A., et al. Characterizing thalamo-cortical disturbances in schizophrenia and bipolar illness. *Cereb Cortex* 24, 3116-3130 (2014).

Insel, T., et al. Research domain criteria (RDoC): toward a new classification framework for research on mental disorders. *Am J Psychiatry* 167, 748-751 (2010).

Yang, G.J., et al. Altered Global Signal Topography in Schizophrenia. *Cereb Cortex* (2016).

Shen, W.W. A history of antipsychotic drug development. *Compr Psychiatry* 40, 407-414 (1999).

Tamminga, C.A., et al. Clinical phenotypes of psychosis in the Bipolar-Schizophrenia Network on Intermediate Phenotypes (B-SNIP). *Am J Psychiatry* 170, 1263-1274 (2013).

Anticevic, A., et al. Global Prefrontal and Fronto-amygdala Dysconnectivity in Bipolar I Disorder with Psychosis History. *Biological Psychiatry* 73, 565-573 (2012).

Anticevic, A., et al. Global resting-state functional magnetic resonance imaging analysis identifies frontal cortex, striatal, and cerebellar dysconnectivity in obsessive-compulsive disorder. *Biol. Psychiatry* 75, 595-605 (2013).

Cole, M.W., Anticevic, A., Repovs, G. & Barch, D.M. Variable global dysconnectivity and individual differences in schizophrenia. *Biological Psychiatry* 70, 43-50 (2011).

Yeo, B.T., et al. The organization of the human cerebral cortex estimated by intrinsic functional connectivity. *J Neurophysiol* 106, 1125-1165 (2011).

Glasser, M.F., et al. A multi-modal parcellation of human cerebral cortex. *Nature* 536, 171-178 (2016).

Hawrylycz, M.J., et al. An anatomically comprehensive atlas of the adult human brain transcriptome. *Nature* 489, 391-399 (2012).

Burt, J.D., M; Eckner, WJ; Navejar, NM; Ji, JL; Martin, WJ; Bernacchia, A; Anticevic, A; Murray, JD. Hierarchy of transcriptomic specialization across human cortex captured by myelin map topography. *Nature Neuroscience* 21, 1251-1259 (2017).

International Search Report and Written Opinion of the International Searching Authority directed to related International Patent Application No. PCT/US2019/022110, mailed Jul. 25, 2019; 17 pages.

Sunkin, S., et al. Allen Brain Atlas: an integrated spatio-temporal portal for exploring the central nervous system. *Nucleic Acids Research* 41, D996-D1008 (Jan. 2013; published online Nov. 28, 2012).

* cited by examiner

Examples of Behavioral Features

*Demographic Characteristics, Symptom Scores, Cognitive Performance Collected via Rating Scales, Questionnaires and Clinician Impression*

| Characteristic | HCS (N=202) M | S.D. | PROB (N=436) M | S.D. | BPP (N=150) M | S.D. | SADP (N=119) M | S.D. | SCZP (N=167) M | S.D. |
|---|---|---|---|---|---|---|---|---|---|---|
| Age (years) | 37.18 | 12.18 | 35.33 | 12.31 | 36.29 | 12.94 | 35.86 | 11.87 | 34.16 | 11.99 |
| Gender (% male) | 42.08% | - | 48.62% | - | 31.33% | - | 44.54% | - | 67.07% | - |
| Parental education (years) | 13.35 | 3.42 | 13.67 | 3.43 | 14.16 | 3.44 | 13.05 | 3.95 | 13.62 | 2.93 |
| Participant's education | 14.76 | 2.27 | 13.47 | 2.34 | 14.22 | 2.31 | 13.25 | 2.22 | 12.93 | 2.28 |
| Handedness (% right) | 85.64% | - | 85.78% | - | 83.33% | - | 88.24% | - | 86.23% | - |
| Signal-to-noise (SNR) | 231.03 | 82.70 | 218.34 | 93.44 | 229.78 | 100.09 | 230.93 | 93.83 | 198.10 | 83.13 |
| % Frames Flagged | 2.81% | 3.99% | 6.17% | 9.09% | 6.41% | 9.67% | 5.32% | 9.32% | 6.57% | 8.35% |
| Medication (CPZ equivalents) | - | - | 443.20 | 402.92 | 318.61 | 321.06 | 514.43 | 462.70 | 490.64 | 395.76 |
| PANSS Positive Symptoms | 7.03 | 0.30 | 15.66 | 5.35 | 12.87 | 4.35 | 18.19 | 5.20 | 16.37 | 5.15 |
| PANSS Negative Symptoms | 7.01 | 0.16 | 14.59 | 5.10 | 12.01 | 3.66 | 15.55 | 4.52 | 16.22 | 5.68 |
| PANSS General Psychopathology | 16.04 | 0.36 | 31.45 | 8.67 | 28.72 | 8.20 | 34.57 | 8.70 | 31.67 | 8.30 |
| PANSS Total Psychopathology | 30.0842 | 0.61 | 61.67 | 16.32 | 53.59 | 13.69 | 68.22 | 15.72 | 64.26 | 16.04 |
| BACS Cognitive Composite Score (Z) | -0.02 | 1.13 | -1.22 | 1.20 | -0.83 | 1.19 | -1.30 | 1.10 | -1.52 | 1.19 |

FIG. 2A

*Cognitive Paradigm Deployed via Computerized Assessment*

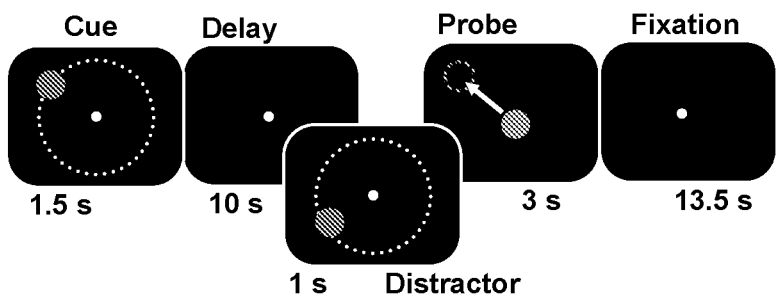

Cue 1.5 s — Delay 10 s — 1 s Distractor — Probe 3 s — Fixation 13.5 s

FIG. 2B

*Eye Tracking Deployment in Laboratory, Clinic or Inside the Scanner*

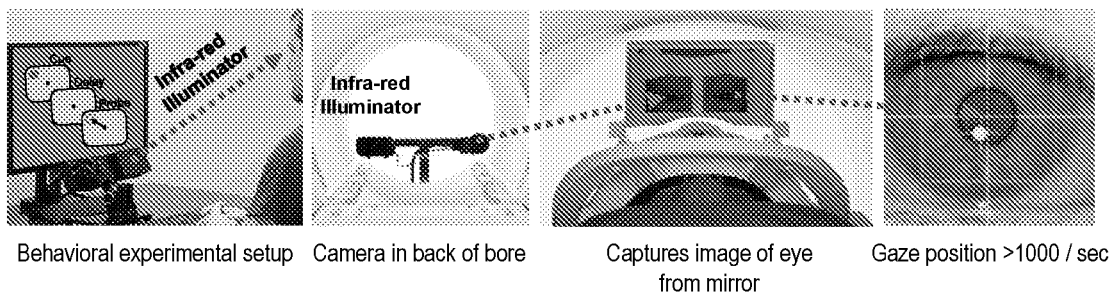

Behavioral experimental setup | Camera in back of bore | Captures image of eye from mirror | Gaze position >1000 / sec

FIG. 2C

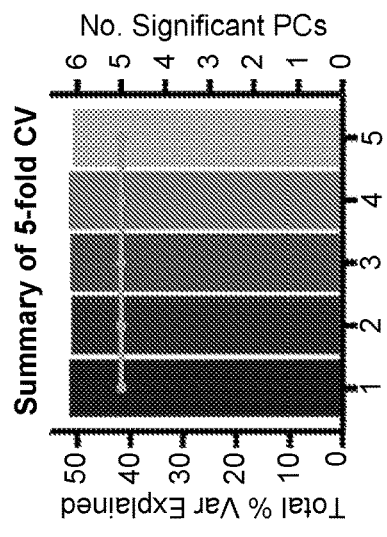
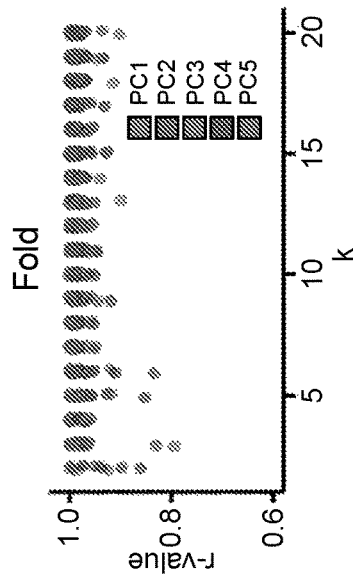
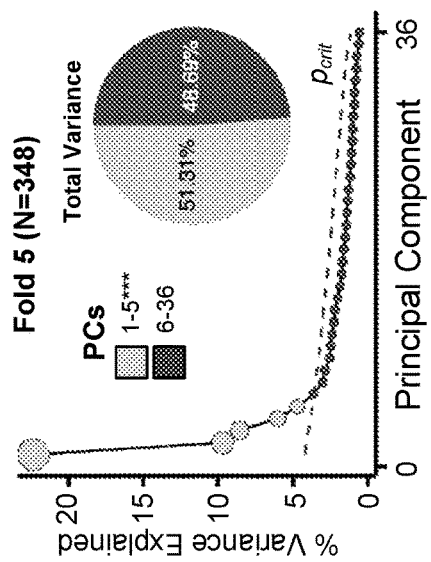
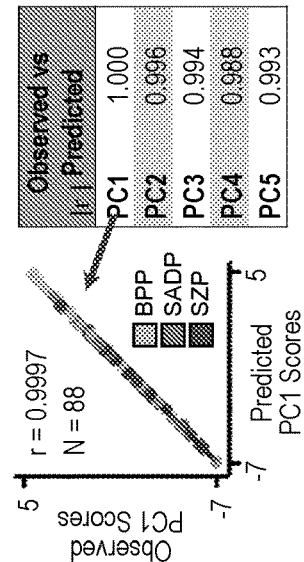
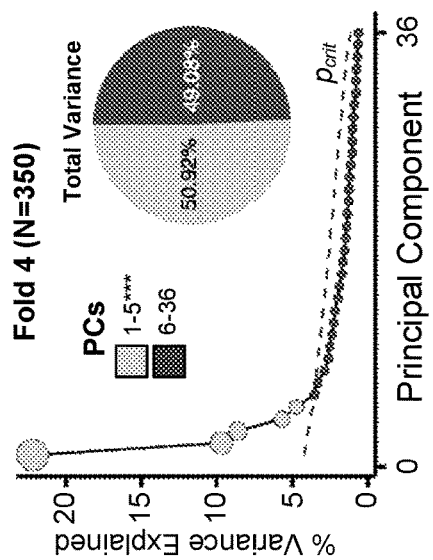
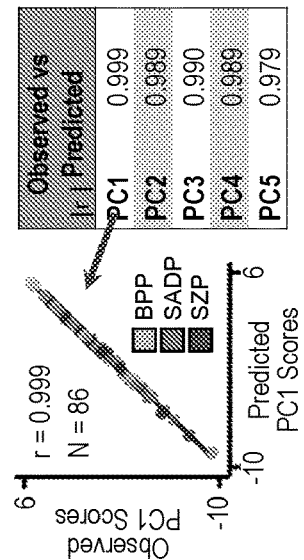
FIG. 5D  FIG. 5E  FIG. 5F  FIG. 5G

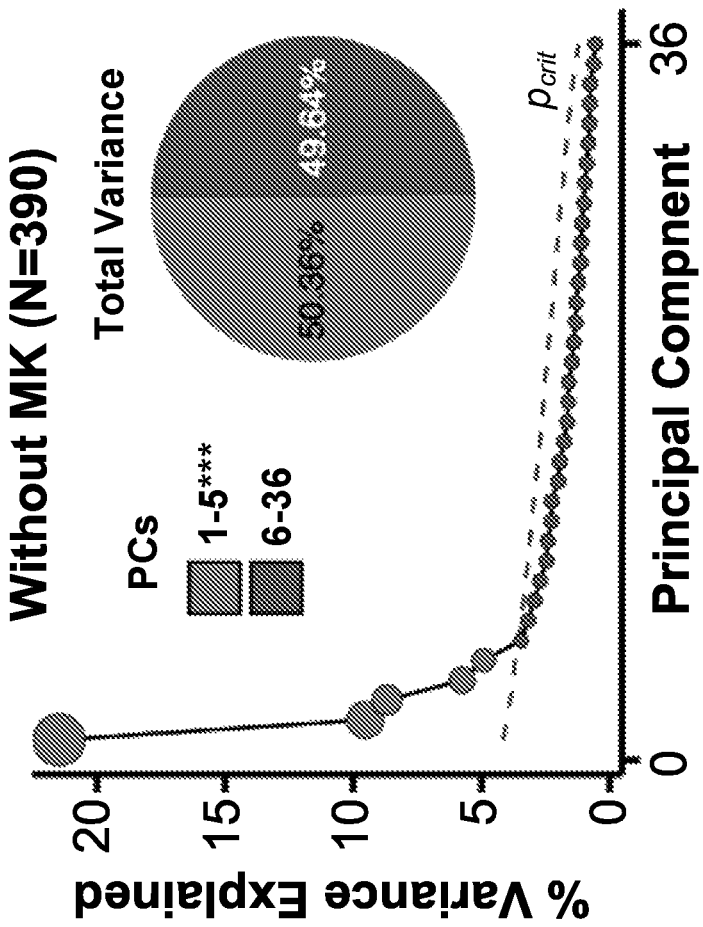
FIG. 6A
FIG. 6B
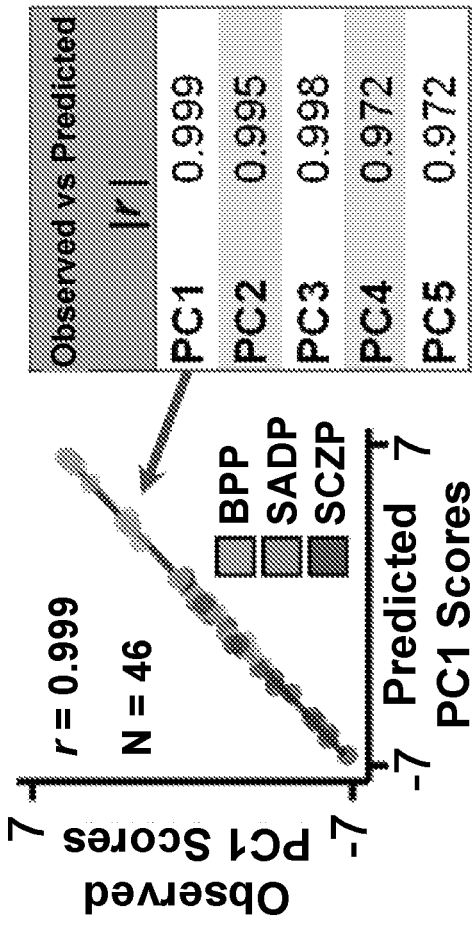
FIG. 6C

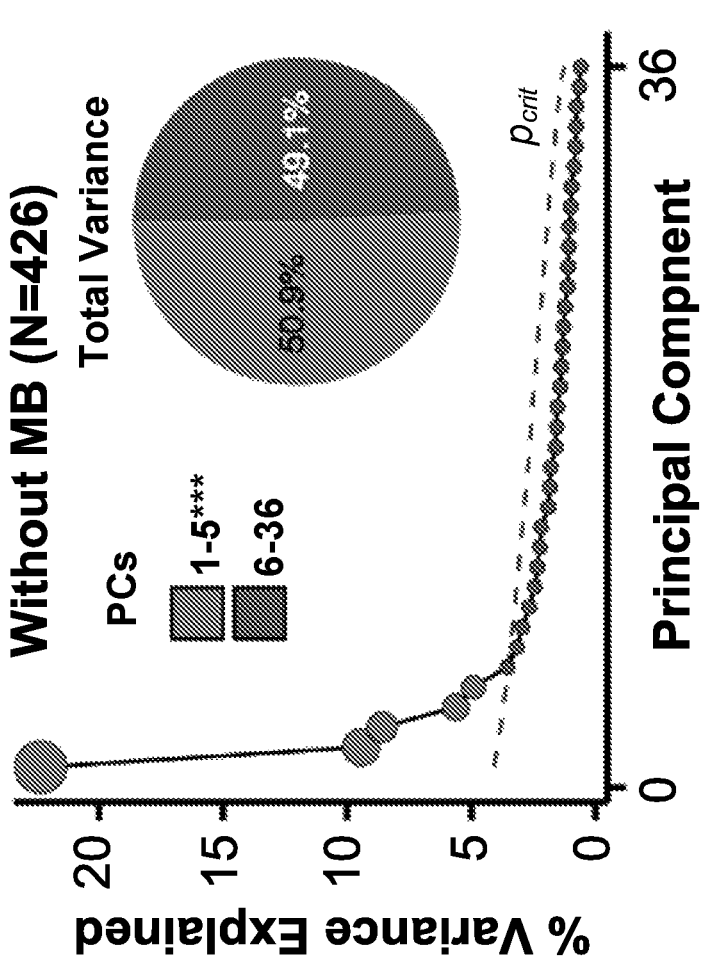
FIG. 6D
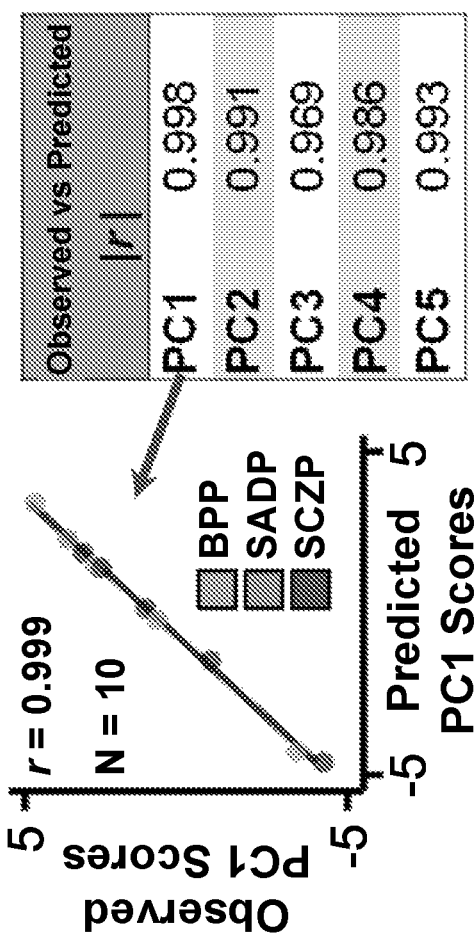
FIG. 6E
FIG. 6F

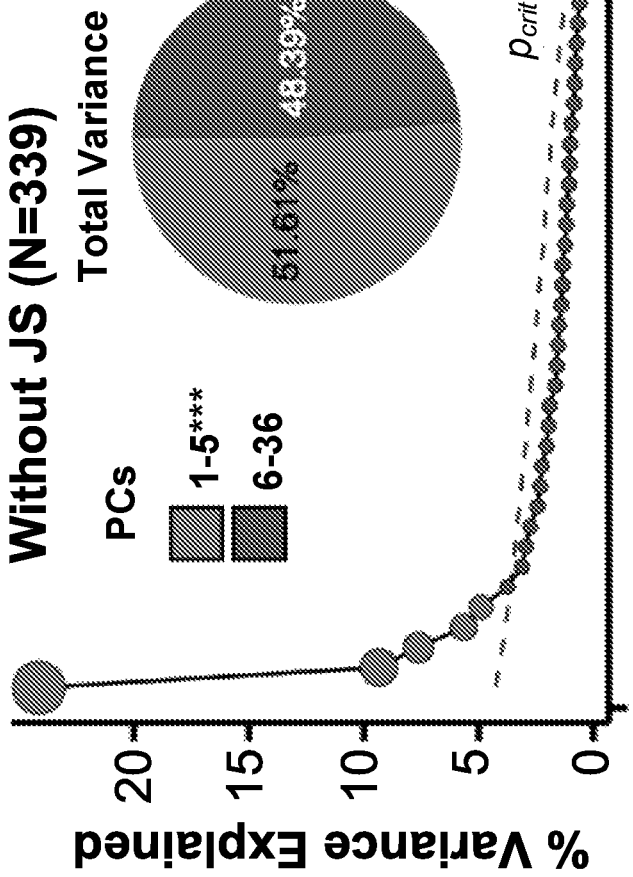
FIG. 6G
FIG. 6H
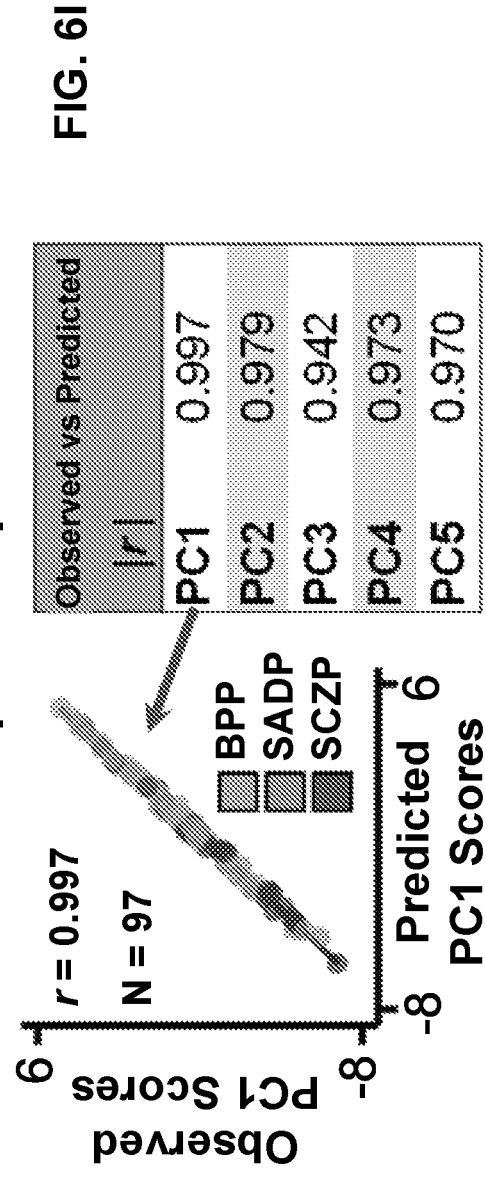
FIG. 6I

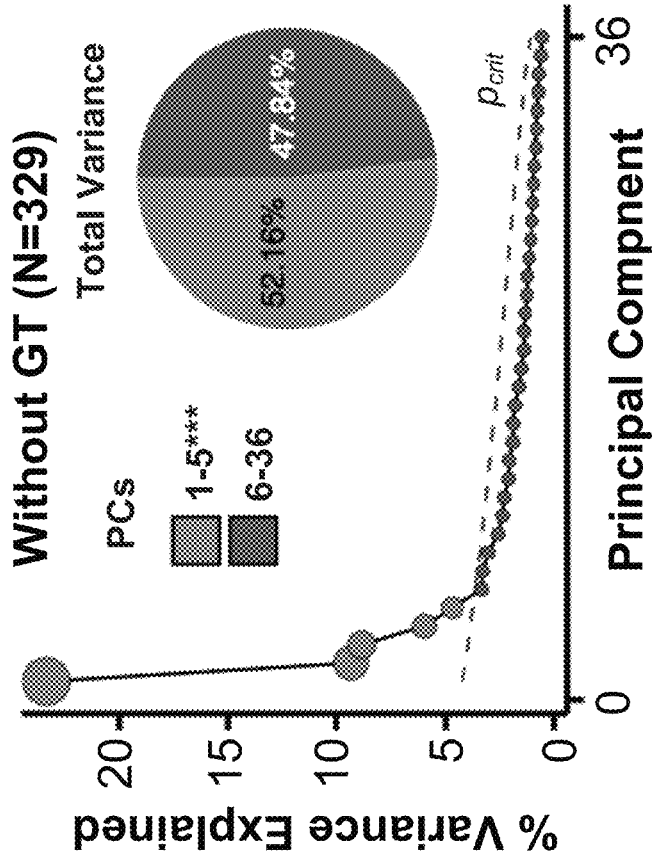
FIG. 6J
FIG. 6K
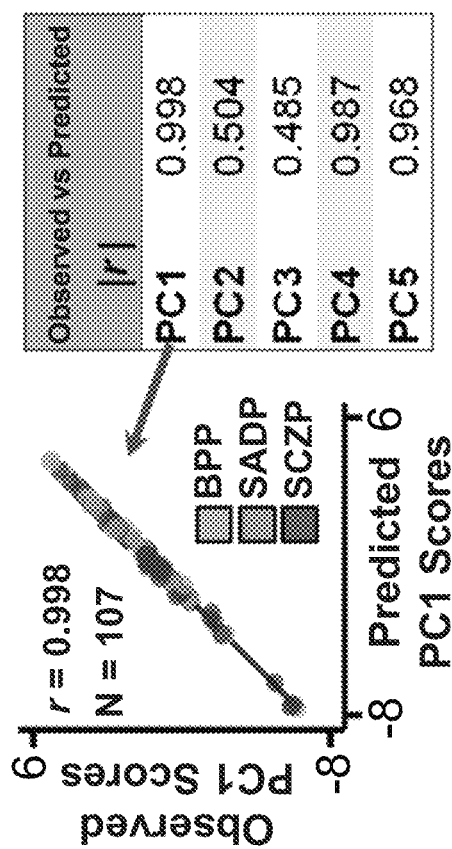
FIG. 6L

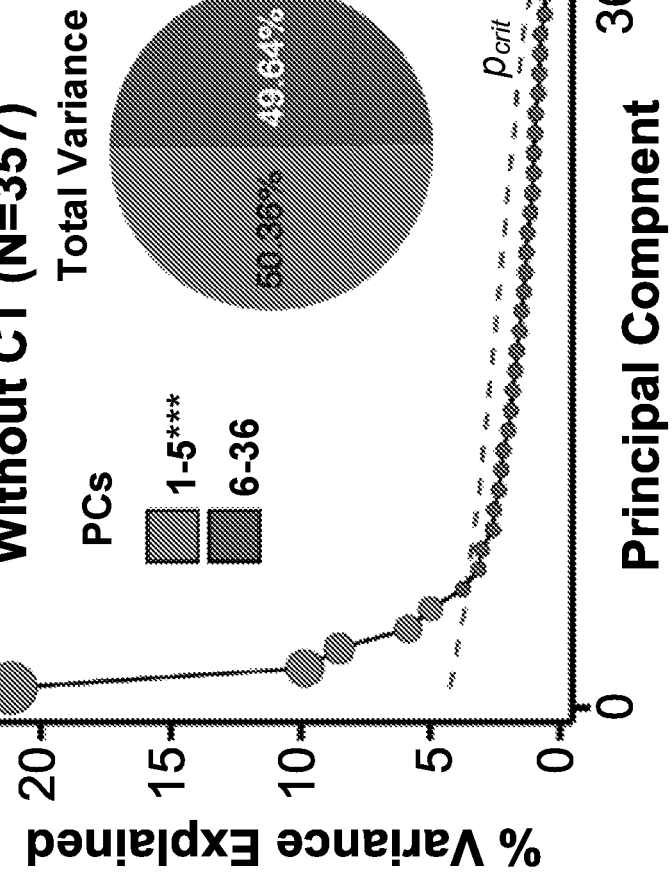
FIG. 6P
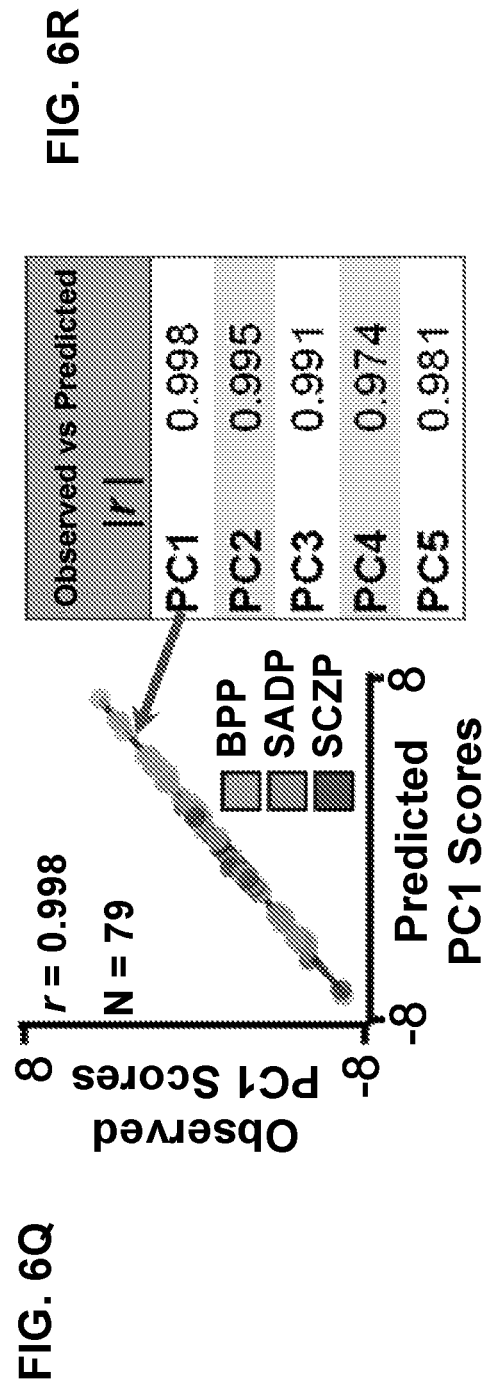
FIG. 6Q
FIG. 6R

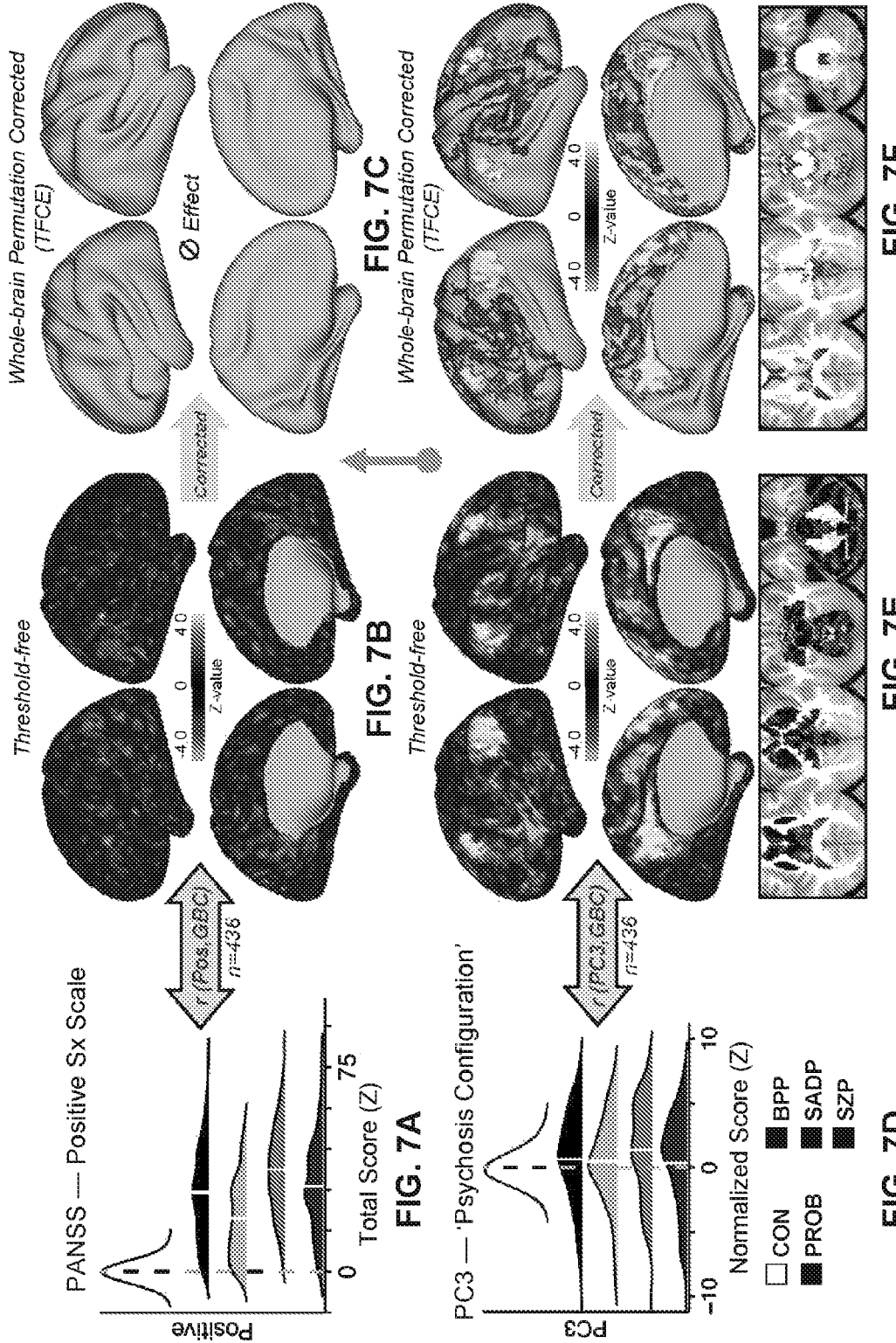

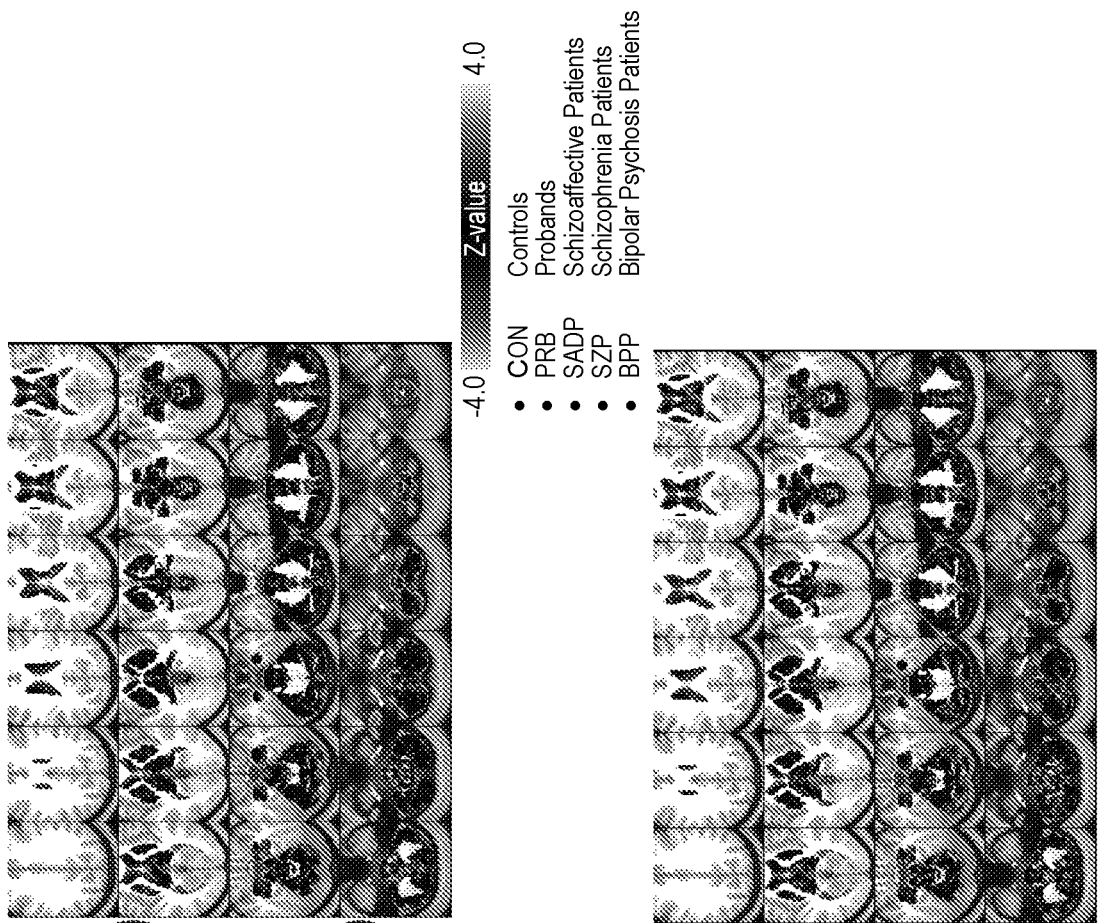
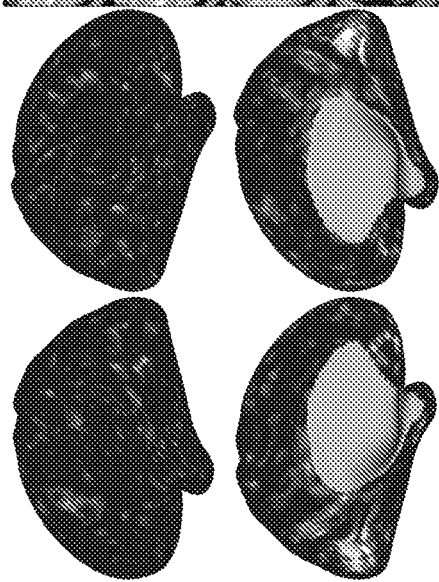
FIG. 8A
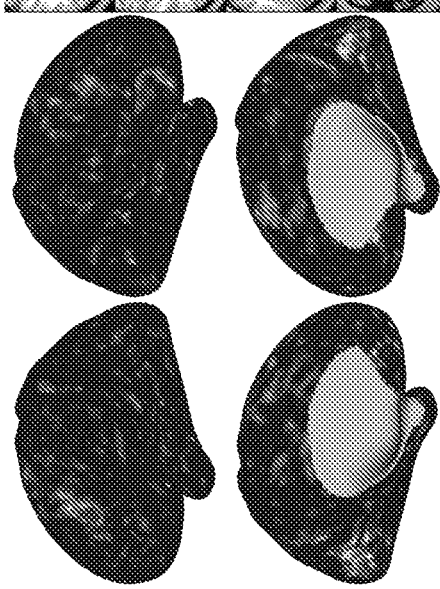
FIG. 8B

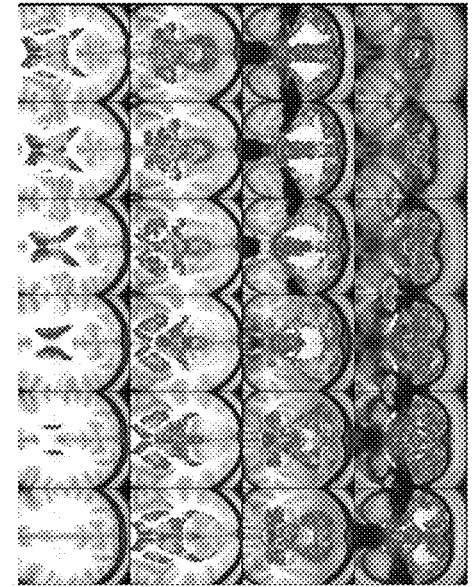 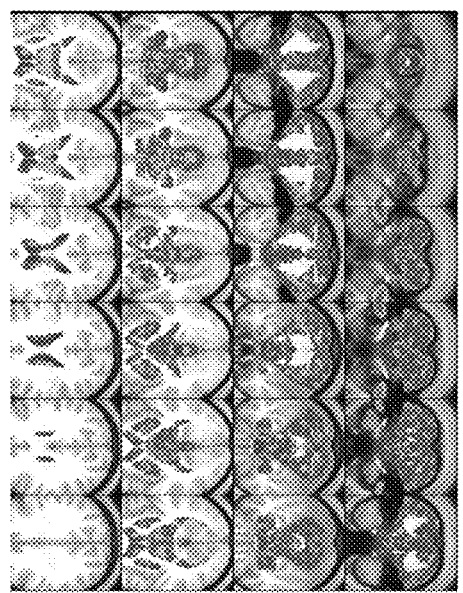
FIG. 9A
FIG. 9B

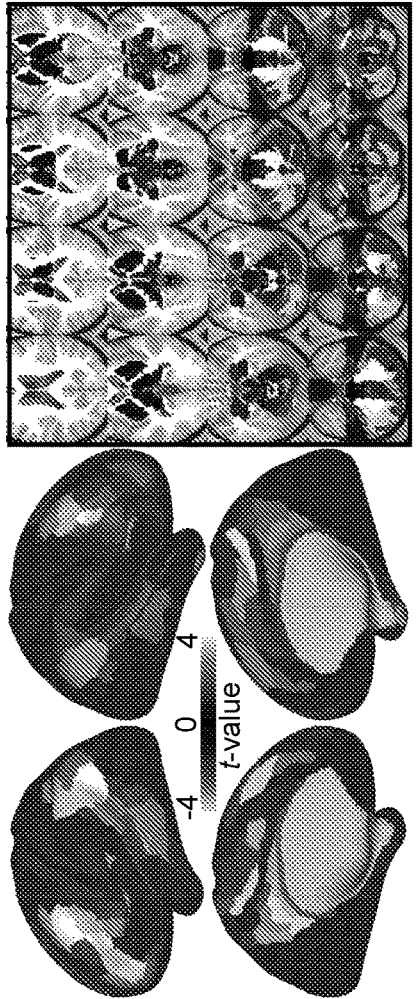
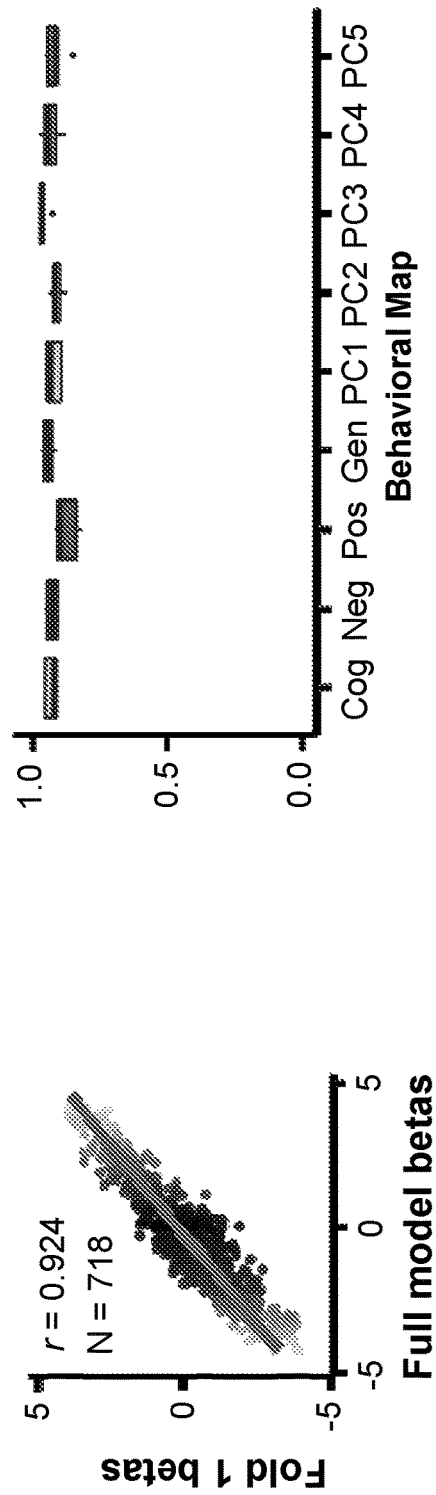
FIG. 11A
FIG. 11B
FIG. 11C

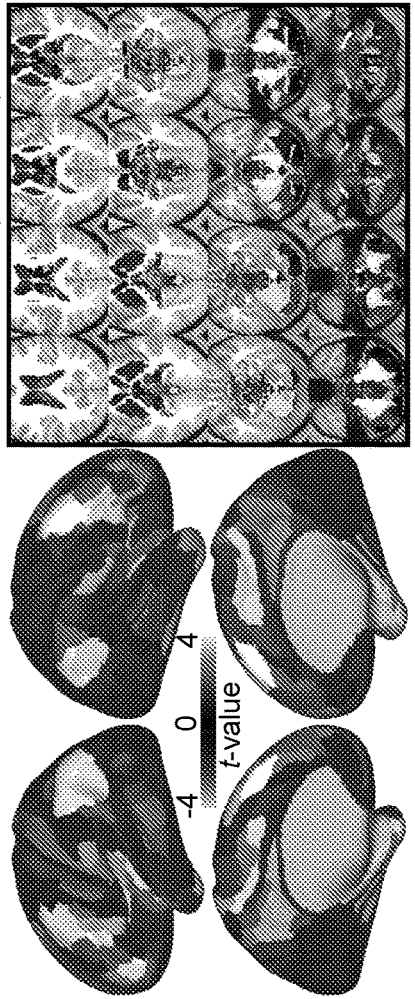
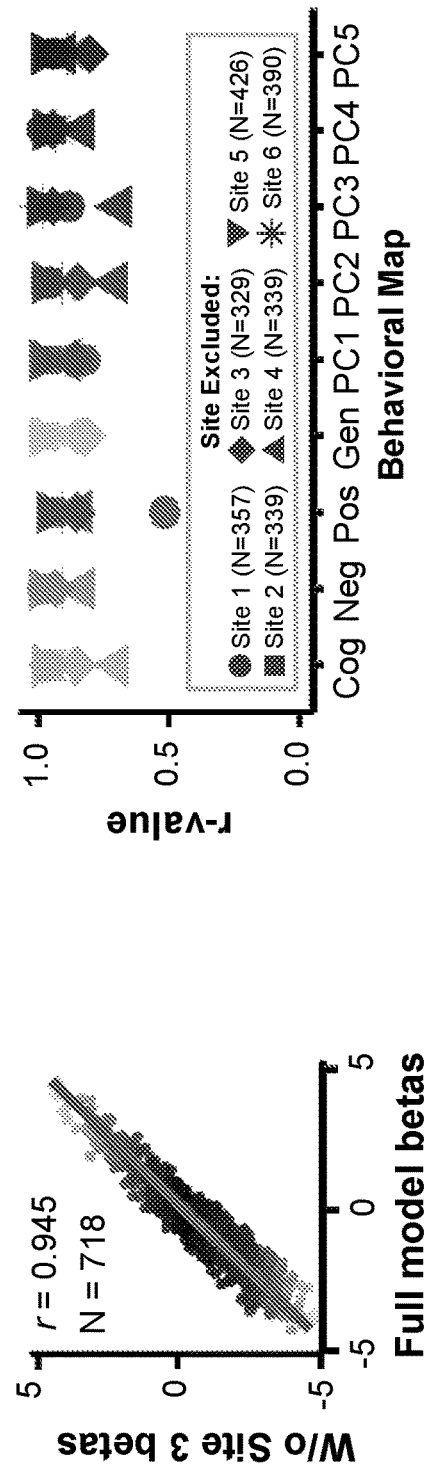
FIG. 11D
FIG. 11E
FIG. 11F

FIG. 12C

Correlation Matrix of IC and PC Scores Across Subjects

|  | IC1 | IC2 | IC3 | IC4 | IC5 |
|---|---|---|---|---|---|
| PC1 | 0.20 | 0.24 | -0.06 | 0.87 | 0.18 |
| PC2 | 0.30 | -0.10 | 0.31 | 0.22 | 0.82 |
| PC3 | 0.13 | 0.62 | -0.66 | 0.29 | 0.21 |
| PC4 | -0.51 | -0.47 | -0.48 | -0.12 | 0.37 |
| PC5 | 0.69 | -0.56 | -0.43 | 0.00 | -0.13 |

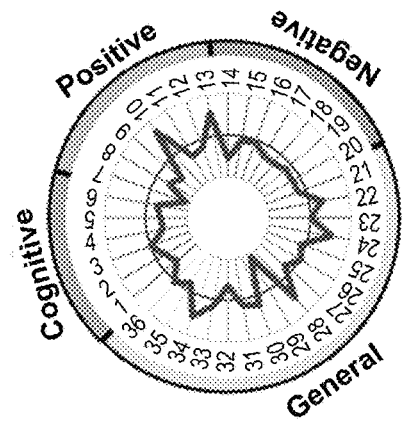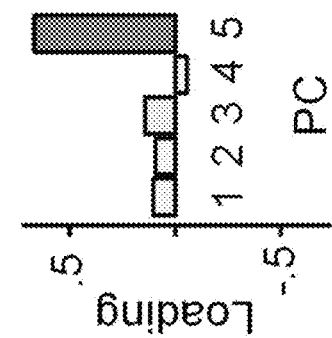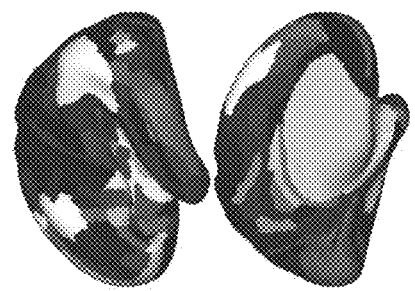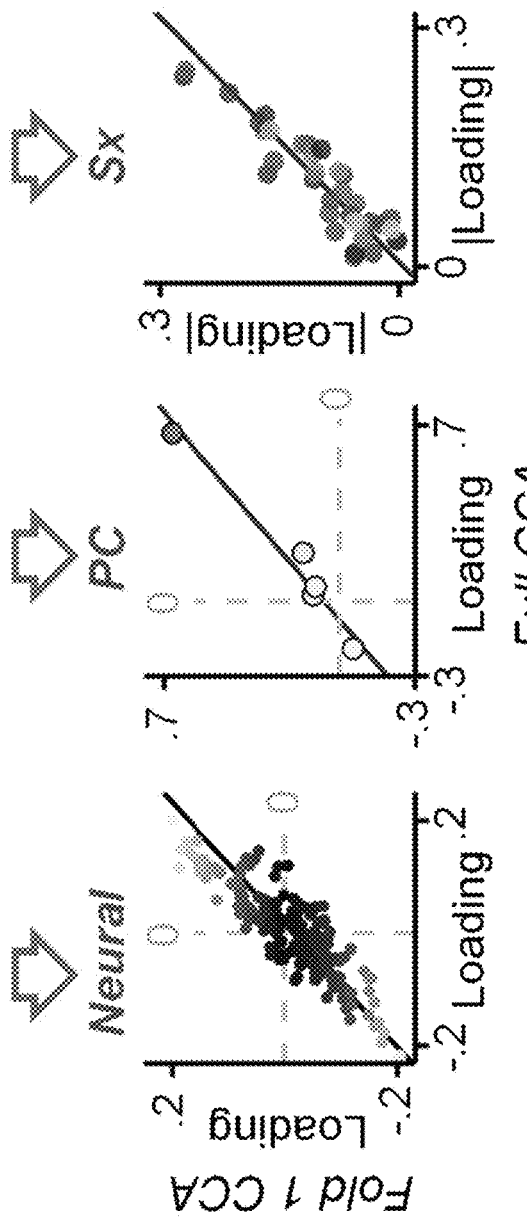
FIG. 14F

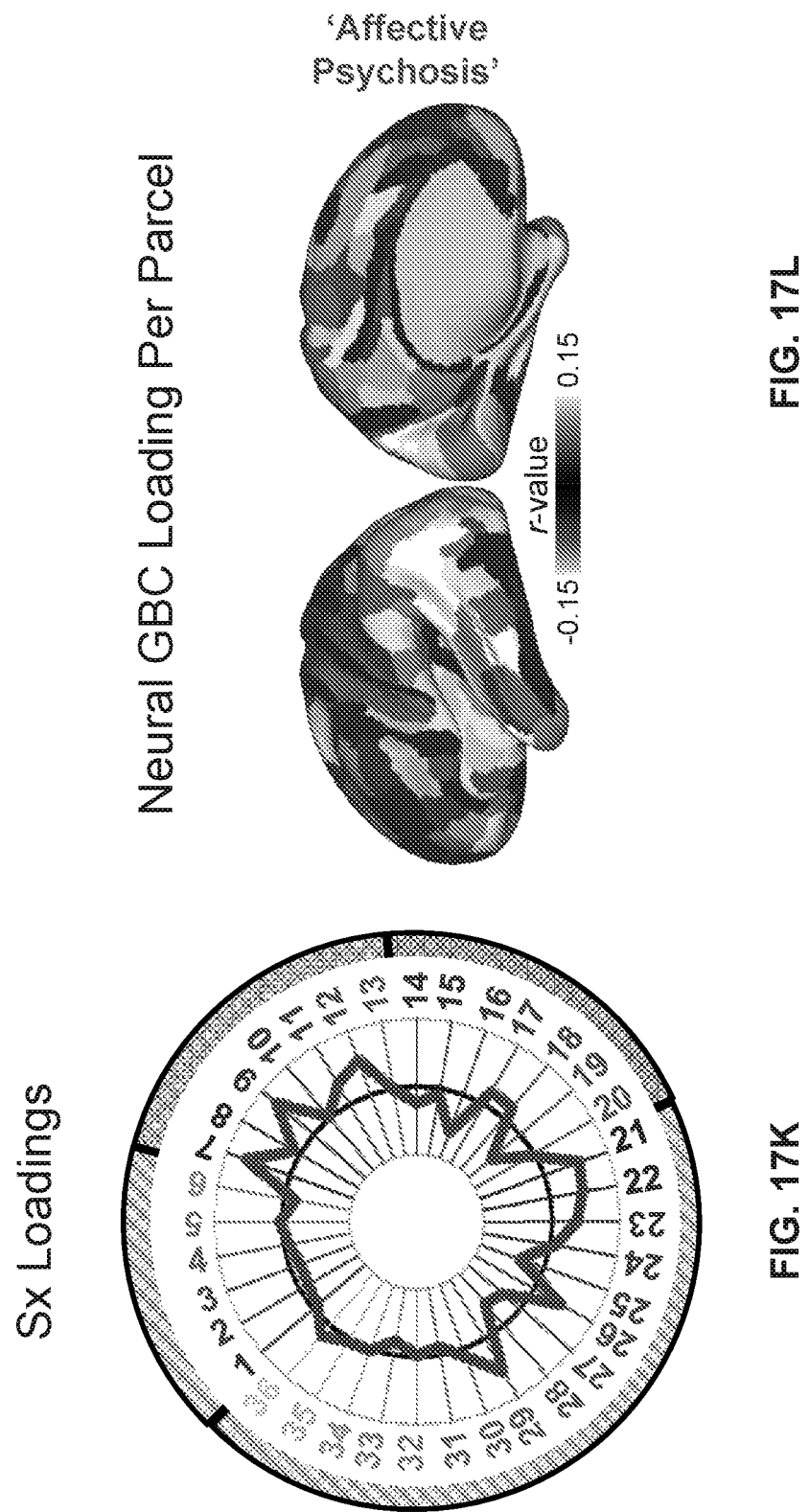

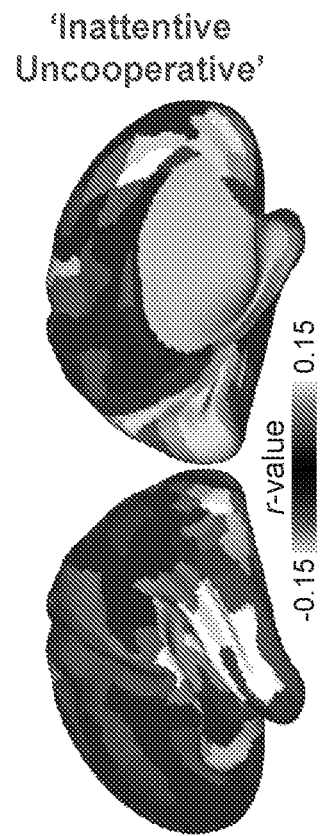
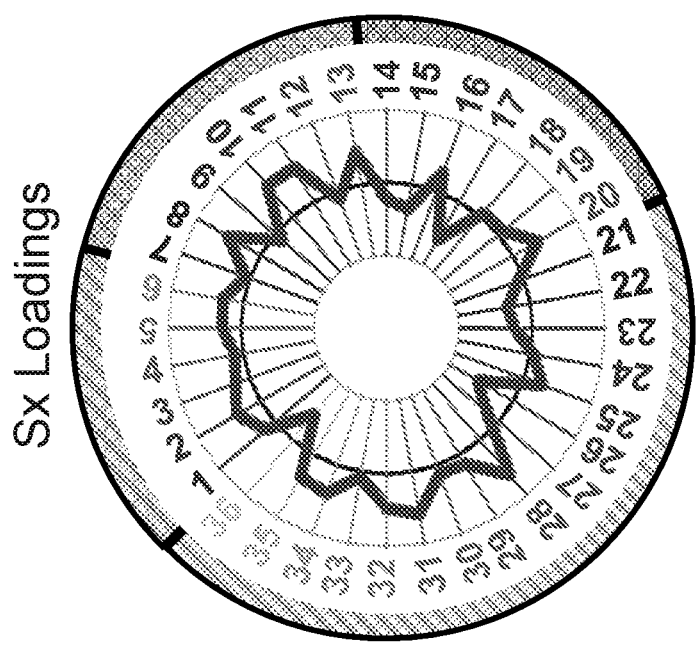
FIG. 17T
FIG. 17S

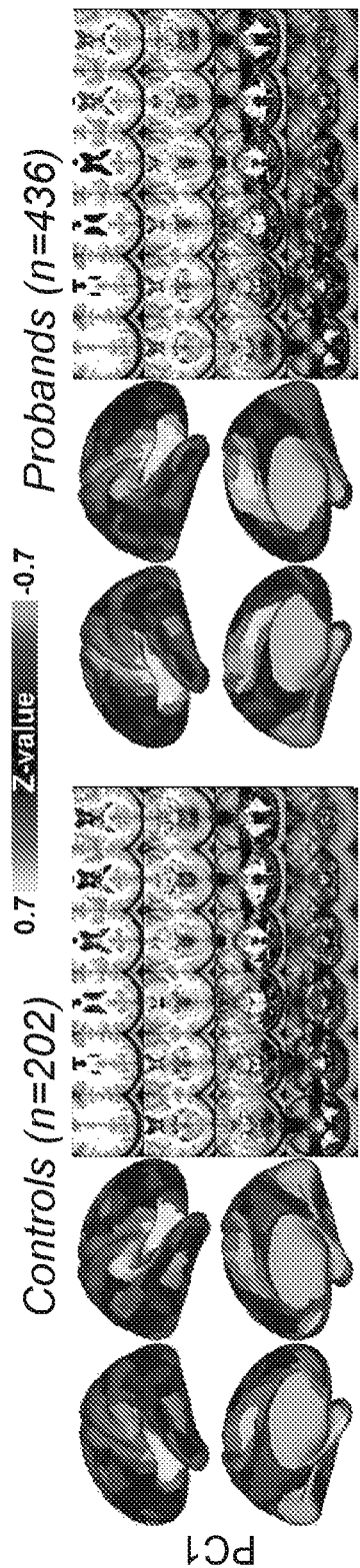
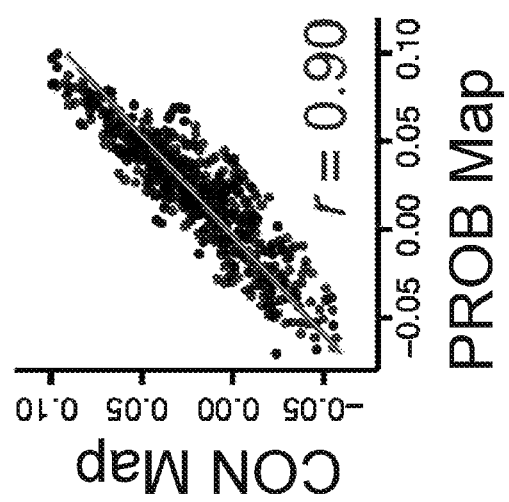
FIG. 19A
FIG. 19B
FIG. 19C

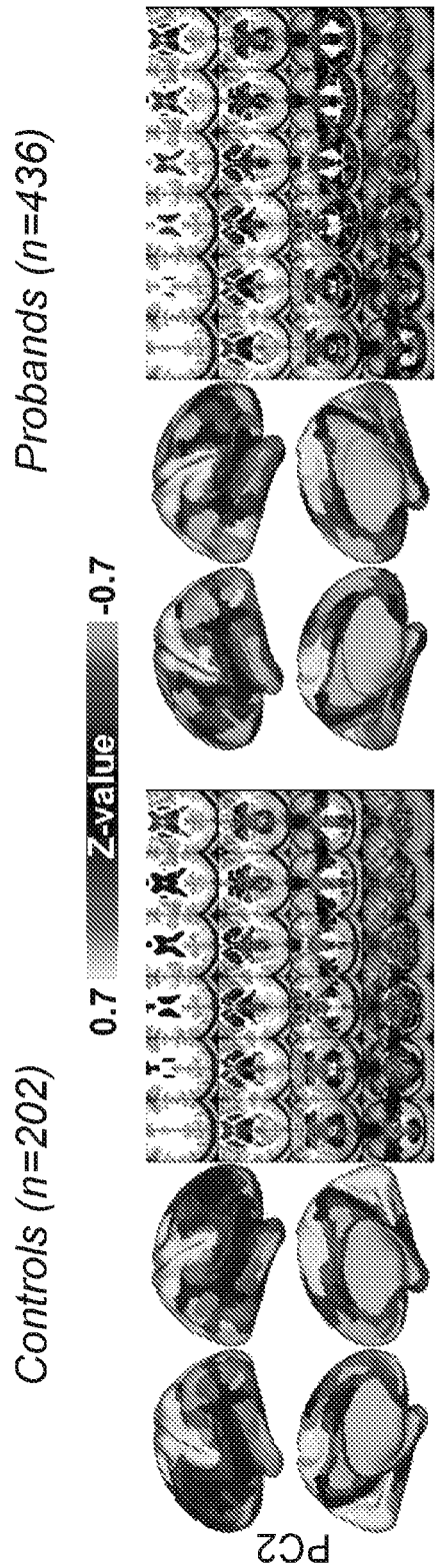
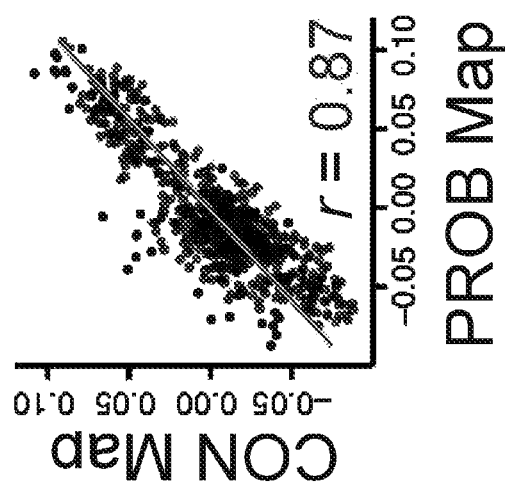
FIG. 19D
FIG. 19E
FIG. 19F

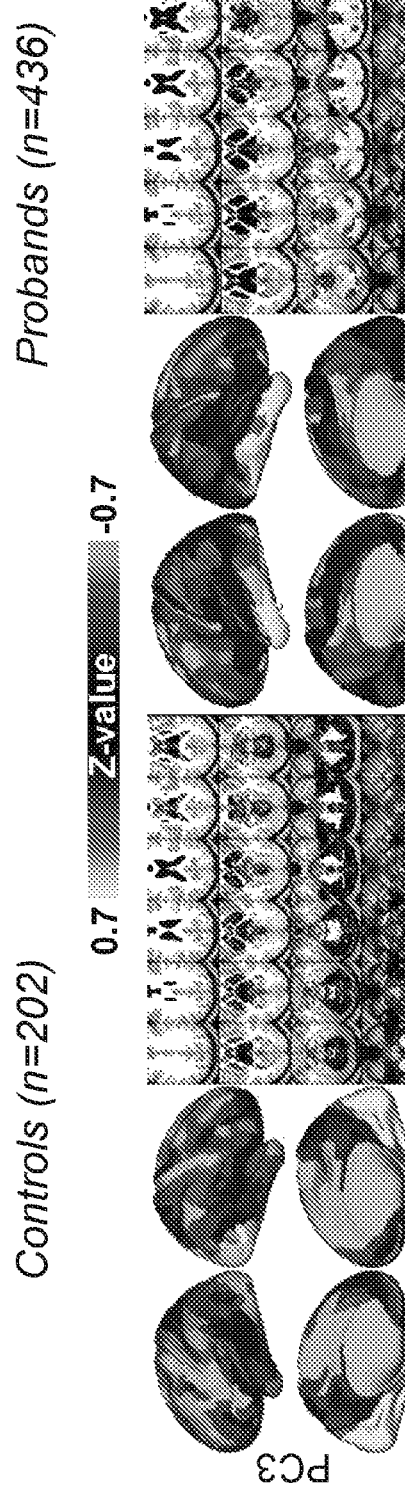
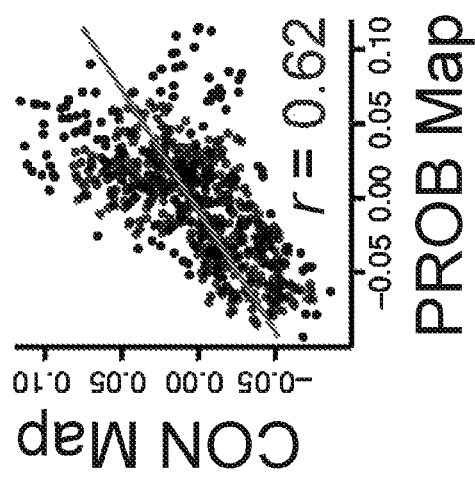
FIG. 19G
FIG. 19H
FIG. 19I

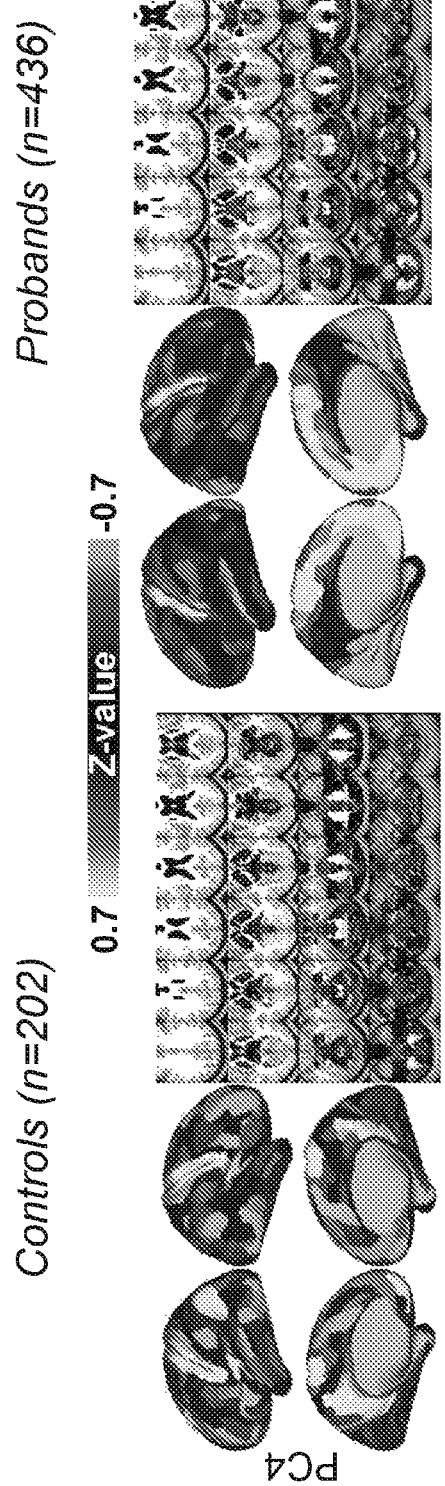
FIG. 19J
FIG. 19K
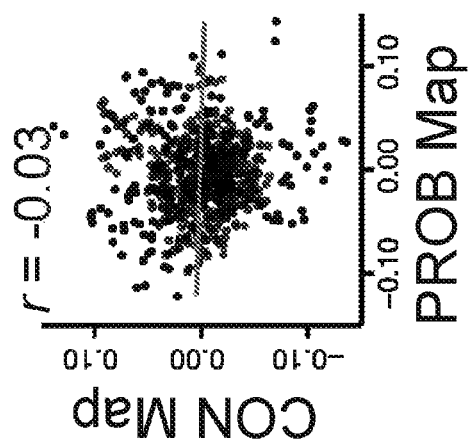
FIG. 19L

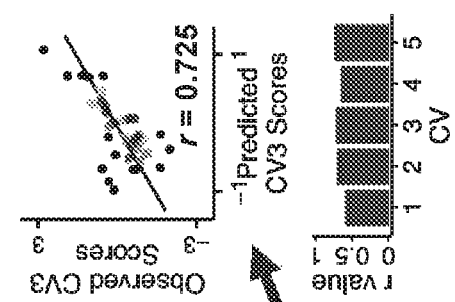
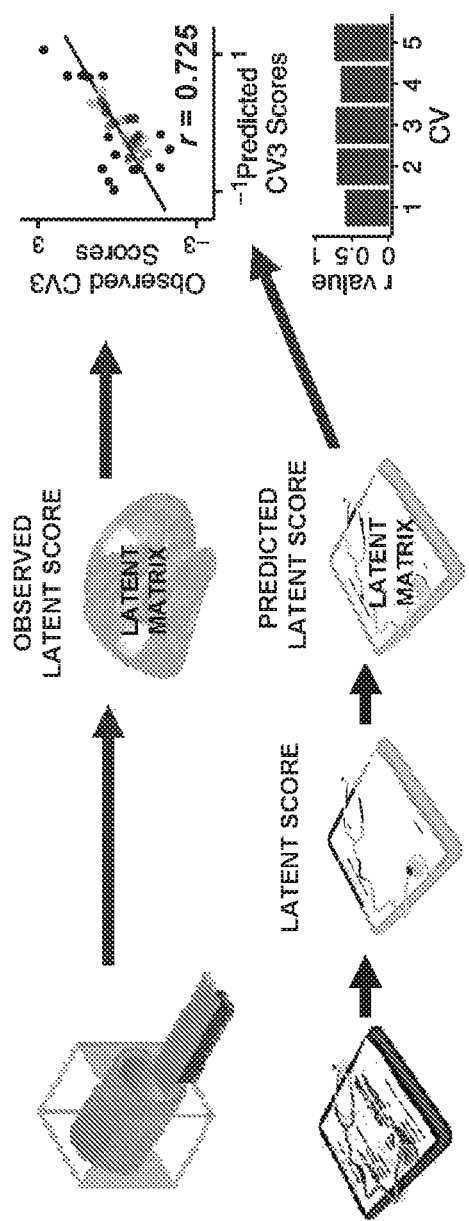
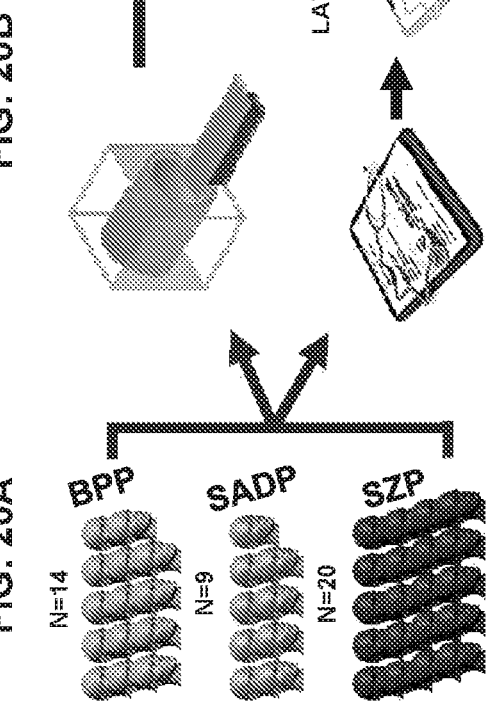
FIG. 20A  FIG. 20B  FIG. 20C  FIG. 20D  FIG. 20E

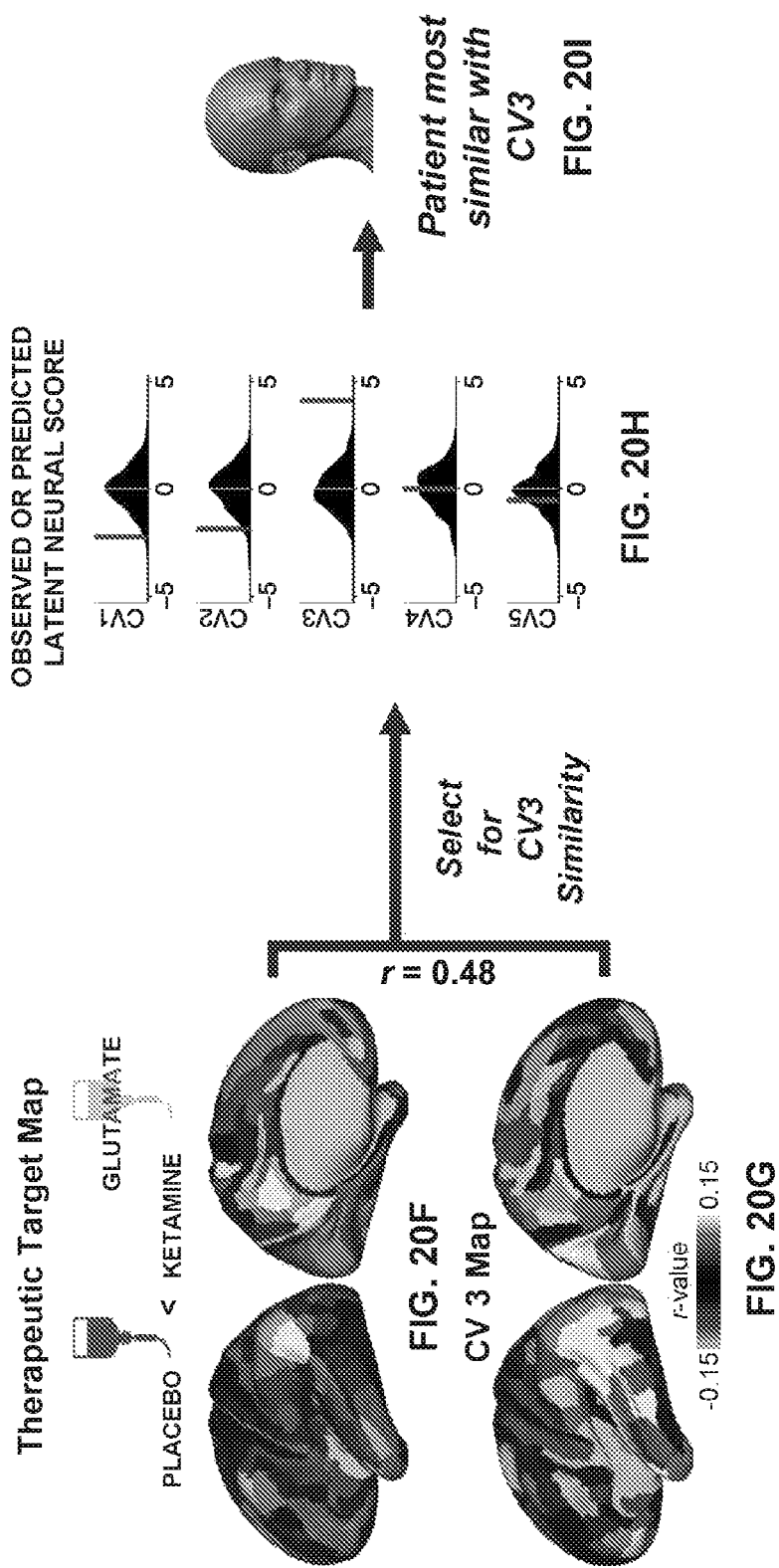

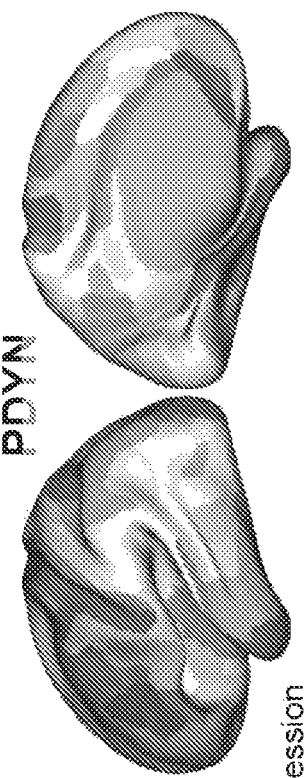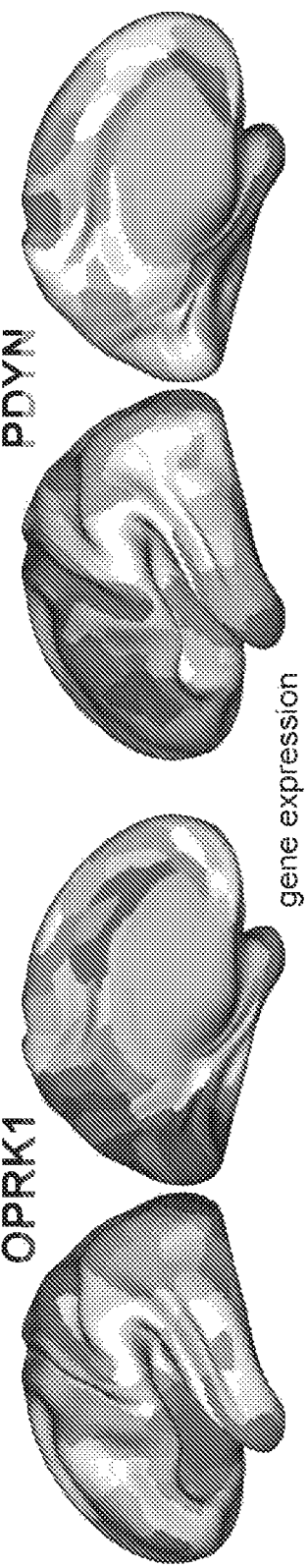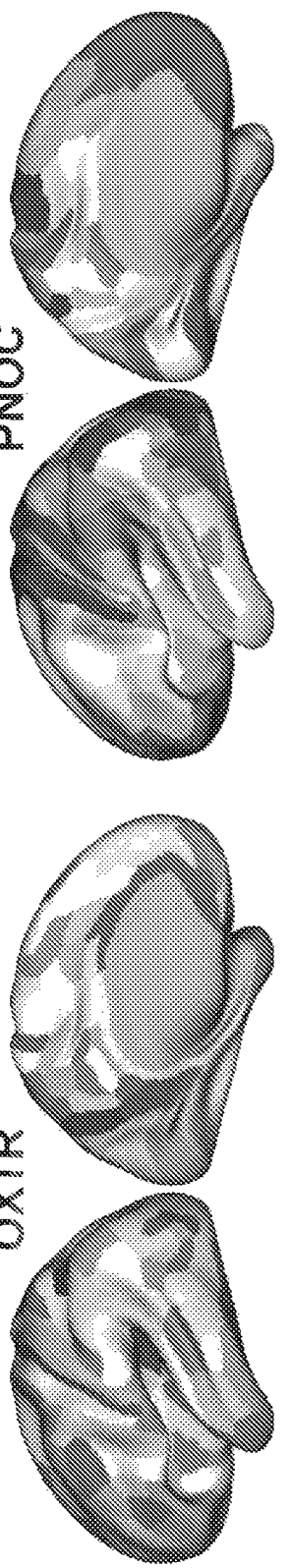
FIG. 21A OPRK1  FIG. 21B PDYN  FIG. 21C OXTR  FIG. 21D PNOC

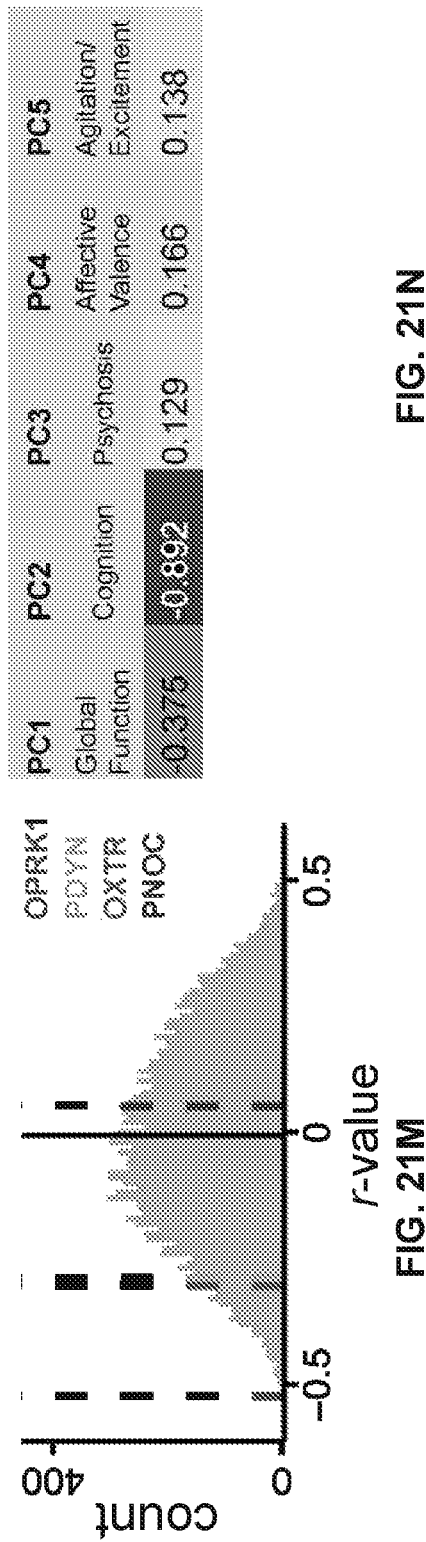
FIG. 21M
FIG. 21N
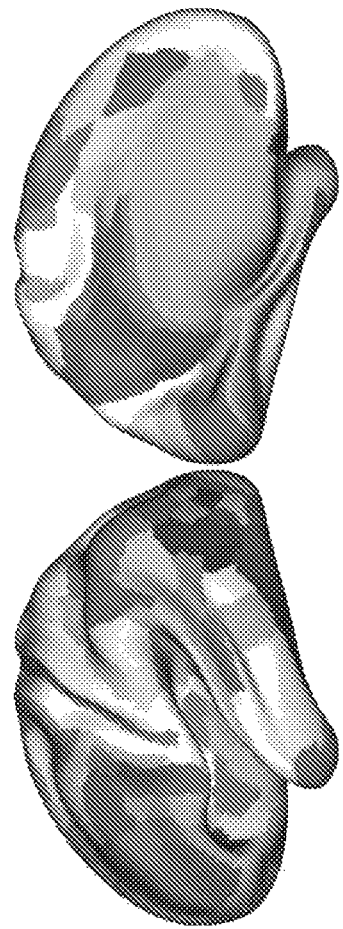
Canonical Variate 4
FIG. 21O

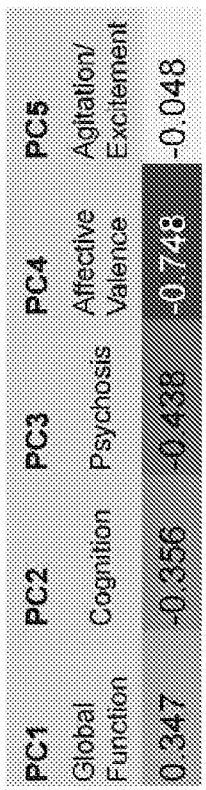
FIG. 21Q
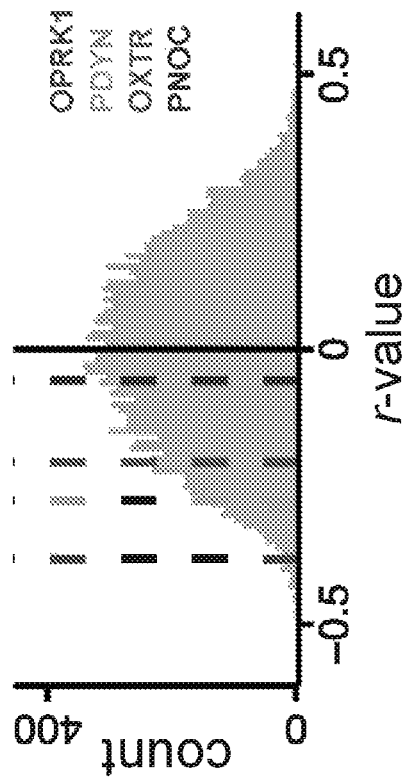
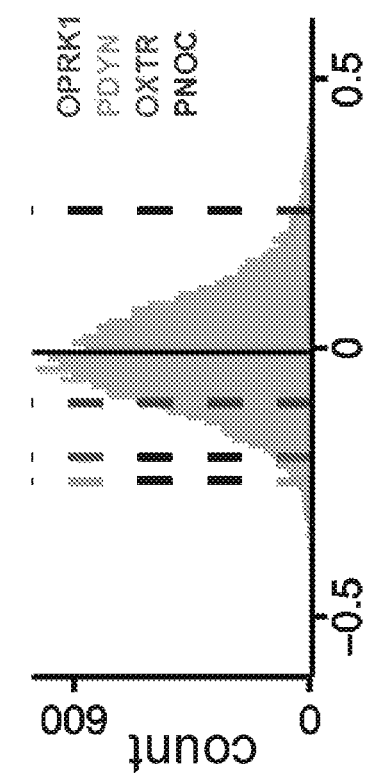
FIG. 21P
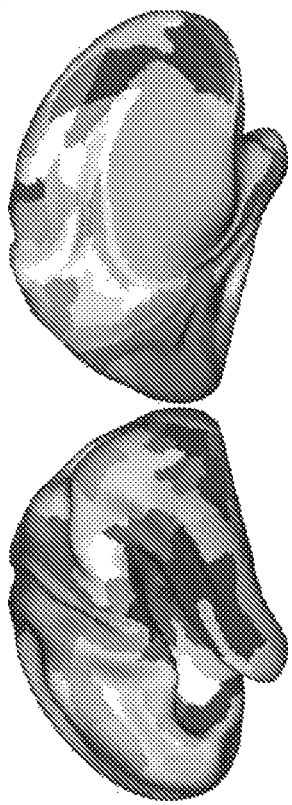
FIG. 21S
Canonical Variate 5
FIG. 21R

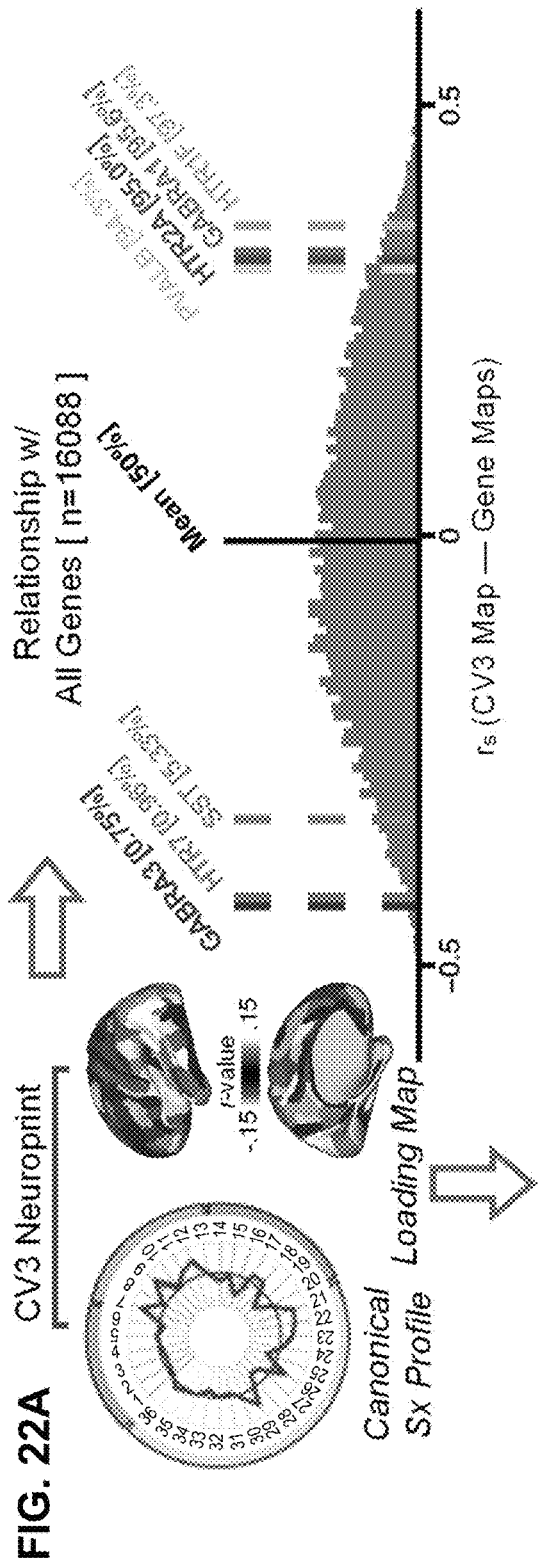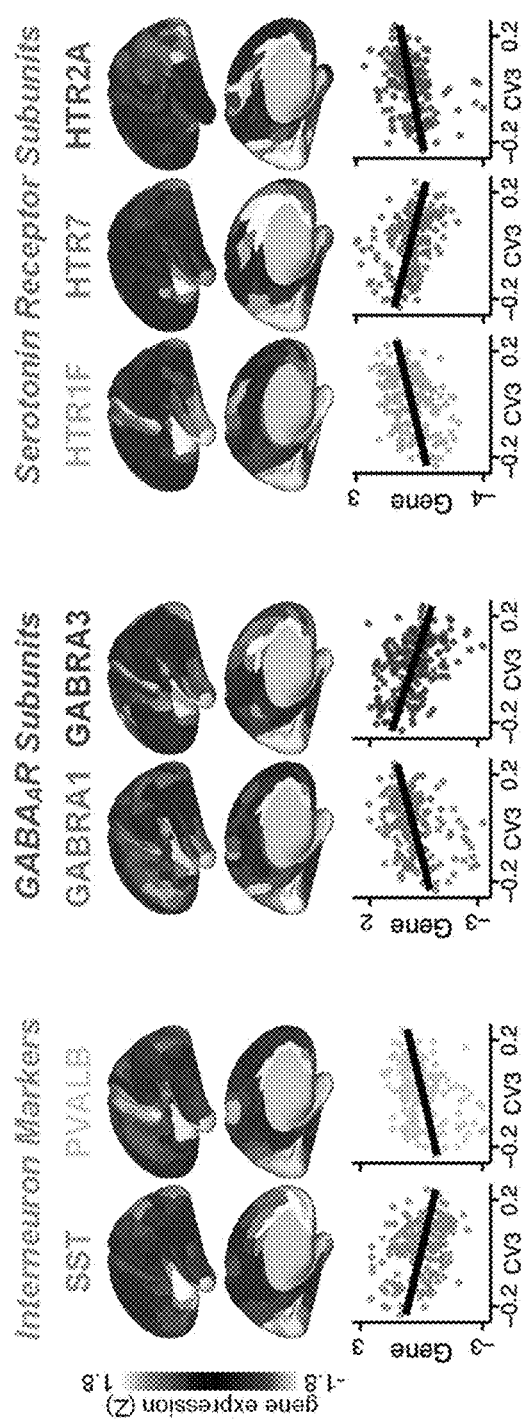
FIG. 22A
FIG. 22B
FIG. 22C
FIG. 22D

Computer Command Line Interface

N-BRIDGE

Neuro-Behavioral Relationships In Dimensional Geometric (N-BRIDGE) Suite
version 0.1.0

LICENSE:
Use of this software is subject to the terms and conditions defined in the file
'LICENSE.md' which is part of this source code package.

- DESCRIPTION:

The Neuro-Behavioral Relationships In Dimensional Geometric Embedding (N-BRIDGE) suite
is a computational neuroinformatics platform which provides a mapping between complex
data-driven meuroimaging maps of the human brain and latent behavioral features.
N-BRIDGE provides a method to associate a data-derived 'behavioral' dimensions to
neuroimaging phenotypes, opening a route to efficient rational bridge between complex
behavioral dimensions and neural circuits. In turn, N-BRIDGE also provides a statistical
predictive framework at the individual level that can be used to bi-directionally map
between the neural and behavioral geometry. The platform is built as a 'stand alone'
set of tools that can work with a generic neuroimaging matrix input.
However, the N-BRIDGE platform is optimized for integration with the NMAP suite
(https://bitbucket.org/hidradev/mnaptools).

```
>nbridge.sh--nbridge_function='prep'\
–
outdata="covmtx,comtx,groupfxbar,groupfxridge,bpcatriplot,bpcaload,bpcascores,bpcascorescon,bpcascre
e,bpcabar,bpcaridge,bpcapie,bp
caradar,bpcascorescon,bicascores,bicaload,bicacormtx,bicapie,bicascree"\
–path=${HOME}"\
–inputbehavior="BehaviorDataDx.dat"\
–controlbehavior="BehaviorDataCON.dat"\
–permutations=1000\
–outprefix="nBridgeDemo"
```

N-BBRIDGE *Prepare* Module

N-BBRIDGE *Initialize* Module

N-BBRIDGE *Project* Module

FIG. 36

Summary Quality Assurance Report for Derived Neuro-behavioral Composite Variable (NB-CV)

Report for Derived NB-CV

*% range (low, high) for Derived NB-CV*

---
- NB-CV (2.5-97.5): 6.578
- BACS(0-95): 6.576
- PANSS Positive (0-95): 5.650
- PANSS Negative (0-95): 5.849
- PANSS General (0-95): 7.313

*Min/Max range for Derived NB-CV*

---
- NB-CV (0 -100): 9.437
- NB-CV max: 4.730
- NB-CV min: - 4.706

*Variance for Derived NB-CV*

---
- NB-CV: 2.724
- BACS: 2.901
- PANSS Positive: 2.934
- PANSS Negative: 3.023
- PANSS General: 4.438

FIG. 37A

SYSTEMS AND METHODS FOR NEURO-BEHAVIORAL RELATIONSHIPS IN DIMENSIONAL GEOMETRIC EMBEDDING (N-BRIDGE)

STATEMENT REGARDING FEDERALLY-SPONSORED RESEARCH AND DEVELOPMENT

This invention was made with U.S. Government support under grant R01 MH112189 awarded by National Institutes of Health (NIH). The U.S. Government has certain rights in the invention.

BACKGROUND

Field of the Invention

Embodiments herein relate to systems and methods for mapping multi-dimensional relationships between neural and behavioral features in humans.

Background Art

Mental disorders are one of the top causes of disability worldwide. However, treatment outcomes are poor for many psychiatric conditions, and available forms of treatment often have limited efficacy. For example, many commonly prescribed antipsychotic medications, which primarily act through antagonism of dopamine D2 receptors in the dorsal striatum of the brain, are only effective at treating select "positive" symptoms that present in a subgroup of patients with psychosis-spectrum disorders[1]. Because of the heterogeneity within groups of patients with the same diagnosis, a key challenge lies in matching patients with effective treatments. Understanding the link between specific behaviors and deviations in neural circuitry is thus critical to developing and prescribing effective treatments at an individualized level for patients with psychiatric symptoms.

SUMMARY

Described herein are example methods and systems for neuro-behavioral relationships in dimensional geometric embedding (referred to herein as "N-BRIDGE"), which includes a comprehensive, extensible, data-driven analytic framework for mapping the multi-dimensional and/or multi-variate relationships between neural and behavioral/phenotypic features in individual or groups of humans. Specifically, N-BRIDGE allows mapping of variations along newly-defined data-driven behavioral/phenotypic latent and/or manifest weighted composite dimensions/axes that capture the geometry of behavioral/phenotypic variation to variation in multi-dimensional combination of neural areal features (e.g. voxels, areas or networks). This bi-directional data-driven mapping allows for the robust identification of neuro-behavioral latent and/or manifest weighted composite and/or manifest weighted composite variables that capture clinically and therapeutically relevant information along complex behavioral/phenotypic dimensions. This multi-dimensional mapping can in turn allow for neurobiologically-grounded definition of robust therapeutic neural targets that quantitatively vary in relation to alterations in behavioral/phenotypic dimensions. Capturing the newly-defined data-driven behavioral dimensions obtained via N-BRIDGE reveals a qualitatively novel and substantially more quantitatively robust mapping of neural feature variation onto behavioral/phenotypic dimensions relative to existing approaches, which directly impacts clinically and therapeutically relevant use for specific patients. Furthermore, the newly defined behavioral/phenotypic dimensions, while robustly mapping neural circuit variation, do not necessarily reveal differences between pre-existing psychiatric diagnostic groups defined using conventional categorical approaches. Put differently, the resulting neural-behavioral multi-dimensional geometry would have been quantitatively invisible to any prior approach using either existing psychiatric diagnoses or any one single pre-existing clinical scale. Importantly, using the neural-behavioral multi-dimensional geometry mapping obtained via N-BRIDGE, it is possible to make subject-specific, quantitative predictions about individuals with the same clinical/psychiatric diagnosis but markedly different behavioral profiles and/or neural profiles, with respect to therapeutically relevant targets.

Understanding the mapping between the natural geometry of behavioral/phenotypic features and neural features further enables more targeted recruitment of patients for clinical trials investigating specific therapeutics (e.g., drugs). Furthermore, the multi-dimensional behavioral/phenotypic to neural feature mapping informs the identification of pharmacological targets for developing drugs or therapeutics for specific behavioral/phenotypic profiles, which may not be evident using either existing psychiatric diagnoses or any one single pre-existing clinical scale. Finally, this multi-dimensional behavioral/phenotypic to neural feature mapping, when applied to the individual subject level, provides an assisted selection of behavioral/clinical/symptom measures that quantitatively pinpoint variation in a specific neural circuit. Conversely, when applied to the individual subject-level, the multi-dimensional behavioral/phenotypic to neural feature mapping provides an assisted selection of specific neural features that in turn quantitatively map onto behavioral/clinical/symptom measures. This individual-level quantitative framework confers a fundamental technical advantage for patient segmentation who present with neuro-behavioral alterations along one or more behavioral and/or neural features.

The framework itself may also be iteratively applied to existing behavioral and neuroimaging data to inform and refine use of existing therapeutics which may have not been optimally targeted. Additionally, the ability to match patients to clinical trials and identify pharmacological targets for drug development with higher rates of success has massive economic upside for enterprises that develop and refine clinical trials (i.e. millions of dollars in savings per trial). In turn, the opportunity to develop and refine an individual-level quantitative framework via the present invention confers a fundamentally more rapid and cost-effective way of identifying how to effectively treat individuals with neuro-behavioral alterations based on their specific and unique profile of neuro-behavioral alterations (e.g., not pre-grouping individuals into a category or syndrome or defining their treatment based solely on a single pre-existing clinical scale of behavior).

In the embodiments presented herein, a method for treating a patient based on neuro-behavioral mapping is described. The method includes receiving, from a user interface of a computing device, behavioral data of a patient corresponding to mental health or cognitive status of the patient, predicting, by at least one processor of the computing device, a neural feature map for the patient representative of neural data based on the behavioral data, determining, by the at least one processor, a therapeutic associated with the neural feature map, and treating the patient with the therapeutic associated with the neural feature map.

In another embodiment, a method for treating a patient based on neuro-behavioral mapping is described. The method includes receiving, from a user interface of a computing device, neural data of a patient corresponding to neural status of the patient, predicting, by at least one processor of the computing device, a behavioral feature profile for the patient representative of behavioral data based on the neural data, determining, by the at least one processor, a therapeutic associated with the behavioral feature profile, and treating the patient with the therapeutic associated with the behavioral feature profile.

In another embodiment, a method for prognosticating a treatment for a patient based on neuro-behavioral mapping is described. The method includes receiving, from a user interface of a computing device, behavioral data of a patient corresponding to mental health or cognitive status of the patient, predicting, by at least one processor of the computing device, a neural feature map for the patient representative of neural data based on the behavioral data, determining, by the at least one processor, at least one neural therapeutic target with a quantitative score indicating correspondence with the neural feature map above a predetermined threshold that the patient will likely respond to, and prognosticating, by the at least one processor, a therapeutic associated with the at least one neural therapeutic target for a current treatment of the patient based on behaviors the patient is presenting.

In another embodiment, a method for prognosticating a treatment for a patient based on neuro-behavioral mapping is described. The method includes receiving, from a scanning or recording device, neural data of a patient corresponding to the neural status of that patient, predicting, by at least one processor of the computing device, a behavioral feature profile for the patient representative of behavioral data based on the neural data, determining, by the at least one processor, at least one therapeutic target with a quantitative score indicating correspondence with the behavioral feature profile above a predetermined threshold that the patient will likely respond to, and prognosticating, by the at least one processor, a therapeutic associated with the at least one behavioral feature profile for treatment of the patient based on the patient's presently obtained neural data.

In another embodiment, a method for forecasting clinical status for an individual based on neuro-behavioral mapping is described. The method includes receiving, from a user interface of a computing device, behavioral data of an individual corresponding to mental health or cognitive status of the individual, predicting, by at least one processor of the computing device, a neural feature map for the individual representative of neural data based on the behavioral data, and forecasting, by the at least one processor, a quantitative correspondence of similarity of the neural feature map with a predetermined neural feature map corresponding to a pre-existing patients' neuro-behavioral mapping, wherein the quantitative correspondence indicates a future occurrence of a clinical status.

In another embodiment, a method for forecasting a clinical status for an individual based on neuro-behavioral mapping is described. The method includes receiving, from a scanning or recording device, neural data of an individual corresponding to the neural status of the individual, predicting, by at least one processor of the computing device, a behavioral feature profile for the individual representative of behavioral data based on the neural data; and forecasting, by the at least one processor, a quantitative correspondence of similarity of the behavioral feature profile with a predetermined behavioral feature profile corresponding to a pre-existing patients' neuro-behavioral mapping, wherein the quantitative correspondence indicates a future occurrence of a clinical status.

In another embodiment, a method for mapping between one or more behavioral features and neural features in humans is described. The method includes receiving, by a computing device, neural data and behavioral data for each individual in a plurality of individuals at one or more discrete points in time, determining, by at least one processor of the computing device, a multi-dimensional geometry of latent behavioral and neural features based on a statistical analysis of the neural data and behavioral data for each individual, and saving and displaying quantified statistical relationships obtained from the multi-dimensional geometry on an output device of the computing device.

In another embodiment, a method for mapping between one or more behavioral features and neural features in patients presenting mental health symptoms is described. The method includes receiving, by a computing device, neural data and symptom-relevant behavioral data relevant to mental health status for each patient in a plurality of patients at one or more discrete points in time, determining, by at least one processor of the computing device, a multi-dimensional geometry of latent behavioral and neural features based on a statistical analysis of the neural data and symptom-relevant behavioral data for each patient, saving and displaying quantified statistical relationships obtained from the multi-dimensional geometry on an output device of the computing device, and deriving clinical status information and/or treatment-relevant information from the multi-dimensional geometry.

In another embodiment, a system for determining an individual's quantitative score within the established neuro-behavioral mapping is described. The system includes a neural scanning or recording device for obtaining neural data and/or behavioral recording device for obtaining behavioral data, a computing device including a graphical user interface, memory, and at least one processor, in which the neural scanning or recording device, the behavioral recording device and the computing device are communicatively coupled via a network. The neural scanning or recording device and/or the behavioral recording device is configured to process the neural data and/or the behavioral data to output neural and/or behavioral latent feature scores for the individual within a predetermined multi-dimensional neuro-behavioral geometry. In some embodiments, the neural scanning or recording device is configured to scan or record the individual's brain, and output at least one of neural data. In some embodiments, the behavioral recording device is configured to record the individual's behavioral data and output the behavioral data. The at least one processor of the computing device is configured to receive the neural data from the neural scanning or recording device and/or the behavioral data from the behavioral recording device, project the individual's neural data and/or the behavioral data into the predetermined multi-dimensional neuro-behavioral geometry of latent behavior and neural features, generate outputs via the graphical user interface indicating at least one of the individual's projection scores within the predetermined multi-dimensional neuro-behavioral geometry, and save at least one of the scores in the memory of the computing device.

In another embodiment, a method for identifying individuals with similar neuro-behavioral latent scores based on their quantitative proximity in a neuro-behavioral geometry is described. The method includes receiving, from a scanning or recording device, neural data of an individual corresponding to a neural status of the individual, receiving, from a user interface of a computing device, behavioral data of the individual corresponding to mental health or cognitive status of the individual, determining, by at least one processor of the computing device, a behavioral feature profile for the individual based on the behavioral data, determining, a neural feature map for the individual based on the neural data, determining, by the at least one processor, a quantitative proximity of behavioral and neural feature scores of individuals within a plurality of individuals based on the behavioral feature profile and/or the neural feature map, and identifying, by the at least one processor, individuals with quantitatively similar neuro-behavioral latent scores based on their quantitative proximity in the neuro-behavioral geometry.

In another embodiment, a method for mapping between one or more behavioral features and neural features in humans is described. The method includes receiving, by a computing device, neural data and phenotypic data for each individual in a plurality of individuals at one or more discrete points in time, determining, by at least one processor of the computing device, a multi-dimensional geometry of latent behavioral feature data based on a statistical analysis of the neural data and phenotypic data for each individual, quantifying statistical relationships of the neural data and phenotypic data for each individual, by the at least one processor of the computing device, to map the one or more behavioral features and the neural features, the quantifying including a multi-dimensional analysis of the neural data and phenotypic data for each individual, and displaying the quantified statistical relationships on an output device of the computing device.

In an embodiment, the method includes first performing a data reduction procedure of the phenotypic or behavioral feature data across the plurality of individuals.

In another embodiment, the method includes quantifying the statistical relationships between multi-dimensional neural feature data and the behavioral/phenotypic feature data such as to define axes in a multi-dimensional geometry, which can be used to inform prediction of functional impairment along specific behavioral/phenotypic and neural dimensions for a single individual or group of individuals.

In another embodiment, the method includes quantifying the statistical relationships between multi-dimensional neural feature data and the behavioral/phenotypic feature data such as to define axes in a multi-dimensional geometry, which can be used to predict specific phenotypic features of individual humans using the multi-dimensional neural feature data, irrespective of functional impairment.

In another embodiment, the method includes quantifying the statistical relationships between multi-dimensional neural feature data and the behavioral/phenotypic feature data such as to define axes in a multi-dimensional geometry, which can be used to predict specific neural features of individual humans using the multi-dimensional behavioral/phenotypic feature data, irrespective of functional impairment.

In another embodiment, the method includes predicting treatment outcome of specific individual humans in relation to variation along multi-dimensional behavioral/phenotypic or neural feature data.

In another embodiment, the method includes identifying optimal targets for treatment outcome for specific individual humans with variation along multi-dimensional phenotypic or neural feature data.

In another embodiment, the method includes predicting progression or change of behavioral/phenotypic or neural feature data over time.

In another embodiment, the individual data comprises phenotypic or behavioral characteristics for each individual in the plurality of individuals.

In another embodiment, the phenotypic or behavioral characteristics for each individual further comprise data regarding detailed assessment of complex behavioral or phenotypic features using one or more assessment instruments.

In another embodiment, the latent phenotypic or behavioral feature data for each individual further comprise data derived from the data reduction procedures using detailed assessment of complex behavioral or phenotypic features obtained from one or more assessment instruments for each individual in the plurality of individuals.

In another embodiment, the neural data comprise multiple areal/regional features such as voxels, areas, neural networks, electrodes from an electrophysiological recording device or other areal features of invasive or noninvasive imaging data for each individual in the plurality of individuals.

In another embodiment, the latent phenotypic or behavioral feature data represents behavior variations along a given latent dimension derived via a data reduction procedure.

In another embodiment, any independent individual for whom there is available detailed assessment of complex behavioral or phenotypic features obtained from one or more assessment instruments can be 'projected' as a point in the multi-dimensional latent feature space to obtain a 'score' along a given latent dimension derived via a data reduction procedure.

In another embodiment, neural data of the cerebral and/or cerebellar cortices are mapped to two-dimensional surfaces for each individual in the plurality of individuals, whereas subcortical neural data are mapped onto appropriate volumetric structures for each individual in the plurality of individuals, thus yielding a neural map.

In another embodiment, neural data are appropriately cleaned and de-noised prior to statistical quantification to improve the signal-to-noise ratio and to attenuate sources of spurious artefactual signal.

In another embodiment, neural data comprise regional summary measures derived from invasive or noninvasive methods across multiple neural areas.

In another embodiment, quantifying the statistical relationships of multi-dimensional neural-phenotypic data can be validated using statistical cross-validation procedures (for example, leave-one-out or k-fold) within and across independent data collection sites and samples.

In another embodiment, data regarding treatment outcome of individuals with variation along multi-dimensional phenotypic or neural feature data are collected over time either continuously or at discrete time points.

In another embodiment, phenotypic and neural data of the same individual human is collected at multiple time points via detailed assessment using one or more assessment instruments.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE
DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

FIG. 2A illustrates example table comprising examples of behavioral, clinical, cognitive, and demographic characteristics of patients and healthy control subjects (CON), according to embodiments of the present disclosure.

FIG. 2B illustrates an example diagram showing a cognitive paradigm deployed via computerized assessment for obtaining behavioral features, according to embodiments of the present disclosure.

FIG. 2C illustrates an example diagram showing an eye tracking deployment, an example of behavioral data collection, in a laboratory, clinic, or inside a scanner, according to embodiments of the present disclosure.

FIGS. 5A-5K illustrate example diagrams showing k-Fold cross-validation for behavioral principal component analysis (PCA), according to embodiments of the present disclosure.

FIGS. 7A-7J illustrate example diagrams relating symptom axes to neural connectivity, according to embodiments of the present disclosure.

FIGS. 9A-9D illustrate example diagrams showing between-group differences in functional connectivity of the frontoparietal control network (FPCN), according to embodiments of the present disclosure.

FIGS. 11A-11F illustrate example diagrams showing the robustness of neural-behavioral mapping across individuals, according to embodiments of the present disclosure.

FIGS. 12A-12I illustrate example diagrams showing the use of independent component analysis (ICA) as an alternative method of dimensionality-reduction for behavioral data, according to embodiments of the present disclosure.

FIGS. 14A-14H illustrate example diagrams showing k-Fold cross-validation for establishing the neuro-behavioral geometry by means of canonical correlation analysis, according to embodiments of the present disclosure.

FIGS. 20A-20I illustrate example diagrams showing a process of using latent scores from the neuro-behavioral geometry to provide a therapeutic prognosis for a new individual.

FIGS. 22A-22G illustrate example pharmaceutical candidates for targeting specific neuroprints using gene expression maps, according to embodiments of the present disclosure.

Figure 24:
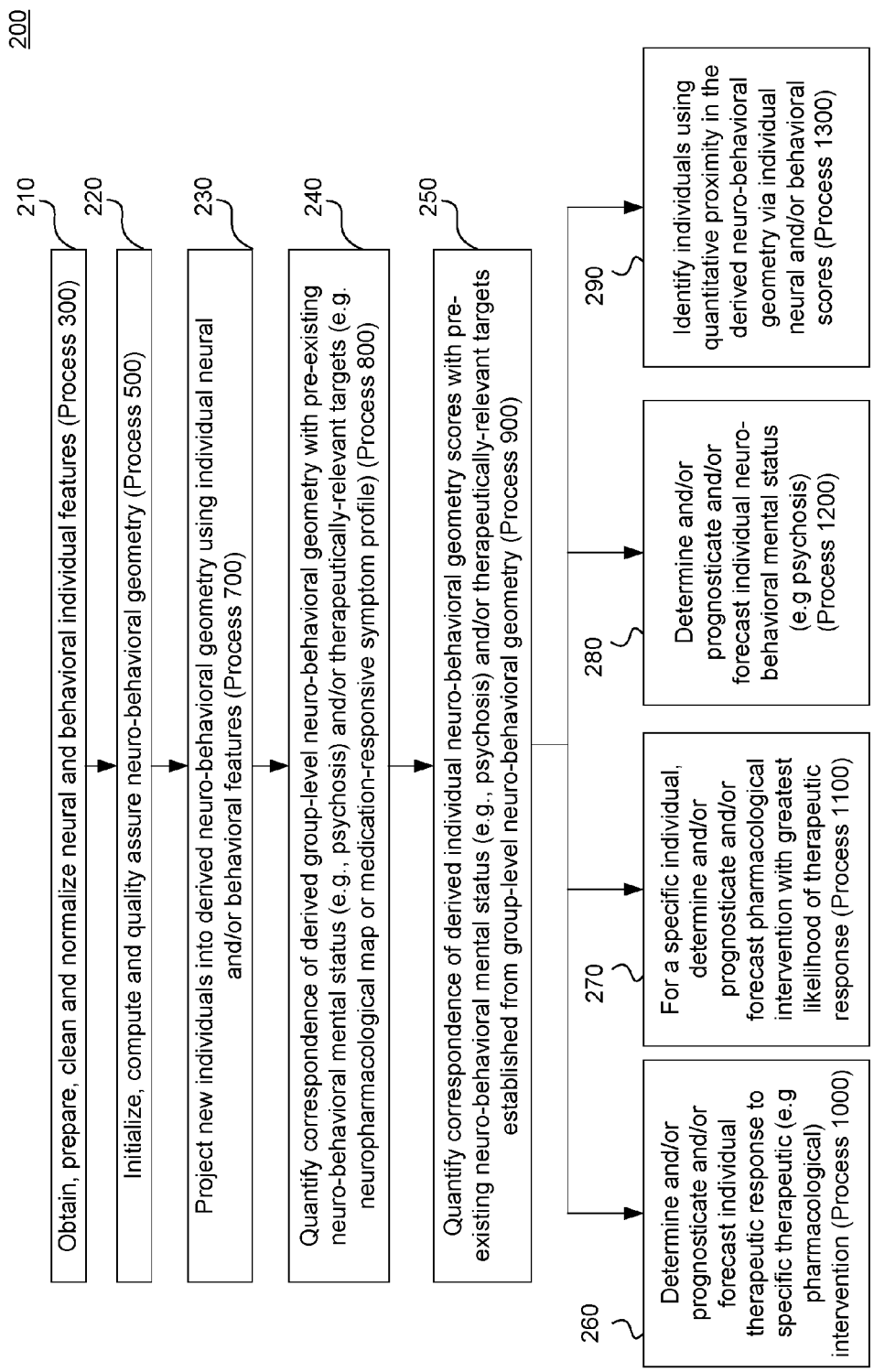

FIG. 24 illustrates an example flowchart diagram of a process by which a neuro-behavioral geometry may be derived from neural and behavioral features and used to determine, prognosticate, and/or forecast treatment response for a given individual, individual response to a specific treatment, individual neuro-behavioral mental status, and/or the quantitative proximity of individuals in the neuro-behavioral geometry according to embodiments of the present disclosure.

Figure 25:
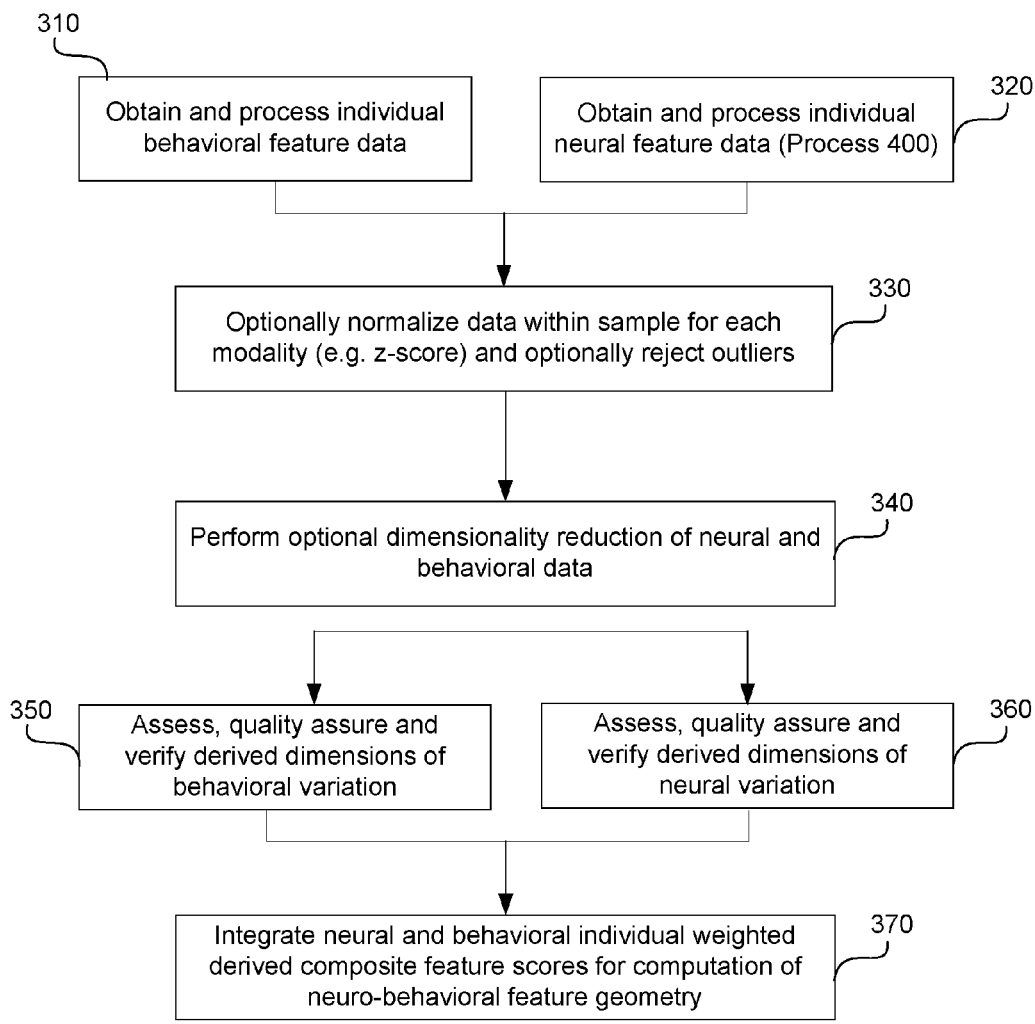

FIG. 25 illustrates an example flowchart diagram of a process by which neural and behavioral features may be obtained in preparation for establishing a neuro-behavioral geometry.

Figure 26:
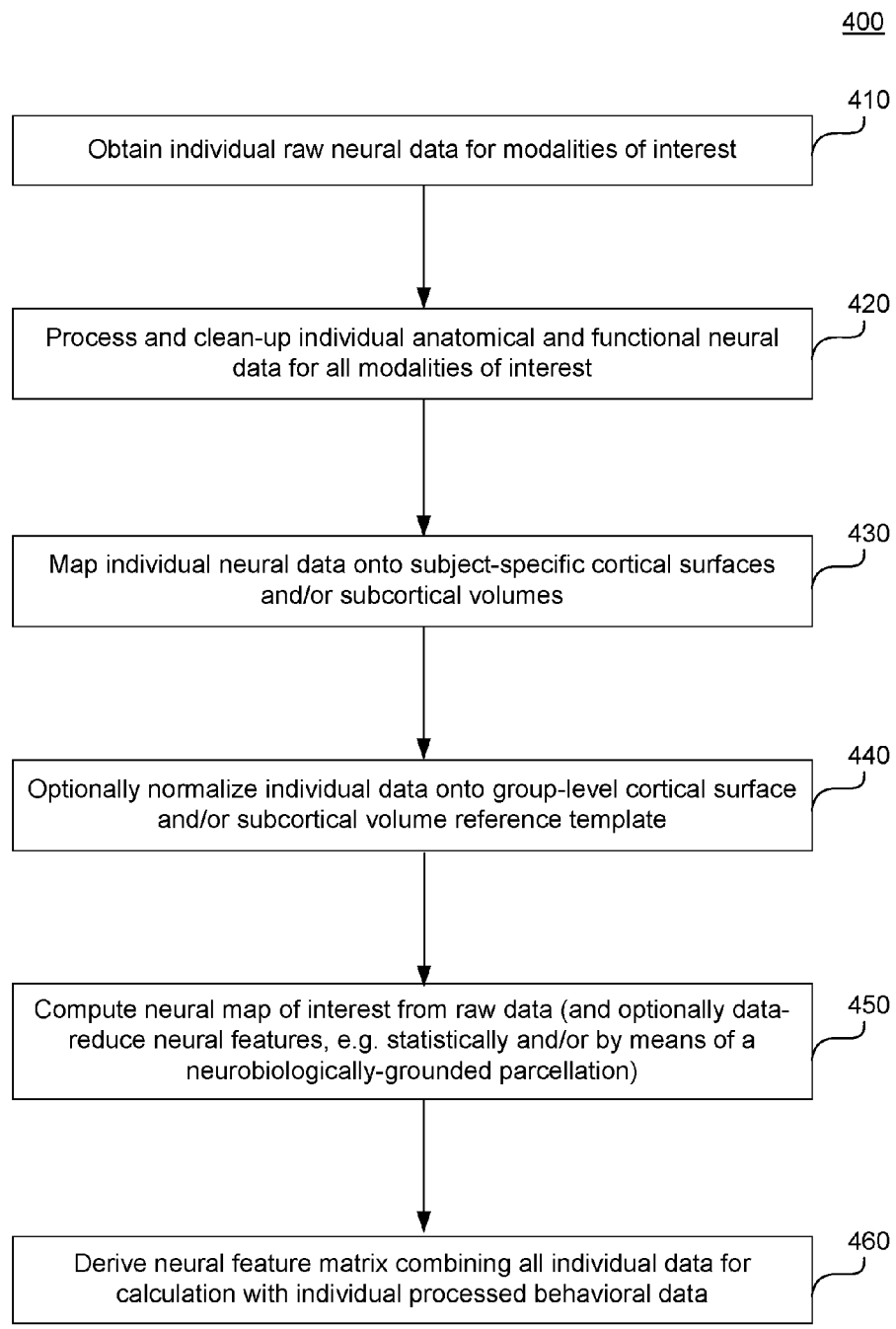

FIG. 26 illustrates an example flowchart diagram of a process by which neural features may be processed and prepared for use in a neuro-behavioral geometry, according to embodiments of the present disclosure.

Figure 27:
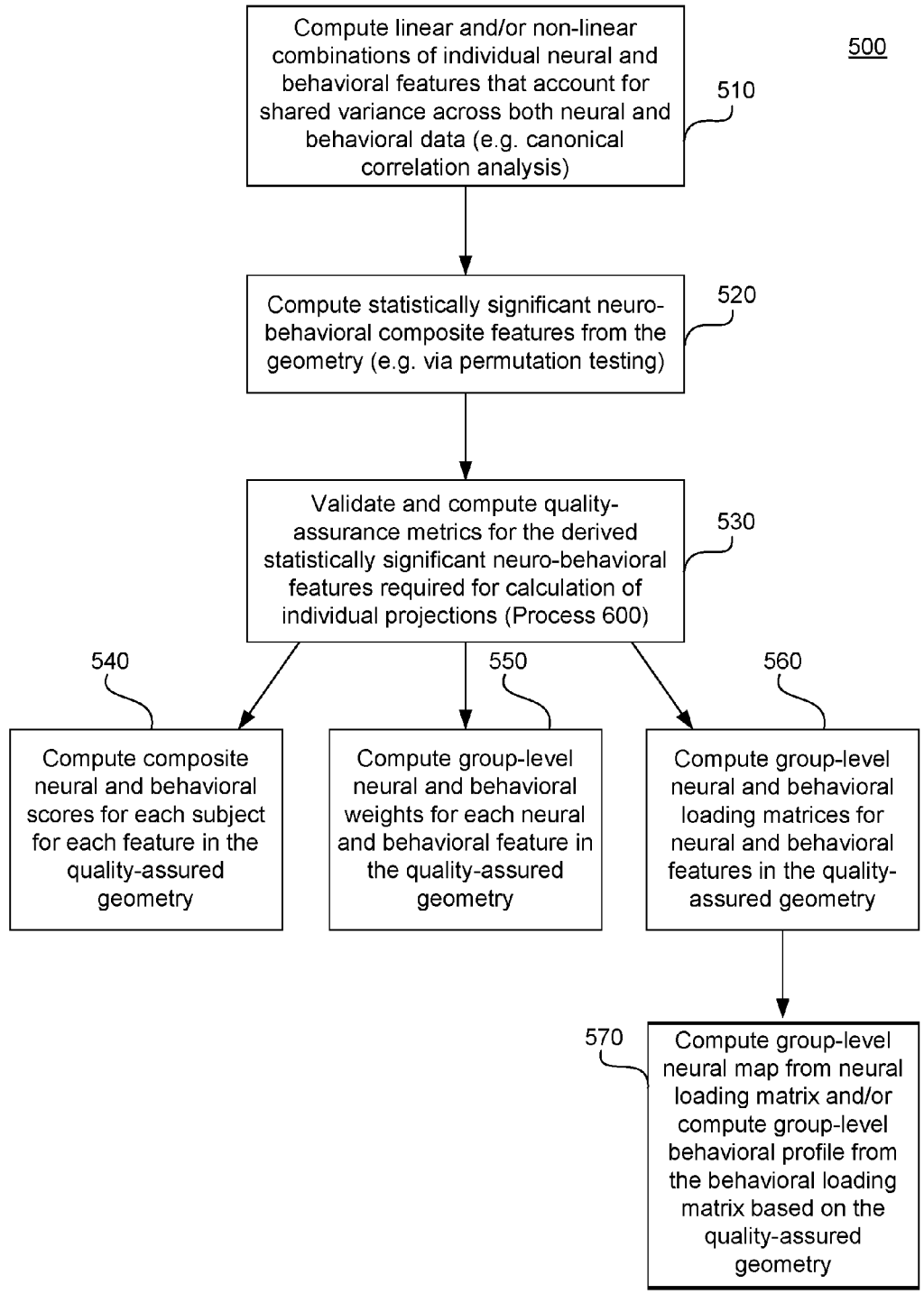

FIG. 27 illustrates an example flowchart diagram of a process by which neural and behavioral features are used to compute and establish neuro-behavioral geometry, according to embodiments of the present disclosure.

Figure 28:
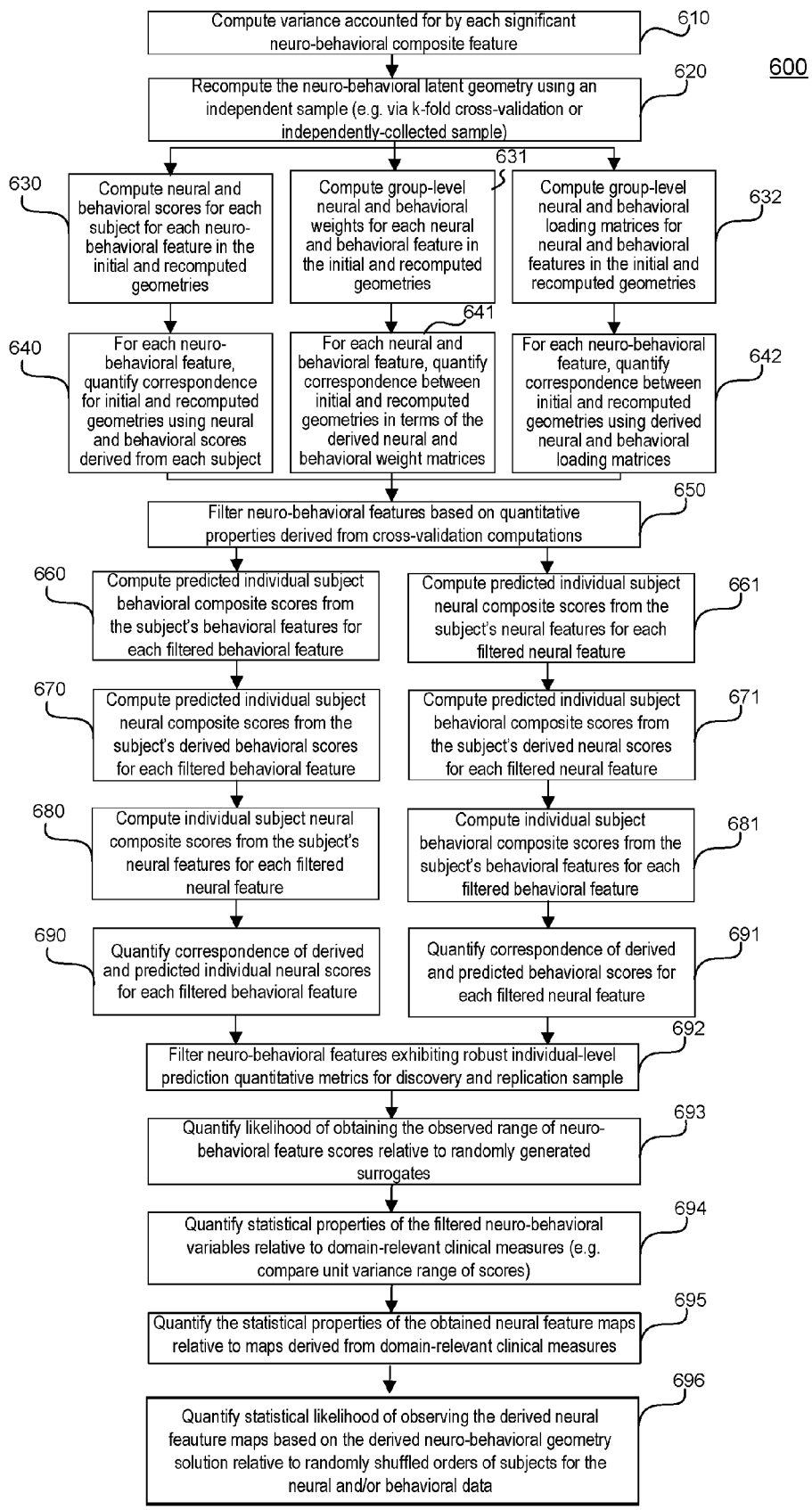

FIG. 28 illustrates an example flowchart diagram of a process by which a neuro-behavioral geometry may be validated and quality-assured, according to embodiments of the present disclosure.

Figure 29:
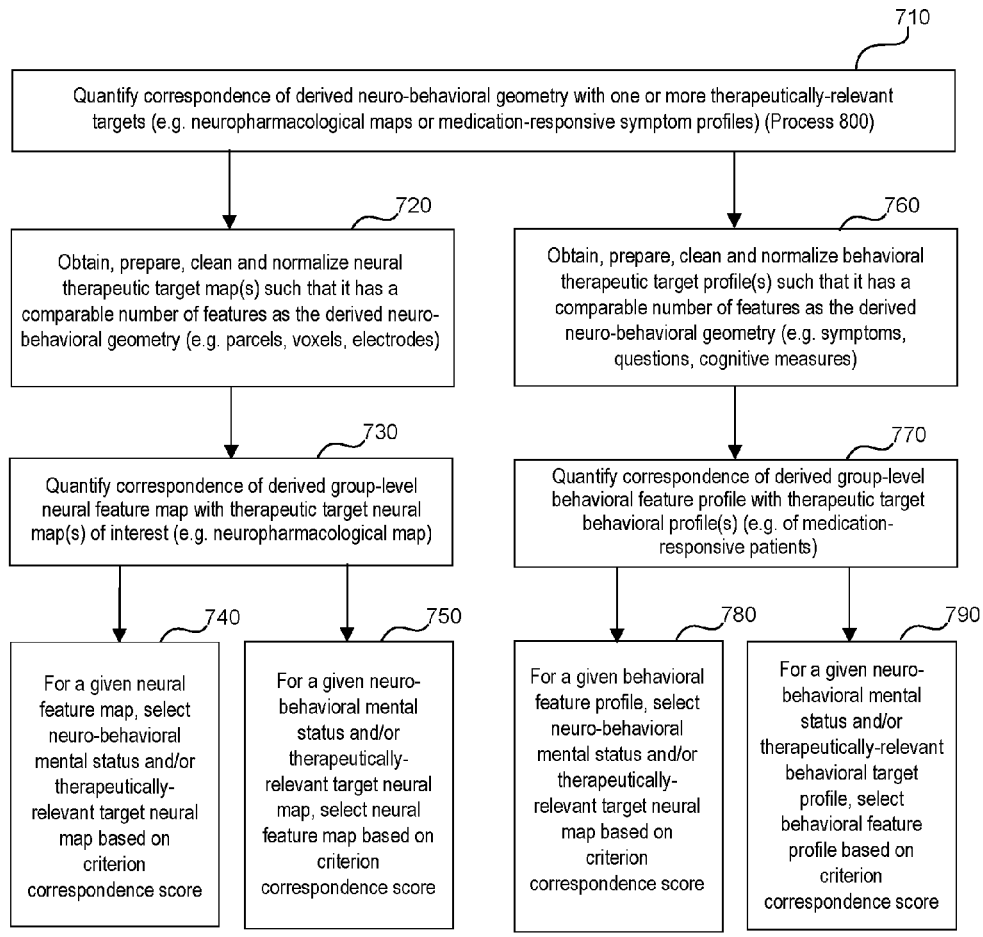

FIG. 29 illustrates an example flowchart diagram of a process by which neural and behavioral latent group-level features may be related to candidate therapeutic targets and/or a neuro-behavioral mental status, according to embodiments of the present disclosure.

Figure 30:
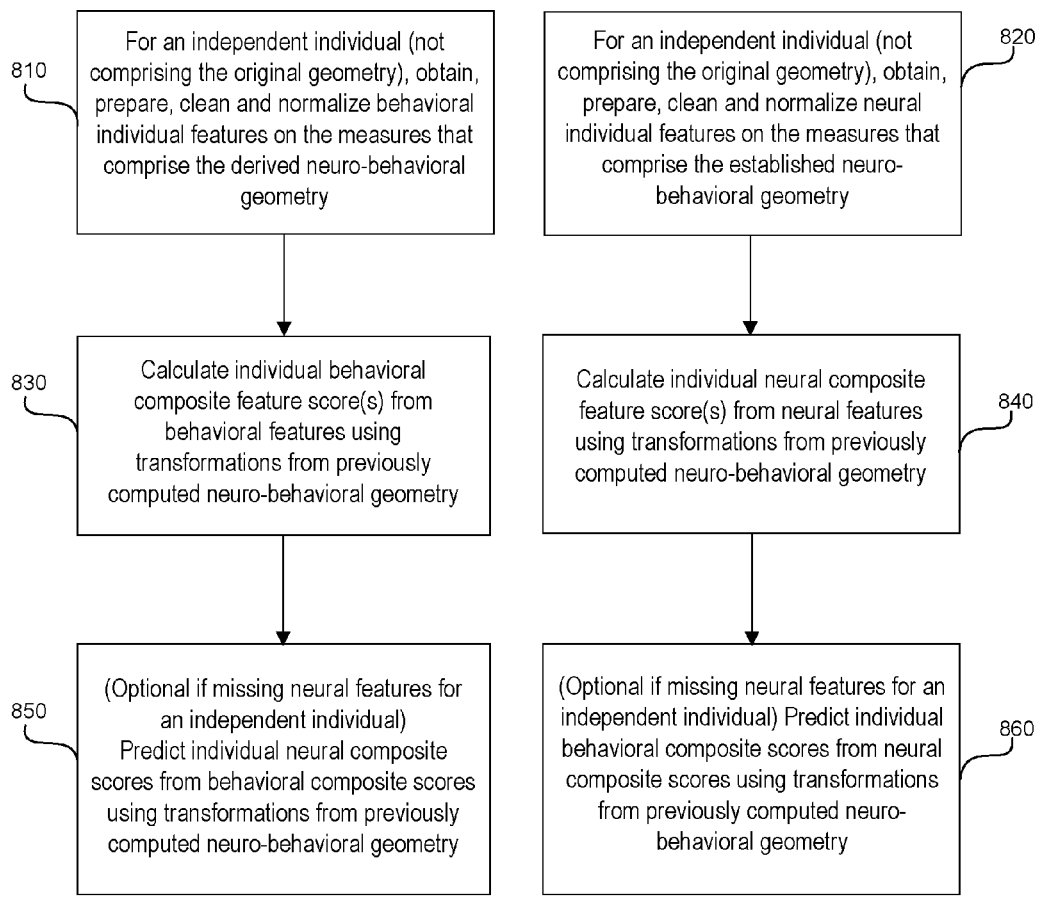

FIG. 30 illustrates an example flowchart diagram of a process by which neural and/or behavioral features from an independent individual may be used to compute latent scores under the neuro-behavioral geometry, according to embodiments of the present disclosure.

Figure 31:
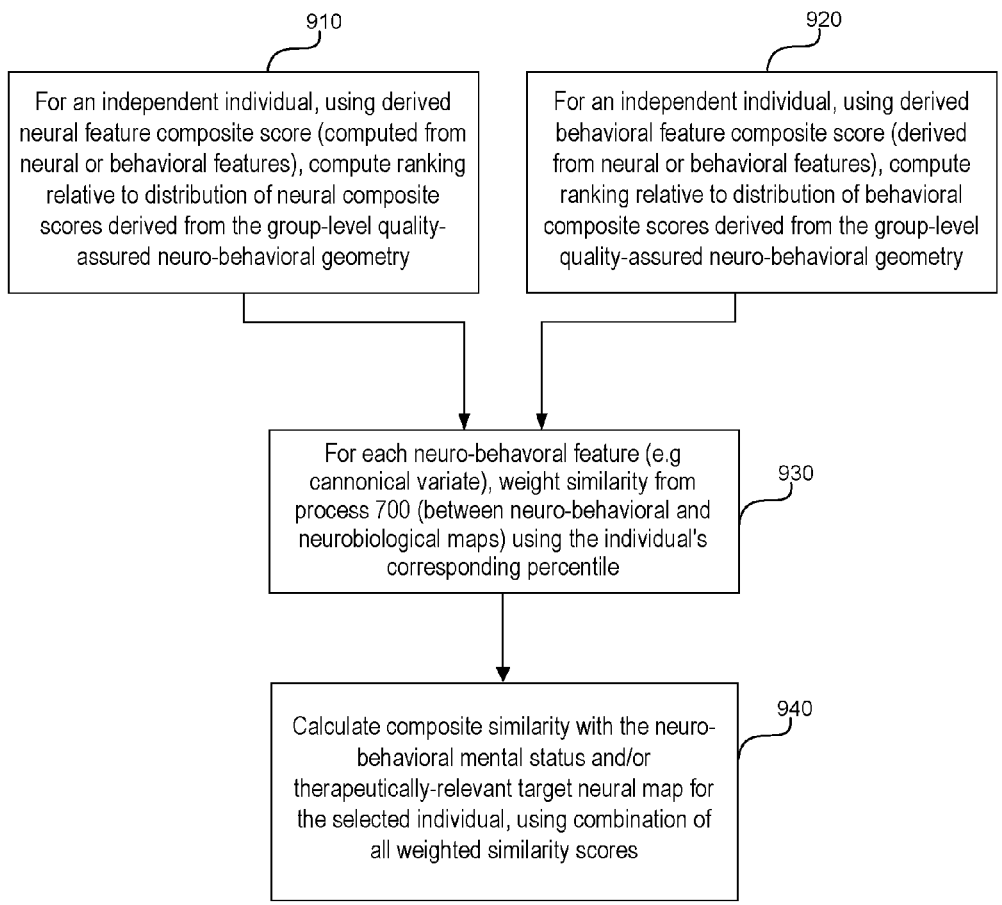

FIG. 31 illustrates an example flowchart diagram of a process by which neural and/or behavioral scores from an independent individual may be used to compute a similarity score with a neuro-behavioral mental status neural therapeutic target(s) of interest, according to embodiments of the present disclosure.

Figure 32:
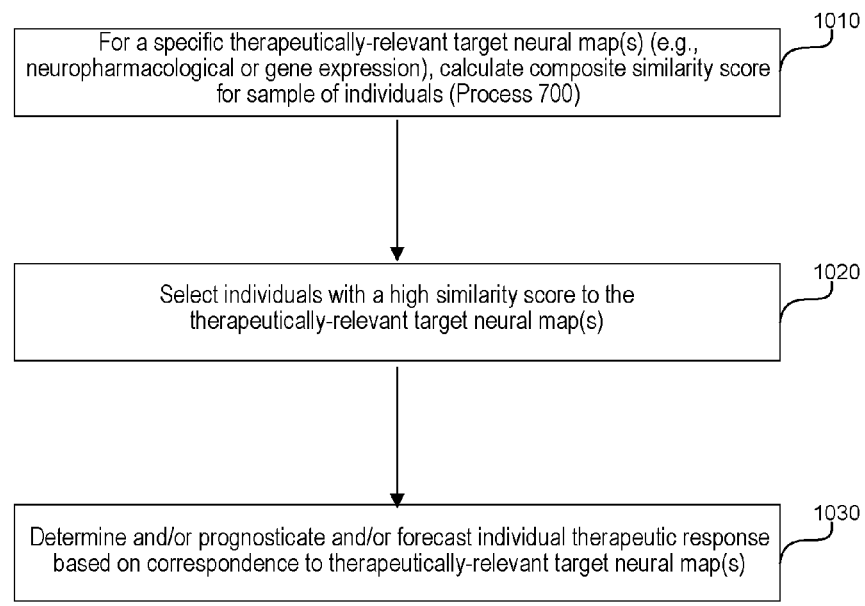

FIG. 32 illustrates an example flowchart diagram of a process of determining, prognosticating, or forecasting individual response to a particular therapeutic, based on neuro-behavioral mapping, according to embodiments of the present disclosure.

Figure 33:
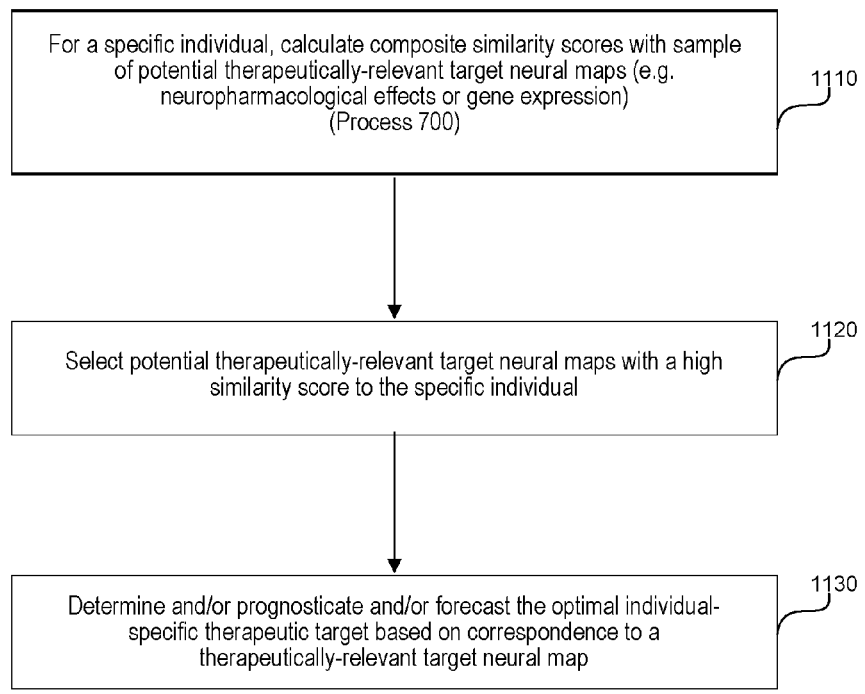

FIG. 33 illustrates an example flowchart diagram of a process of determining, prognosticating, or forecasting a therapeutic for an individual based on neuro-behavioral mapping, according to embodiments of the present disclosure.

Figure 34:
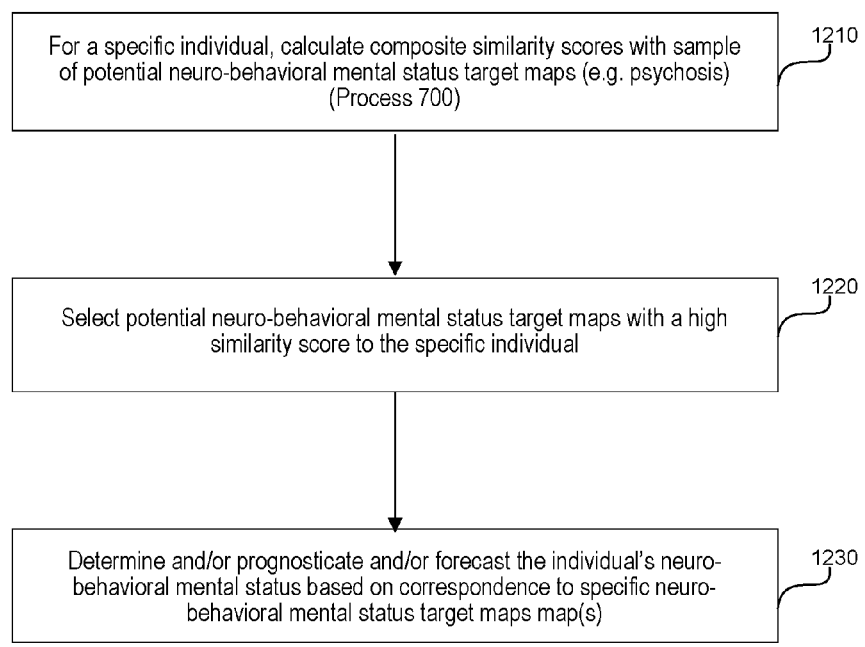

FIG. 34 illustrates an example flowchart diagram of a process of determining, prognosticating, or forecasting a mental health status for an individual based on neuro-behavioral mapping, according to embodiments of the present disclosure.

Figure 35:
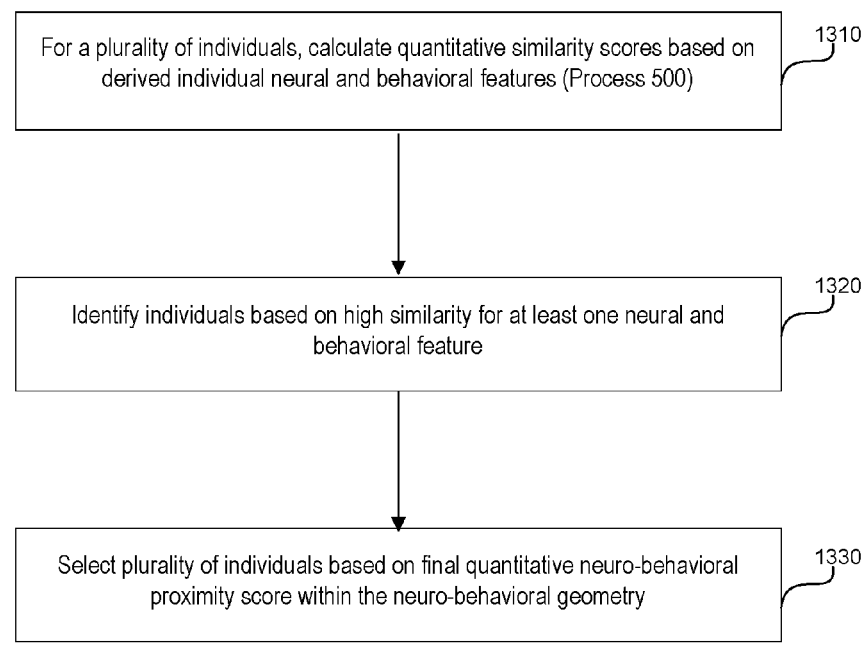

FIG. 35 illustrates an example flowchart diagram of a process of identifying individuals based on quantitative proximity in the neuro-behavioral geometry, according to embodiments of the present disclosure.

FIG. 36 illustrates an example of a user interface for performing the steps of the invention, according to embodiments of the present disclosure.

Figure 37B:
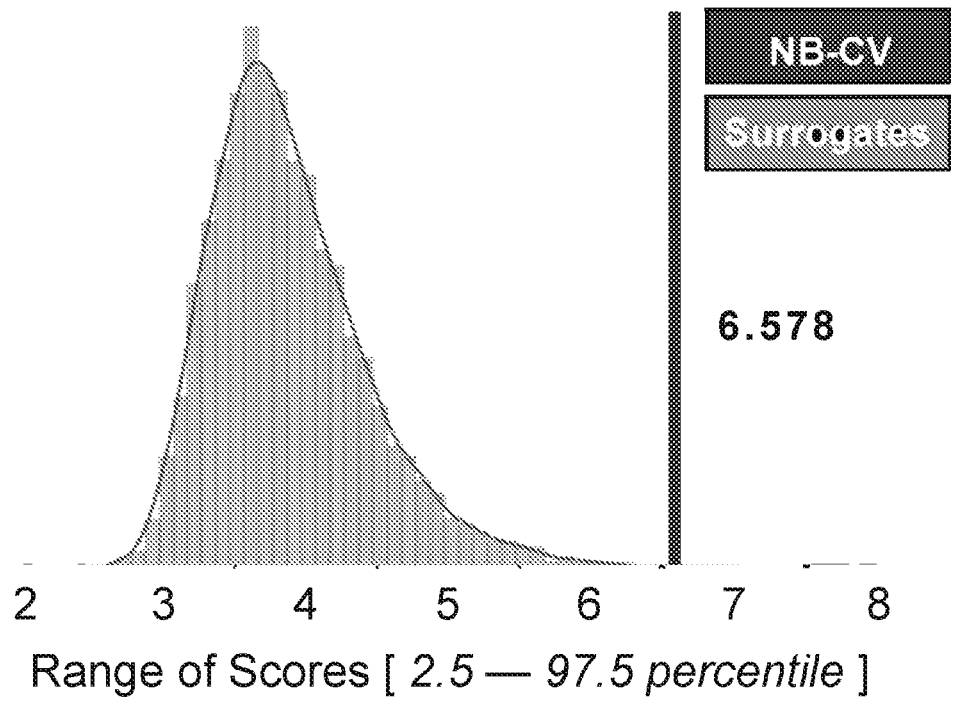
Figure 37C:
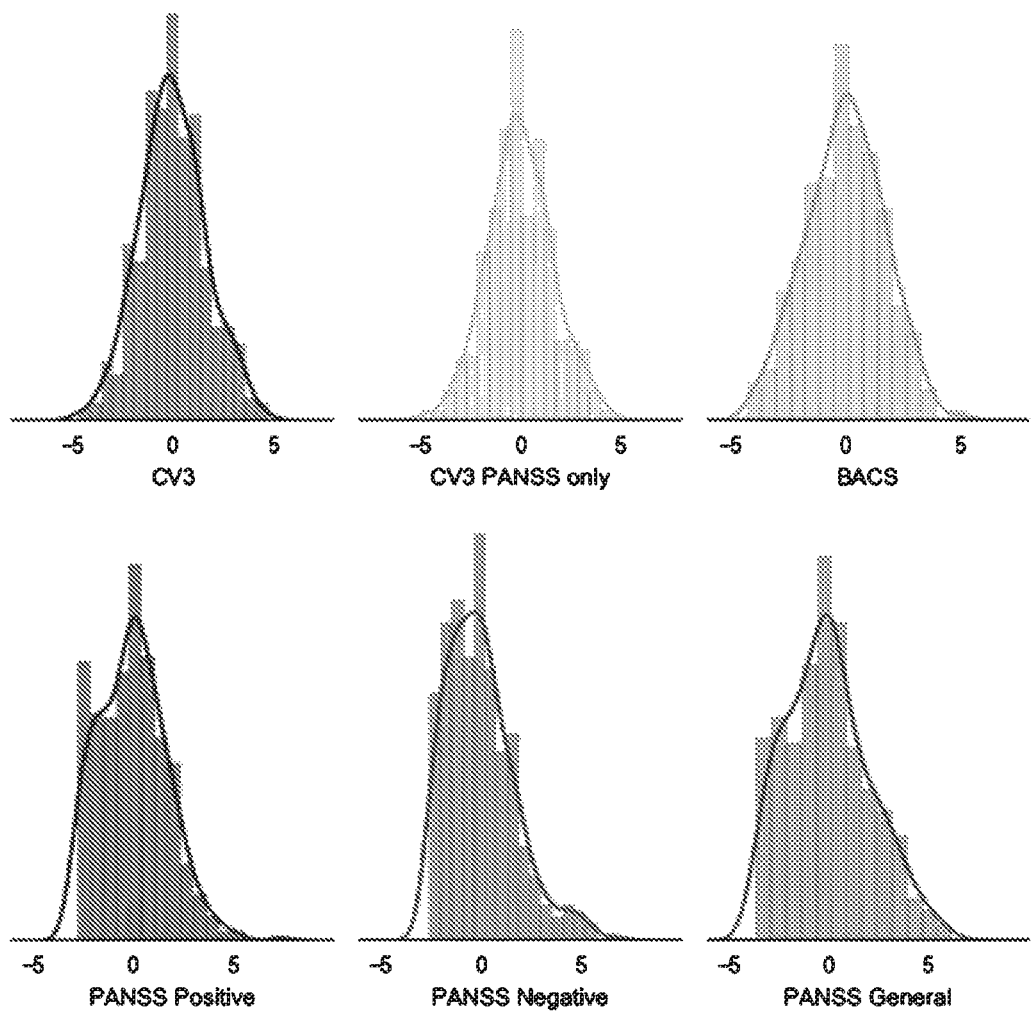

FIGS. 37A-37C illustrate examples of outputs of the neuro-behavioral geometry from an exemplar user interface, according to embodiments of the present disclosure.

Figure 38:
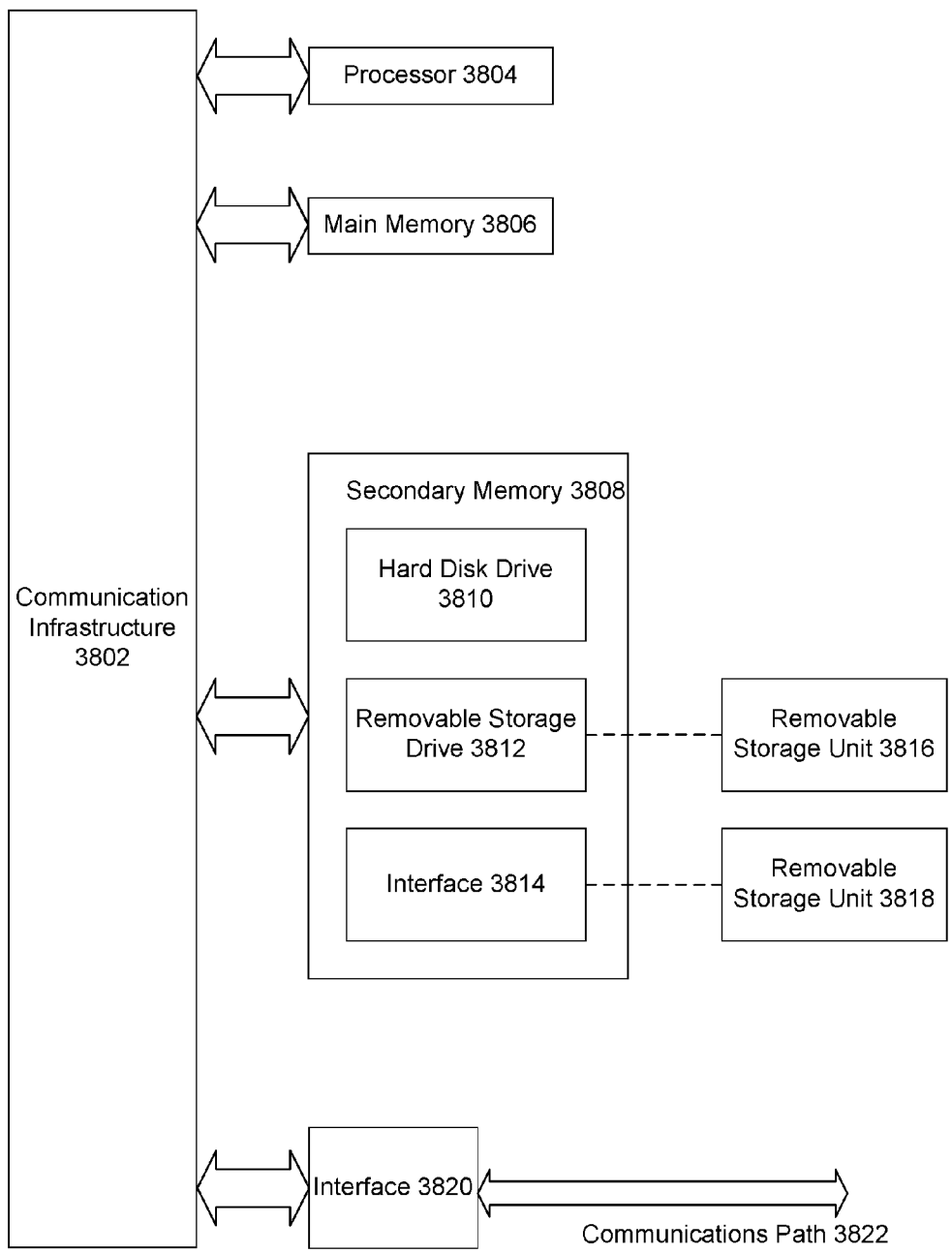

FIG. 38 illustrates a block diagram of an example computer system that may be used to perform various aspects of the present disclosure.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the present invention. The scope of the present invention is not limited to the disclosed embodiment(s).

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Definition of Terms

As used herein, the term "projecting" or "projection" refers to the process of mapping a data point from one n-dimensional geometry to another by means of applying a mathematical transform.

As used herein, the term "neural feature map" or "brain feature map" or "neural data map" refers to an assignment of a numerical value to specific brain locations/regions from a given assessment or analysis, from neural data of a particular modality. Examples of neural features include, but are not limited to: functional connectivity (e.g. global brain connectivity, seed-based connectivity derived from blood oxygen level-dependent imaging functional magnetic resonance imaging (BOLD fMRT)); functional activation (e.g. task-based BOLD fMRT); structural measures (e.g., volume of subcortical neural structures, probabilistic tractography from diffusion-weighted imaging (DWI), myelin content, cortical curvature, cortical thickness); metabolic measures (e.g., positron-emission tomography (PET)); electrophysiological measures (e.g., electroencephalogram (EEG) or magnetoencephalography (MEG)). In some embodiments, other imaging modalities may be utilized to obtain neural data of an individual.

As used herein, the term "behavioral measure" refers to a quantitative measure of a behavioral phenotype. Examples of behavioral measures include, but are not limited to: assessments of symptom severity for a particular psychiatric disorder or domain of psychiatric disorders, either clinician-observed or self-reported (e.g. questionnaires, Positive and Negative Syndrome Scale (PANSS), Beck Depression Inventory (BDI)); assessments of cognitive ability (e.g. the Brief Assessment of Cognition in Schizophrenia (BACS) or Penn Matrix Test (PMAT)); quantitative assessments of task performance (e.g. accuracy or reaction time); physiological responses (e.g. eye movement, heart rate, galvanic skin response).

As used herein, the term "behavioral feature profile" refers to a configuration of quantified behaviors.

As used herein, the term "therapeutically relevant map" or "neural therapeutic feature map" refers to a map with spatial information regarding the potential efficacy of a therapeutic target(s) at each brain location. Examples of therapeutically relevant maps include, but are not limited to: neuropharmacological maps showing the neural response to a pharmacological intervention, such as ketamine; gene expression maps showing levels of expression of particular genes at each brain location; PET maps showing the binding of radioligands to specific neuroreceptors of interest (e.g. dopamine D2 receptors).

As used herein, the term "mental health" refers to an individual's psychological status, reflecting cognitive, behavioral, emotional states and traits. Examples of measures of mental health include but are not limited to: cognitive ability; mood; level of psychosis; and personality.

As used herein, the term "predict/prediction" refers to the process of computing a statistical inference for a measure or quantity, based on current information.

As used herein, the term "prognosticate/prognostication" refers to the prediction of diagnostic status and/or treatment response, based on current information.

As used herein, the term "forecast" refers to the process of computing a statistical inference for a measure or quantity for a time point in the future, based on current information.

As used herein, the term "neuro-behavioral mapping" refers to an algorithm derived from the calculation that maximizes the shared statistical relationship between behavioral and neural features for a plurality of individuals. In some embodiments, a neuro-behavioral geometry In some embodiments, "pre-existing mapping" may be used synonymously with "neuro-behavioral mapping."

As used herein, the term "latent" refers to a variable, and/or feature, and/or state, and/or statistical model, and/or geometry that may be directly observed and/or inferred and may reflects some composite weighted linear and/or non-linear score derived from the original neural and/or behavioral data. In some embodiments, "latent" may be used synonymously with "weighted composite" and/or "manifest weighted composite".

As used herein, the term "neuro-behavioral geometry" refers to the derived mathematical solution that incorporates neural and behavioral features into a set of neural and behavioral latent and/or manifest weighted composite variables derived from a plurality of individuals.

As used herein, the term "latent neural feature map" refers to a map of neural information wherein the neural information comprises neural data mathematically transformed with respect to the neuro-behavioral geometry.

As used herein, the term "latent behavioral feature profile" refers to a configuration of behavioral information wherein the behavioral information comprises behavioral data mathematically transformed with respect to the neuro-behavioral geometry.

As used herein, the term "latent neural score" refers to the computed or predicted neural measure for an individual's representation in the neuro-behavioral geometry.

As used herein, the term "latent behavioral score" refers to the computed or predicted behavioral measure for an individual's representation in the neuro-behavioral geometry.

As used herein, the term "neural status" refers to an individual's neural condition. Neural status may comprise states or traits of an individual's neural system. Examples of measures of neural status include but are not limited to: degree of synchrony of specific neural circuits, myelin content, volume of neural structures, cortical thickness, functional coupling of specific neural regions.

As used herein, the term "therapeutic" refers to the process of affecting clinical status. Examples of measures of therapeutics include, but are not limited to, pharmaceutical agents, cognitive behavioral therapy, deep brain stimulation.

As used herein, the terms "treating" or "treatment" or "therapy" refer to partially or completely alleviating, ameliorating, improving, relieving, delaying onset of, inhibiting progression of, reducing severity of, reducing incidence of one or more symptoms or features of disease, or any combination thereof. Thus, in general, the term "treatment" refers to countering the effects caused as a result of the disease or pathological condition of interest in a subject including (i) inhibiting the progress of the disease or pathological condition, in other words, slowing or stopping the development or progression thereof, or one or more symptoms of such disorder or condition; (ii) relieving the disease or pathological condition, in other words, causing said disease or pathological condition, or the symptoms thereof, to regress; (iii) stabilizing the disease or pathological condition or one or more symptoms of such disorder or condition, (iv) reversing the disease or pathological condition or one or more symptoms of such disorder or condition to a normal state, (v) preventing the disease or pathological condition or one or more symptoms of such disorder or condition, and (vi) any combination thereof. In some embodiments, the term "treatment" may refer to the general process of receiving a therapeutic.

As used herein, the term "preventing" refers to partially or completely delaying onset of an disease, disorder and/or condition; partially or completely delaying onset of one or more symptoms, features, or clinical manifestations of a particular disease, disorder, and/or condition; partially or completely delaying onset of one or more symptoms, features, or manifestations of a particular disease, disorder, and/or condition; partially or completely delaying progression from a particular disease, disorder and/or condition; and/or decreasing the risk of developing pathology associated with the disease, disorder, and/or condition.

As used herein, the term "effective amount" is that amount sufficient to effect beneficial or desired results. In some aspects, the beneficial or desired results are, for example, clinical results, and, as such, an "effective amount" depends upon the context in which it is being applied. The term "effective amount" can be used interchangeably with "effective dose," "therapeutically effective amount," or "therapeutically effective dose."

Introduction

Understanding the link between variation along specific behaviors or multi-dimensional behavioral features and variation in neural features is critical to developing and administering effective treatments at an individualized level for individuals with behavioral health concerns (e.g. psychiatric symptoms or help-seeking behaviors related to mental health). Currently, much of the research in psychiatry operates under the fundamental assumption that traditional clinical/diagnostic groups, typically defined by sets of co-occurring symptoms, are the gold standard for describing behavioral—and therefore neural—variation in individuals. Diagnostic groups in psychiatry are defined by sets of co-occurring behavioral symptoms, as outlined in the Diagnostic and Statistical Manual of Mental Disorders (DSM) [2]. However, attempts to robustly characterize the neural substrates of these predefined diagnostic groups have thus far been unsuccessful, suggesting that these sets of symptoms do not map to biologically meaningful mechanisms. There is ample evidence that the underlying neural perturbations do not fully obey DSM diagnostic boundaries. For example, compared to schizophrenia, patients with bipolar disorder exhibit similar, but attenuated, bi-directional patterns of disruption in whole-brain thalamic dysconnectivity along a dimensional axis[3]. These axes of variation may not be observable in studies that examine properties only in patients within DSM-defined boundaries. Hence, it is necessary to first define dimensions of behavioral/phenotypic variation that map onto dimensions of neural variation.

In light of this, the NIMH's Research Domain Criteria (RDoC) initiative adopts a 'dimensional' approach to characterizing aspects of psychiatric disorders, aimed at defining the range and distribution of human functioning using neurobiologically-grounded methodology[4]. However, one major downside to this approach is that it ignores the categorical features that are present in psychiatry. Furthermore, it fails to concurrently, in the same individual, to consider the multi-dimensional variation of behavioral/phenotypic and neural features, which may be imbedded in multi-dimensional geometry. For example, patients with schizophrenia exhibit increased power in low frequency blood oxygen level—dependent (BOLD) signal and increased variance in the spontaneous fluctuations of the BOLD signal over time, while patients with bipolar disorder do not[5]. Hence evidence suggests that the neural signatures of neuropsychiatric conditions possess both categorical and continuous/dimensional properties. Reconciling these distinct mappings between multi-dimensional behavioral and neural features geometric is therefore a fundamental step towards advancing conceptualization of the relationships between the brain and behavior, which directly informs design of effective treatments for punctate neural features that map onto sets of altered behavioral features. There is, therefore, a pressing need to develop a unified quantitative statistical framework for describing the complex multidimensional geometry of behavior and how it relates to the brain in humans. Moreover, it remains unknown if use of pre-existing clinical scales to define either categories or dimensions is the optimal approach in such situations. In other words, it may be possible that defining the proper mapping between the behavioral variation and neural variation does not follow any specific pre-defined clinical symptom definition designed a priori nor any predefined diagnostic category. Instead, it may be possible that natural variation in multi-dimensional behavioral/phenotypic features follows some complex 'latent' combination of symptom features that are essential to consider in unison to properly delineate variation in the key neural circuits.

Many currently prescribed first-line therapies in the field of mental health were serendipitous discoveries in psychiatry[6]. Characterizing how and which specific sets of symptoms map to neural circuitry is a key step towards developing targeted and effective treatments for psychiatric disorders. Once specific neural circuits and/or regions are mapped to variation along specific behaviors in psychiatric patients, the basic biological features of these circuits/regions (such as gene expression or neuronal properties) can be further characterized and used to inform targeted treatment development for such punctate neural features.

Example Embodiments

Figure 1:
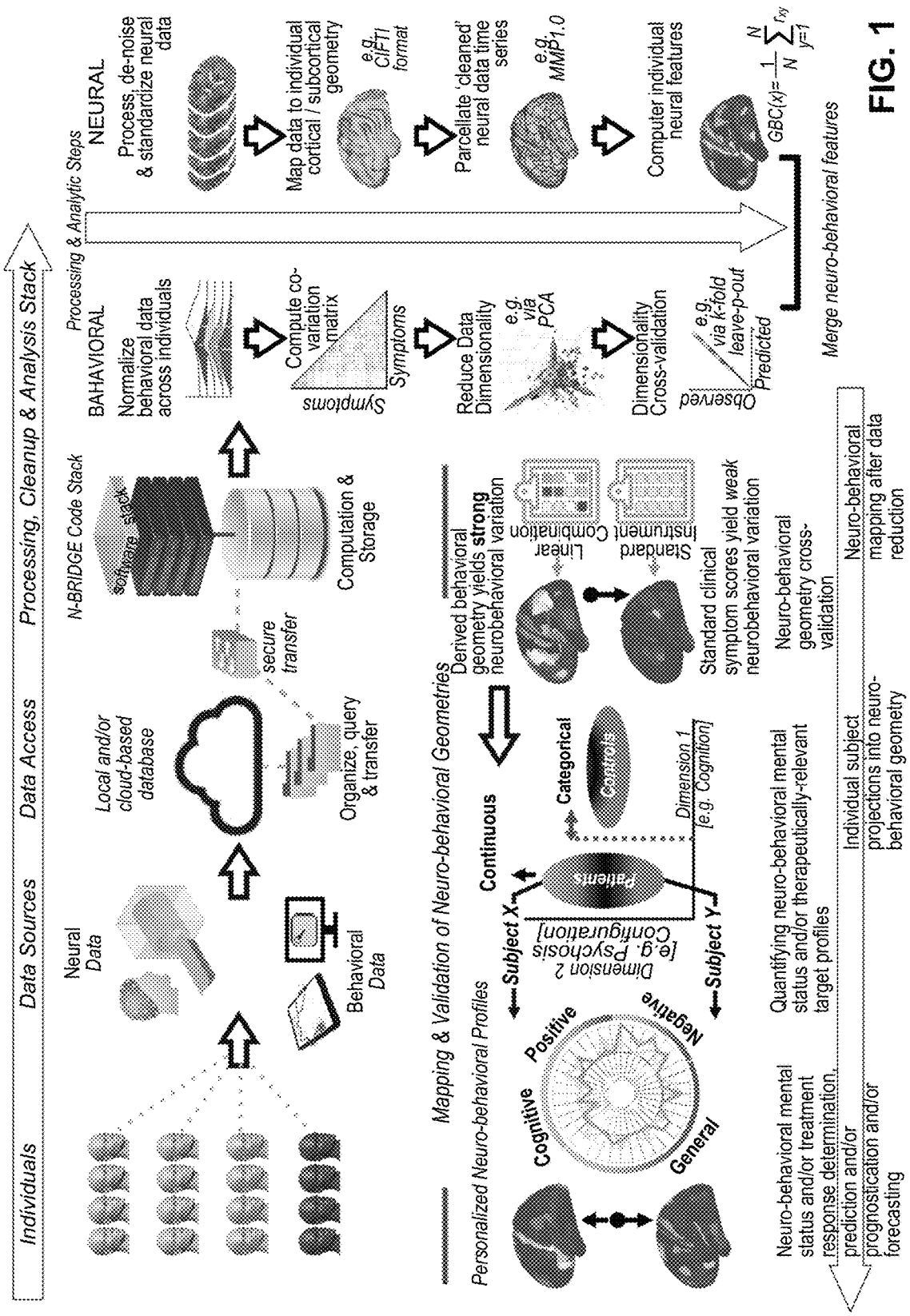
FIG. 1 illustrates an example schematic of determining a treatment for a patient based on neuro-behavioral mapping, according to embodiments of the present disclosure.

FIG. 1 illustrates an example schematic of determining a treatment for a patient based on neuro-behavioral mapping, according to embodiments of the present disclosure. In particular, FIG. 1 shows a high-level overview of N-BRIDGE, illustrating how behavioral data and/or neural data is obtained from a plurality of individuals, such as by imaging modalities (e.g., MM, EEG, MEG, or the like) or behavioral assessment (e.g., behaviors identified via computer tests administered to patients by clinicians, behaviors obtained by observation by an individual, measurements corresponding to behaviors a patient exhibits or reports to a doctor, or the like) and utilized for generating a neural-behavioral multi-dimensional geometry mapping. In some embodiments, behavioral data and/or neural data (e.g., neuroimaging data) may undergo processing, transformation, and analysis steps, as will be described further below, prior to mapping and validation of a neuro-behavioral geometry. The resulting neural-behavioral multi-dimensional geometry mapping may ultimately be used to determine therapeutics associated with distinct neural/behavioral features, predict treatments for patients, and generate recommendations for treating patients.

Described herein are a series of data-driven methods, in which independent behavioral dimensions have been identified that map to specific neural circuits in a public dataset of 436 psychosis-spectrum patients, including 150 individuals with a formal diagnosis of bipolar disorder with psychosis (BPP), 119 individuals with a formal diagnosis of schizoaffective disorder (SADP), and 167 individuals with a formal diagnosis of schizophrenia (SZP) and 202 healthy control subjects without a diagnosis or history of psychiatric illness. Additionally, the generalizability of the present disclosure is demonstrated with an independent public dataset of 339 young adults without a diagnosis of psychiatric illness.

FIG. 2A illustrates an example table comprising examples of relevant behavioral, clinical, cognitive, and demographic characteristics of patients (PROB, all proband patients) and healthy control subjects (HCS), according to embodiments of the present disclosure. In particular, FIG. 2A illustrates an example table with behavioral data comprising demographic characteristics, symptom scores, and cognitive performance collected via rating scales, questionnaires, and clinician impression. The data used here is obtained from the publicly available Bipolar-Schizophrenia Network for Intermediate Phenotypes (B-SNIP) dataset, which is made available via the National Institutes of Mental Health Data Archive (NDA) as collection #2274[7]. First, a data-reduction procedure via principal component analysis (PCA) across all available measures of behavior was performed to identify dimensions/axes along which variation in behavior is maximal in patients across all available measures of behavior or phenotypic measures. These behavioral dimensions yield a set of 'latent' dimensions/axes within which each individual can be projected. In turn, each individual can be assigned a 'score' along one or more of these latent dimensions, which can then mapped to areal neural features in the same individuals. This can be done using any invasive or non-invasive neural feature measure that can yield a neural map (such as by using functional magnetic imaging (fMRI) data).

In some embodiments, a patient or a doctor may utilize a user interface of a computing device to provide behavioral data corresponding to the patient. The behavioral data may include any measurements corresponding to behaviors a patient exhibits or reports to a doctor. In other cases, behavioral data may be obtained by observation of the patient by an individual (e.g., doctor, medical assistant, or the like) or by selection of answers to questions on a computing device.

For example, a clinician may ask a patient a series of open-ended questions and provide the patient with rating levels to identify the severity of a condition for each question. The patient may provide answers to the questions, in which the answers include rating levels selected by the patient. In another example, a patient may be given a test (e.g., a test on a computer or a test administered by a clinician) to measure the patient's short-term and long-term memory abilities, such as by asking the patient to recall various numbers or names over time. In yet another example, a clinician may ask a patient a series of questions regarding behaviors, such as how often a patient smokes each day, how many alcoholic beverages a patient drinks, and the like.

FIG. 2B illustrates an example diagram showing a cognitive paradigm deployed via computerized assessment for obtaining behavioral features, according to embodiments of the present disclosure. For example, a patient may utilize a user interface of a computing device for a computerized cognitive assessment to measure cognitive processes, such as memory, attention, problem solving, decision making, and the like. In some embodiments, a questionnaire-based assessment to assess a patient's mental health or cognitive status may be implemented on a computing device, a tablet, a mobile device, or the like. For example, a computing device may present a plurality of questions to a user (e.g., an individual, a patient, or a clinician) on a display of the computing device, and the computing device may receive one or more answers to the series of questions via a user interface of the computing device. In particular, the one or more answers may be selected by the user via the user interface of the computing device.

FIG. 2C illustrates an example diagram showing an eye tracking deployment in a laboratory, clinic, or inside a scanner, according to embodiments of a present disclosure. For example, an infrared illuminator may be utilized to measure eye movements of a patient over time, while using a computing device or while in a scanning device. The eye movement or eye tracking measurements may be useful in providing insight and useful data for measuring cognitive processes of the patient.

FIGS. 3A-3F illustrates example diagrams of behavioral variation of psychopathy and cognition, according to embodiments of the present disclosure. FIGS. 3A-3F are described as the following: (a) Distributions of symptom severity for each of the subject groups, for traditional symptom factors. Right bar plots show group-level total mean BACS composite cognitive performance PANSS positive symptoms, Negative symptoms, General symptoms, and of probands differentiated using traditional diagnostic categories (BPP, yellow bar, N=150; SADP, orange bar, N=119; SZP, red bar, N=167), as well as across all patients (black, N=436) and controls (white, N=202. Error bars show standard deviation. Abbreviations: CON, controls; PROB, all probands; BPP, bipolar disorder with psychosis; SADP, schizoaffective disorder with psychosis; SZP, schizophrenia with psychosis. (b) Correlations between 36 measures of psychopathy and cognitive behavior across all patients (N=436). Measures include 30 items from the Positive and Negative Syndrome Scale (PANSS) and 6 items from the Brief Assessment of Cognition in Schizophrenia (BACS). (c) Screeplot showing the total proportion of variance explained by each of the principal components (PC) from the principal component analysis (PCA) performed across all 36 behavioral measures in 436 patients. The size of each point is proportional to the variance explained by that PC. The first five PCs (green) were determined to be significant using a permutation test. Inset shows the proportion of variance both accounted and not accounted for by the five significant PCs. Together, these five PCs capture 50.93% of the total variance in behavior in the sample. (d) Distribution plots of PC scores for each of the subject groups for the five significant PCs. PC scores were normalized relative to the control group. Of note, PC3 does not exhibit mean-shifts for any of the diagnostic groups, indicating no categorical separation but substantial kurtosis (i.e. variation) across the psychosis spectrum. (e) Loadings of each of the 36 behavioral measures on the first five PCs. Each PC ('Global Dysfunction', 'Cognition', 'Psychosis Configuration', 'Affective Valence', 'Agitation/Excitement') is named for its most strongly weighted measures. (f) Plot of the behavioral PCA with the first three significant PCs as axes. The vectors show the projection of standard symptom axes in this PC space, illustrating that these axes are not the same as the data-driven PC axes and hence do not reflect maximal behavioral variation in psychosis-spectrum disorders. Points shown are the centroids for each of the subject groups.

Figure 3A:
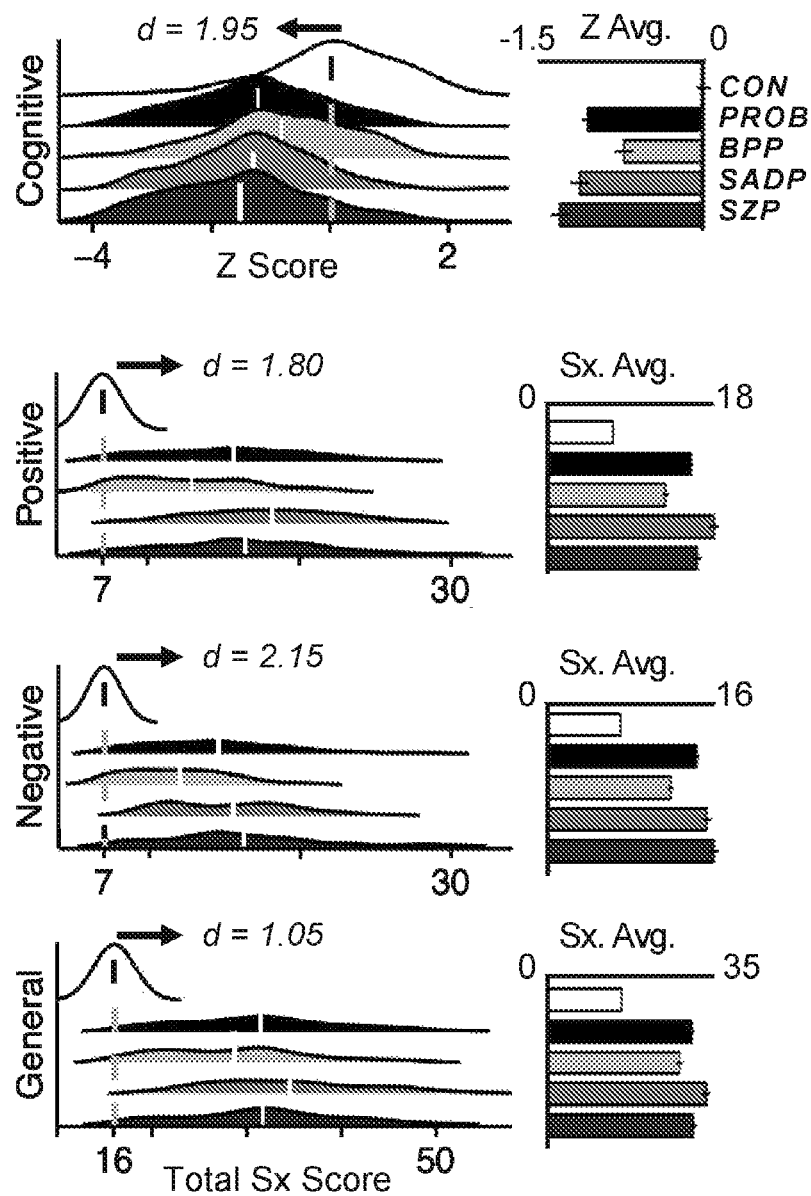
FIGS. 3A-3F illustrate example diagrams of the multi-dimensional behavioral variation of psychopathology and cognition, according to embodiments of the present disclosure.
Figure 3B:
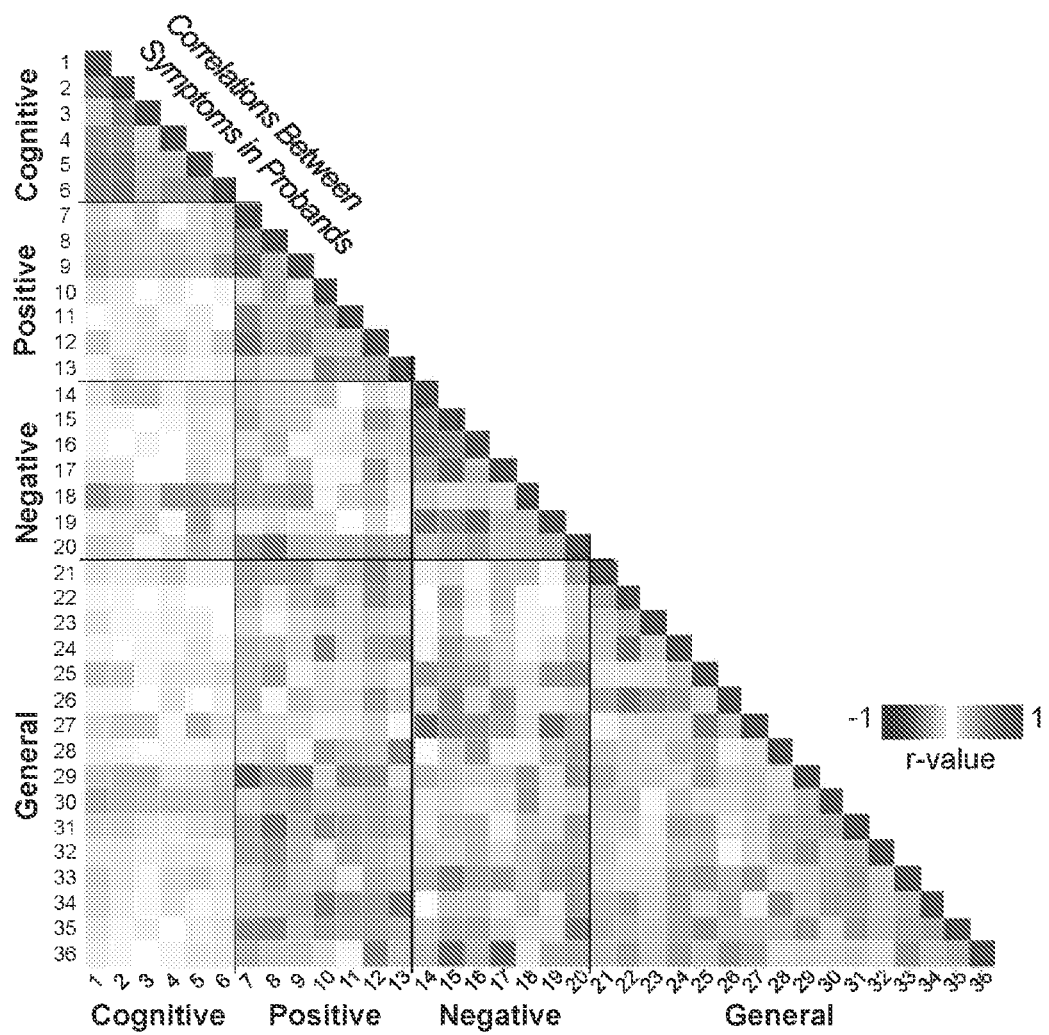
Figure 3C:
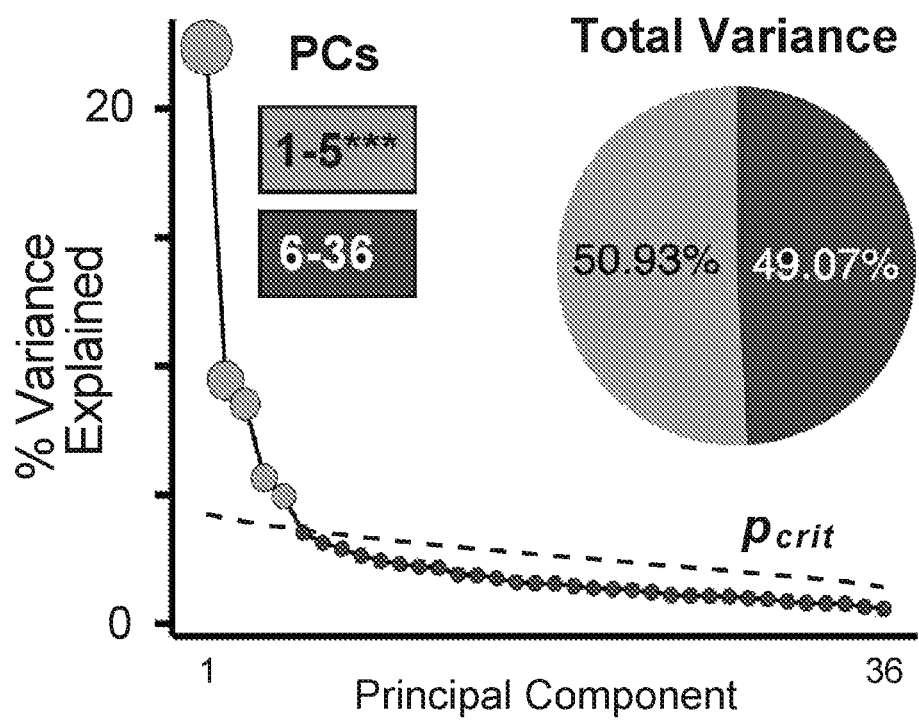
Figure 3D:
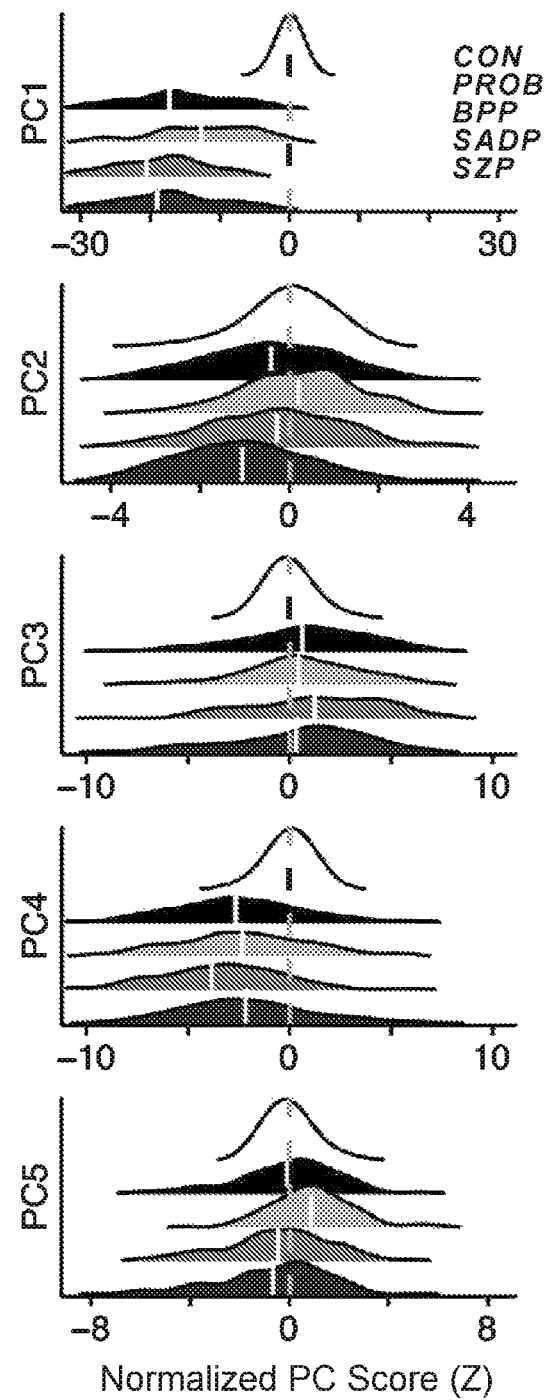
Figure 3E:
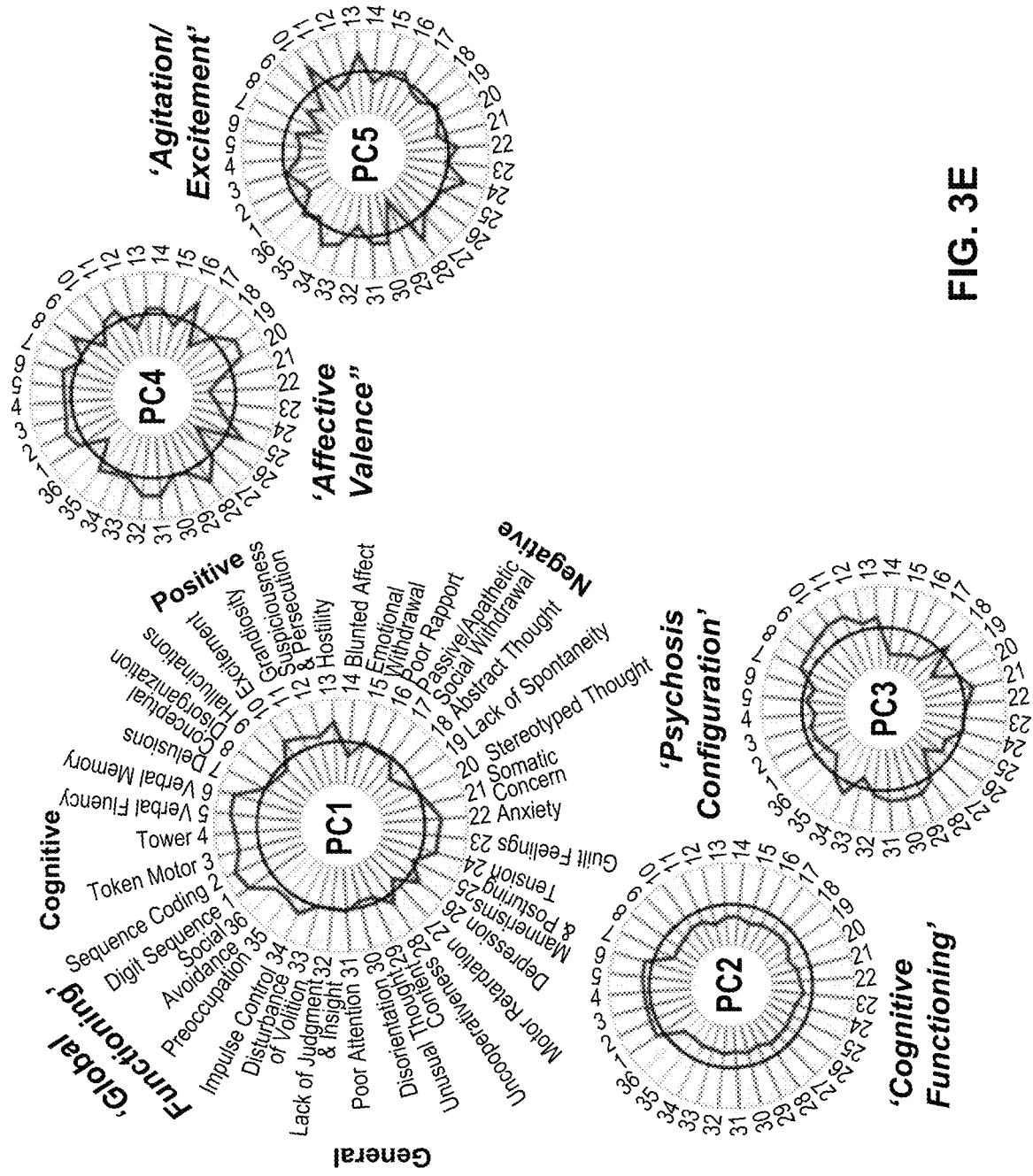
Figure 3F:
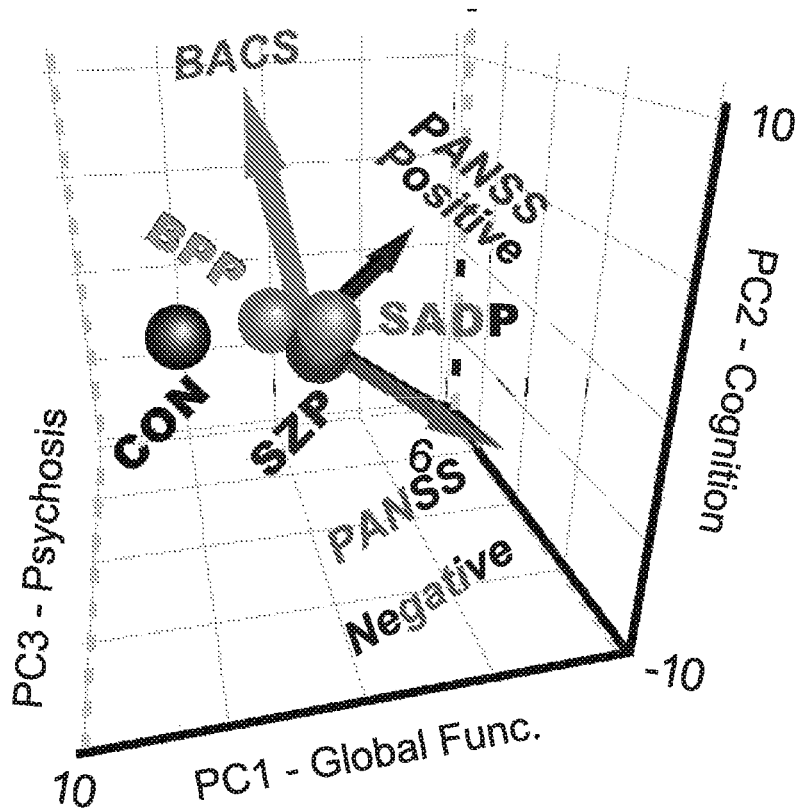

Importantly, these axes are not parallel to the axes of traditional clinical symptom dimensions that are derived from pre-existing clinical scales used in psychiatry, and do not reflect DSM-defined categorical diagnostic boundaries (See FIG. 3F and FIG. 4). This illustrates that the current "gold standard" for defining symptom dimensions in psychiatry is not optimal for capturing true behavioral variation in patients neither based on existing diagnostic schemes nor predefined clinical symptom measures. This results in a 'mismatch' between dimensions of behavior and putative disrupted neural circuits.

Figure 4C:
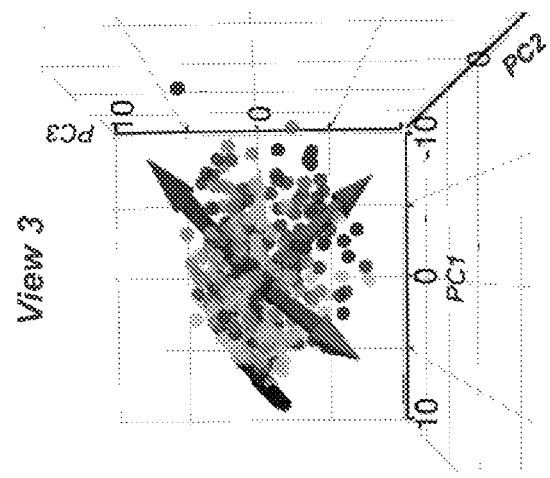
FIGS. 4A-4F illustrate example diagrams showing distinct angles of the geometry of multi-dimensional behavioral variation, according to embodiments of the present disclosure.
Figure 4B:
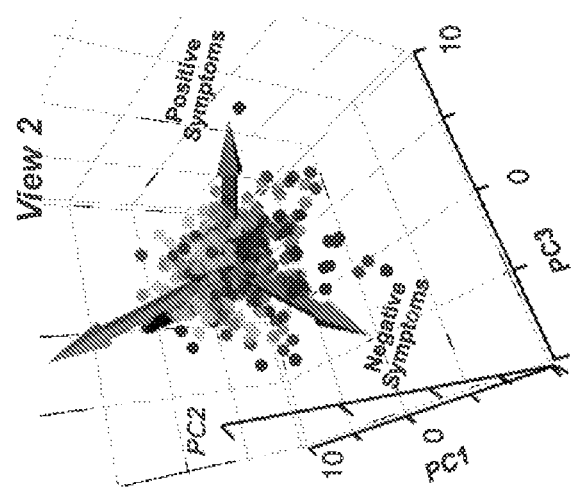
Figure 4A:
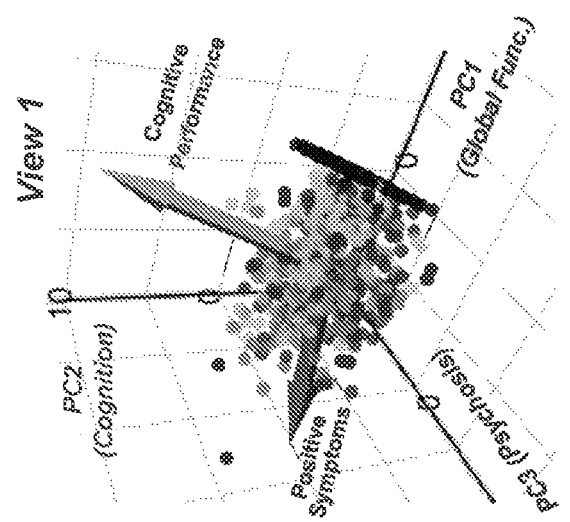
Figure 4F:
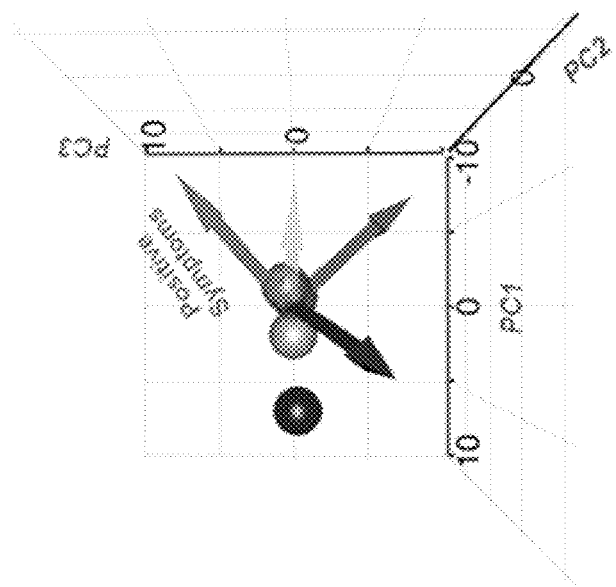
Figure 4E:
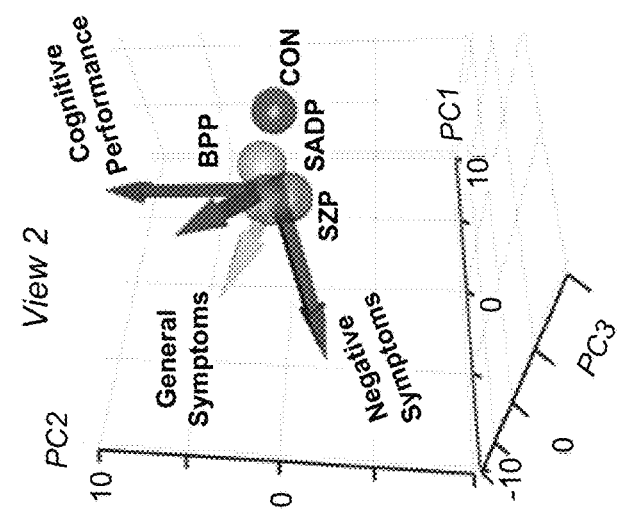
Figure 4D:
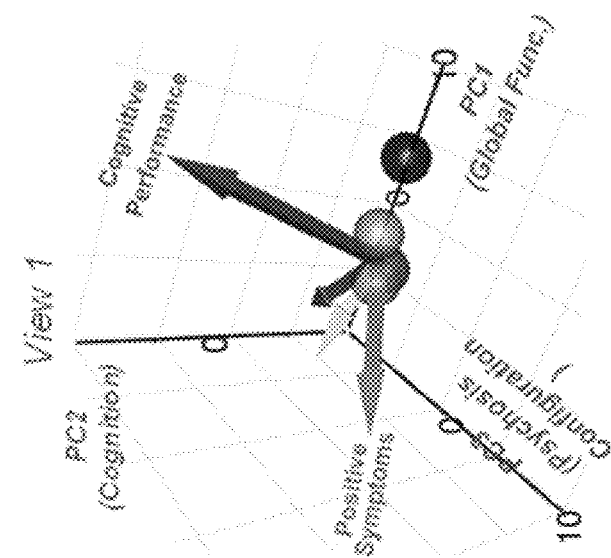
Figures 5A, 5B, 5C:
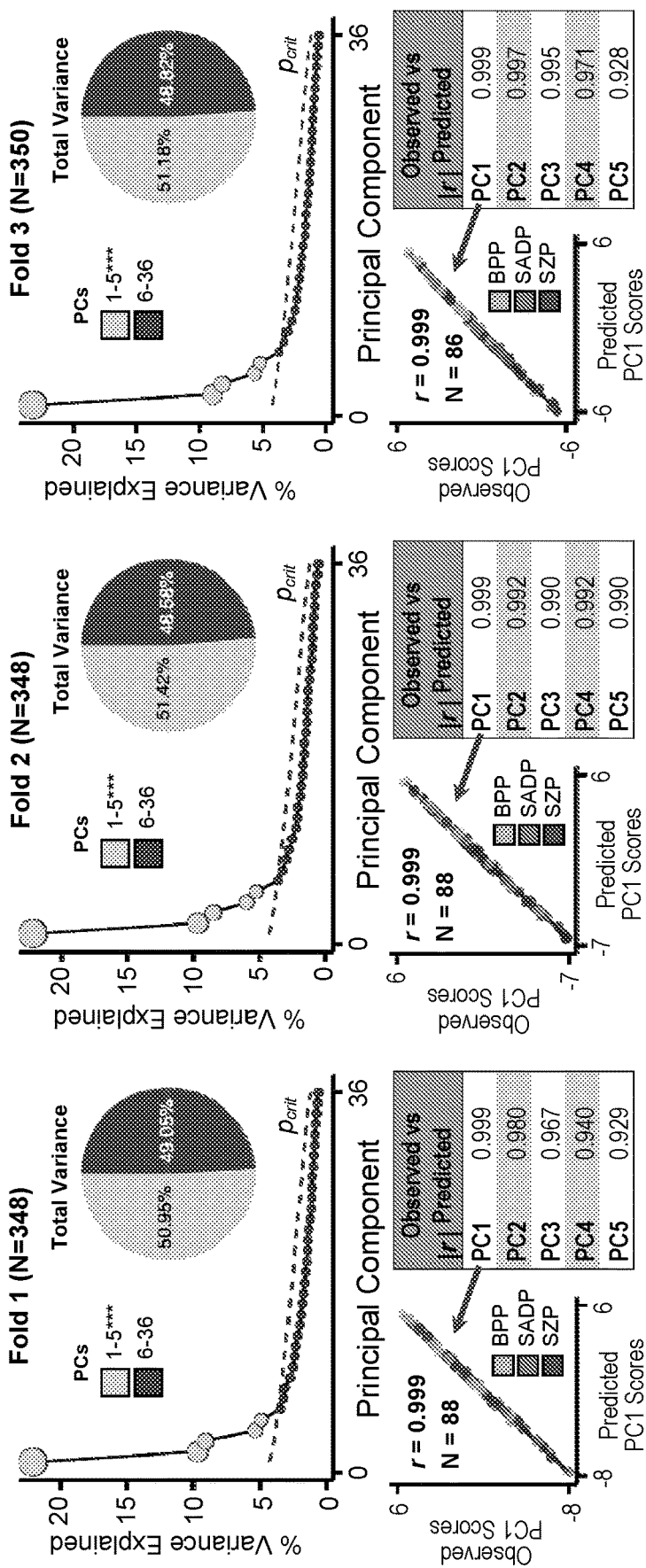
Figures 5H, 5I:
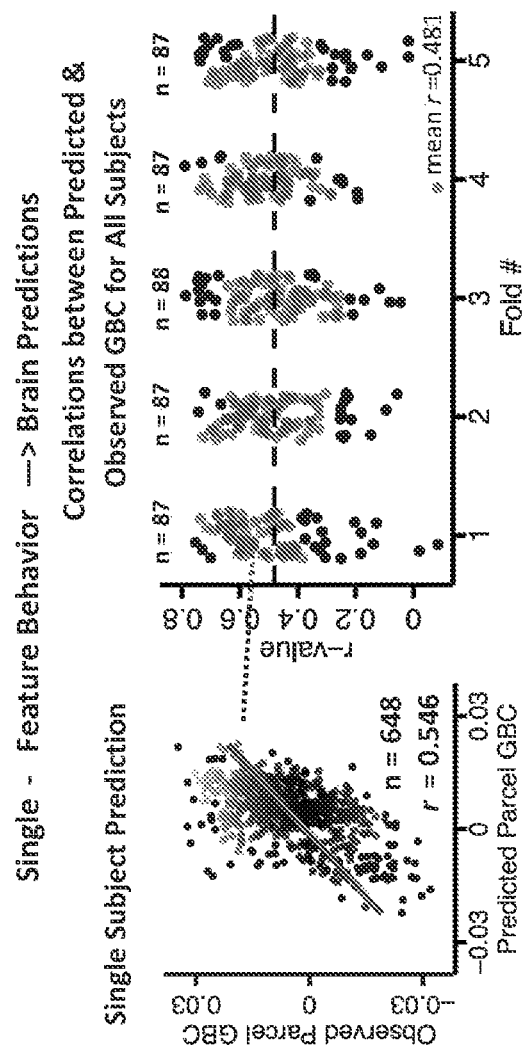
Figures 5J, 5K:
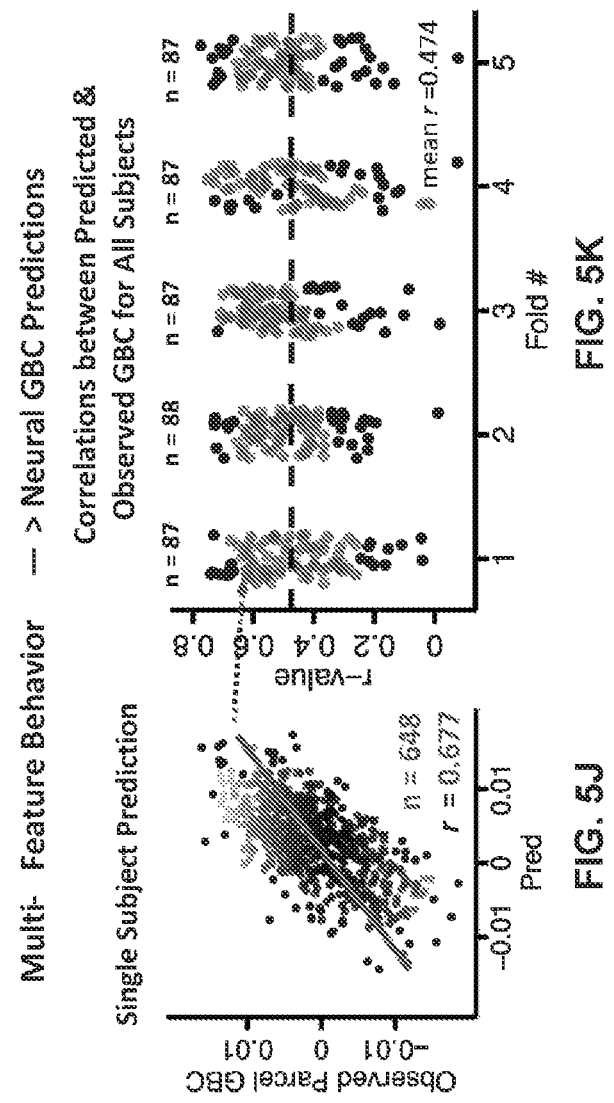

FIGS. 4A-4F illustrates example diagrams showing distinct angles of the geometry of symptom variation, according to embodiments of the present disclosure. In particular, FIGS. 4A-4F show alternative views of the tri-plot in the diagram of FIG. 3G, showing the relationship between the three principal axes of variation in behavior and standard clinical symptom factors. Each point represents an individual subject projected into the principal component (PC) space. FIGS. 4D-4F show alternative views of the tri-plot in diagrams of FIGS. 4A-4C, where each sphere represents the mean of each a priori clinical group. Notably, using these behavioral dimensions allows for prediction of how individual subjects in a left-out sample fit into the geometry with a high degree of accuracy (e.g., FIGS. 5 and 6).

FIGS. 5A-5K illustrate example diagrams showing k-Fold cross-validation for behavioral principal component analysis (PCA), according to embodiments of the present disclosure. FIGS. 5A-5K illustrate the results from a 5-fold cross-validation analysis to test the stability of the PCA solution. Subjects were first randomly assigned to one of 5 subsets. Each subset of subjects was then used as an independent 'test sample' in a PCA that was derived from the other 4 subsets. FIGS. 5A-5K are described as the following: FIGS. 5A-5E illustrate the results from a 5-fold cross-validation analysis to test the stability of the PCA solution. Subjects were first randomly assigned to one of 5 subsets. Each subset of subjects was then used as an independent 'test sample' in a PCA that was derived from the other 4 subsets. (a) Proportion of variance explained by each of the PCs in a PCA of all 36 behavioral measures, excluding a subset of 88 subjects. The number of significant PCs determined via a permutation test and the total proportion of variance explained by these PCs are all comparable to the full model shown in panel p. To obtain a 'predicted' PC score for the 88 subjects in the excluded subset, the loadings from the model obtained from the other 348 subjects were used. The 'observed' PC scores are the scores from the full model of the same 88 subjects. The scatterplot shows that the predicted and observed scores for PC1 are highly correlated (r=0.999), suggesting that the PCA solution is stable and predictive at the individual-subject level. Similarly, predicted and observed scores are highly correlated for all five PCs. (b-e) The results of the PCA are also highly comparable and predictive for the other four folds. (f) Plot summarizing the total proportion of variance explained and the number of significant PCs obtained from each of the 5 k-fold cross-validation sets. (g) Plot summarizing the r-values for each of the 5 PCs across k from 2 to 20. Each point represents the correlation between predicted and observed scores for one cross-validation fold (i.e. there are a total of (20 folds*5 PCs)=100 points for k=20). The solution is highly stable even at k=2 (where the model is trained on half the sample and tested on the other half), with the weakest correlation being 0.75 and only two folds reporting a correlation weaker than r=0.9. (h) Results of predicting single-subject GBC from a simple regression on a single behavioral PC. Each point in the scatterplot represents the GBC value of a single parcel for a single subject. First, a regression of parcel GBC against the PC3 scores was computed in a subset of 349 subjects. Then, the parcel GBC for each of the remaining 87 subjects in the left-out sample was predicted using this regression model. The correlation between the predicted and observed GBC was 0.55 across all neural parcels for this exemplar subject. (i) Results of predicting single-subject GBC from a simple regression on a single behavioral PC, for all subjects across all folds in a 5-fold cross-validation (dotted arrow points to the subject illustrated in panel (j). The mean correlation across all subjects is 0.48 (horizontal black dashed line), which is high considering that this example shows the mapping from a single behavioral dimension to a complex multidimensional neural space. A similar process can be employed using multiple behavioral dimensions to achieve a more accurate prediction of neural feature data from behavioral data. (j) Results of predicting single-subject GBC from a multiple regression on all five behavioral PCs. Each point in the scatterplot represents the GBC value of a single parcel for a single subject. First, a regression of parcel GBC against all 5 PC scores was computed in a subset of 349 subjects. Then, the parcel GBC for each of the remaining 87 subjects in the left-out sample was predicted using this multiple regression model. (k) Results of predicting single-subject GBC from a simple regression on a single behavioral PC, for all subjects across all folds in a 5-fold cross-validation.

Figures 6M, 6N, 6O:
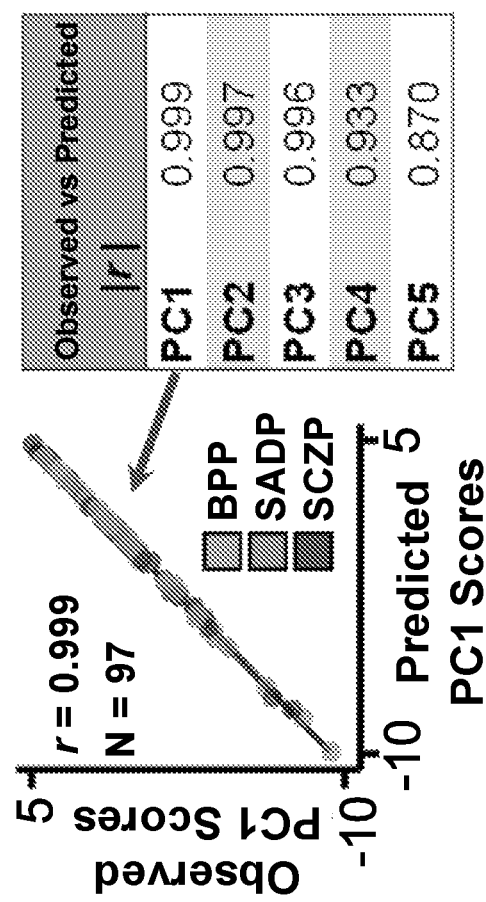
FIGS. 6A-6R illustrate example diagrams of evaluating site effects in behavioral PCA, according to embodiments of the present disclosure.
Figure 7H:
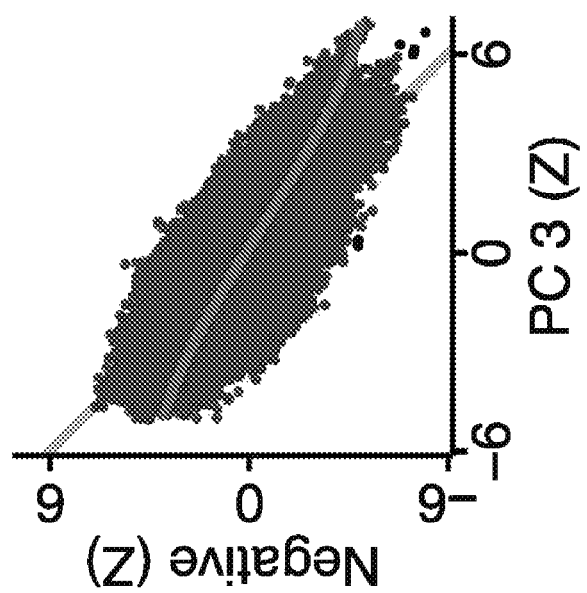
Figure 7G:
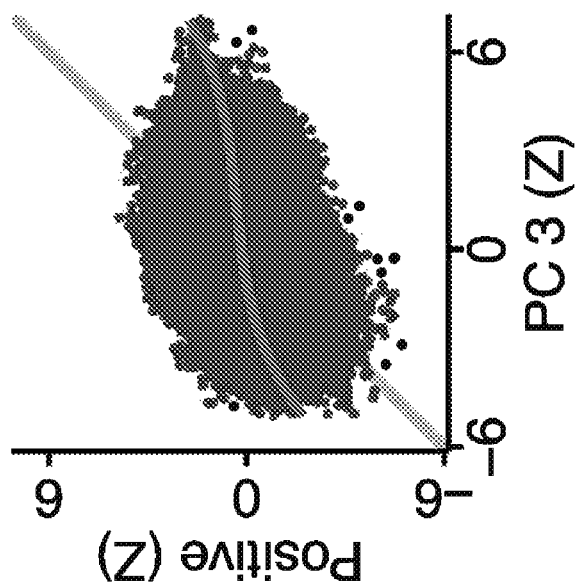
Figure 7J:
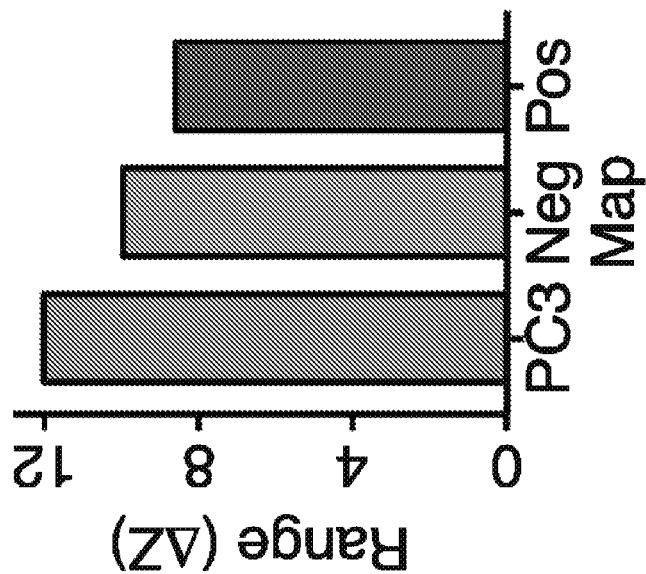
Figure 7I:
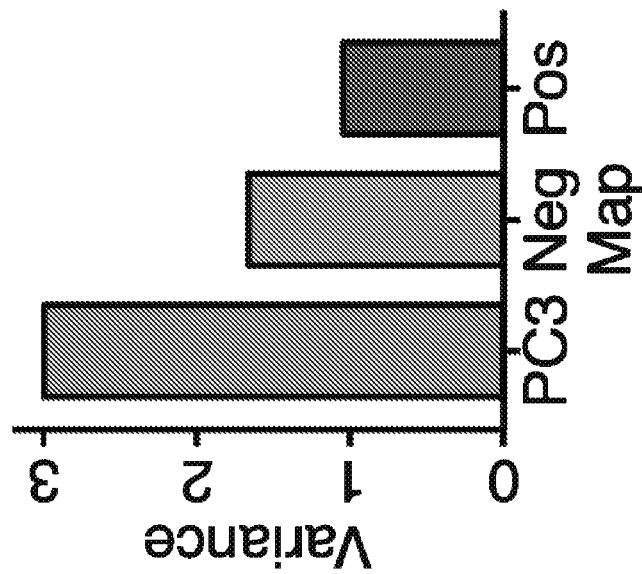

FIGS. 6A-6R illustrates example diagrams of evaluating site effects in behavioral PCA, according to embodiments of the present disclosure. FIGS. 6A-6R are described as the following: (a) Proportion of variance explained by each of the PCs in a PCA of all 36 behavioral measures, excluding one of the six sites at which data was collected. The number of significant PCs determined via a permutation test and the total proportion of variance explained by these PCs are all comparable to a full model (shown in FIGS. 3A-3F). (b) To obtain a 'predicted' PC score for the 46 subjects in the excluded site, the loadings from the model obtained from the other 390 subjects were used. The 'observed' PC scores are the scores from the full model of the same 88 subjects. The scatterplot shows that the predicted and observed scores for PC1 are highly correlated (r=0.999), suggesting that the PCA solution is stable and robustly predictive at the individual-subject level. (c) Predicted and observed scores are highly correlated for all five PCs. (d-r) The results of the PCA are also highly comparable for the other 5 sites, suggesting that site differences in evaluating patient symptoms are not driving the variation in behavior.

Importantly, variation along the identified behavioral dimensions relate to variation in specific neural circuits. These robust relationships between brain and behavior are not observed using traditional diagnostic groups or symptom categories (FIGS. 7A-7J). The ability to map distinct neural circuitry underlying data-driven behavioral variation has not been demonstrated with previous frameworks. One such example of neural-behavioral mapping in the disclosed geometry is demonstrated using an unbiased data-driven measure that quantifies the relationships between spontaneous fluctuations of the blood-oxygenation-level-dependent (BOLD) signal from any one region (i.e. functional connectivity), termed global brain connectivity (GB C)[8],[9],[10]. GBC can be calculated by computing the average strength of the statistical relationship between a given voxel (or area) and all other voxels (or areas) and is therefore unbiased as to the location of a possible alteration in connectivity (i.e. it is data-driven). Consequently, GBC maps can be computed for each individual subject and yield an area neural map provide a fully unbiased and data-driven validation of the variation along the PCA-derived behavioral/phenotype geometry (FIGS. 7A-7J).

FIGS. 7A-7J illustrates example diagrams relating symptom/behavior axes to neural connectivity, according to embodiments of the present disclosure. FIGS. 7A-7J are described as the following: (a) Distribution of total PANSS positive symptoms for each of the subject groups (white=controls; black=all patients; yellow=bipolar disorder; orange=schizoaffective disorder; red=schizophrenia). Distributions are normalized to the control group to reflect variation around the mean of the control group. (b) Relationship between PANSS positive symptoms and global brain connectivity (GBC) across all patients (N=436) at each brain location. (c) No regions survived non-parametric family-wise error (FWE) correction at p<0.05 using a permutation test with threshold-free cluster enhancement (TFCE). Note that the marked difference in PANSS positive symptom score between control and patient groups (Cohen's d=1.95) does not map to a corresponding neural circuit with any appreciable precision. (d) Distribution of scores for the 'Psychosis Configuration' PC for each of the subject groups, again normalized to the control group. (e) Relationship between the 'Psychosis Configuration' PC score and GBC across all patients (N=436) at each brain location. (f) Regions that were significant at p<0.05 after FWE correction via TFCE. Critically, although there is only a small difference between control and patient groups (relative to the within-group spread) in behavioral scores along the 'Psychosis' axis, a clear set of neural circuits relating to the variation along the 'Psychosis' PC axis emerges in panel f. The disclosed data-driven behavioral geometry mapping allows for mapping natural variation in any behavioral dimension via a data-reduction technique onto neural features that can reveal more robust variation along a population of individual, which is otherwise 'invisible' when using preexisting clinical scales or diagnostic groups. (g) Comparison of values in the PC3 vs Positive Symptom map for every grey coordinate. Sigmoidal distribution indicates an improvement in the z-statistics of the PC3 map relative to Positive map. (h) Similarly, the sigmoidal distribution of the PC3 vs Negative map indicates an improvement in statistics of the PC map. (i) Comparison of the variance between the PC3, Negative and Positive symptom map Z-scores. The variance of the PC3 values is greatest, indicating a greater spread in the distribution of Z-scores and regions with a stronger statistical relationship with GBC. (j) Comparison of the range between the PC3, Negative and Positive symptom map Z-scores. Similarly, the range of the PC3 values is greatest, indicating a greater spread in the distribution of Z-scores and regions with a stronger statistical relationship with GBC.

Figures 8C, 8D:
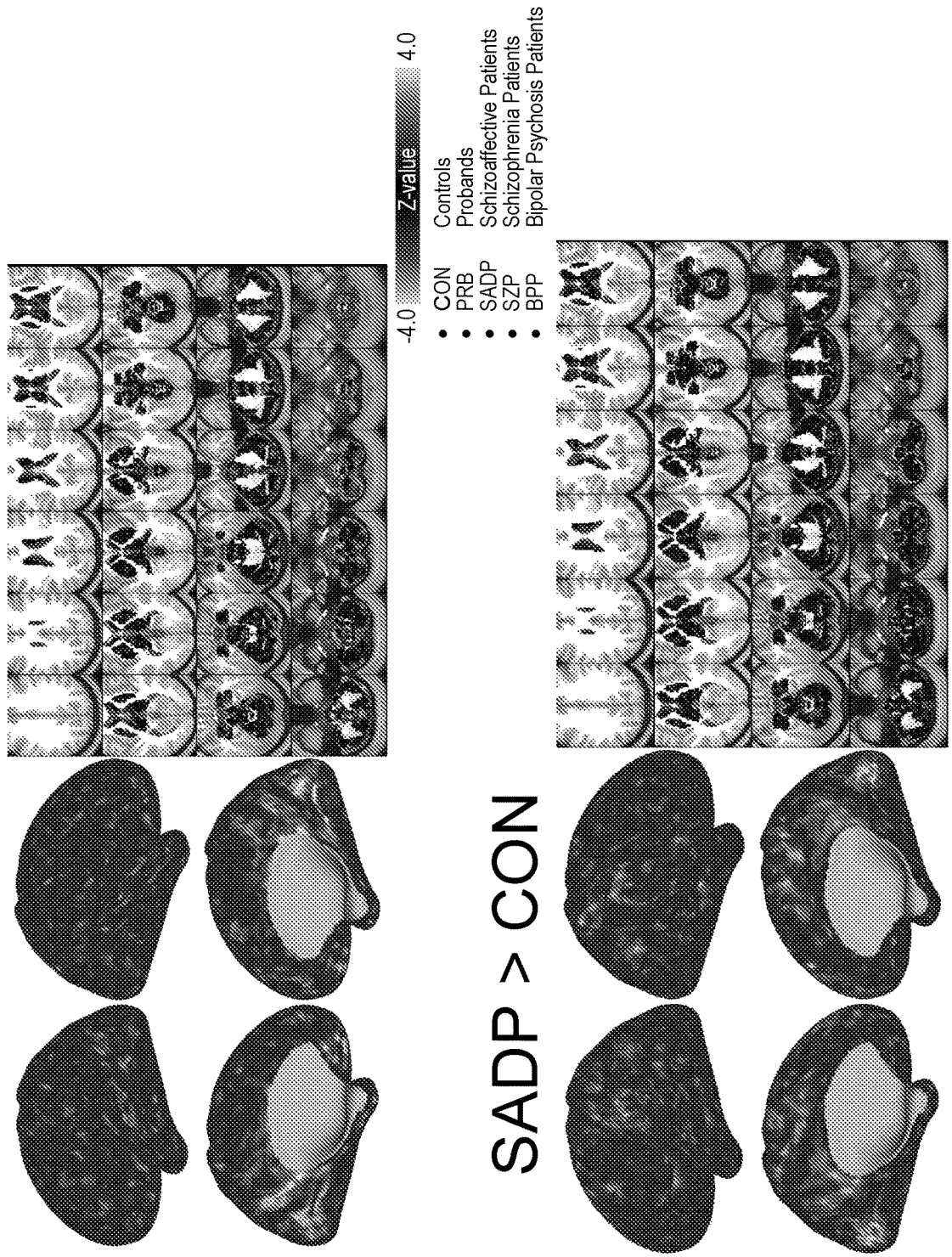
FIGS. 8A-8P illustrate example diagrams relating diagnostic categories and symptom axes to neural features, according to embodiments of the present disclosure.
Figure 8E:
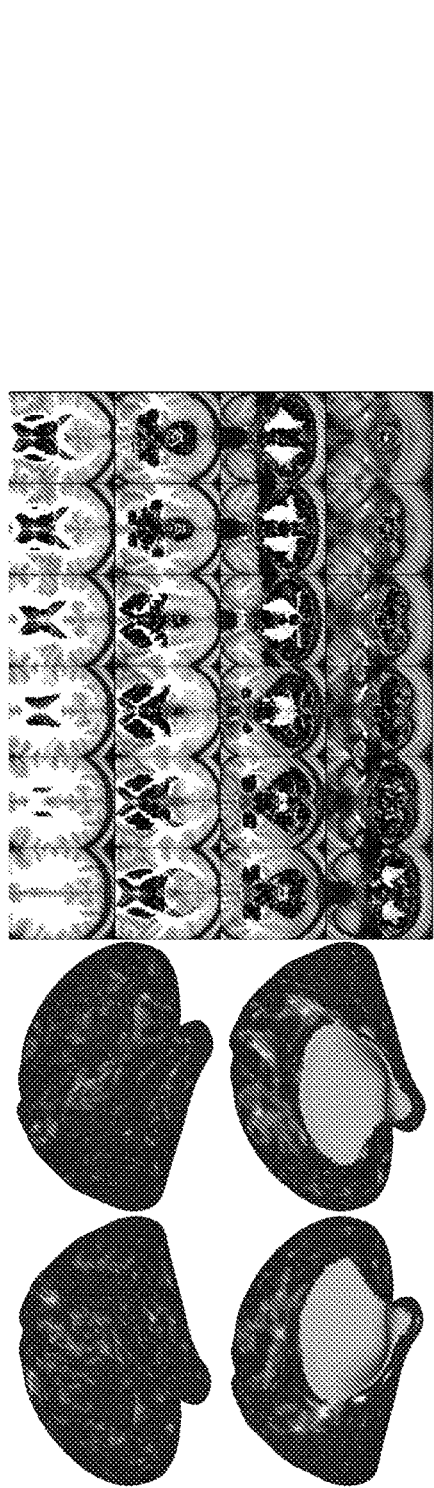
Figure 8F:
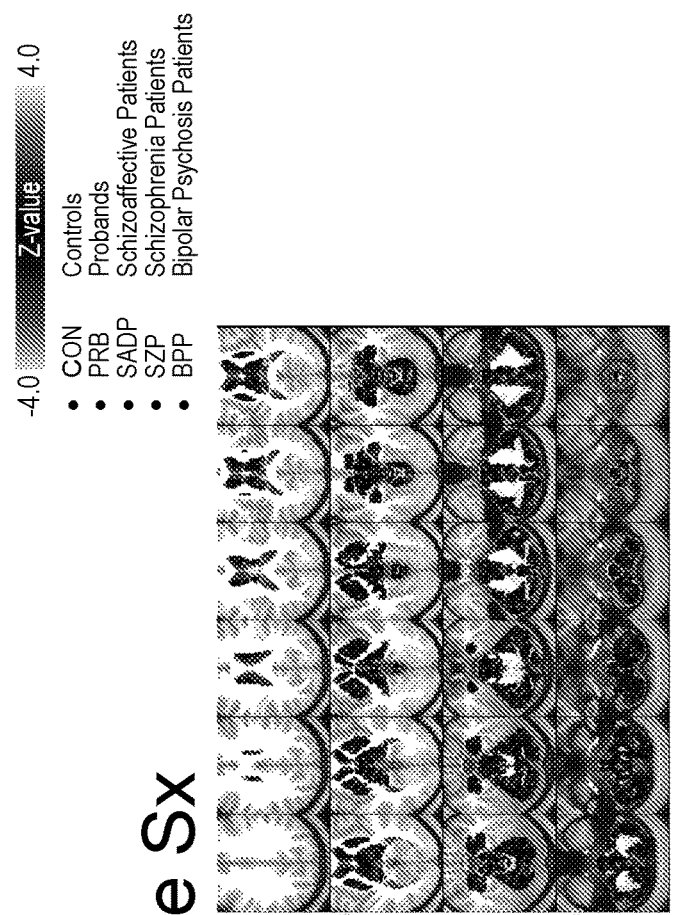
Figure 8G:
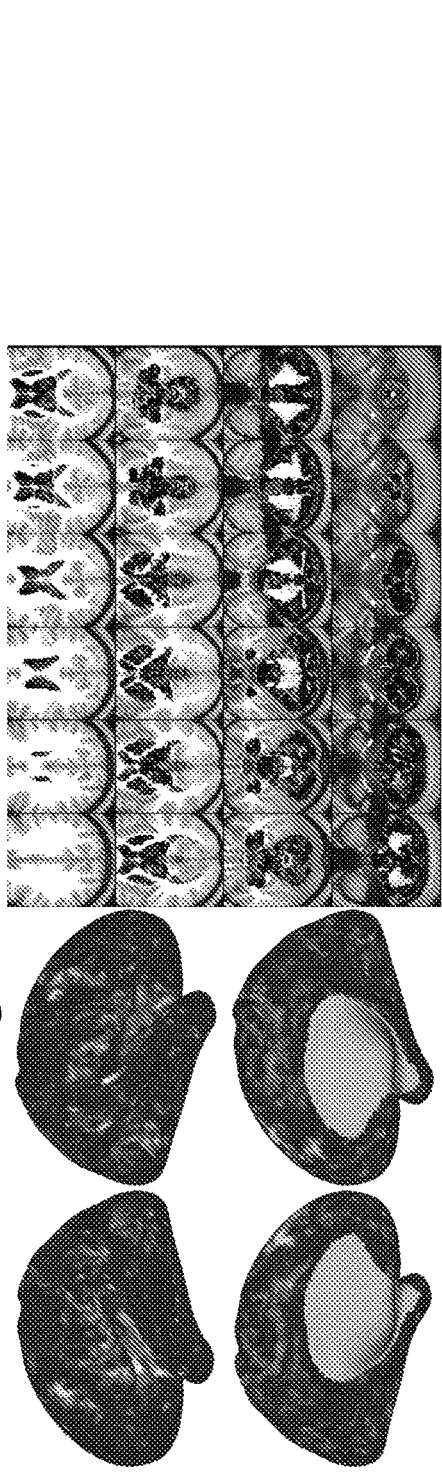
Figure 8H:
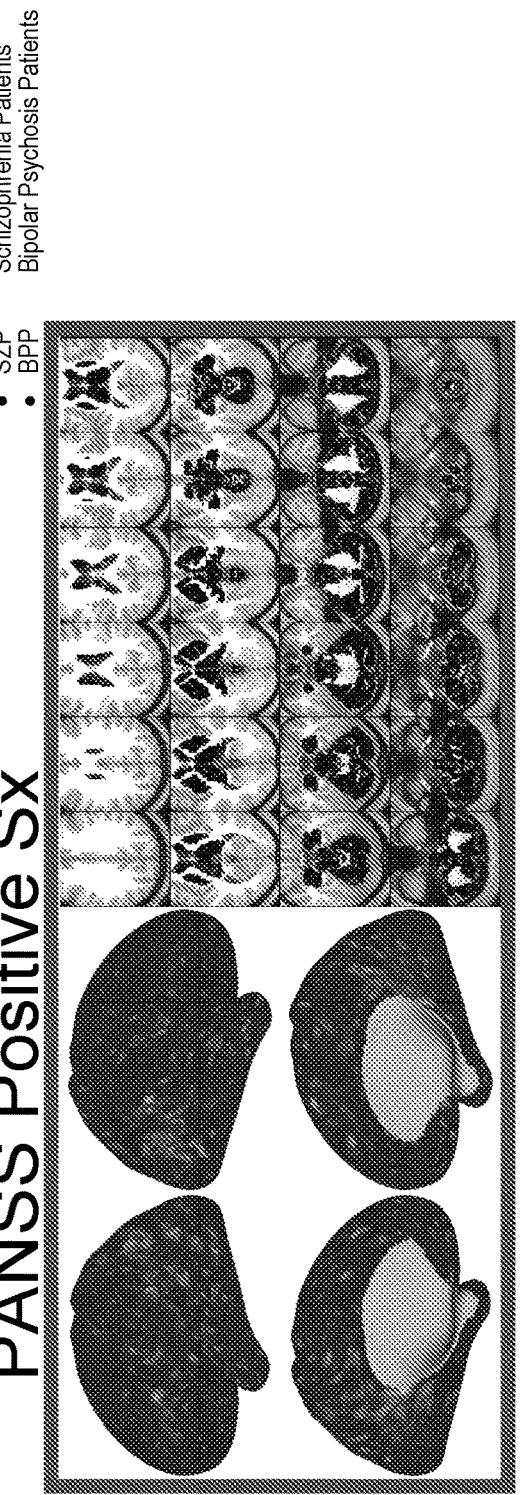
Figure 8I:
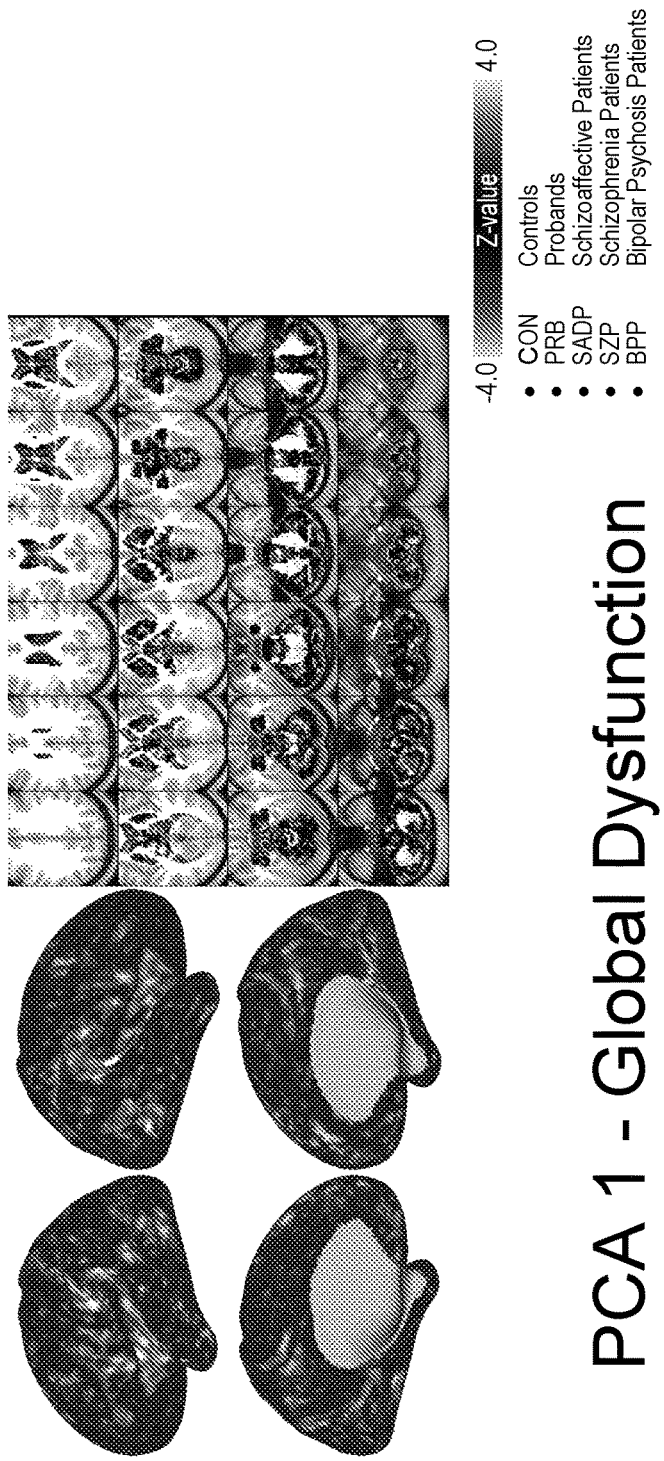
Figure 8J:
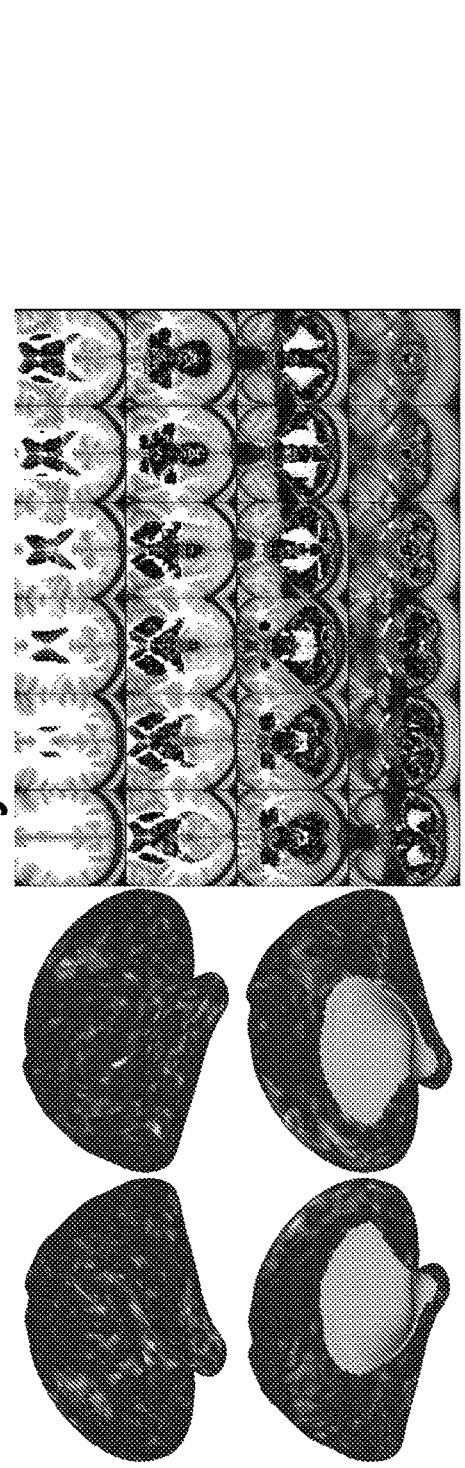
Figure 8K:
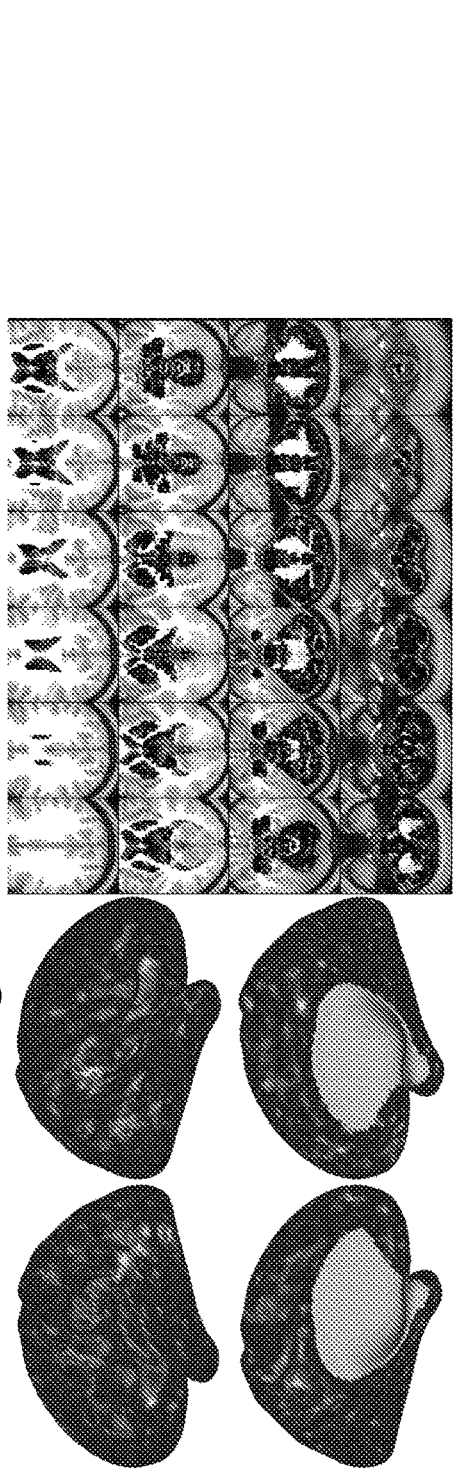
Figure 8L:
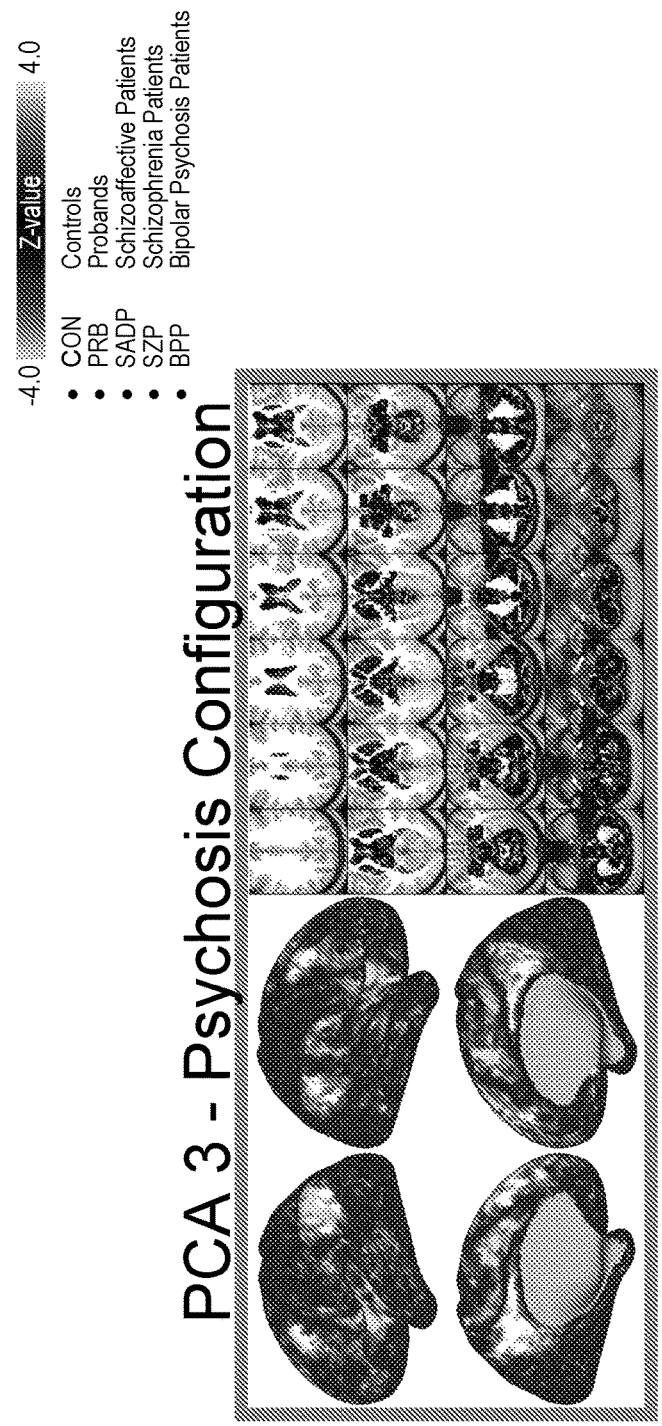
Figure 8M:
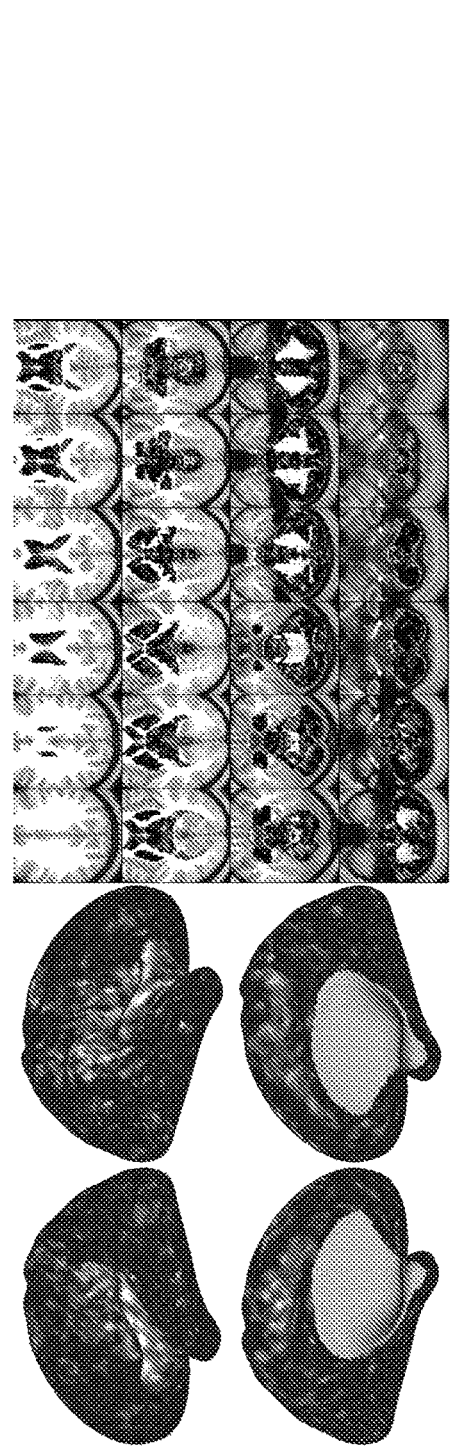
Figure 8N:
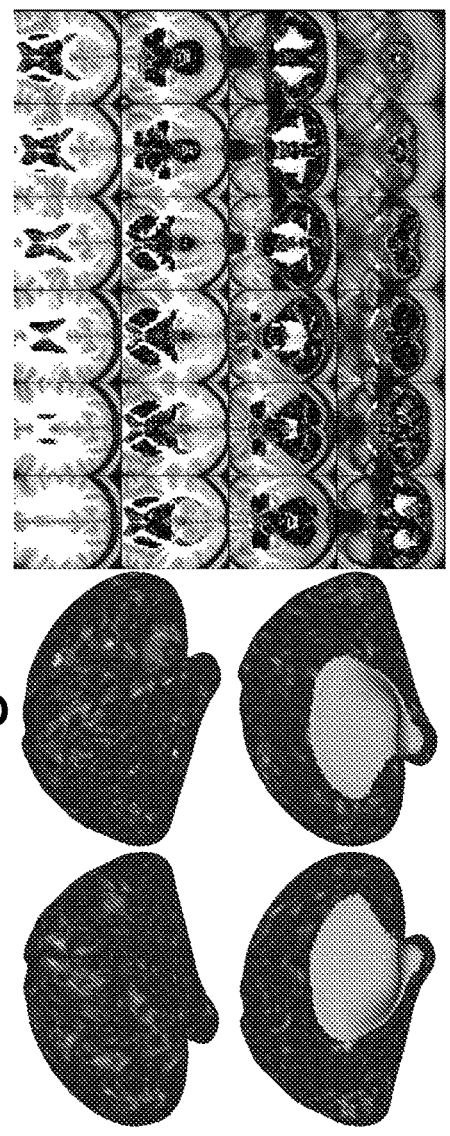
Figure 8O:
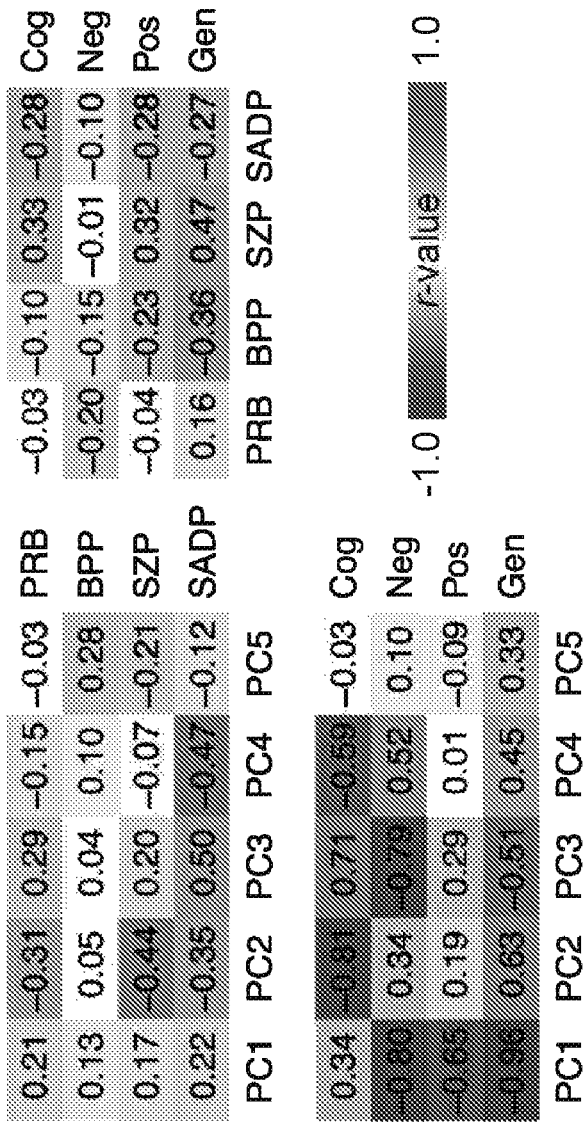
Figure 8P:
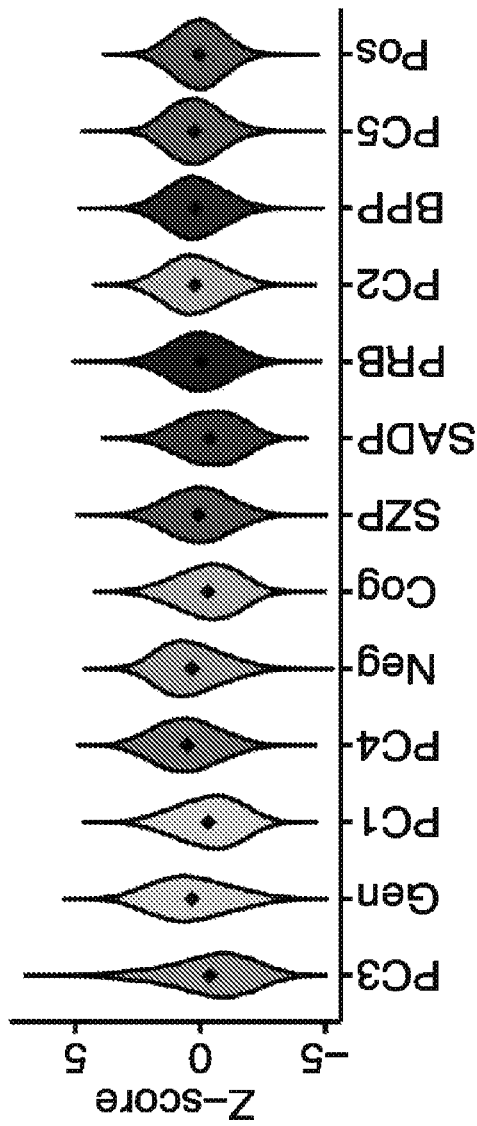
Figure 9C:
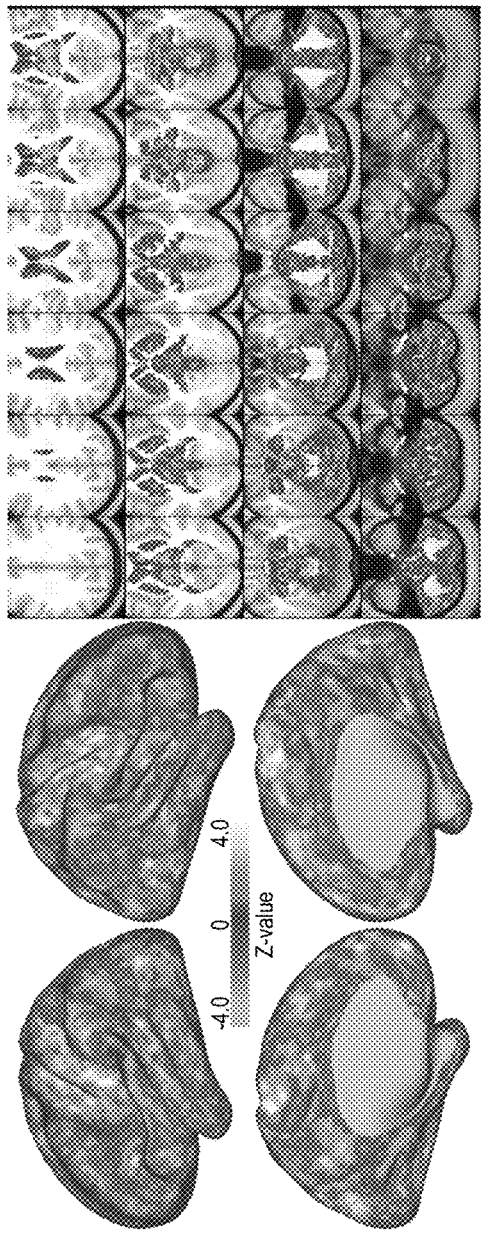
Figure 9D:
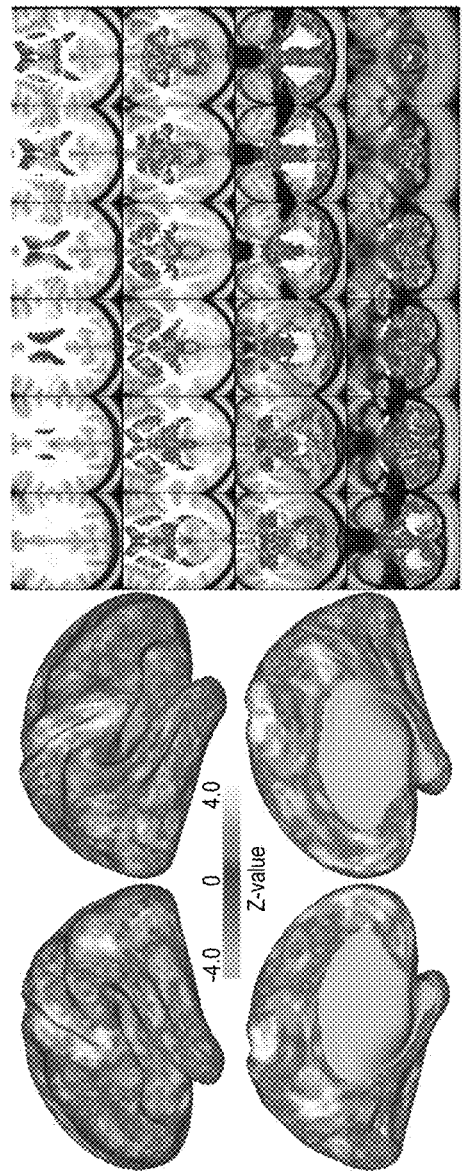
Figures 10A, 10B, 10C:
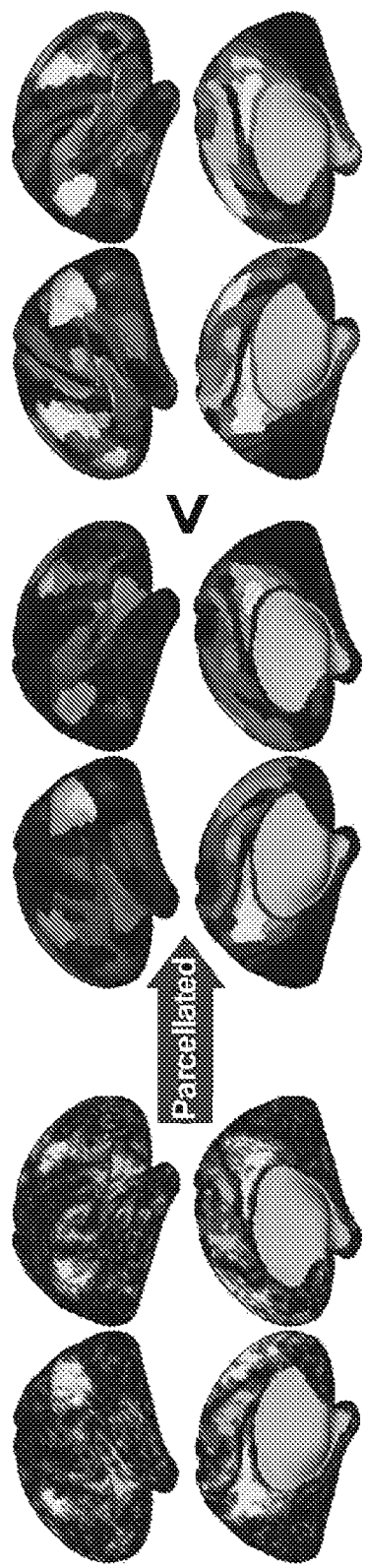
FIGS. 10A-10D illustrate examples of performing data-reduction on neural features, according to embodiments of the present disclosure.
Figure 10D:
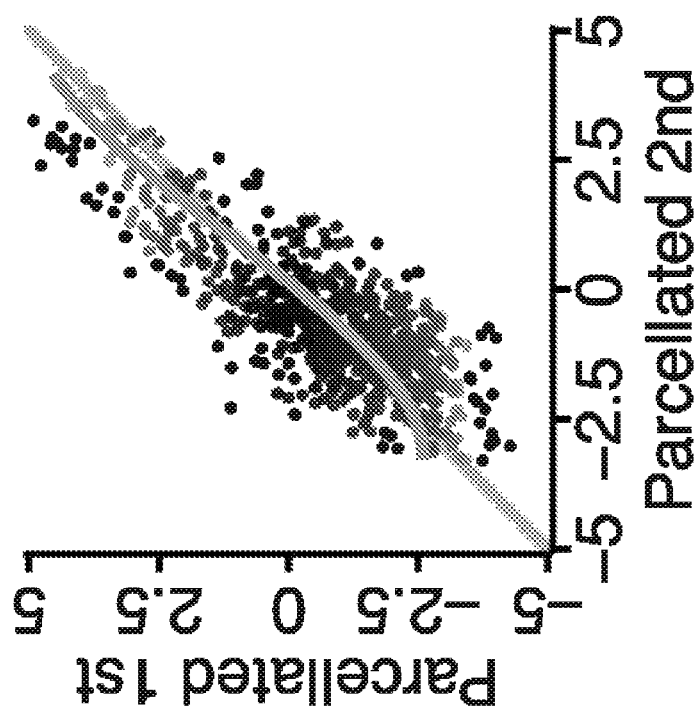
Figures 12A, 12B:
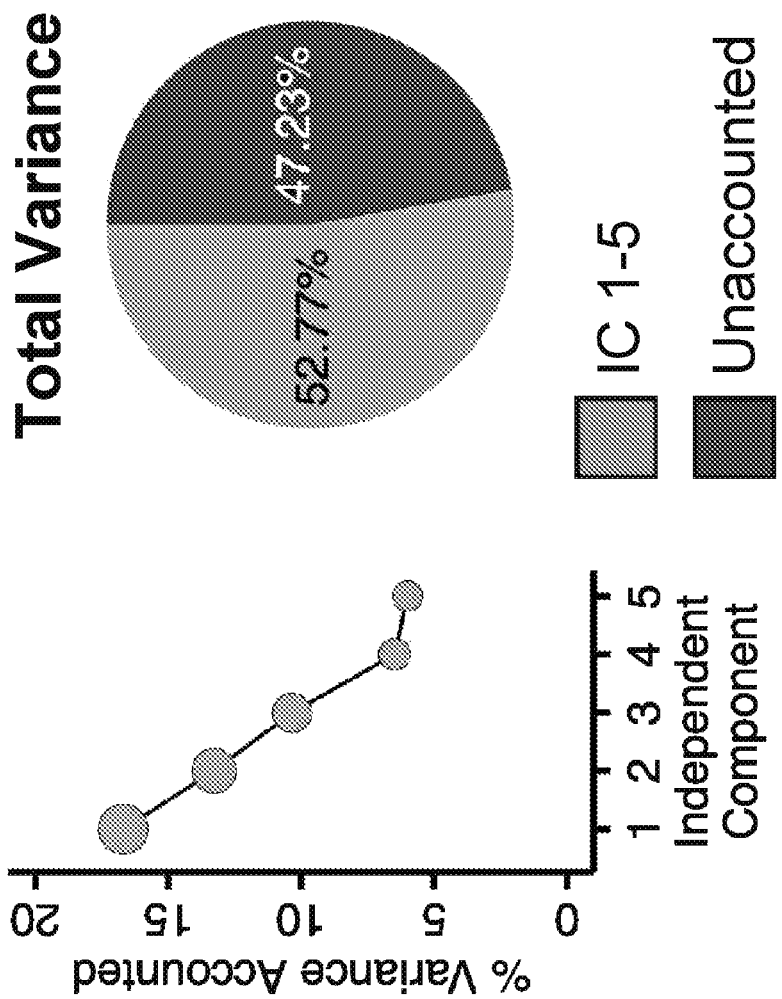
Figures 12D, 12E:
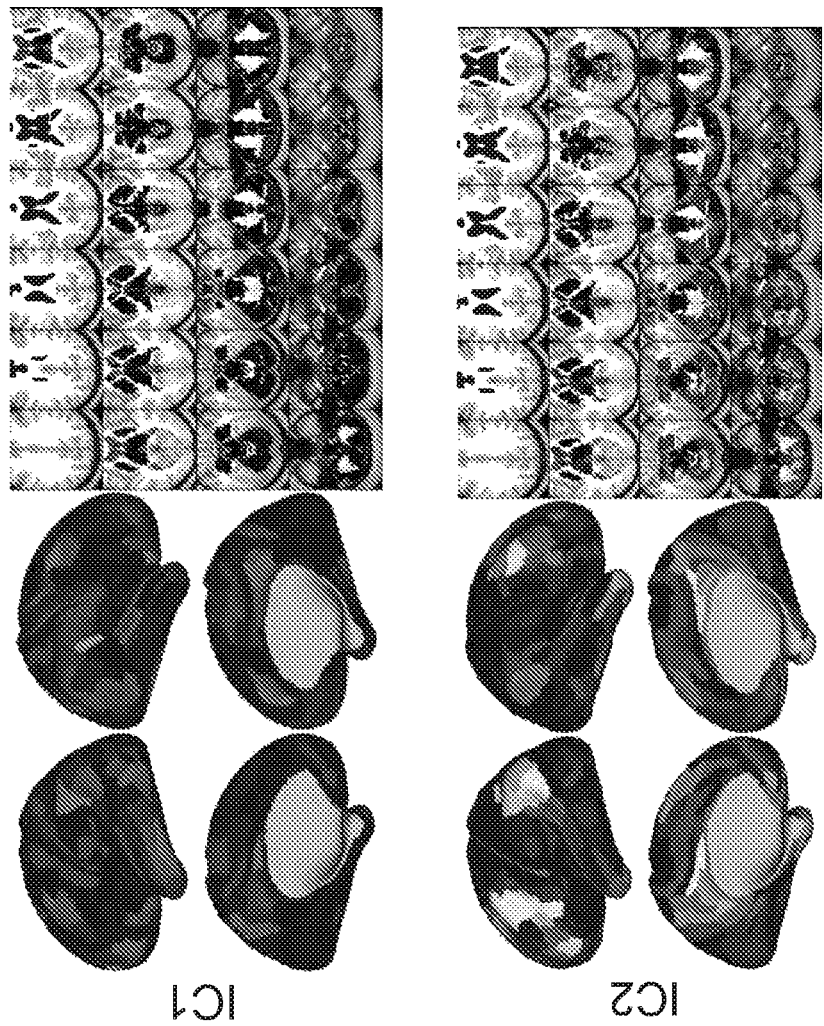
Figures 12F, 12G:
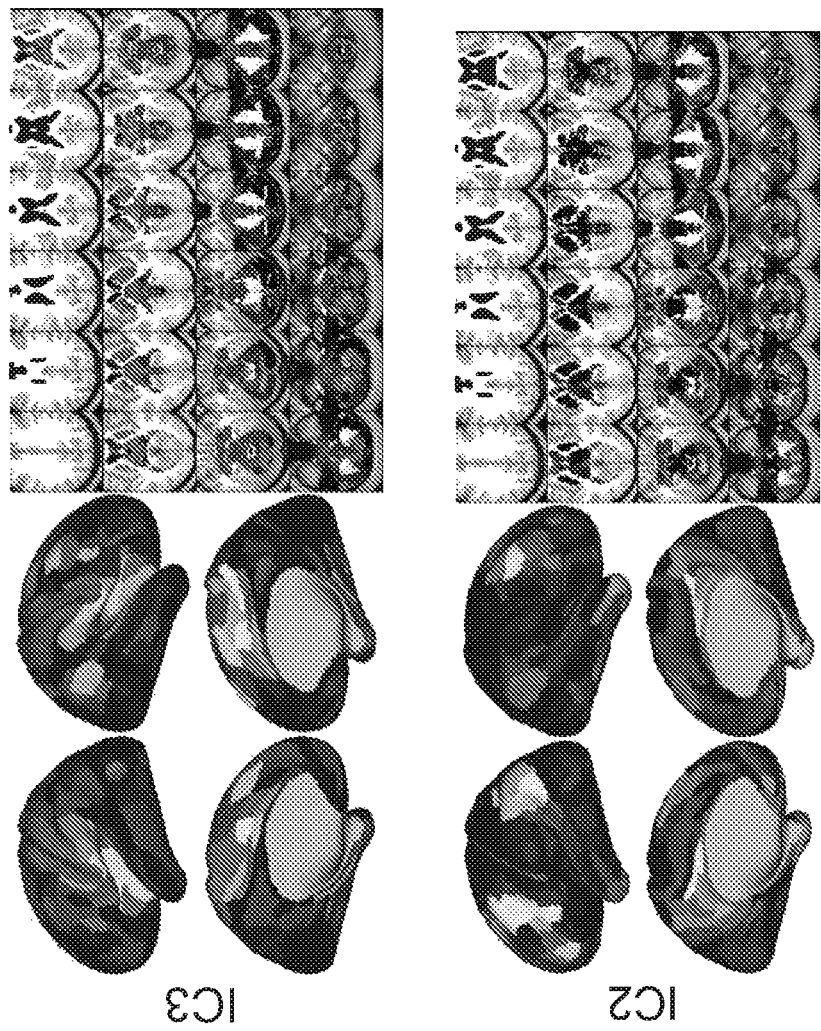
Figures 12H, 12I:
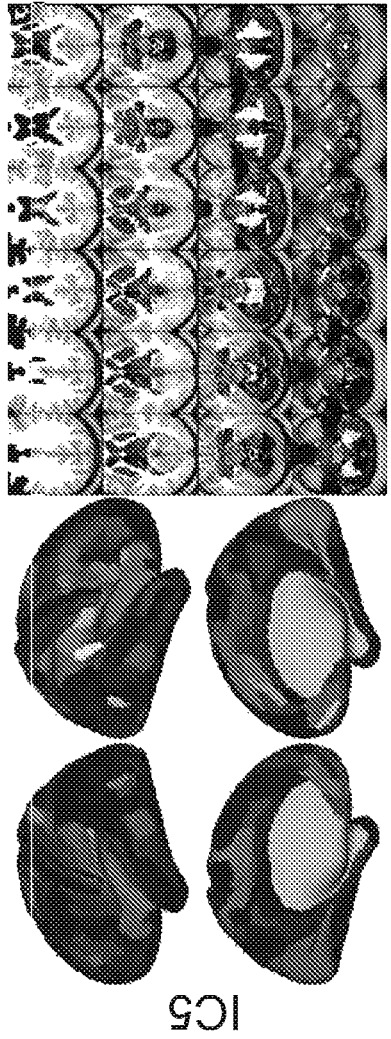

FIGS. 8A-8P illustrate example diagrams relating diagnostic categories and symptom axes to neural features, according to embodiments of the present disclosure. FIGS. 8A-8P are described as the following: Z-scored map of a t-test for the difference in group mean GBC between traditional diagnostic patient groups: (a) all probands (PRB) versus all healthy controls (CON); (b) patients with bipolar disorder (BPP) versus healthy controls (CON); (c) patients with schizophrenia (SZP) versus healthy controls (CON); (d) patients with schizoaffective disorder (SADP) versus healthy controls (CON). (e) Z-scored map of the F-test for the difference in group mean GBC between patients in all 3 diagnostic groups (BPP, SZP, SADP). Z-scored map of the regression against GBC, across all probands, of traditional symptom/behavioral scales: (f) BACS cognitive composite performance score; (g) PANSS total negative symptom score; (h) PANSS total positive symptom score; (i) PANSS total general symptom score. Z-scored map of the regression against GBC, across all probands, of data-derived behavioral dimension scores: (j) PC1 score; (k) PC2 score; (l) PC3 score; (m) PC4 score; (n) PC5 score. (o) Correlation matrices showing the similarity between maps in A-N. (p) Note that although there are strong correlations between the PC maps and the traditional symptom maps, the statistical properties of the PC maps are greatly improved, suggesting a stronger mapping between neural and behavioral variation.

Critically, the disclosed framework also allows for the natural and quantitative capture of neural features that reflect a categorical divide between patients and controls. FIGS. 9A-9D show one example of a neural characteristic that is distinctly different between individuals with and without a psychosis-spectrum diagnosis. Previous studies have shown that schizophrenia-associated disruptions in functional connectivity are most pronounced in higher order associative regions of the brain, such as those of the fronto-parietal control network (FPCN) implicated in higher-order executive functioning. These studies showed that functional connectivity derived by computing statistical variation from such FPCN executive regions exhibits a robust pattern of hyper-connectivity with sensorimotor regions and hypo-connectivity with prefrontal/associative regions in patients with schizophrenia relative to healthy controls. As shown in FIG. 9A-9D, this affected neural circuit is similarly disrupted in all psychosis spectrum disorder patients irrespective of the specific diagnosis, suggesting that it is a marker of a categorical distinction between healthy individuals and those with psychosis, which may serve as a solid categorical classifier. However, such a classifier, no matter how many features it included, would be unable to detect multi-dimensional variation along dimensions of latent and/or manifest weighted composite features in both behavioral and neural spaces.

Put differently, the flexibility to embed both categorical and continuous behavioral and neural features within the same multi-dimensional geometry is not present in previous frameworks (such as the DSM or RDoC), which limits the ability to map multi-dimensional complex human behavior and variation in psychiatric conditions onto neural feature variation. The N-BRIDGE framework therefore provides a unified mapping between the multi-dimensional geometry of data-driven behavioral variation and the multi-dimensional geometry of data-driven neural variation.

FIGS. 9A-9D illustrate example diagrams showing between-group differences in functional connectivity of the fronto-parietal control network (FPCN), according to embodiments of the present disclosure. FIGS. 9A-9D are described as the following: (a) Unthresholded map of differences in whole-brain functional connectivity seeded from the FPCN between controls (N=202) and all patients (N=436). Yellow/orange highlight areas to which the FPCN is hyper-connected in patients relative to controls; regions hypo-connected in patients are shown in blue. The FPCN seed was defined using a well-validated functional parcellation derived from an independent dataset of 1,000 individuals[11]. (b) Unthresholded map of differences in FPCN-seed connectivity between controls (N=202) and patients with a diagnosis of bipolar disorder (N=150). (c) Unthresholded map of differences in FPCN-seed connectivity between controls (N=202) and patients with a diagnosis of schizoaffective disorder (N=119). (d) Unthresholded map of differences in FPCN-seed connectivity between controls (N=202) and patients with a diagnosis of schizophrenia (N=167). Note the remarkably high similarity between all four maps.

FIGS. 10A-10D illustrate examples of performing data-reduction on neural features, according to embodiments of the present disclosure. FIGS. 10A-10D are described as the following: (a) Example analysis of behavioral data with complete, unreduced high-dimensional neural data (in this example, regression of a behavioral score on to a neural map with over 90,000 features). (b) Map of data from (a) parcellated after performing analysis. (c) Example of the same analysis performed on the same neural data, where neural features which were first dimension-reduced using a neurobiologically-based parcellation. (d) A comparison of the maps in B and C shows that the statistics of the same analysis are improved after a principled neurobiologically-grounded means of data-reducing neural features, likely attributable to an improvement in signal-to-noise of the neural data after parcellation.

FIGS. 11A-11F illustrate example diagrams showing the robustness of neural-behavioral mapping in psychosis spectrum individuals, according to embodiments of the present disclosure. FIGS. 11A-11F are described as the following: (a) Normalized coefficient map from regression of individual subject scores along Principal Component (PC) 3, the "Psychosis" behavioral dimension, onto neural parcellated GBC data of a subset of patients with formal psychosis-spectrum diagnoses. Five-fold cross-validation was performed by first randomly partitioning subjects into 5 subsets. Regression of the behavioral dimension PC3 scores was then performed on all but one subset of subjects (N=349). The greater the magnitude of the coefficient for a parcel, the stronger the statistical relationship between GBC of that parcel and the "Psychosis" behavioral dimension. A clear neural circuit emerges, whereby specific neural regions show a strong positive relationship with the Psychosis dimension, and other regions show a strongly negative relationship. (b) Scatterplot showing the correlation between the value of each parcel in the regression model computed using all except Fold 1 subjects and the full sample model (as seen in FIGS. 7A-7J). The resulting normalized coefficient map from the leave-one-fold-out model is highly similar to that from the full sample regression model. (c) Summary figure of 5-fold cross-validation of the regression of all five PC scores and traditional symptom scales. Boxplots show the range of r-values between coefficient maps for each fold and the full model. Regression of behavioral scores for all 9 measures on to parcellated GBC data (each time leaving out one subset of subjects) also result in highly similar maps of neural-behavioral relationships, demonstrating that the relationship between behavior and neural GBC is highly robust and not driven by a small subset of individuals. (d) Normalized coefficient map from regression of individual subject scores along Principal Component (PC) 3, the "Psychosis" behavioral dimension, onto neural parcellated GBC data of subjects from all but one of the six sites at which data were collected. Here, Site 3 is excluded as an exemplar as it has the largest sample size (and therefore may exert the greatest influence on the results of the full model). (e) Scatterplot showing the correlation between the value of each parcel in the regression model computed using all except Site 3 subjects and the full sample model (as seen in FIGS. 2A-2C). The resulting normalized coefficient map from the leave-one-site-out model is highly similar to that from the full sample regression model. (f) Summary figure of leave-one-site-out validation of the regression of all five PC scores and traditional symptom scales. Boxplots show the range of r-values between coefficient maps for each site and the full model. Regression of behavioral scores for all 9 measures on to parcellated GBC data (each time leaving out subjects from one site) also result in highly similar maps of neural-behavioral relationships, demonstrating that the relationship between behavior and neural GBC is highly robust and not driven by a specific site.

FIGS. 12A-12I illustrate example diagrams showing the use of independent component analysis (ICA) as an alternative method of dimensionality-reduction for behavioral data. FIGS. 12A-12I are described as the following: (a) Screeplot showing the total proportion of variance explained by each independent component (IC) in a five-component solution. performed across all 36 behavioral measures in 436 patients. The size of each point is proportional to the variance explained by that IC. (b) Pie chart shows the proportion of variance both accounted and not accounted for by the five ICs. Together, these five ICs capture 52.77% of the total variance in behavior in the sample. (c) Correlation matrix showing correlations of individual subject scores for the 5 significant principal components (PCs) from the PCA solution shown in FIGS. 3A-3F and the five ICs from the ICA solution, across all 436 subjects. (d-h) Relationships across all patients (N=436) at each brain location between global brain connectivity (GBC) and IC score, for ICs 1-5. Values shown in each brain parcel is the Z-scored regression coefficient of IC score on to parcel GBC, across all 436 subjects. (i) Correlation matrix showing correlations of individual parcel regression coefficients for the 5 significant PCs and the five ICs (shown in D-H), across all 718 neural parcels.

Figure 13A:
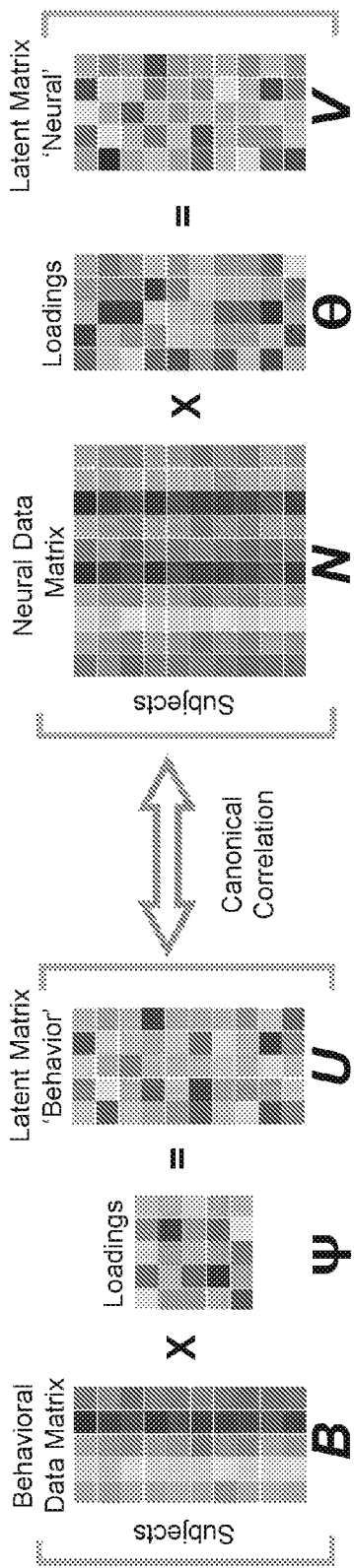
FIGS. 13A-13J illustrate example diagrams showing canonical correlation analysis (CCA) of behavioral and neural features, according to embodiments of the present disclosure.
Figure 13B:
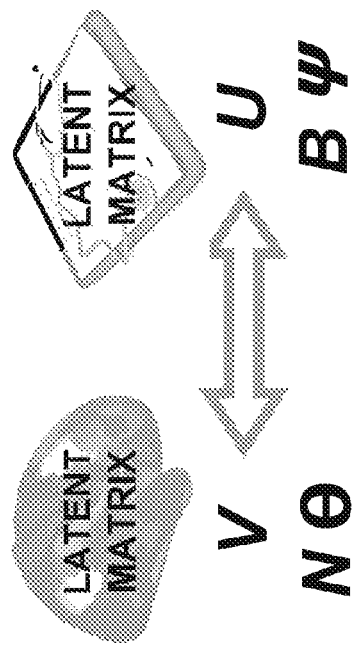
Figures 13C, 13D:
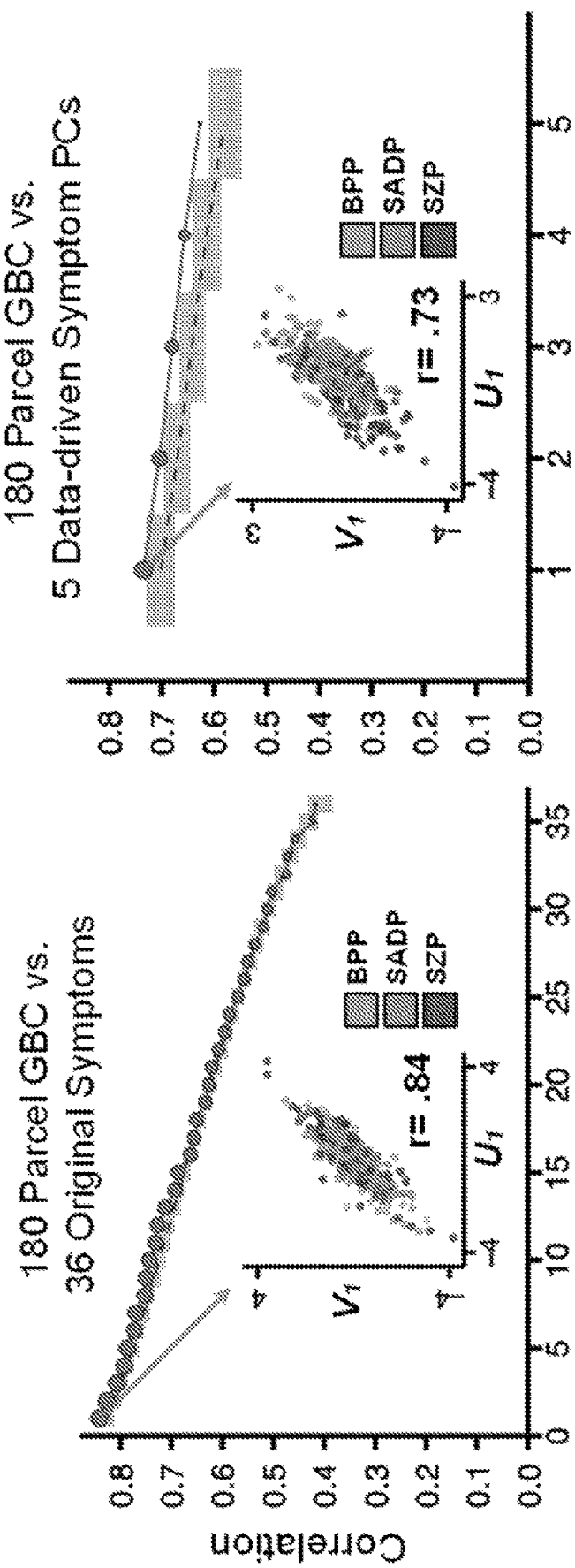
Figure 13F:
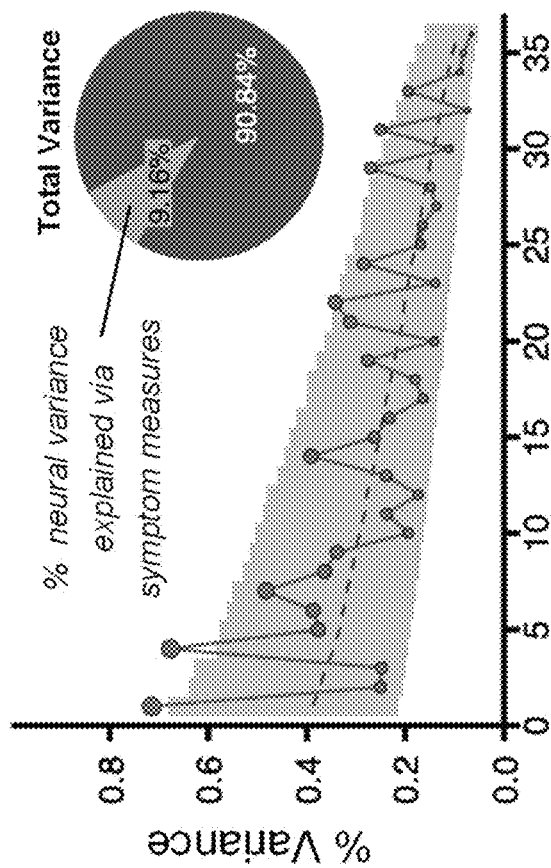
Figure 13E:
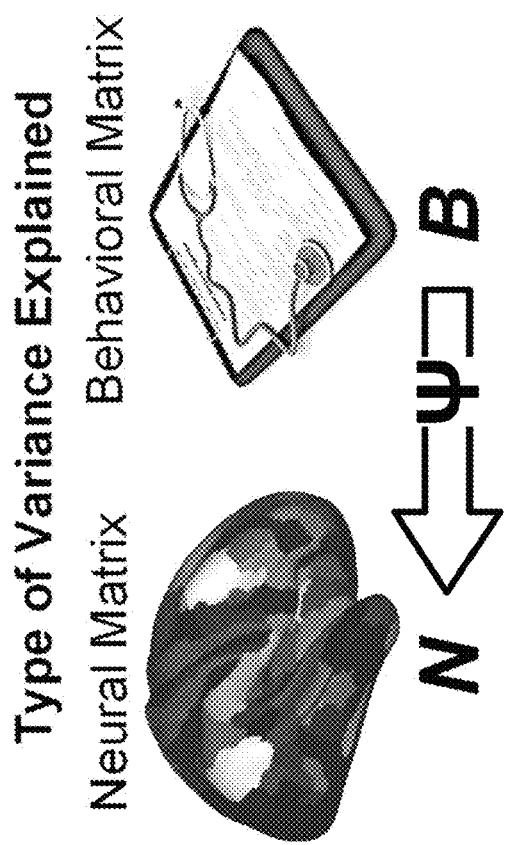
Figures 13G, 13H:
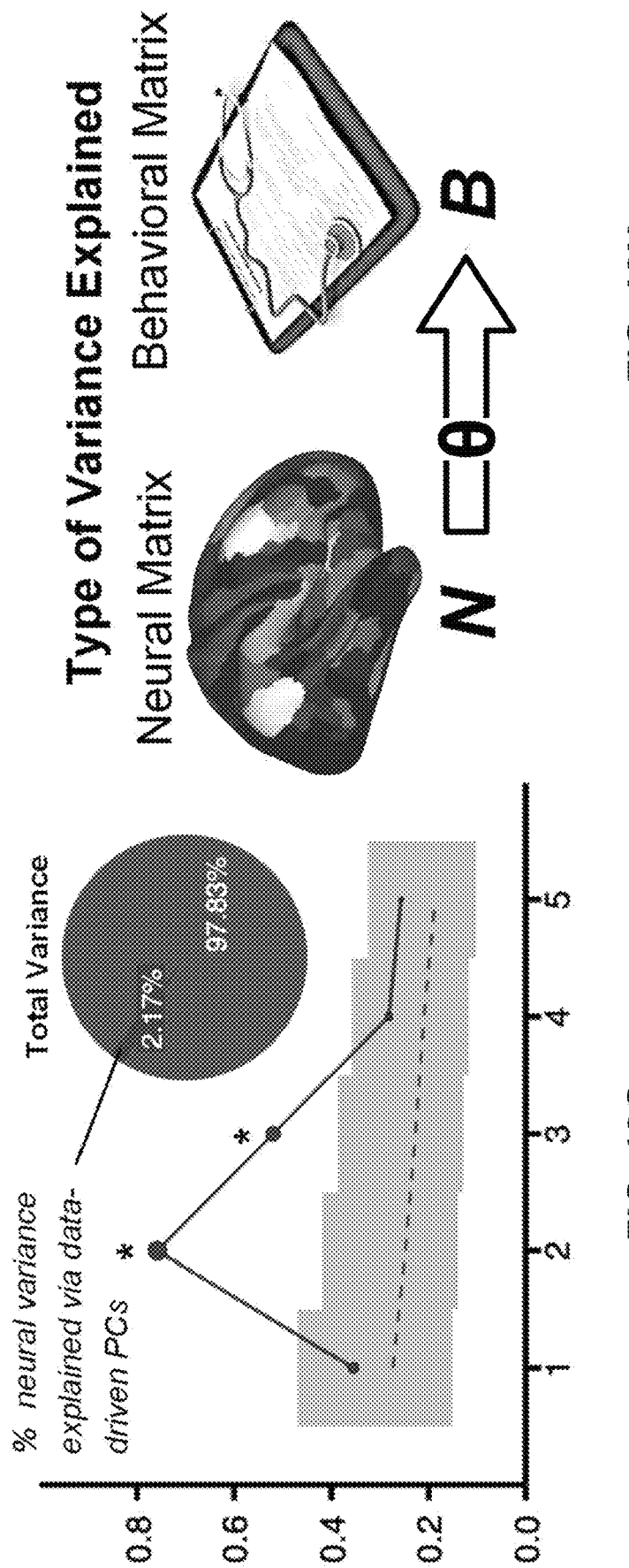

The present disclosure additionally demonstrates the utility of mapping data-derived behavioral dimensions to neural circuitry by using canonical correlation analysis (CCA), a multivariate data-driven approach to characterizing the relationships between two sets of multi-dimensional variables. CCA examines simultaneously the relationships between multiple independent variables and multiple dependent variables by identifying linear combinations of each variable set that maximizes the correlations between the two sets, making it a powerful statistical technique for studying the many-to-many geometry mapping between neural and behavioral features. The application of the CCA process in the present disclosure is illustrated in FIG. 13A.

Figure 13J:
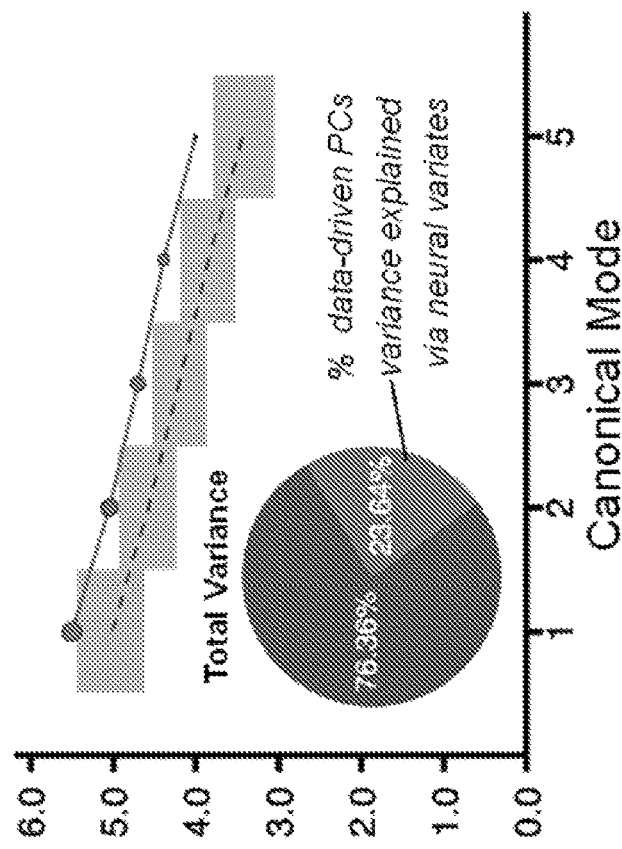
Figure 13I:
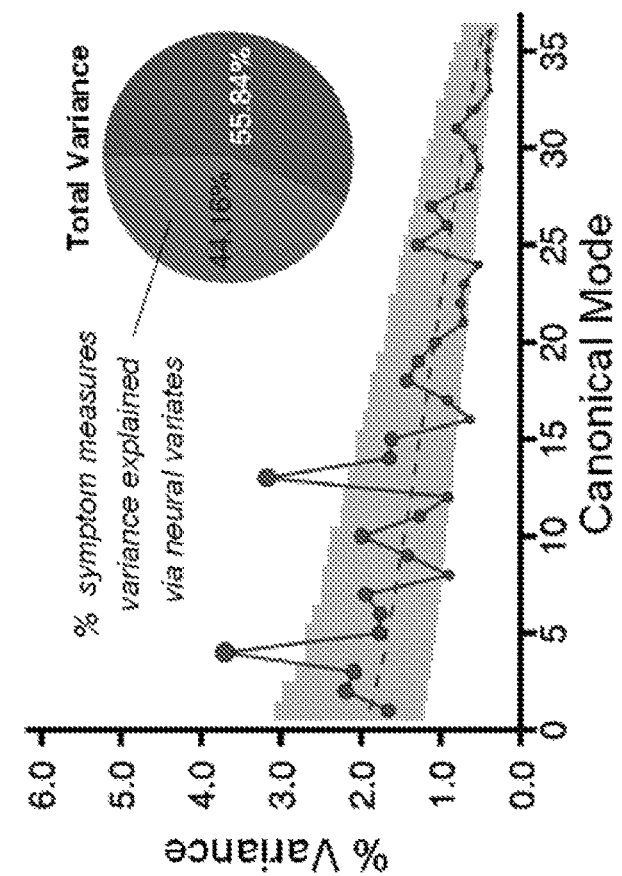
Figure 14A:
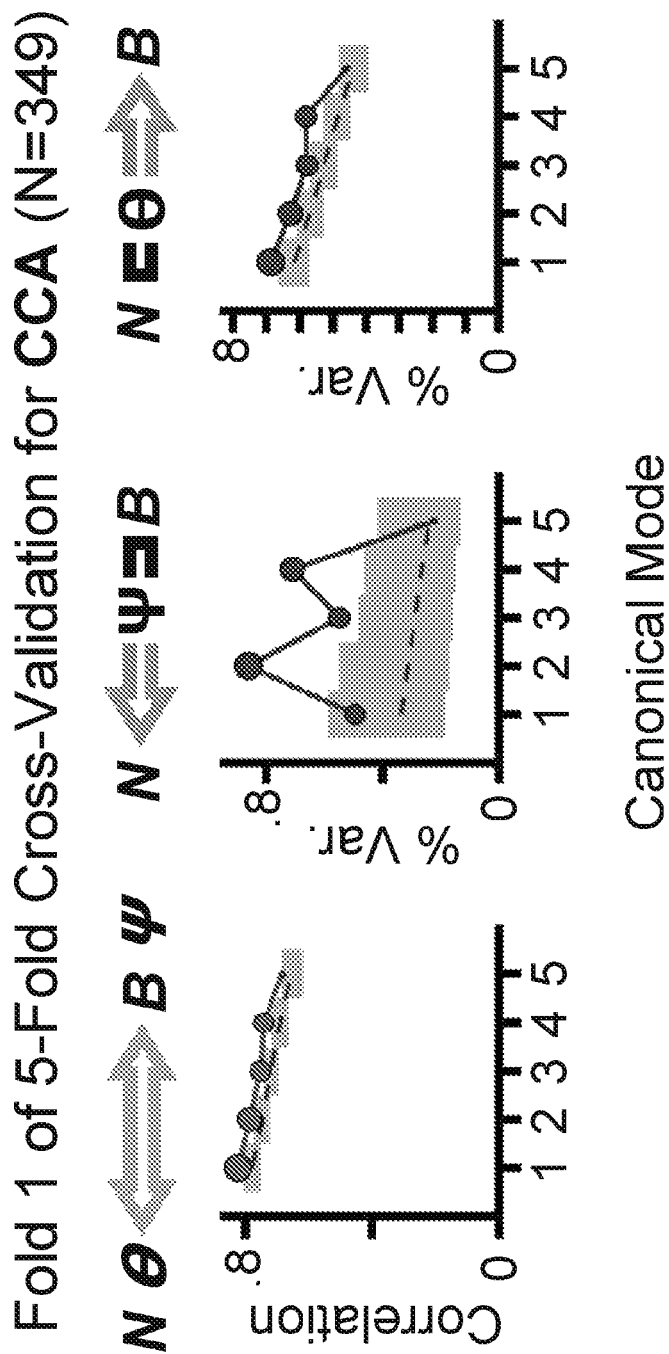
Figure 14B:
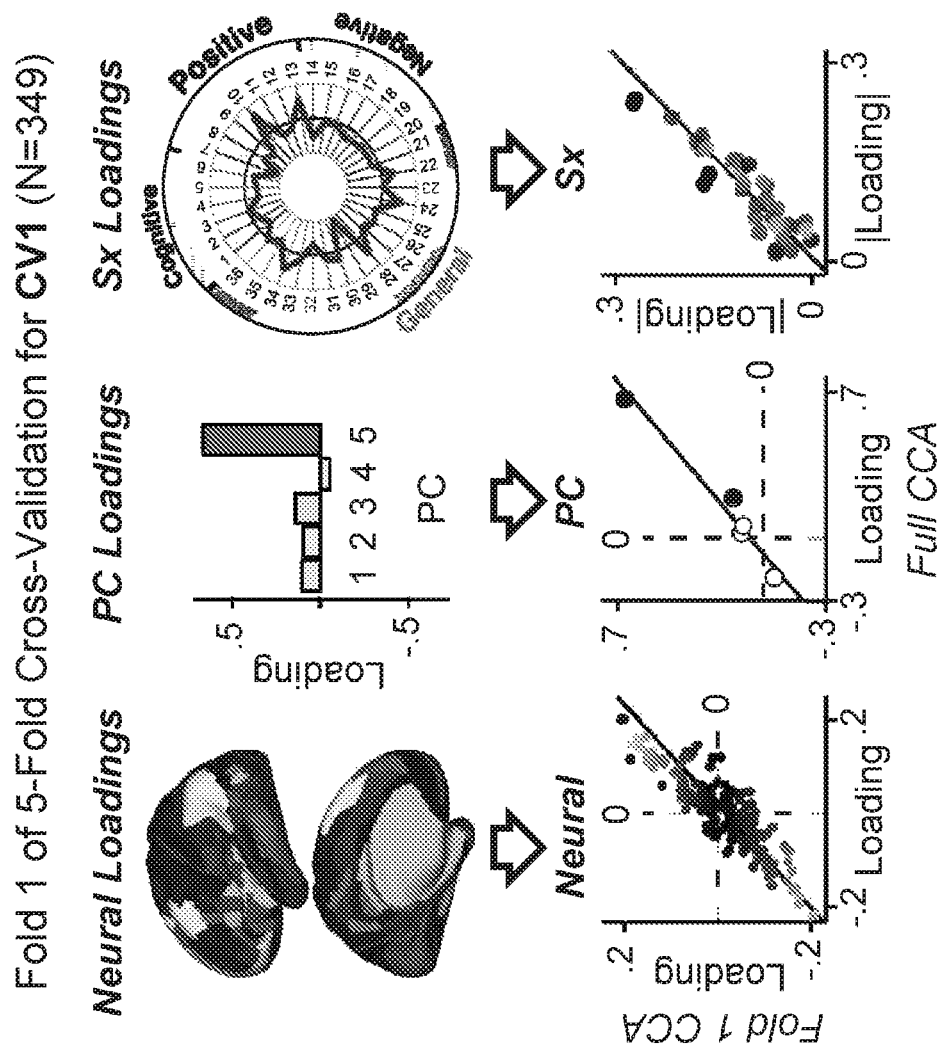
Figure 14C:
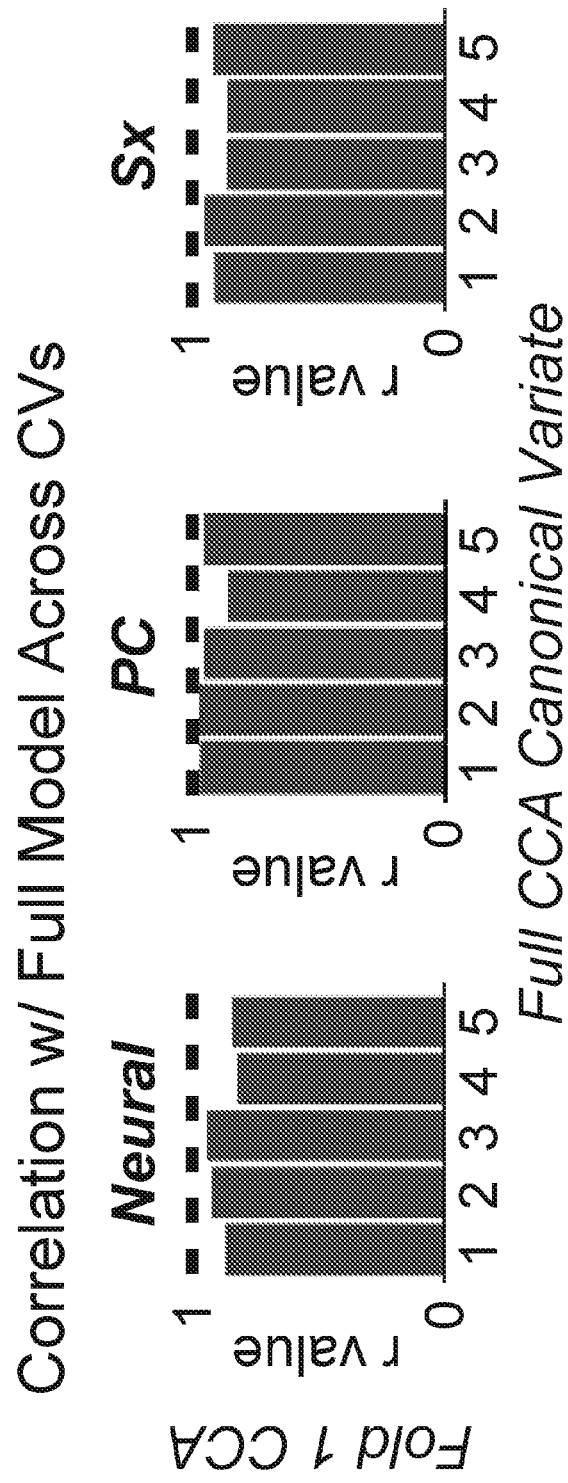
Figure 14D:
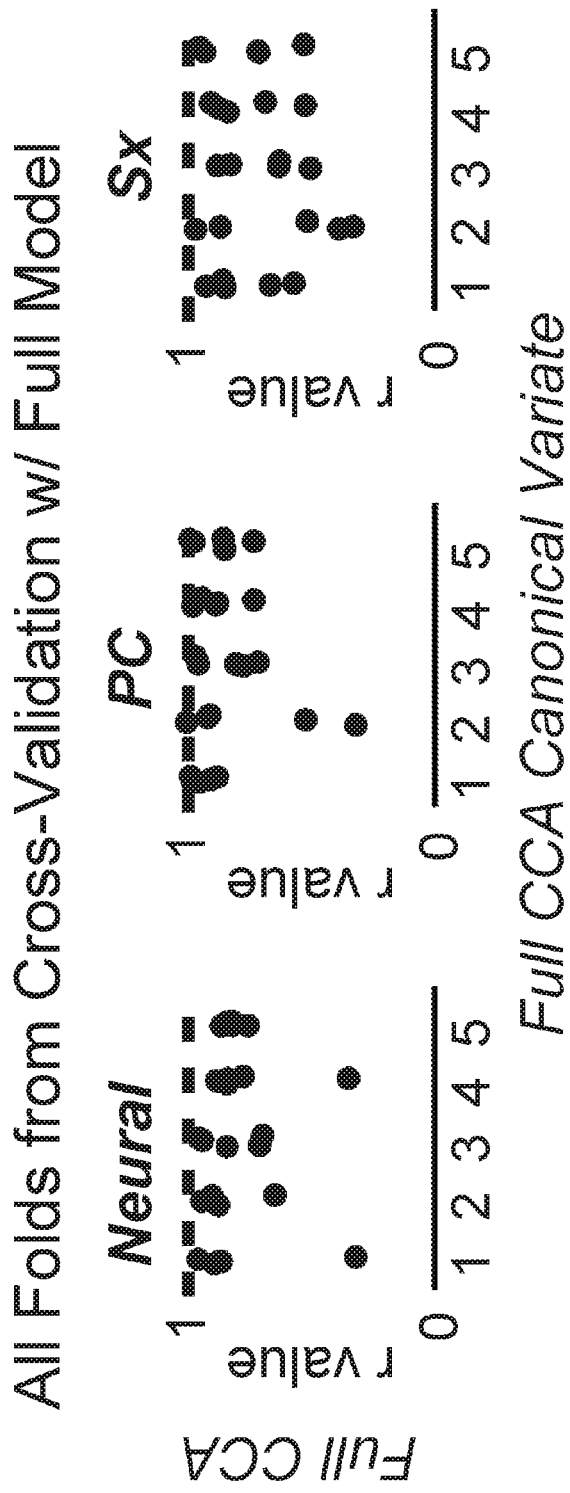
Figure 14E:
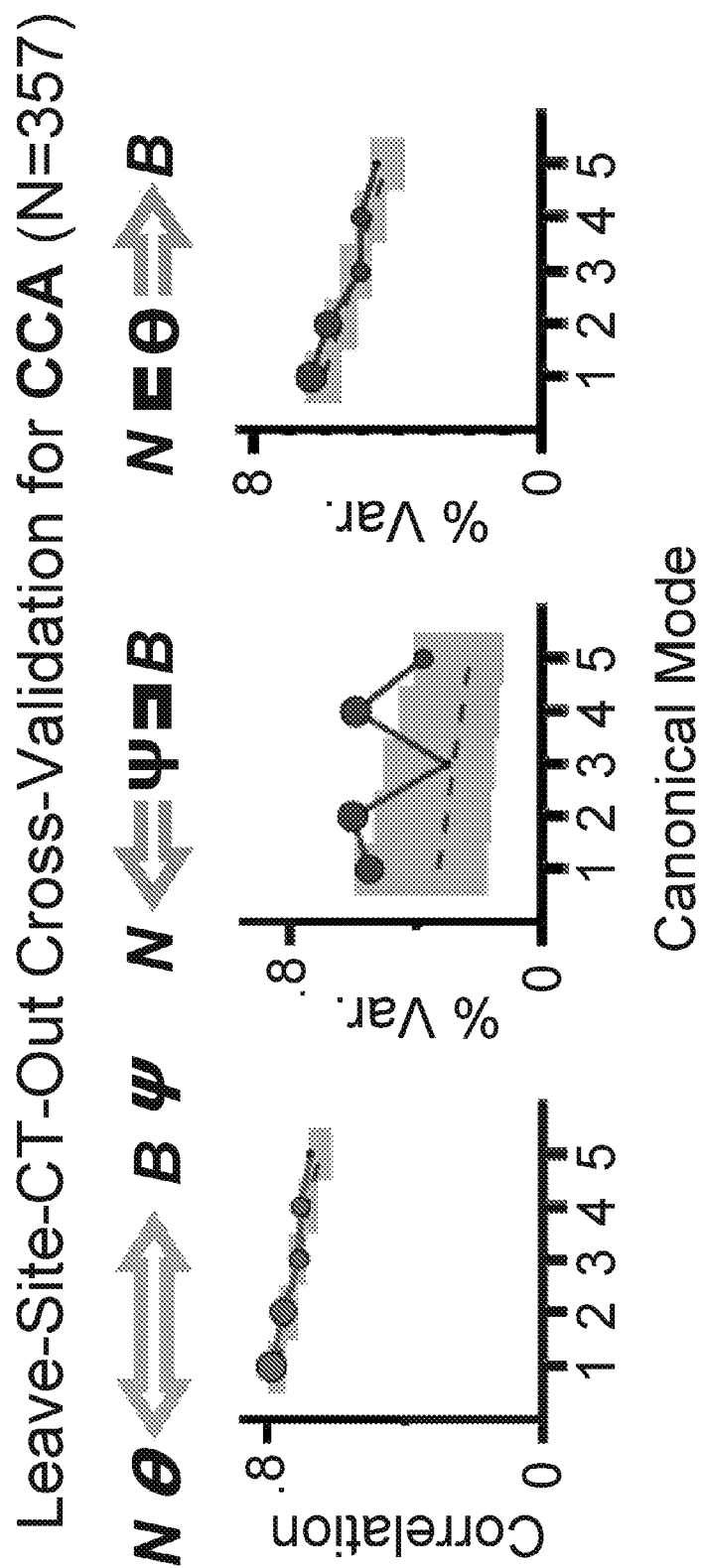
Figure 14G:
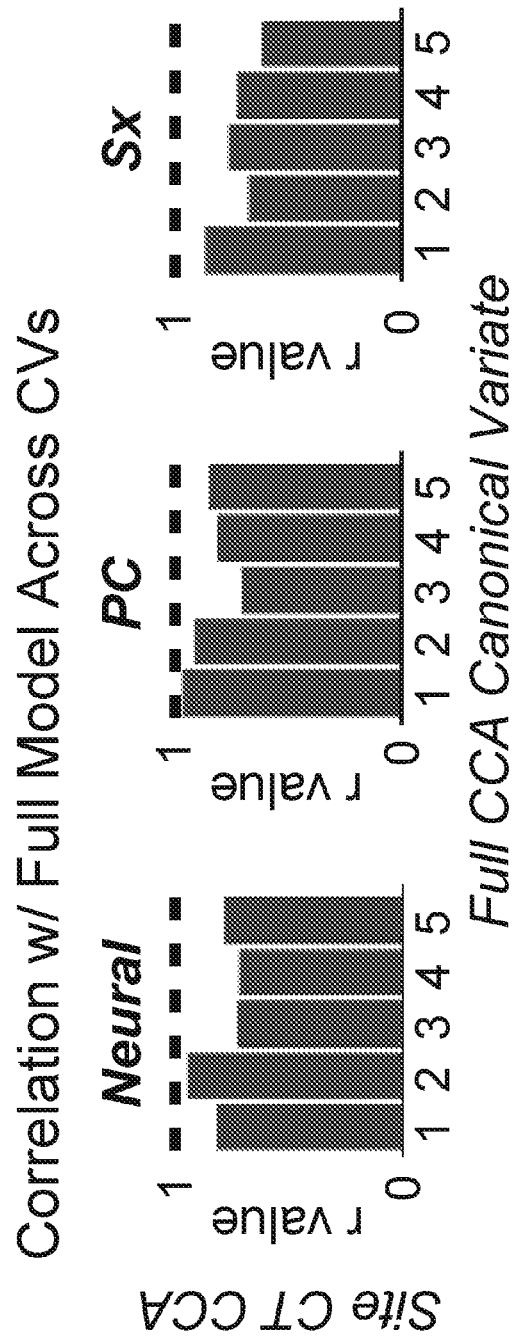
Figure 14H:
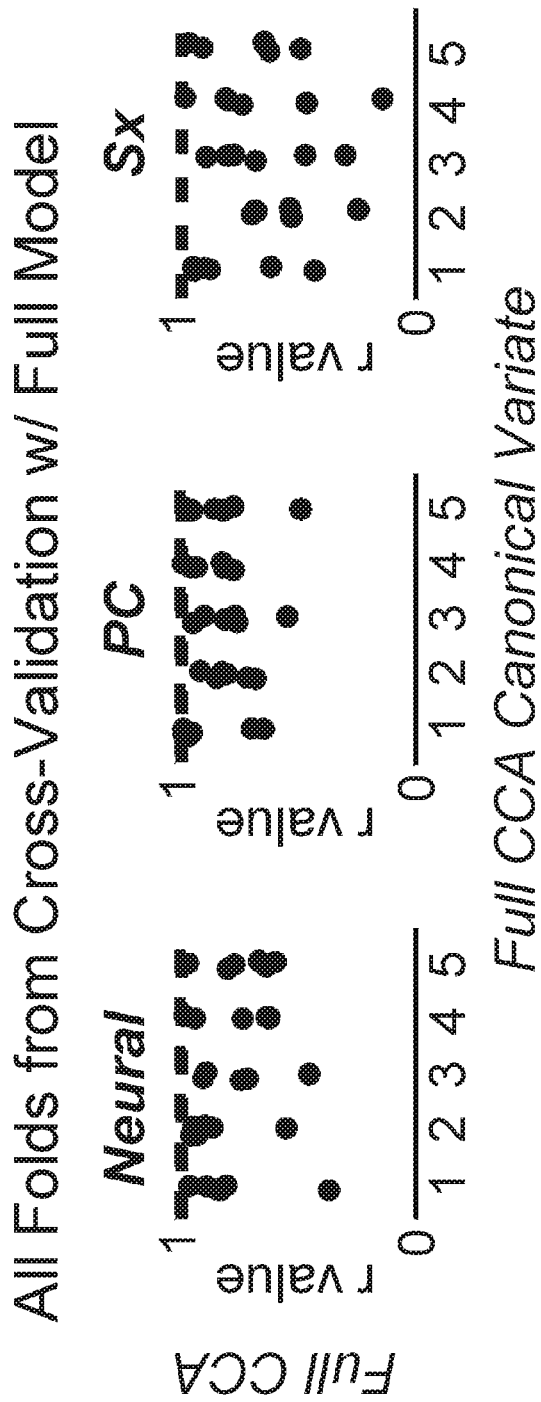
Figure 15A:
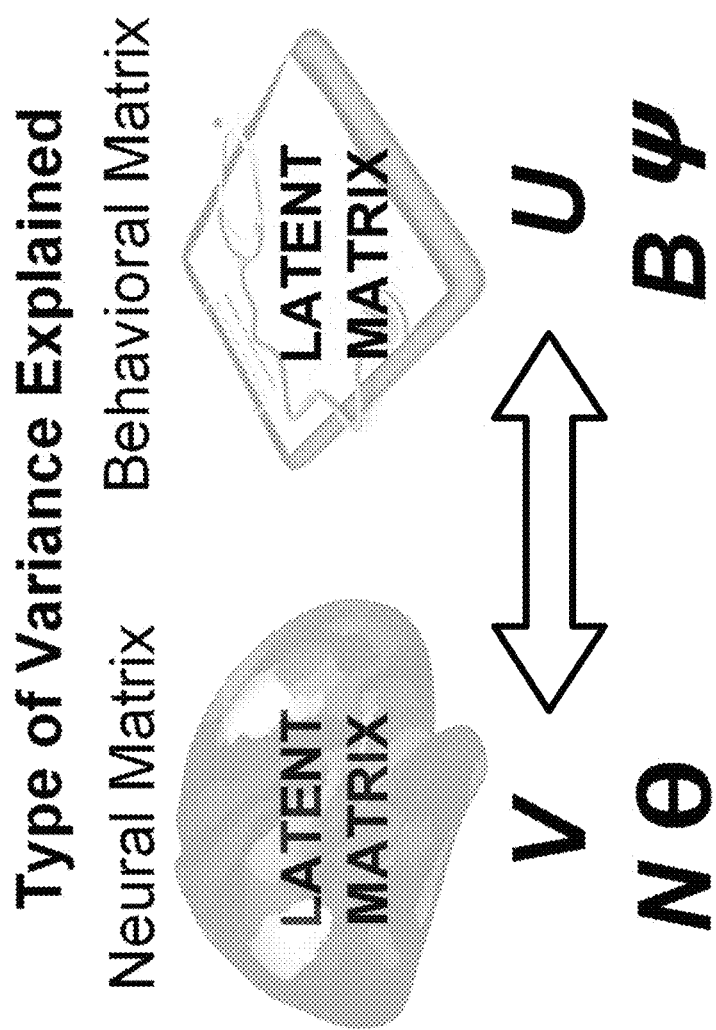
FIGS. 15A-15I illustrate example diagrams showing canonical correlation analysis (CCA) of behavioral and network-level neural features, according to embodiments of the present disclosure.
Figures 15B, 15C:
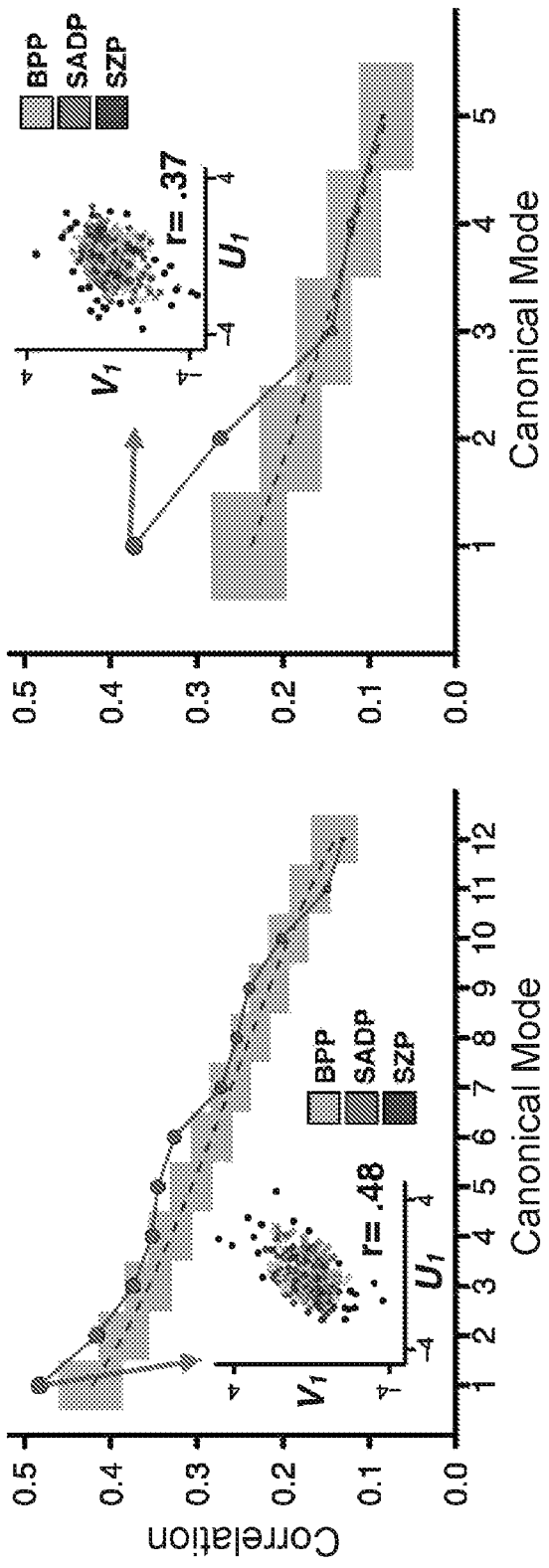
Figure 15D:
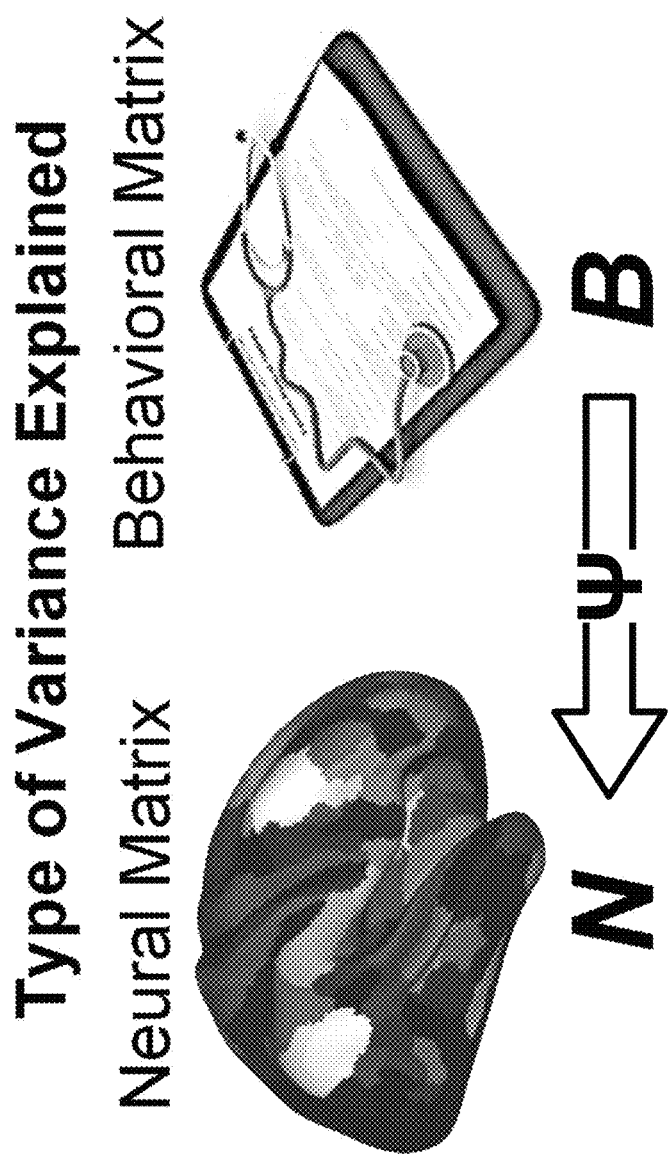
Figures 15E, 15F:
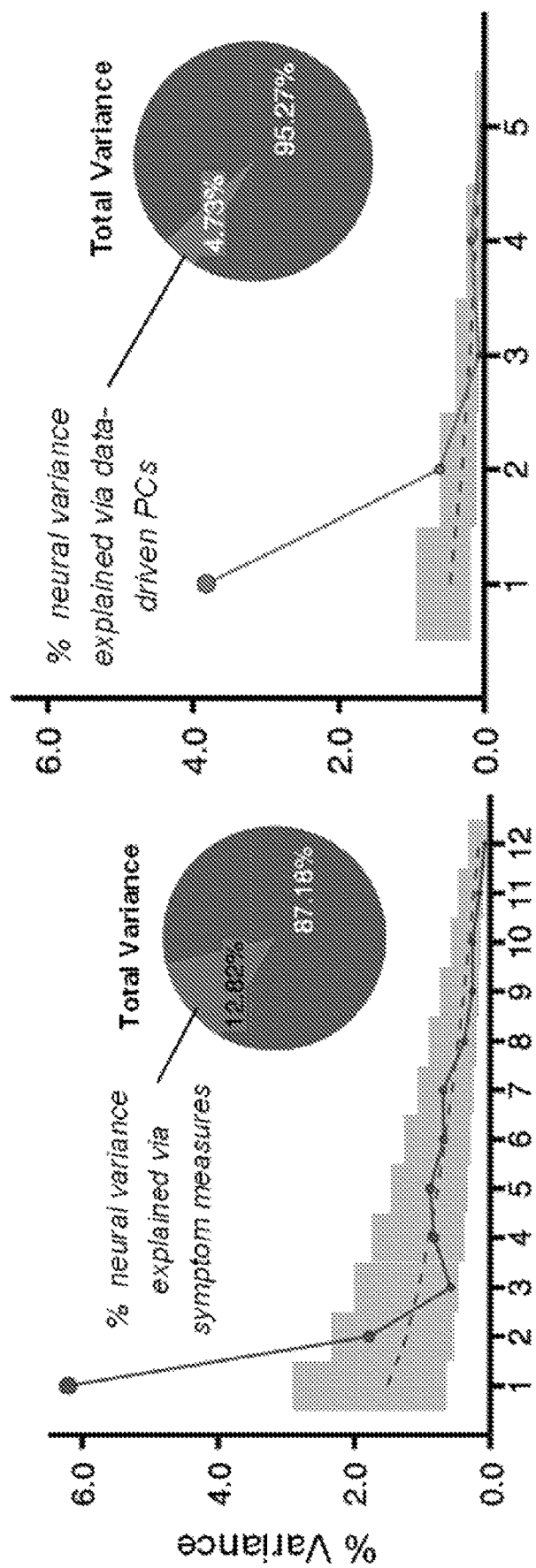
Figure 15G:
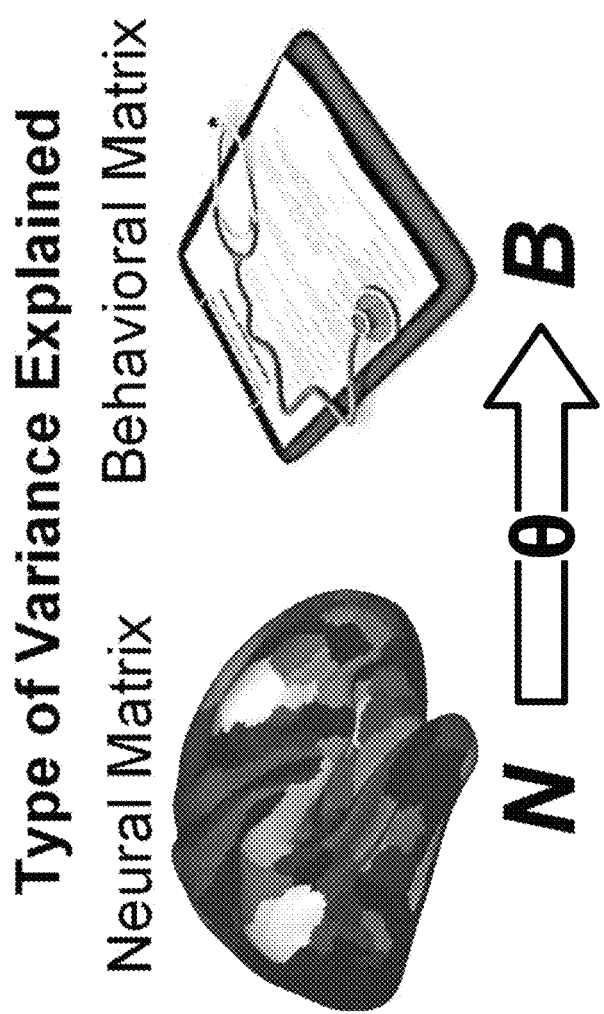
Figures 15H, 15I:
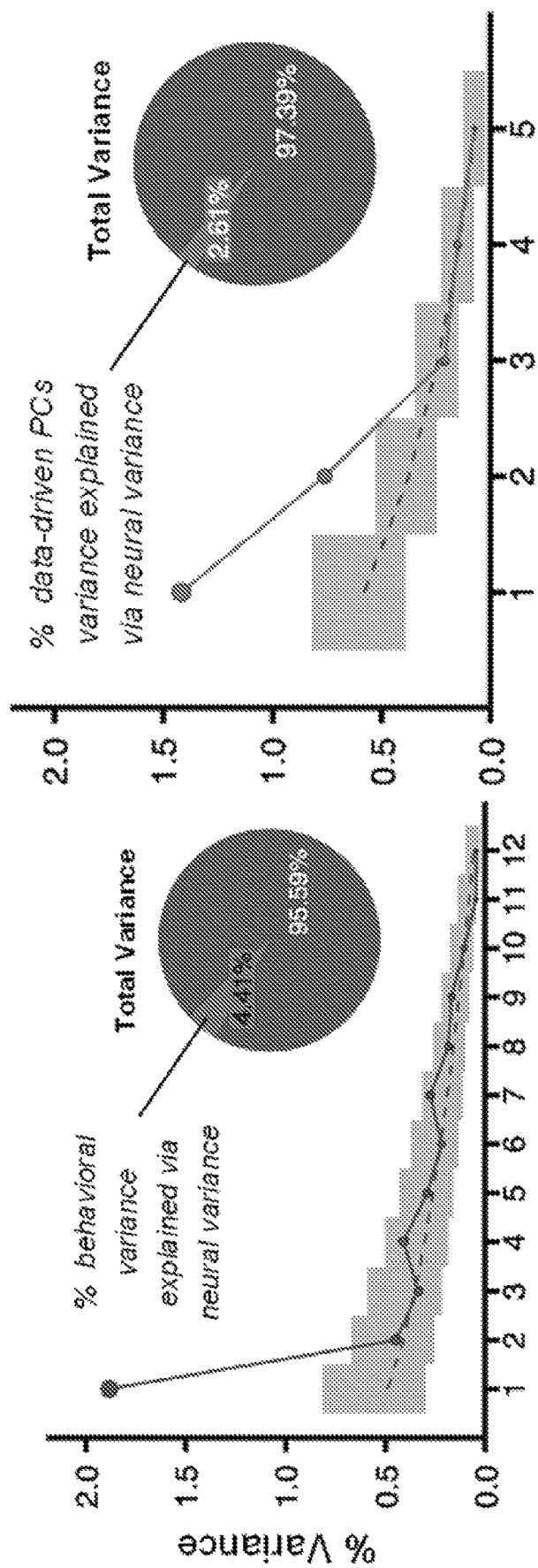
Figure 16A:
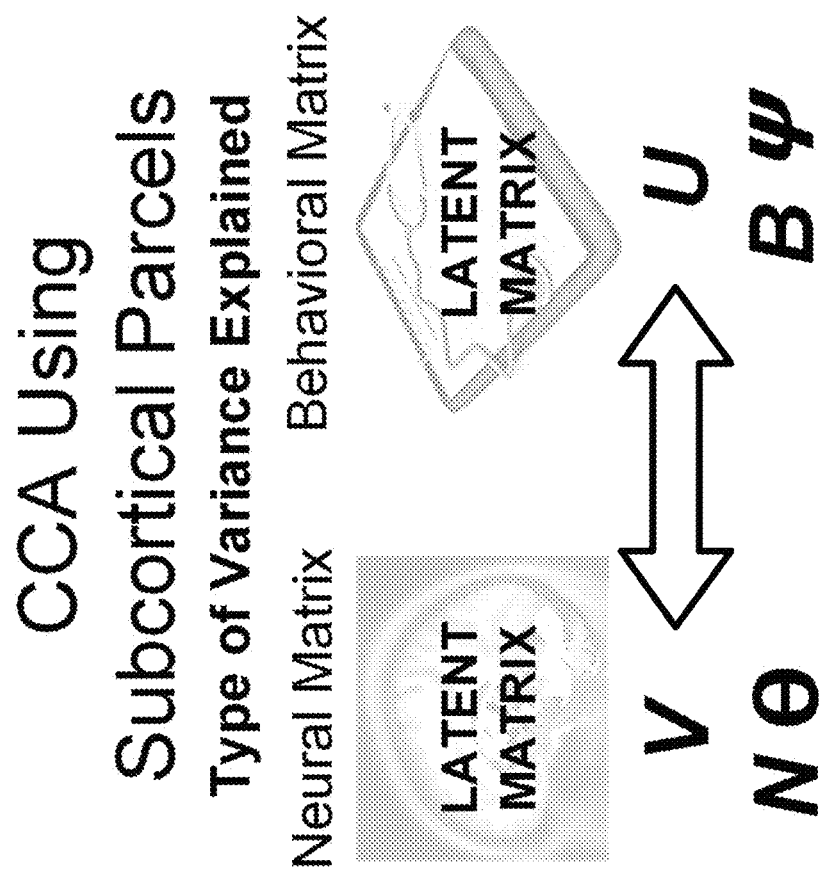
FIGS. 16A-16I illustrate example diagrams showing canonical correlation analysis (CCA) of behavioral and subcortical neural features, according to embodiments of the present disclosure.
Figures 16B, 16C:
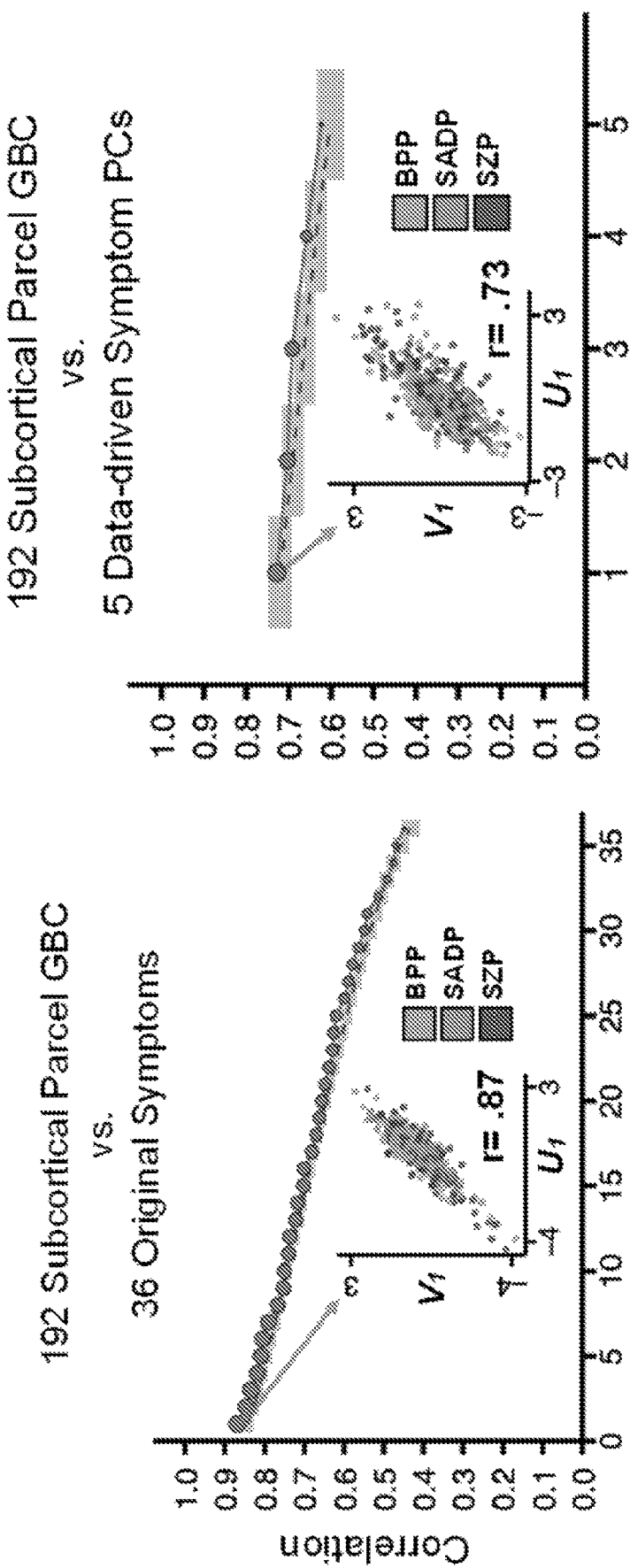
Figure 16D:
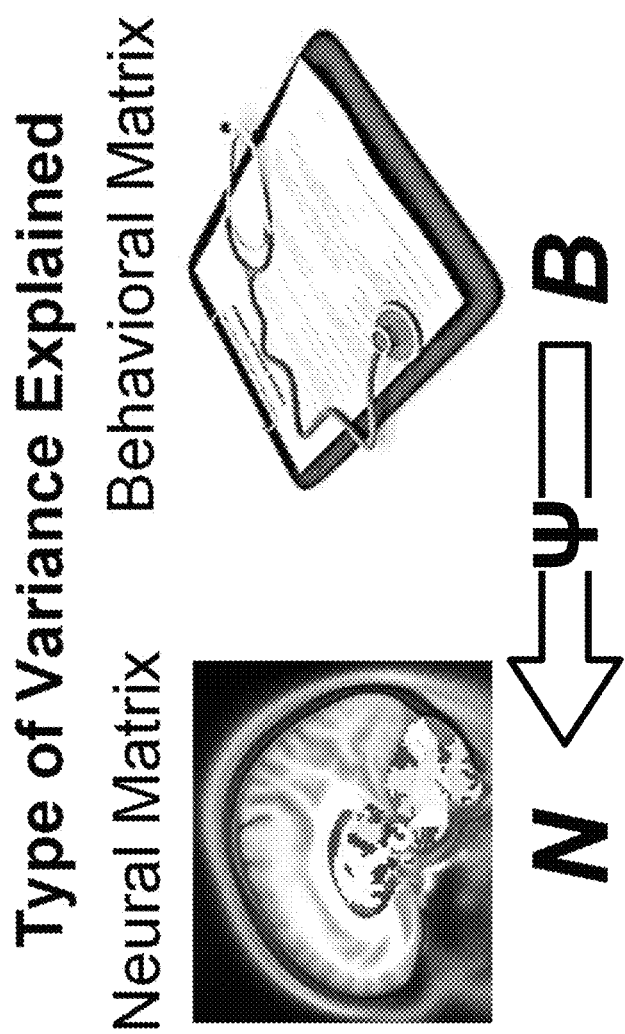
Figure 16F:
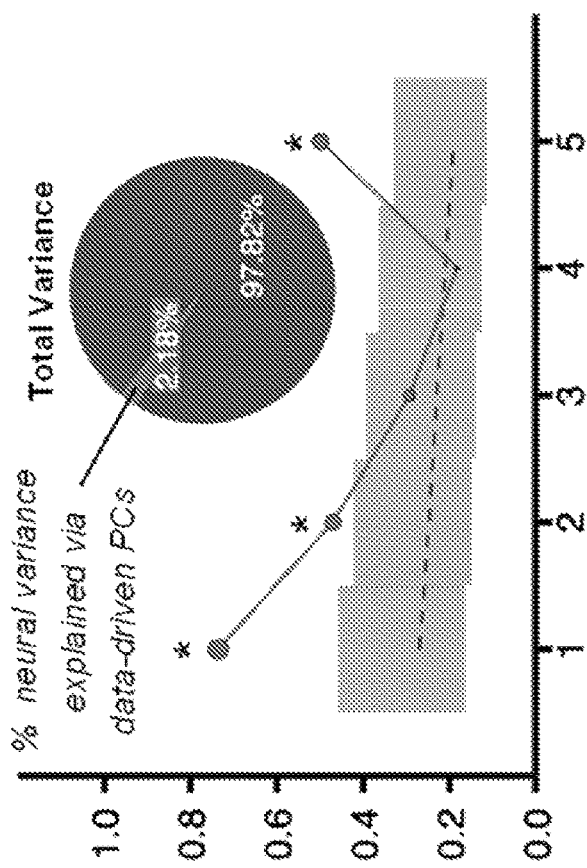
Figure 16E:
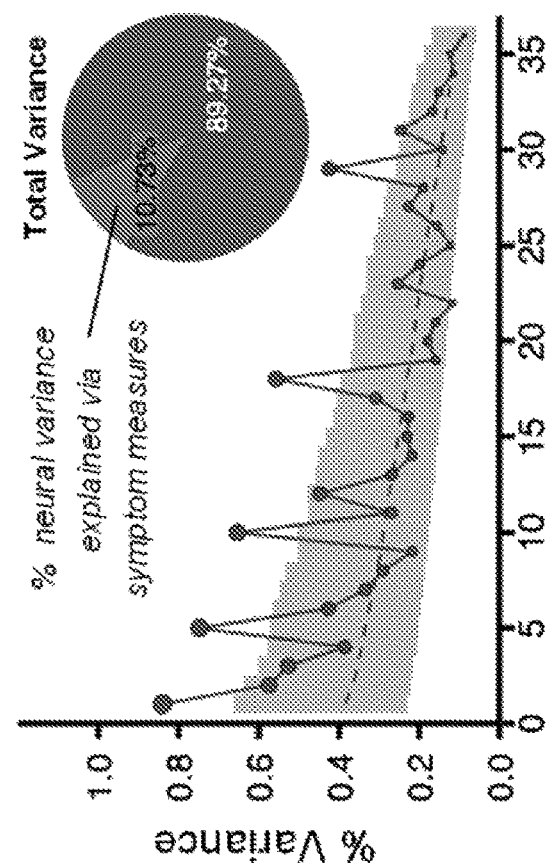
Figure 16G:
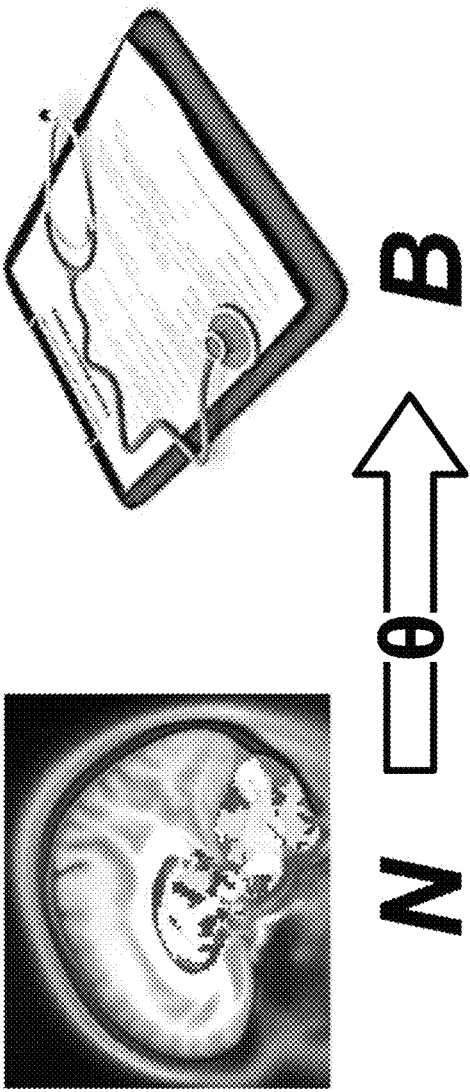
Figures 16H, 16I:
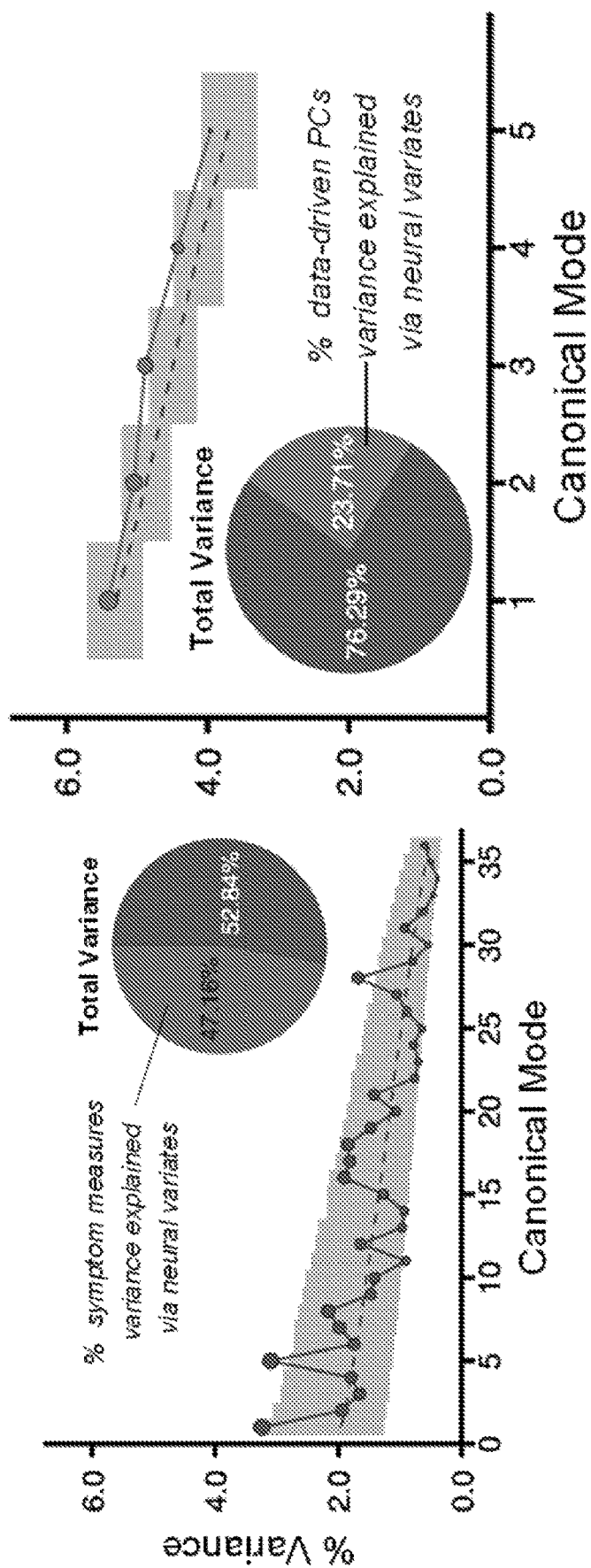

To highlight the importance of using behavioral dimensions that faithfully capture the axes of natural behavioral variation, the results of a CCA performed between neural features and all 36 behavioral measures are compared with a CCA performed between neural features and scores along the 5 identified data-driven behavioral PC dimensions across all patients. Here the neural features used in both CCAs are the mean GBC averaged within each of 180 cortical parcels[12]. Results demonstrate that a comparable amount of behavioral variance in the PCs can be explained (FIG. 13J) despite having far fewer features than the full set of behavioral measures (FIG. 13I).

FIGS. 13A-13J illustrate example diagrams showing canonical correlation analysis (CCA) of behavioral and neural features, according to embodiments of the present disclosure. FIGS. 13A-13J are described as the following: (a) Conceptual illustration of the CCA process. CCA maximizes the correlation between linear combinations of two sets of variables (in this case, a matrix B of behavioral measures and a matrix N of neural measures for each subject). CCA solves for transformation matrices $\Psi$ and $\Theta$ such that the correlations between the linearly transformed 'latent' matrices U and V are maximal. Each row in U and V is known as a canonical variate; each corresponding pair of canonical variates (e.g. $U_1$ and $V_1$) is referred to as a canonical mode. (b) The correlations between the transformed latent matrices U and V are maximized. U is a linear composite of behavioral data matrix B scaled by the weights in $\Psi$; similarly, V is the linear composite of N transformed by $\Theta$. (c) Screeplot showing the correlations between the canonical variates of a CCA performed between 180 neural features (symmetrized cortical parcel GBC) and all 36 behavioral measures. Dashed black line shows the null calculated via a permutation test with 5000 shuffles; grey bars show 95% confidence interval. Inset illustrates the correlation (r=0.85) between the canonical variates of the first mode, $U_1$ and $V_1$ (note that the correlation is not driven by a separation between categorical diagnoses). The canonical modes are independent from each other; the correlation between each subsequent pair of variates is computed from the residuals of the previous pair. (e) The correlation between the neural data N and the transformed behavioral data matrix $B\Psi$ reflects the amount of variance in N that can be explained by behavioral canonical variates V. (f) Screeplot showing the proportion of neural variance explained by each of the behavioral canonical variates in a CCA performed between 180 neural features (symmetrized cortical parcel GBC) and all 36 behavioral measures. Dashed black line shows the null calculated via a permutation test with 5000 shuffles; grey bars show 95% confidence interval. Inset shows the total proportion of neural variance explained by the behavioral variates. (g) Screeplot of the proportion of neural variance explained by each of the behavioral canonical variates in a CCA performed between 180 neural features (symmetrized cortical parcel GBC) and the 5 PCs of behavior. (h) The correlation between the behavioral data B and the transformed neural data matrix N$\Theta$ reflects the amount of variance in B that can be explained by neural canonical variates U. (i) Screeplot showing the proportion of behavioral variance explained by each of the neural canonical variates in a CCA performed between 180 neural features (symmetrized cortical parcel GBC) and all 36 behavioral measures. Dashed black line shows the null calculated via a permutation test with 5000 shuffles; grey bars show 95% confidence interval. Inset shows the total proportion of behavioral variance explained by the neural variates. (j) Screeplot of the proportion of total behavioral variance explained by each of the neural canonical variates in a CCA performed between 180 neural features (symmetrized cortical parcel GBC) and the 5 PCs of behavior. Note that although the CCA using behavioral PCs has far fewer dimensions, each neural variate explains a higher amount of total behavioral variance than neural variates in g, suggesting that the identified PCs of behavior capture variation in symptoms with far fewer features, which in turn more robustly relates to neural variation. Thus, bi-directional mapping between the multi-dimensional neural feature space to the multi-dimensional behavioral/phenotype feature space is possible via the N-BRIDGE framework. However, the key observation here is that the multi-dimensional neural feature information contains substantially more predictive power for the variation of the multi-dimensional behavioral/phenotype features. This is important because to optimize the prediction for any independent individual human, both neural and behavioral feature data should be used concurrently to first map the multi-dimensional neural-behavioral geometry and then use it to project both neural and behavioral data for any independent individual along the defined axes.

FIGS. 14A-14H illustrate example diagrams showing k-fold cross-validation for establishing the neuro-behavioral geometry by means of canonical correlation analysis, according to embodiments of the present disclosure. FIGS. 14A-14H are described as the following: FIGS. 14A-14E illustrate the results from a 5-fold cross-validation analysis to test the stability of the CCA solution. Subjects were first randomly assigned to one of 5 subsets. Each subset of subjects was then used as an independent 'test sample' in a CCA that was derived from subjects in the other 4 subsets. (a) Results of a CCA performed in a sub sample of N=349 subjects. Left: screeplot showing the correlations between the canonical variates of a CCA performed between 180 neural features (symmetrized cortical parcel GBC) and the 5 behavioral principal components in N=349 subjects. Middle: Screeplot of the proportion of neural variance explained by each of the behavioral canonical variates in a CCA performed between 180 neural features (symmetrized cortical parcel GBC) and the 5 PCs of behavior. Right: Screeplot of the proportion of total behavioral variance explained by each of the neural canonical variates in a CCA performed between 180 neural features (symmetrized cortical parcel GBC) and the 5 PCs of behavior. Dashed black line shows the null calculated via a permutation test with 5000 shuffles; grey bars show 95% confidence interval. Note that the outcome of this CCA is highly similar to the full sample CCA shown in FIGS. 14A-14H. (b) Comparison of the first canonical variate (CV1) in a CCA performed in a subsample of N=349 subjects with CV1 from the full model performed with N=436 subjects. Left: neural factor loadings for CV1 obtained from the subsample (Fold 1) CCA and from the full sample CCA are highly correlated, at r=0.85. Middle: Behavioral factor loadings are also highly correlated between the Fold 1 CCA and the full CCA, at r=0.85. Right: Additionally, absolute values of individual behavioral item weights associated with CV1 are highly correlated between the Fold 1 CCA and the full CCA. (c) Summary of correlation values between Fold 1 CCA and full CCA results, as in FIG. 14B, across all 5 CVs. Note that the neural and behavioral factor loadings as well as individual behavioral item weights are highly preserved between the sample CCA and the full model. (d) Summary of correlation values between all 5 subsample CCAs and the full sample CCA, for all 5 CVs. Each of the 5 CVs is plotted along the X-axis; each point represents the correlation between one of the 5-fold subsample CCAs and the full CCA, hence there are 5 points (in the 5-fold cross-validation) for each CV. (e) Results of a CCA performed in a subsample of N=357 subjects, with subjects from one site left out (leave-one-site-out, LOSO). Panels as described in A. (f) Comparison of the first canonical variate (CV1) in a LOSO CCA and the CV1 from the full model performed with N=436 subjects. Panels as described in FIG. 14B. (g) Summary of correlation values between the LOSO CCA and full CCA results, as in panel B, across all 5 CVs. Panels as described in FIG. 14C. (h) Summary of correlation values between all 6 LOSO CCAs and the full sample CCA, for all 5 CVs. Panels as described in FIG. 14D; each point represents the correlation between one of the 6 LOSO CCAs and the full CCA.

FIGS. 15A-15I illustrate example diagrams showing canonical correlation analysis (CCA) of behavioral and network-level neural features, according to embodiments of the present disclosure. FIGS. 15A-15I are described as the following: (a) The correlations between the transformed latent matrices U and V are maximized. U is a linear composite of behavioral data matrix B scaled by the weights in $\Psi$; similarly, $V_1$ is the linear composite of N transformed by $\Theta$. As shown in FIG. 13A, each row in U and V is known as a canonical variate; each corresponding pair of canonical variates (e.g. $U_1$ and $V_1$) is referred to as a canonical mode. (b) Screeplot showing the correlations between the canonical variates of a CCA performed between 12 neural features (mean GBC of 12 whole-brain networks from a neurobiologically-derived functional parcellation) and all 36 behavioral measures. Dashed black line shows the null calculated via a permutation test with 5000 shuffles; grey bars show 95% confidence interval. Inset illustrates the correlation (r=0.48) between the canonical variates of the first mode, $U_1$ and $V_1$ (note that the correlation is not driven by a separation between categorical diagnoses). The canonical modes are independent from each other; the correlation between each subsequent pair of variates is computed from the residuals of the previous pair. (c) Screeplot showing the correlations between the canonical variates of a CCA performed between 12 network neural features and the 5 behavioral principal components. Dashed black line shows the null calculated via a permutation test with 5000 shuffles; grey bars show 95% confidence interval. Inset illustrates the correlation (r=0.37) between the canonical variates of the first mode, $U_1$ and $V_1$. Note that the strength of the correlations is greatly reduced compared to the parcel-level CCA shown in FIG. 13. (d) The correlation between the neural data N and the transformed behavioral data matrix B$\Psi$ reflects the amount of variance in N that can be explained by behavioral canonical variates V. (e) Screeplot showing the proportion of neural variance explained by each of the behavioral canonical variates in a CCA performed between 12 network neural features and all 36 behavioral measures. Dashed black line shows the null calculated via a permutation test with 5000 shuffles; grey bars show 95% confidence interval. Inset shows the total proportion of neural variance explained by the behavioral variates. (f) Screeplot of the proportion of neural variance explained by each of the behavioral canonical variates in a CCA performed between 12 network neural features and the 5 PCs of behavior. (g) The correlation between the behavioral data B and the transformed neural data matrix N$\Theta$ reflects the amount of variance in B that can be explained by neural canonical variates U. (h) Screeplot showing the proportion of behavioral variance explained by each of the neural canonical variates in a CCA performed between 12 network neural features and all 36 behavioral measures. Dashed black line shows the null calculated via a permutation test with 5000 shuffles; grey bars show 95% confidence interval. Inset shows the total proportion of behavioral variance explained by the neural variates. (i) Screeplot of the proportion of total behavioral variance explained by each of the neural canonical variates in a CCA performed between 12 network neural features and the 5 PCs of behavior. Note that although the CCA using behavioral PCs has far fewer dimensions, each neural variate explains a higher amount of total behavioral variance than neural variates in FIG. 15H, suggesting that the identified PCs of behavior capture variance with far fewer features.

FIGS. 16A-16I illustrate example diagrams showing canonical correlation analysis (CCA) of behavioral and subcortical neural features, according to embodiments of the present disclosure. FIGS. 16A-16I are described as the following: (a) The correlations between the transformed latent matrices U and V are maximized. U is a linear composite of behavioral data matrix B scaled by the weights in $\Psi$; similarly, $V_1$ is the linear composite of N transformed by $\Theta$. As shown in FIG. 13A, each row in U and V is known as a canonical variate; each corresponding pair of canonical variates (e.g. $U_1$ and $V_1$) is referred to as a canonical mode. (b) Screeplot showing the correlations between the canonical variates of a CCA performed between 192 subcortical neural features (GBC of 192 parcels from a neurobiologically-derived functional parcellation of the subcortex) and all 36 behavioral measures. Dashed black line shows the null calculated via a permutation test with 5000 shuffles; grey bars show 95% confidence interval. Inset illustrates the correlation (r=0.87) between the canonical variates of the first mode, $U_1$ and $V_1$ (note that the correlation is not driven by a separation between categorical diagnoses). The canonical modes are independent from each other; the correlation between each subsequent pair of variates is computed from the residuals of the previous pair. (c) Screeplot showing the correlations between the canonical variates of a CCA performed between 192 subcortical neural features (GBC of 192 parcels from a neurobiologically-derived functional parcellation of the subcortex) and the 5 behavioral principal components. Dashed black line shows the null calculated via a permutation test with 5000 shuffles; grey bars show 95% confidence interval. Inset illustrates the correlation (r=0.73) between the canonical variates of the first mode, $U_1$ and $V_1$. (d) The correlation between the neural data N and the transformed behavioral data matrix $B\Psi$ reflects the amount of variance in N that can be explained by behavioral canonical variates V. (e) Screeplot showing the proportion of neural variance explained by each of the behavioral canonical variates in a CCA performed between 192 subcortical neural features (GBC of 192 parcels from a neurobiologically-derived functional parcellation of the subcortex) and all 36 behavioral measures. Dashed black line shows the null calculated via a permutation test with 5000 shuffles; grey bars show 95% confidence interval. Inset shows the total proportion of neural variance explained by the behavioral variates. (f) Screeplot of the proportion of neural variance explained by each of the behavioral canonical variates in a CCA performed between 192 subcortical neural features (GBC of 192 parcels from a neurobiologically-derived functional parcellation of the subcortex) and the 5 PCs of behavior. (g) The correlation between the behavioral data B and the transformed neural data matrix $N\Theta$ reflects the amount of variance in B that can be explained by neural canonical variates U. (h) Screeplot showing the proportion of behavioral variance explained by each of the neural canonical variates in a CCA performed between 192 subcortical neural features (GBC of 192 parcels from a neurobiologically-derived functional parcellation of the subcortex) and all 36 behavioral measures. Dashed black line shows the null calculated via a permutation test with 5000 shuffles; grey bars show 95% confidence interval. Inset shows the total proportion of behavioral variance explained by the neural variates. (i) Screeplot of the proportion of total behavioral variance explained by each of the neural canonical variates in a CCA performed between 192 subcortical neural features (GBC of 192 parcels from a neurobiologically-derived functional parcellation of the subcortex) and the 5 PCs of behavior. Note that although the CCA using behavioral PCs has far fewer dimensions, each neural variate explains a higher amount of total behavioral variance than neural variates in FIG. 16H, suggesting that the identified PCs of behavior capture variance with far fewer features.

Figures 17A, 17B:
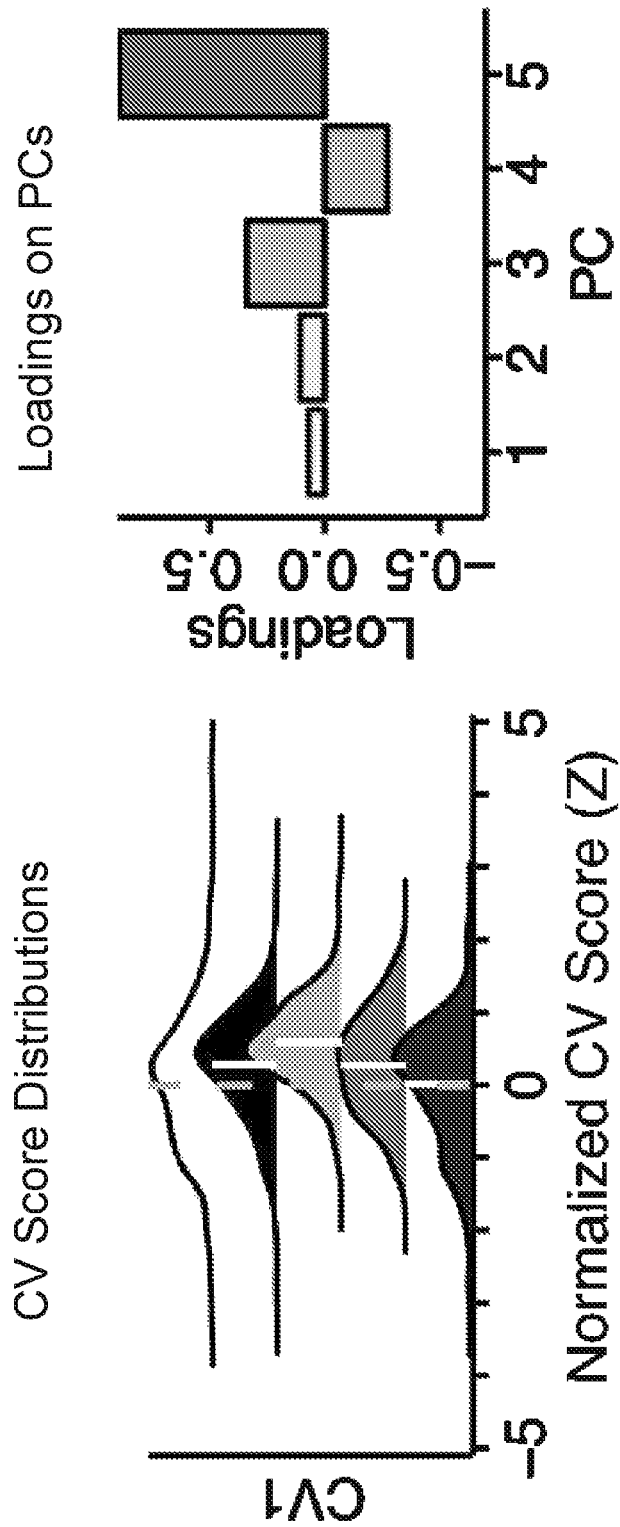
FIGS. 17A-17T illustrate example diagrams showing the characterization of canonical variate symptom configurations, according to embodiments of the present disclosure.
Figures 17C, 17D:
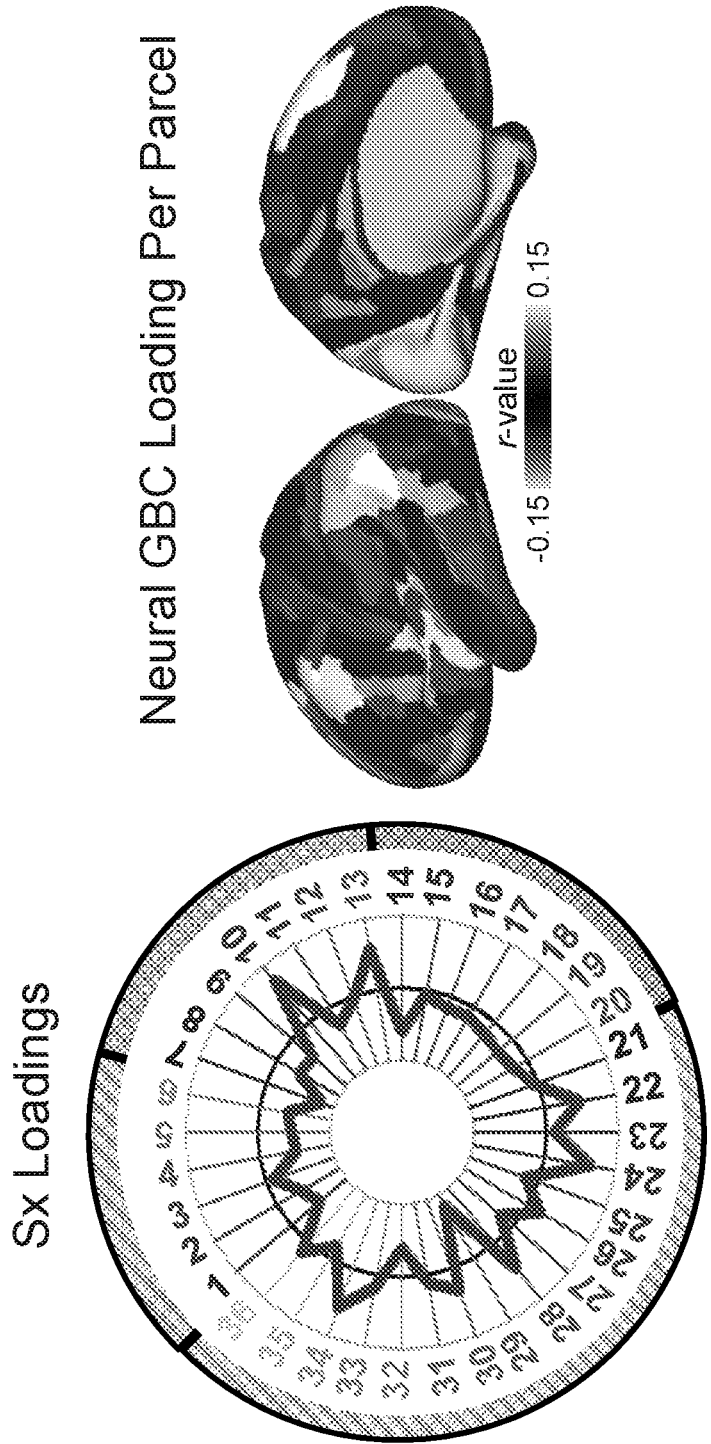
Figures 17E, 17F:
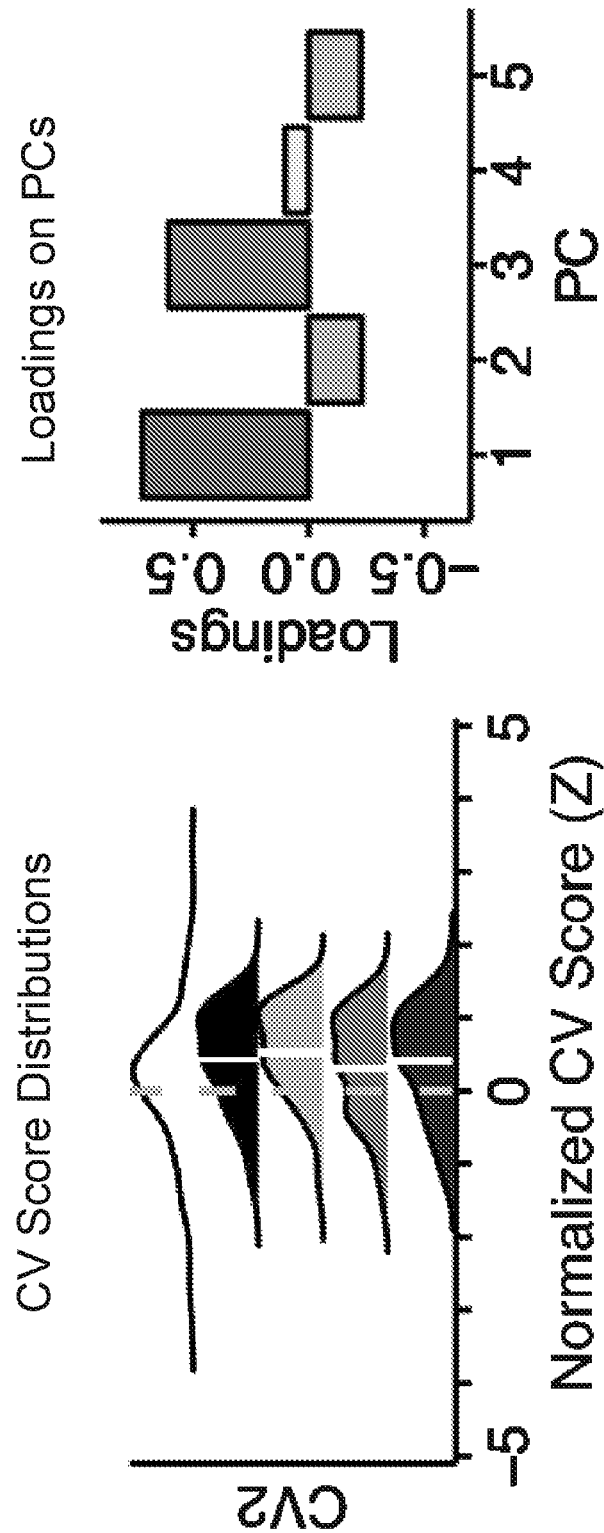
Figures 17G, 17H:
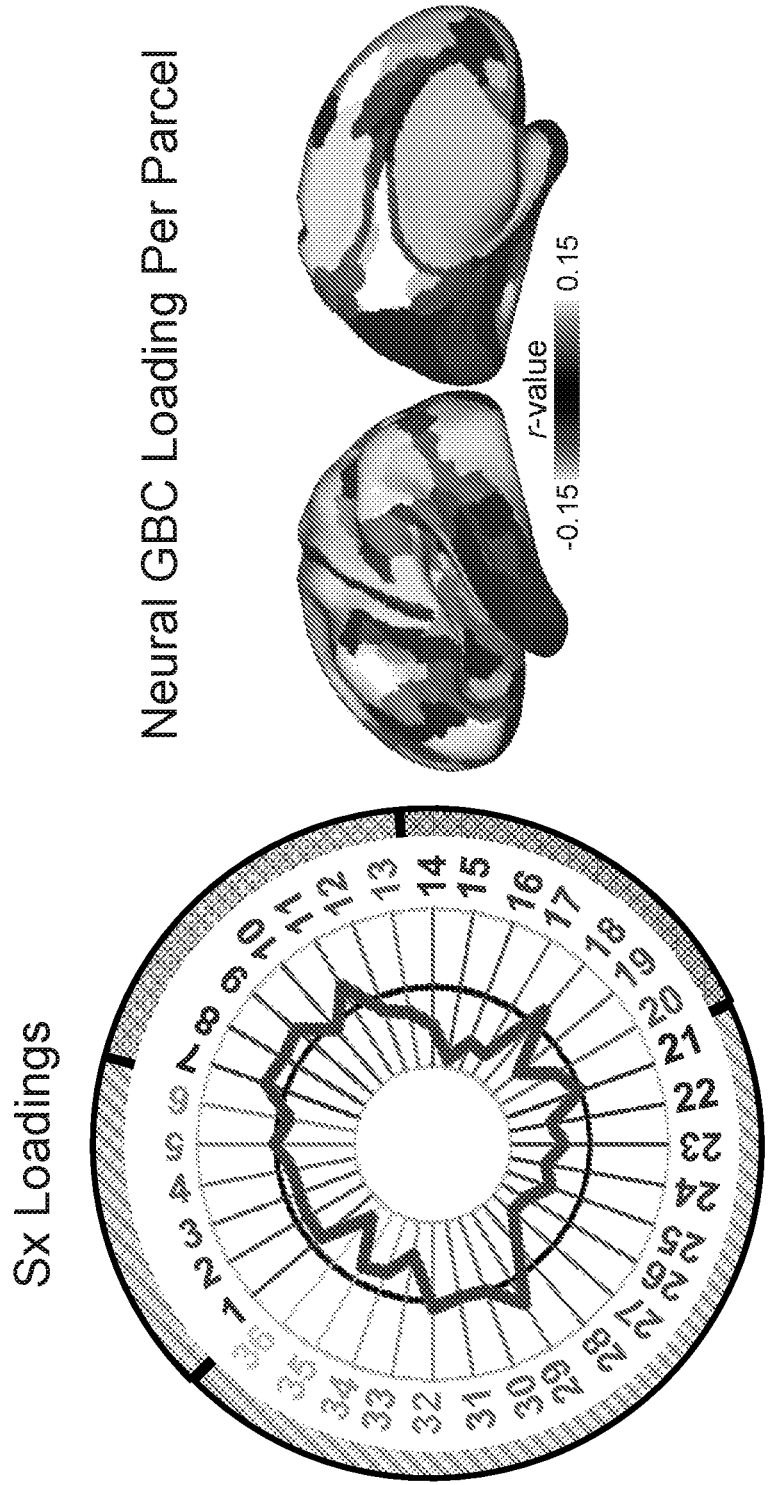
Figures 17I, 17J:
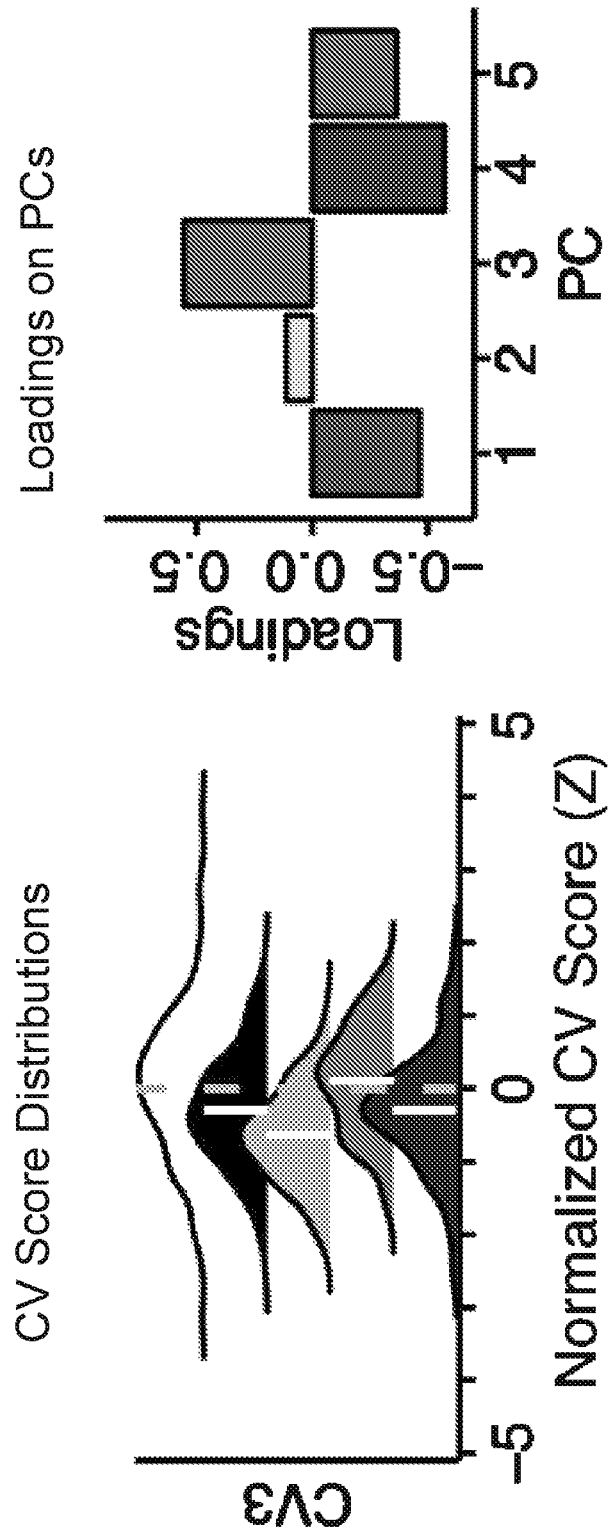
Figures 17M, 17N:
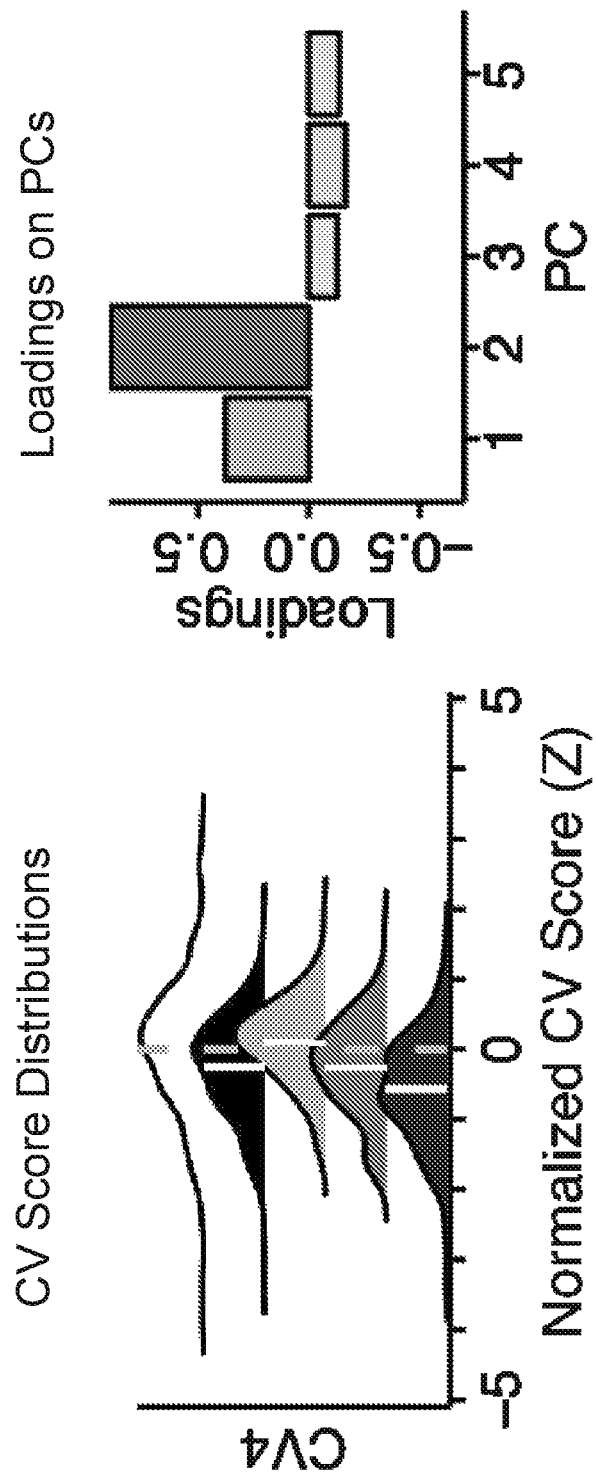
Figure 17P:
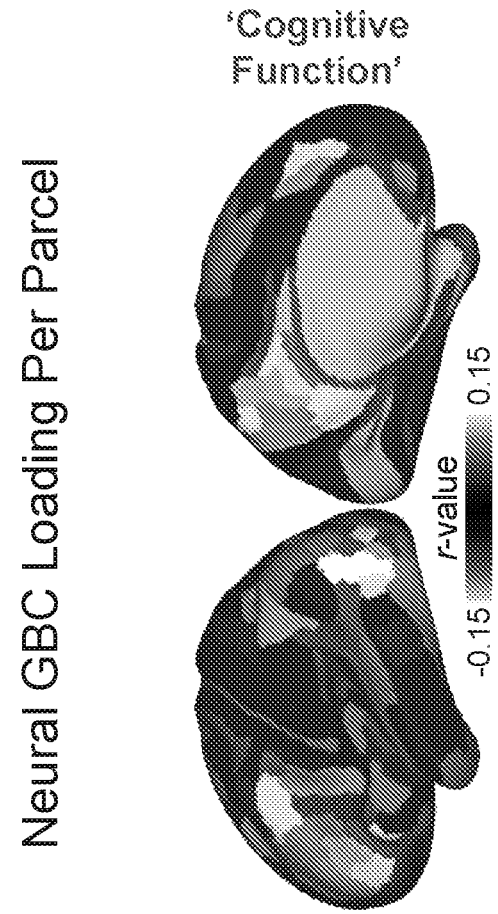
Figure 17O:
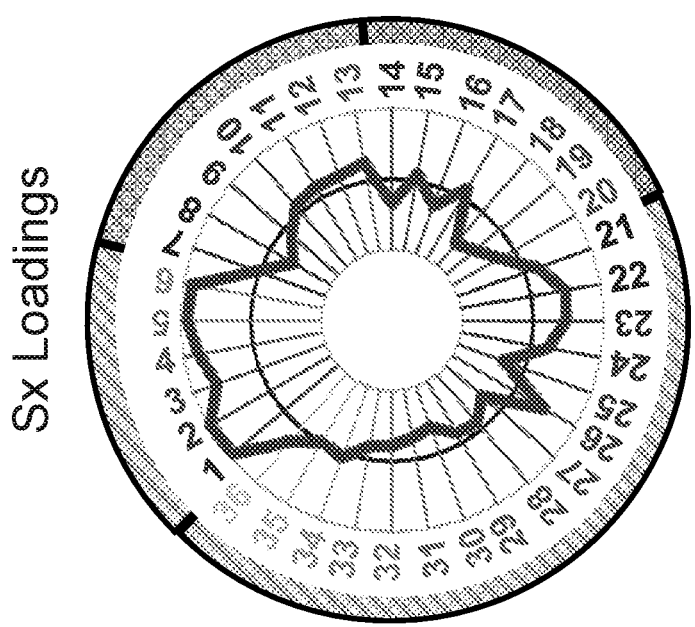
Figures 17Q, 17R:
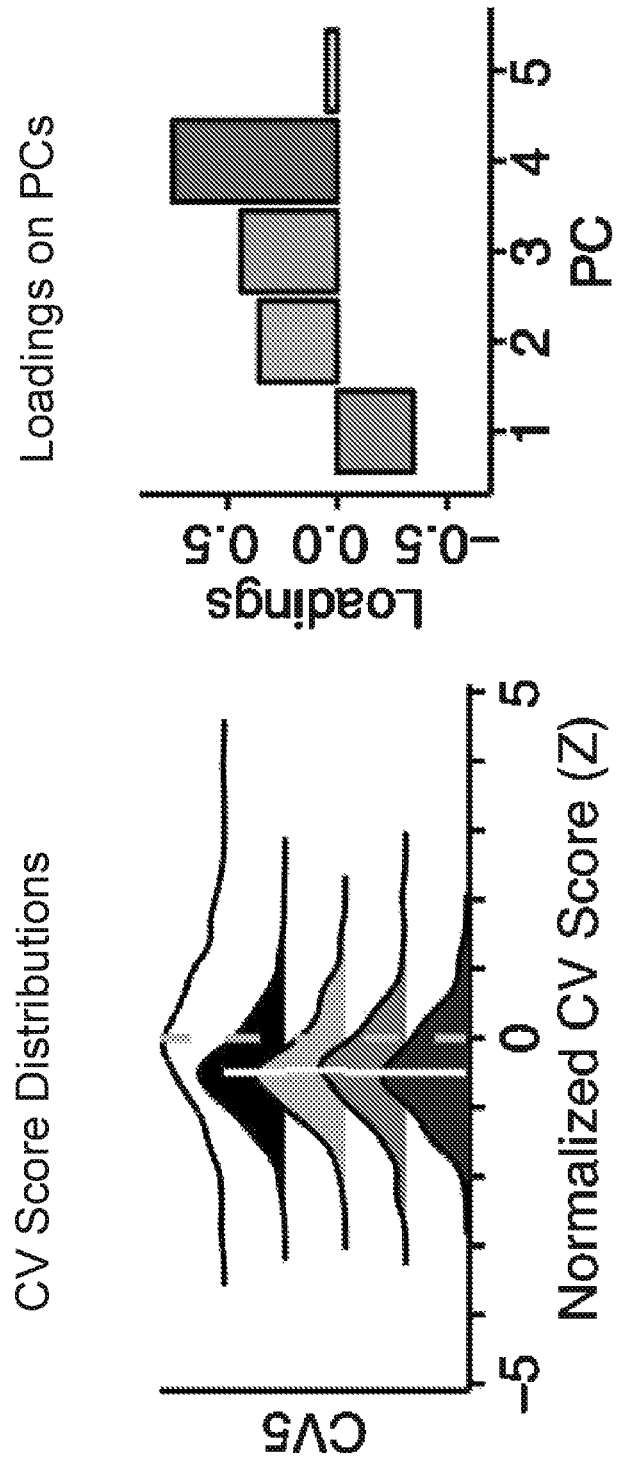
Figures 18A, 18B:
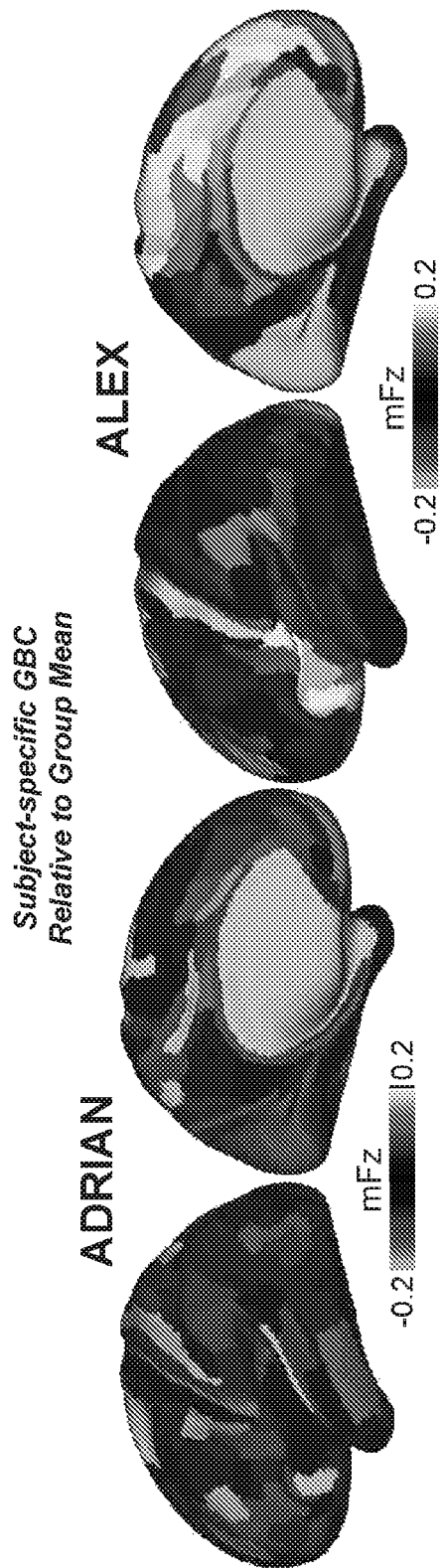
FIGS. 18A-18E illustrate example diagrams showing the characterization of individual subject-specific "neuroprint" profiles of neural and behavioral geometry, according to embodiments of the present disclosure.
Figure 18C:
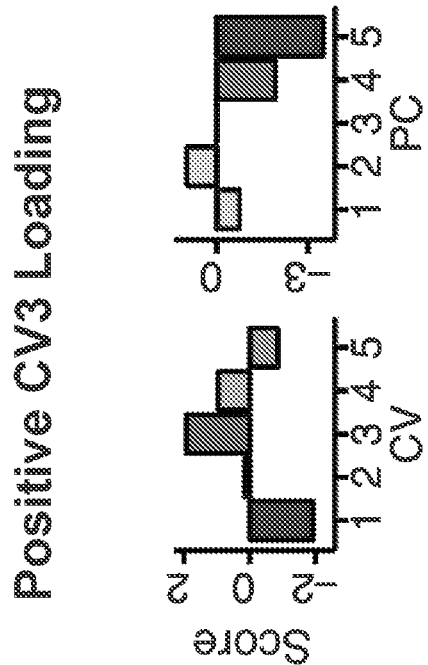
Figure 18D:
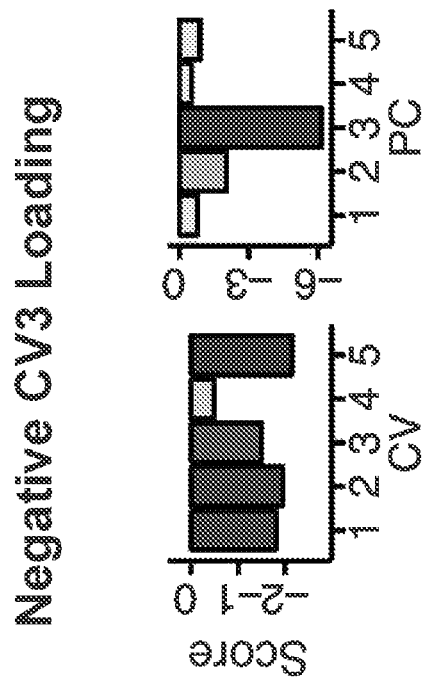
Figure 18E:
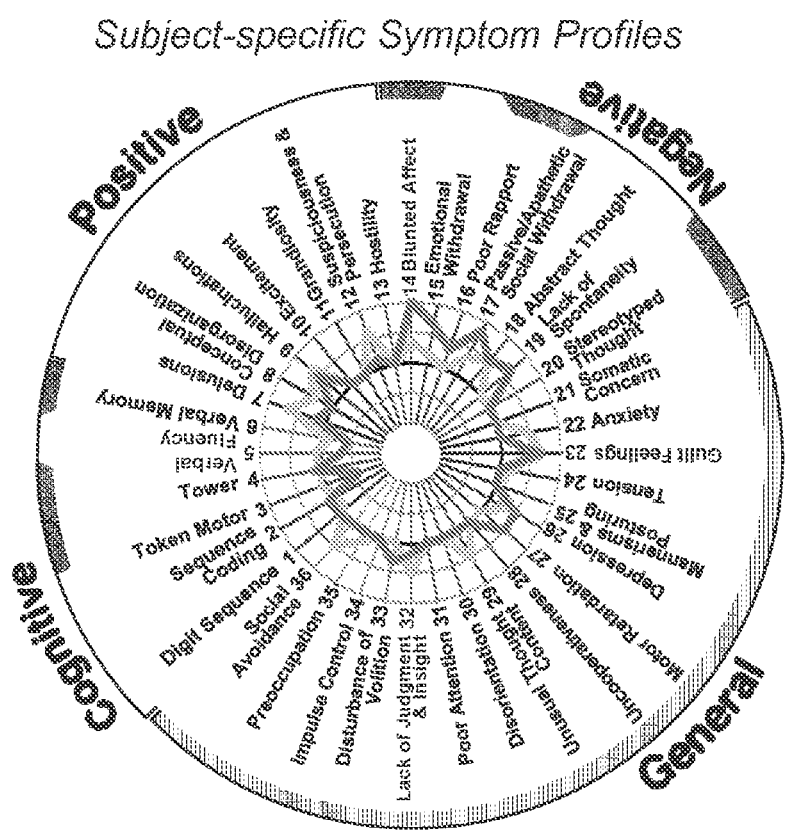

FIGS. 17A-17T illustrate example diagrams showing the characterization of canonical variate symptom configurations, according to embodiments of the present disclosure. FIGS. 17A-17T are described as the following: (a) Distributions of scores for the first canonical variate (CV1) by diagnostic group (white: controls; black: all patients; yellow: bipolar disorder with psychosis; orange: schizoaffective disorder with psychosis; red: schizophrenia). All scores are normalized to controls. (b) Behavioral canonical factor loadings for CV1. (c) Weights of the original behavioral items for CV1. (d) Neural canonical factor loadings for CV1. (e-t) Similar analyses shown for canonical variates 2-5.

FIGS. 18A-18E illustrate example diagrams showing the characterization of individual subject-specific "neuroprint" profiles of neural and behavioral geometry, according to embodiments of the present disclosure. FIGS. 18A-18E are described as the following: (a) Neural features (cortical GBC, demeaned relative to all patients) from an exemplar individual subject, "Adrian". (b) Neural features (cortical GBC, demeaned relative to all patients) from another exemplar subject, "Alex". Note the differences in neural features between Alex and Adrian, which is also reflected in the differences in the behavioral profile of the two subjects. (c) Individual behavioral loading (behavioral principal components and canonical variates) profile for subject Adrian. (d) Individual behavioral loading profile for subject Alex. Note the differences between the behavioral loading configurations for these two exemplar subjects, for example, in CV3. (e) Radarplot showing the individual symptom profiles for Alex (orange) and Adrian (blue). Although the overall symptom severity is similar, the configuration of symptoms is markedly different for the two subjects. The NBRIDGE framework provides a method for mapping the relationships between particular behavioral configurations and neural profiles (i.e. "neuroprints").

Figure 19M:
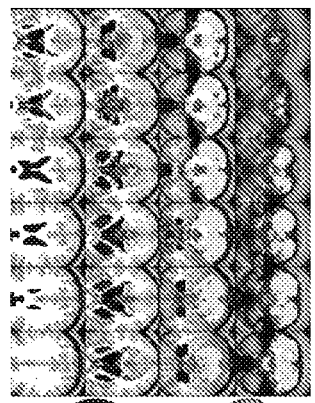
FIGS. 19A-19R illustrate example diagrams showing principal component analysis (PCA) of neural features in control and proband subjects, according to embodiments of the present disclosure.
Figure 19N:
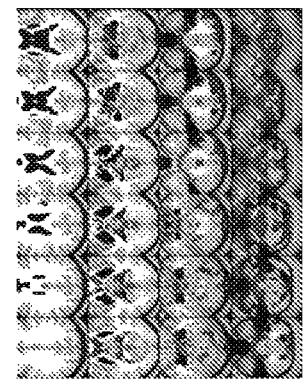
Figure 19O:
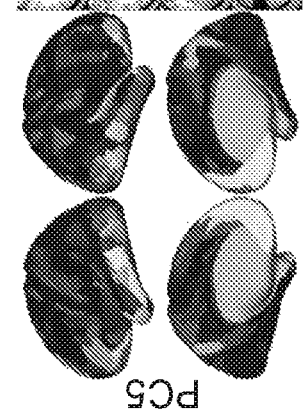
Figure 19Q:
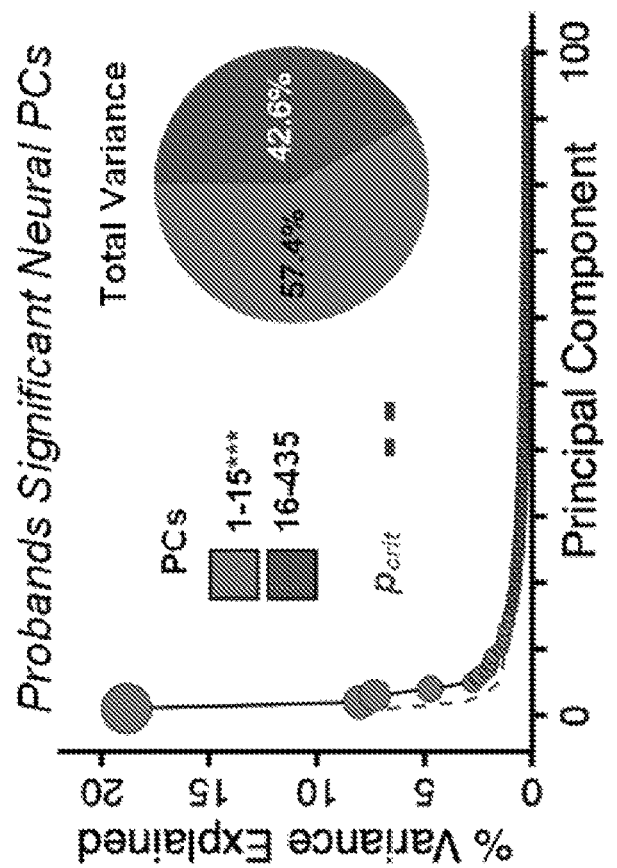
Figure 19P:
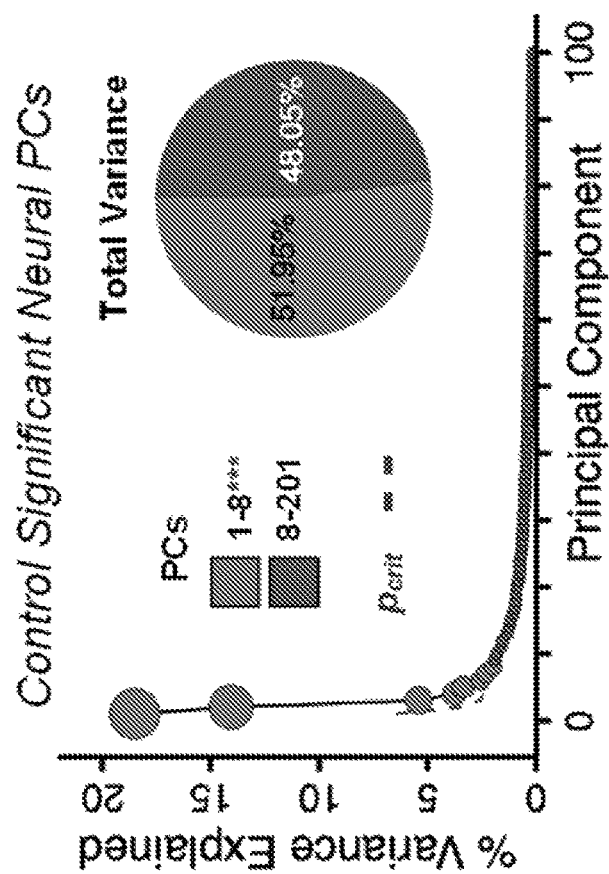
Figure 19R:
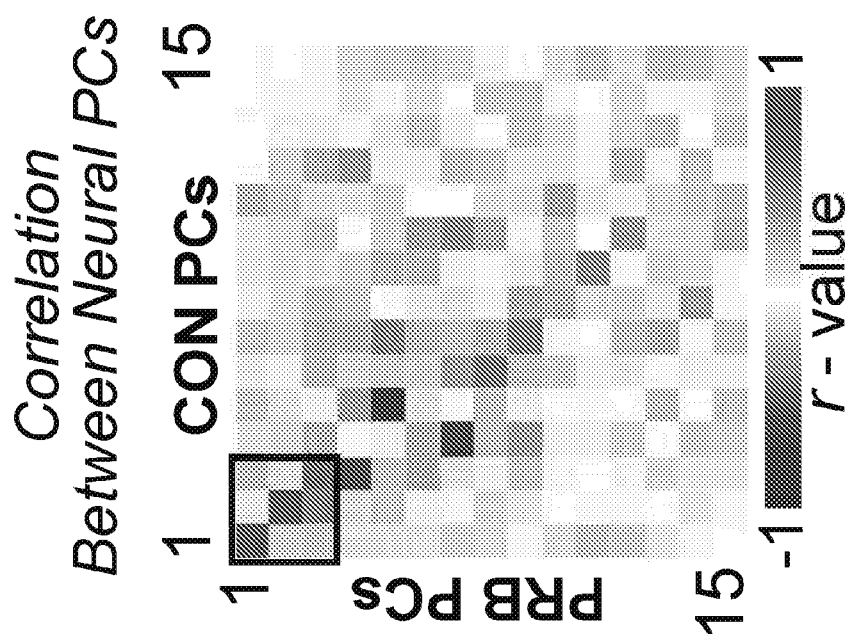

FIGS. 19A-19R illustrate example diagrams showing principal component analysis (PCA) of neural features in control and proband subjects, according to embodiments of the present disclosure. FIGS. 19A-19R are described as the following: (a) Results of PCA performed on neural features (718 whole-brain parcel GBC) across all control subjects (N=202). (b) Results of PCA performed on neural features (718 whole-brain parcel GBC) across all proband subjects (N=436). (c) Note that the first neural principal component (PC) in control subjects (FIG. 19A) and in proband subjects (FIG. 19B) are highly similar (r=0.90 across parcels). This may reflect a component of neural variance common across all humans. (d-i) The second and third PCs are also similar between control and proband subjects. (j-l) The fourth PC is markedly dissimilar between control and proband subjects, suggesting that this component may reflect neural variance which deviates in individuals with psychiatric symptoms. (m-o) The fifth PC is also highly dissimilar between controls and probands, also possibly reflecting diagnosis-relevant differences in neural variance. (p) Screeplot showing the total proportion of variance explained by the first 100 PCs from the PCA performed across all 718 neural features in 202 control subjects. The size of each point is proportional to the variance explained by that PC. The first 8 PCs (green)

were determined to be significant using a permutation test. Inset shows the proportion of variance both accounted and not accounted for by the 8 significant PCs. Together, these 8 PCs capture 51.95% of the total variance in neural GBC in the sample. (q) Screeplot showing the total proportion of variance explained by the first 100 PCs from the PCA performed across all 718 neural features in 436 proband subjects. The size of each point is proportional to the variance explained by that PC. The first 15 PCs (green) were determined to be significant using a permutation test. Inset shows the proportion of variance both accounted and not accounted for by the 15 significant PCs. Together, these five PCs capture 57.4% of the total variance in neural GBC in the sample. (r) Correlations between the first 15 neural PCs in controls (CON) and patients (PRB). The first 3 PCs are common across both control and proband subjects, possibly reflecting common components of human neural variance. After this, the PCs diverge, possibly reflecting differences in neural variance of healthy individuals and those with psychiatric symptoms.

The mapping identified using the disclosed neuro-behavioral framework ultimately yields a neural map that can define a set of neural features (e.g. areas, circuits, systems, etc.), which can then be mapped to specific additional neural features with spatial information. An example here is neuropharmacological maps derived from administering an agent of known molecular mechanism, such as ketamine.

FIGS. 20A-20I illustrate example diagrams showing a process of using latent scores from the neuro-behavioral geometry to provide a therapeutic prognosis for a new individual. FIGS. 20A-20I show an exemplar process by which the neuro-behavioral prediction can be validated and are described as follows: (a) First, the CCA was performed in all available subjects. This is referred to as the "full CCA". Next, a training set of 90% of these subjects was randomly selected, and a CCA was performed in this training set ("training CCA"). A simple regression was performed between training set neural scores and training set behavioral scores, to derive a weight for prediction in panel C. The remaining 10% of left-out subjects comprised the test set. (b) Neural features are used to compute latent neural scores, per the established neuro-behavioral geometry. Here, the 'observed' latent neural scores for the test set are the scores obtained for those subjects from the full CCA. (c) Behavioral latent scores for test set subjects were computed from behavioral data using weights from the training CCA. These behavioral latent scores were then used to predict the latent neural scores using the simple regression from the training set, without leveraging neural data from the test set. (Note that the regression here was performed solely to derive a weight in order to demonstrate that the behavioral CCA score is predictive of the neural CCA score and is not a step or in place of the CCA.) Here, the 'predicted' neural latent scores are computed by using the test subjects' behavioral data and the weight matrix derived from the training CCA. (d) Predicted latent neural scores are highly similar to observed neural scores computed from neural data. The correlation accuracy is ~0.7. (e) Summary of r-values for all 5 CVs. (f) A therapeutically relevant map, for example a map of the change in neural GBC pre- and post-ketamine infusion, can be used to provide a direct link to molecular mechanisms which affect neural circuits in the same manner as one or more of the group neural feature maps (e.g. CV3 neural map in panel (g).) (h) The neural latent scores (either computed from available neural features or predicted from behavioral scores) can be using to identify subjects which are most similar to particular neuro-behavioral profile, for example CV3. Here, the predicted neural latent scores of an individual from a fully independent dataset are shown relative to the distribution of neural latent scores for all original subjects used to derive the geometry. In this example, as ketamine is a non-selective NMDAR antagonist, the framework would predict that the subject in (i), who is highly similar to CV3 and therefore ketamine intervention, would respond to glutamatergic agonism.

Another example is the ability to quantify gene expression profiles from a genome-wide transcriptional atlas, the publicly available Allen Human Brain Atlas (AHBA)[13]. Briefly, the AHBA contains levels of expression of 20,737 genes obtained from six postmortem human brains using DNA microarray probes sampled from hundreds of neuroanatomical loci. Note that because no significant interhemispheric differences were found in cortical gene expression in the first two donor brains, only the left hemisphere was profiled for all six brains. The expression of each gene was then mapped to the 180 unilateral cortical parcels from Glasser et al. (2016)[12] and Z-scored for each individual subject. Finally, a group-level map for each gene was computed by averaging its Z-scored expression level per parcel across all subjects[14]. These parcellated gene expression maps can then be compared with the neural maps identified from the disclosed neuro-behavioral geometry. In this case, such a mapping can allow identification of molecular targets for specific axes of variation in the overall multi-dimensional phenotype-neural geometry, which can reveal therapeutic targets otherwise invisible to prior approaches that fail to consider the optimally derived multi-dimensional phenotype-neural geometry (e.g. such as the DSM, RDoC or using pre-existing single or multiple clinical scales).

Figure 21F:
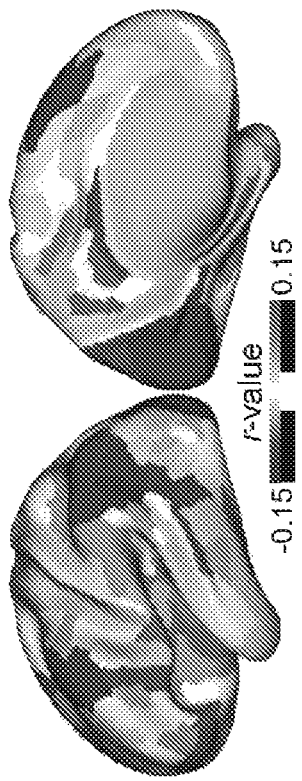
FIGS. 21A-21S illustrate example diagrams showing correlation with gene expression maps, according to embodiments of the present disclosure.
Figure 21E:
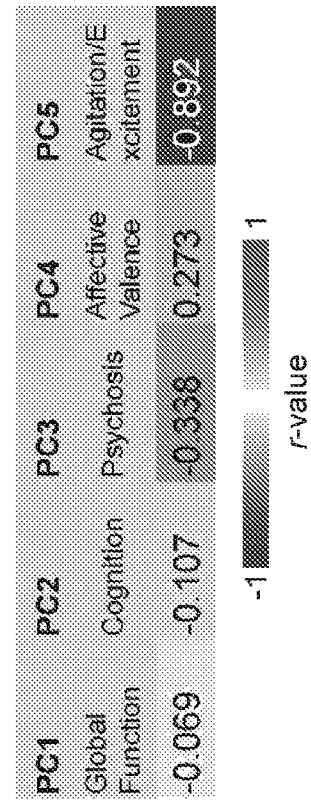
Figures 21G, 21H:
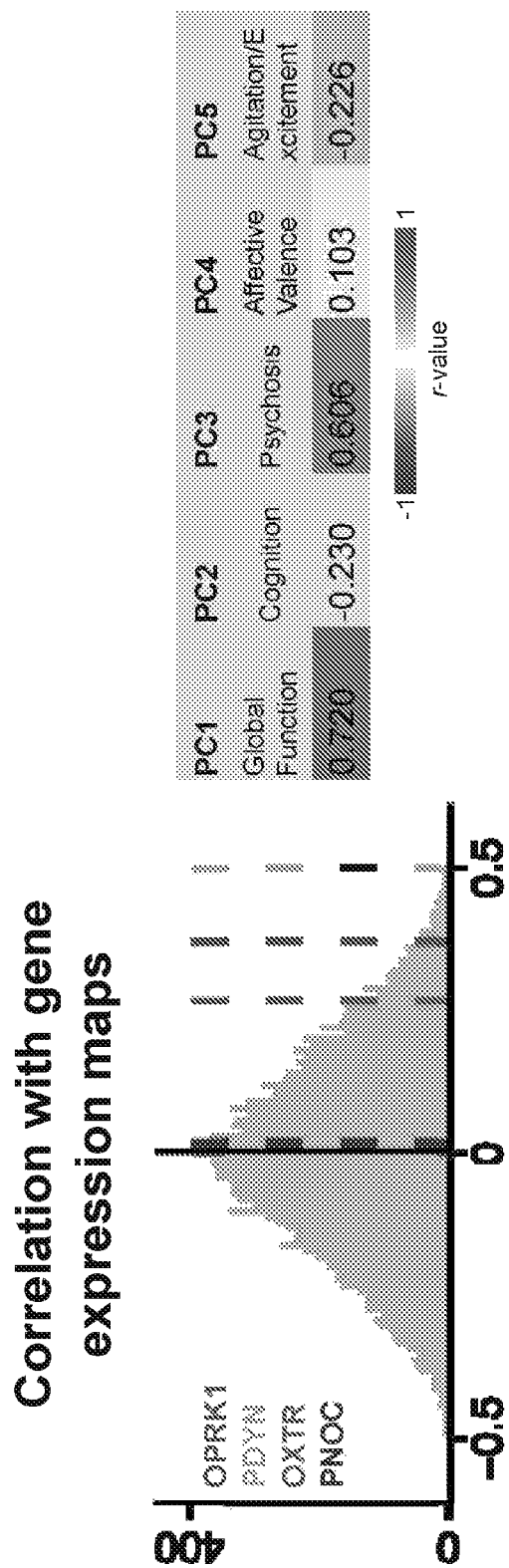
Figure 21J:
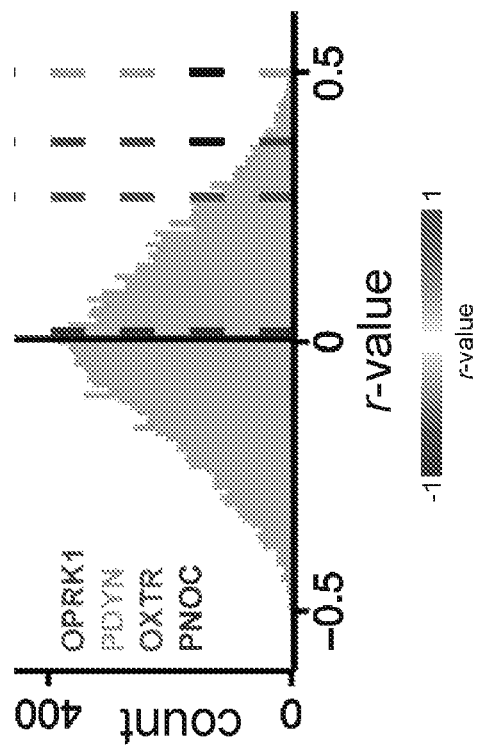
Figure 21I:
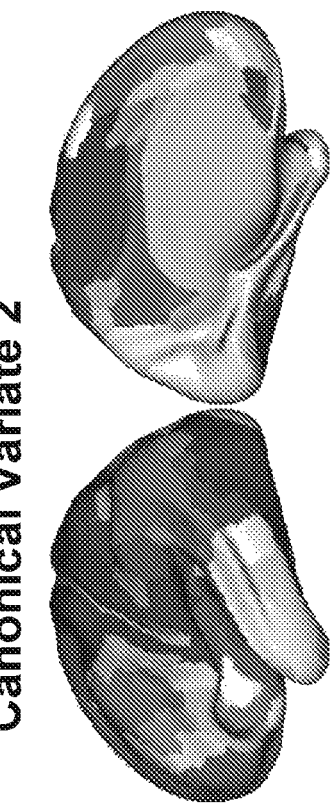
Figures 21K, 21L:
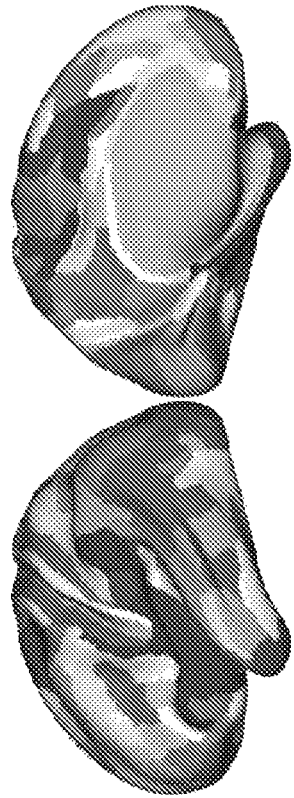
Figure 22E:
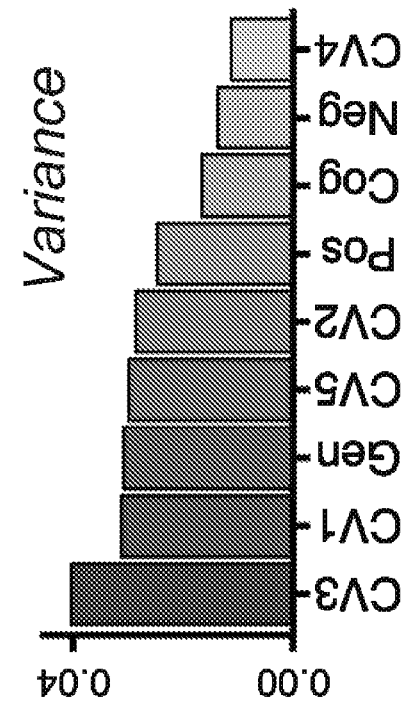
Figure 22F:
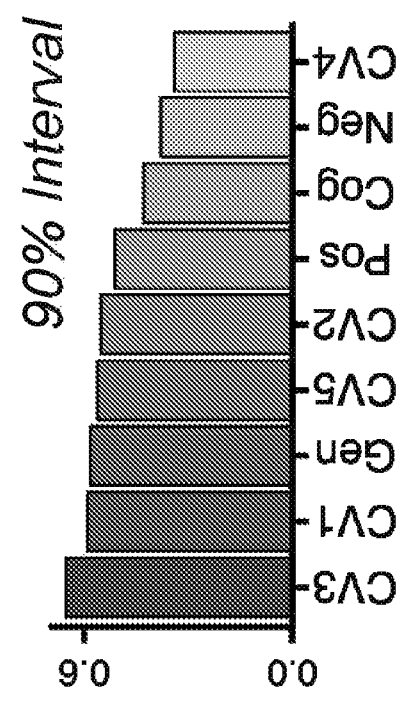
Figure 22G:
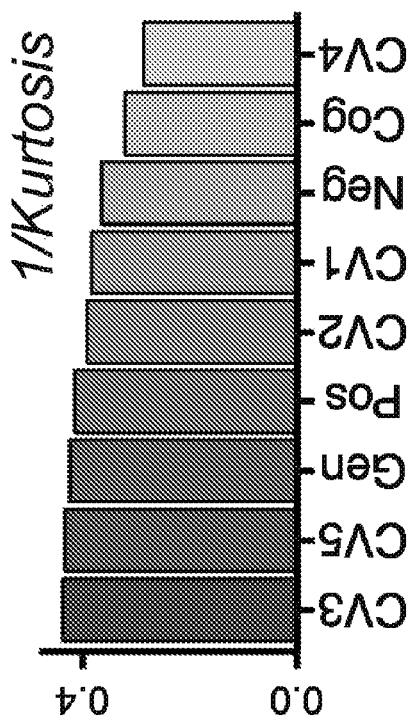

The disclosed geometry allows for specific gene expression profiles to be mapped to neural and behavioral profiles. For illustrative purposes, four genes of interest have been highlighted in FIGS. 21A-21S: OPRK1, which encodes the opioid receptor kappa 1; PDYN, which encodes prodynorphin; OXTR, oxytocin receptor; and PNOC, prepronociceptin protein. FIGS. 21A-21S show the expression maps for these four genes—a high positive value indicates a high expression of the gene in that cortical parcel. As an intuitive example, Canonical Variate 4 is highly correlated with behavioral PC1 and PC2 (Global Functioning and Cognition) but not PC3, PC4, or PC5 (FIG. 21N), indicating that the neural map shown in FIG. 21O is associated with high functioning and high cognitive performance and low psychosis and mood deficits. This neural map is highly anti-correlated with cortical expression of the PNOC gene (FIG. 21P, purple dashed line; note that this gene is close to the tail end of the correlation distribution), suggesting that the expression pattern of PNOC in FIG. 21D is related to poor cognitive performance and poor functioning. Critically, this mapping provides the indication that targeting the regulation of PNOC-related ligands may treat cognitive deficits and in turn improve global function. Using this framework, genetic and molecular targets that are associated with specific dimensions of behavioral variation may be identified, along with the development of pharmaceutical agents that may address deficits along axes that maximally capture multi-dimensional phenotype-neural geometry.

FIGS. 21A-21S illustrate example diagrams showing spatial relationships with gene expression maps, according to embodiments of the present disclosure. FIGS. 21A-21S are described as the following: (a) Cortical expression of the OPRK1 gene from the Allen Human Brain Atlas (AHBA). Values indicate Z-scored expression levels; a high positive value indicates high expression of OPRK1 in that region. (b-d) Cortical expression of the PDYN, OXTR, and PNOC genes. (e) Correlation between each of the 5 behavioral PCs and the first behavioral canonical variate (CV). These values reflect the proportion of variance in the behavioral data extracted by CV1. For example, the high positive correlation with PC5 indicates that this CV accounts for most of the variance in the Agitation/Excitement behavioral measures. (f) Correlation between each of the 180 cortical neural parcels and the first neural CV, reflecting the variance contributed by each neural region to this CV. (g) Distribution of correlation values between the neural map in f and the expression maps of 16,088 genes from the AHBA dataset. The position of the four genes of interest shown in a-d are highlighted. Note for example that the expression pattern of PDYN (orange dashed line) is at the tail end of the distribution, and is highly anti-correlated with the neural map of CV1. (h-s) Behavioral and neural variance and correlations with gene expression maps for CV2 to CV5.

FIGS. 22A-22G illustrate example pharmaceutical candidates for targeting specific neuroprints using gene expression maps, according to embodiments of the present disclosure. FIGS. 22A-22G are described as the following: (a) Distribution of correlation values between the CV3 neural loading map and the expression maps of 16,088 genes from the AHBA dataset. The position of 7 genes of interest shown in b-d are highlighted. Note for example that the expression pattern of GABRA3 (purple dashed line) is at the tail end of the distribution, and is highly anti-correlated with the neural map of CV3. The CV3 neuroprint, including the canonical symptom profile and associated loading map, is shown at left. (b) Upper panels show gene expression patterns for two interneuron marker genes, somatostatin (SST) and parvalbumin (PVALB). More positive values (yellow regions) show areas where the gene of interest is more highly expressed. Lower panels show the correlation between the CV3 factor loading map and the gene expression maps, for SST and PVALB. (c) Gene expression maps and parcel-wise correlations with the CV3 map for two GABRAA receptor subunit genes, GABRA1 and GABRA3. (d) Gene expression maps and parcel-wise correlations with the CV3 map for three serotonin receptor subunit genes, HTR1F, HTR7, and HTR2A. (e) Bar plot comparing the 90% interval range (95th percentile-5th percentile) of the distributions of r-values with gene expression maps, shown for the five CV maps and the four symptom factor (Positive, Negative, General, Cognitive) maps. The range is greatest for the distribution of correlation coefficients between the CV3 map and all 16,088 genes, indicating that identifying gene expression similarity using the CV3 map may be statistically superior and more easily resolved compared to the other behavioral maps. (f) Bar plot comparing the variances of the distributions of r-values between the 9 behavioral maps and gene expression maps. The CV3 map again has the highest value, indicating that it is highly correlated and highly anti-correlated with a larger number of gene expression maps and may thus provide superior and more easily resolvable mapping to gene expression patterns. (g) Bar plot comparing the kurtosis of the distributions of r-values between the 9 behavioral maps and gene expression maps. Note that the reciprocal of the kurtosis (1/kurtosis) is plotted so that the distribution with the most and more extreme tail-end values has the highest value (i.e. the CV3 distribution is the most leptokurtic).

Figure 23:
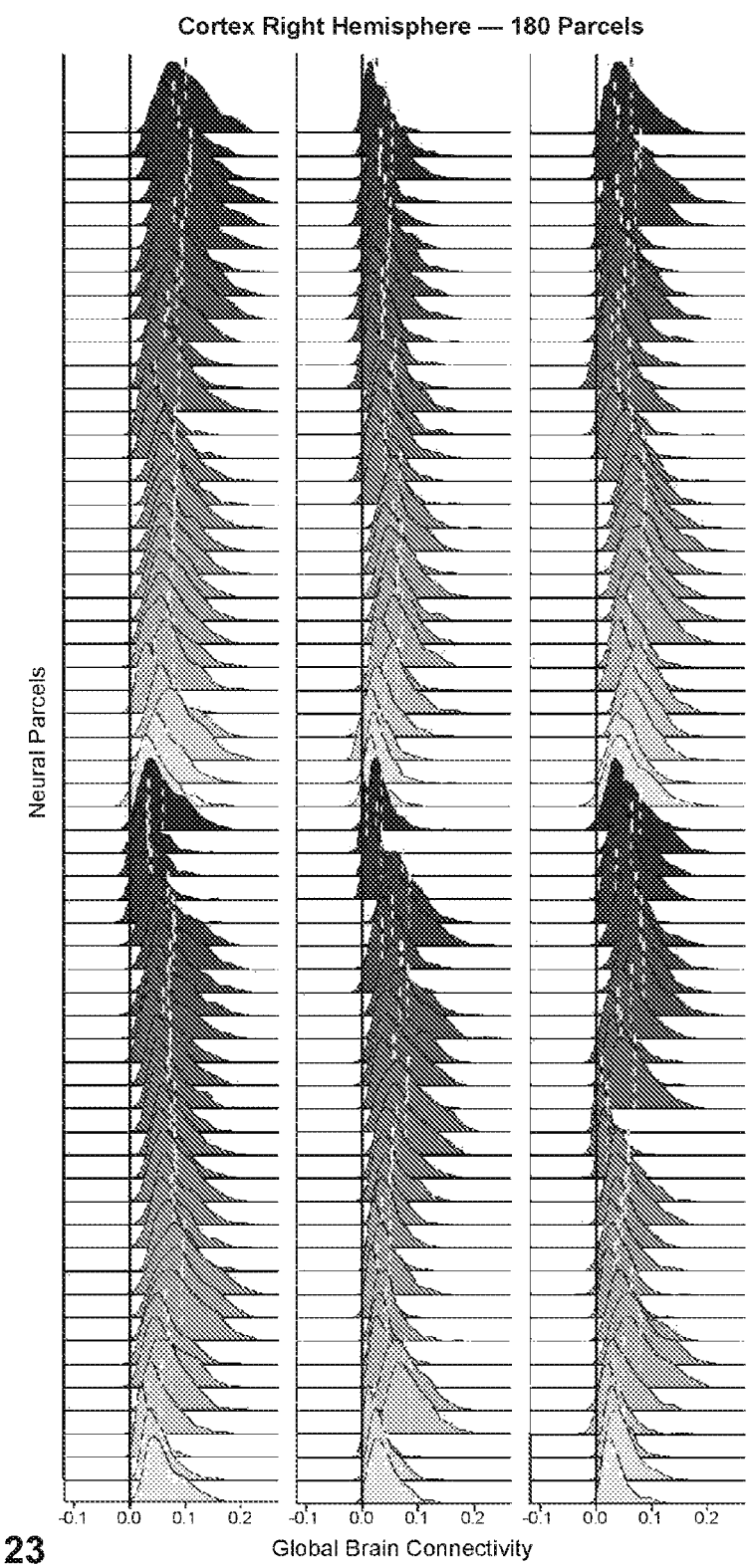
FIG. 23 illustrates example mapping of an exemplar neural feature in a sample of individuals without formal psychiatric diagnoses to delineate the boundaries of functional impairment, according to embodiments of the present disclosure.

FIG. 23 illustrates mapping of an exemplar neural feature in a sample of individuals without formal psychiatric diagnoses obtained from the publicly available Human Connectome Project dataset. These results delineate the concept of defining boundaries of functional impairment, according to embodiments of the present disclosure. FIG. 23 is described as the following: example distributions of parcel GBC from an independent sample of 339 young adults without a diagnosis of psychiatric illness, in 180 parcels of the right cerebral cortex. Each density plot shows the distribution of GBC for a particular parcel across all 339 individuals (i.e. a summary measure of functional connectivity for a particular region of the brain). Dotted grey line shows the mean GBC across all 339 subjects for each parcel; solid black line shows the zero-line for all parcels. Using this method, the distributions of a neural feature for particular neural regions can be quantified in individuals with and without functional and/or behavioral/phenotypic impairment and used to inform quantitative prediction of neural functional and/or behavioral/phenotypic impairment along axes that maximally capture multi-dimensional phenotype-neural geometry. Such a prediction for a specific individual can be quantified by independently obtaining either the neural feature data or the relevant behavioral/phenotypic data, which can then be projected into the axes of the predefined multi-dimensional phenotype-neural geometry.

FIG. 24 illustrates an example flowchart diagram of a process 200 by which a neuro-behavioral geometry may be derived from neural and behavioral features and used to determine, prognosticate, and/or forecast treatment response for a given individual, individual response to a specific treatment, individual neuro-behavioral mental status, and/or the quantitative proximity of individuals in the neuro-behavioral geometry according to embodiments of the present disclosure.

FIG. 25 illustrates an example flowchart diagram of a process 300 by which neural and behavioral features may be obtained in preparation for establishing a neuro-behavioral geometry.

FIG. 26 illustrates an example flowchart diagram of a process 400 by which neural features may be processed and prepared for use in a neuro-behavioral geometry, according to embodiments of the present disclosure.

FIG. 27 illustrates an example flowchart diagram of a process 500 by which neural and behavioral features are used to compute and establish neuro-behavioral geometry, according to embodiments of the present disclosure.

FIG. 28 illustrates an example flowchart diagram of a process 600 by which a neuro-behavioral geometry may be validated and quality-assured, according to embodiments of the present disclosure.

FIG. 29 illustrates an example flowchart diagram of a process 700 by which neural and behavioral latent group-level features may be related to candidate therapeutic targets and/or a neuro-behavioral mental status, according to embodiments of the present disclosure.

FIG. 30 illustrates an example flowchart diagram of a process 800 by which neural and/or behavioral features from an independent individual may be used to compute latent scores under the neuro-behavioral geometry, according to embodiments of the present disclosure.

FIG. 31 illustrates an example flowchart diagram of a process 900 by which neural and/or behavioral scores from an independent individual may be used to compute a similarity score with a neuro-behavioral mental status neural therapeutic target(s) of interest, according to embodiments of the present disclosure.

FIG. 32 illustrates an example flowchart diagram of a process 1000 of determining, prognosticating, or forecasting individual response to a particular therapeutic, based on neuro-behavioral mapping, according to embodiments of the present disclosure.

FIG. 33 illustrates an example flowchart diagram of a process 1100 of determining, prognosticating, or forecasting a therapeutic for an individual based on neuro-behavioral mapping, according to embodiments of the present disclosure.

FIG. 34 illustrates an example flowchart diagram of a process 1200 of determining, prognosticating, or forecasting a mental health status for an individual based on neuro-behavioral mapping, according to embodiments of the present disclosure.

FIG. 35 illustrates an example flowchart diagram of a process 1300 of identifying individuals based on quantitative proximity in the neuro-behavioral geometry, according to embodiments of the present disclosure.

FIG. 36 illustrates an example of a user interface for performing the steps of the invention, according to embodiments of the present disclosure.

FIGS. 37A-37C illustrate examples of outputs of the neuro-behavioral geometry from an exemplar user interface, according to embodiments of the present disclosure. In particular, FIG. 37A illustrates an example summary quality assurance report for a derived neuro-behavioral latent variable. FIG. 37B illustrates an example graph showing a range of scores of randomized 'surrogate' unit vector symptom profiles versus a derived neuro-behavioral latent variable. FIG. 37C illustrates example graphs of unit-variance normalized distributions of derived neuro-behavioral latent variables versus a priori input clinical scales.

Exemplary Computer Implementation

FIGS. 1-35 as described herein are illustrative examples allowing an explanation of the present invention. It should be understood that embodiments of the present invention could be implemented in hardware, firmware, software, or a combination thereof. In such an embodiment, the various components and steps would be implemented in hardware, firmware, and/or software to perform the functions of the present invention. That is, the same piece of hardware, firmware, or module of software could perform one or more of the illustrated blocks (i.e., components or steps).

The present invention can be implemented in one or more computer systems capable of carrying out the functionality described herein. Referring to FIG. 38, an example computer system 3800 useful in implementing the present invention is shown. Various embodiments of the invention are described in terms of this example computer system 3800. After reading this description, it will become apparent to one skilled in the relevant art(s) how to implement the invention using other computer systems and/or computer architectures.

Computer system 3800 includes one or more processors, such as processor 3804. Processor 3804 can be a special purpose or a general purpose digital signal processor. Processor 3804 is connected to a communication infrastructure 3802 (for example, a bus or network). Various software implementations are described in terms of this exemplary computer system. After reading this description, it will become apparent to a person skilled in the relevant art(s) how to implement the disclosure using other computer systems and/or computer architectures.

Computer system 3800 also includes a main memory 3806, preferably random access memory (RAM), and may also include a secondary memory 3808. Secondary memory 3808 may include, for example, a hard disk drive 3810 and/or a removable storage drive 3812, representing a floppy disk drive, a magnetic tape drive, an optical disk drive, solid-state disk, or the like. Removable storage drive 3812 reads from and/or writes to a removable storage unit 3816 in a well-known manner. Removable storage unit 3816 represents a floppy disk, magnetic tape, optical disk, solid-state disk, or the like, which is read by and written to by removable storage drive 3812. As will be appreciated by persons skilled in the relevant art(s), removable storage unit 3816 includes a computer usable storage medium having stored therein computer software and/or data.

In alternative implementations, secondary memory 3808 may include other similar means for allowing computer programs or other instructions to be loaded into computer system 3800. Such means may include, for example, a removable storage unit 3818 and an interface 3814. Examples of such means may include a program cartridge and cartridge interface (such as that found in video game devices), a removable memory chip (such as an EPROM, or PROM) and associated socket, a thumb drive and USB port, and other removable storage units 3818 and interfaces 3814 which allow software and data to be transferred from removable storage unit 3818 to computer system 3800.

Computer system 3800 may also include a communications interface 3820. Communications interface 3820 allows software and data to be transferred between computer system 3800 and external devices. Examples of communications interface 3820 may include a modem, a network interface (such as an Ethernet card), a communications port, a PCMCIA slot and card, etc. Software and data transferred via communications interface 3820 are in the form of signals which may be electronic, electromagnetic, optical, or other signals capable of being received by communications interface 3820. These signals are provided to communications interface 3820 via a communications path 3822. Communications path 3822 carries signals and may be implemented using wire or cable, fiber optics, a phone line, a cellular phone link, an RF link and other communications channels.

As used herein, the terms "computer program medium" and "computer readable medium" are used to generally refer to tangible storage media such as removable storage units 3816 and 3818 or a hard disk installed in hard disk drive 3810. These computer program products are means for providing software to computer system 3800.

Computer programs (also called computer control logic) are stored in main memory 3806 and/or secondary memory 3808. Computer programs may also be received via communications interface 3820. Such computer programs, when executed, enable the computer system 3800 to implement the present disclosure as discussed herein. In particular, the computer programs, when executed, enable processor 3804 to implement the processes of the present disclosure, such as any of the methods described herein. Accordingly, such computer programs represent controllers of the computer system 3800. Where the disclosure is implemented using software, the software may be stored in a computer program product and loaded into computer system 3800 using removable storage drive 3812, interface 3814, or communications interface 3820.

In another embodiment, features of the disclosure are implemented primarily in hardware using, for example, hardware components such as application-specific integrated circuits (ASICs) and gate arrays. Implementation of a hardware state machine so as to perform the functions described herein will also be apparent to persons skilled in the relevant art(s).

CONCLUSION

It is to be appreciated that the Detailed Description section, and not the Abstract section, is intended to be used to interpret the claims. The Abstract section may set forth one or more, but not all exemplary embodiments, and thus, is not intended to limit the disclosure and the appended claims in any way.

The disclosure has been described above with the aid of functional building blocks illustrating the implementation of specified functions and relationships thereof. The boundaries of these functional building blocks have been arbitrarily defined herein for the convenience of the description. Alternate boundaries may be defined so long as the specified functions and relationships thereof are appropriately performed.

It will be apparent to those skilled in the relevant art(s) that various changes in form and detail can be made therein without departing from the spirit and scope of the disclosure. Thus, the disclosure should not be limited by any of the above-described exemplary embodiments, but should be defined only in accordance with the following claims and their equivalents.

REFERENCES

1. Seeman, P. & Lee, T. Antipsychotic drugs: direct correlation between clinical potency and presynaptic action on dopamine neurons. *Science* 188, 1217-1219 (1975).
2. American Psychiatric Association. Diagnostic and Statistical Manual of Mental Disorders, 5th Edition: DSM-5. (American Psychiatric Publishing, Arlington, VA, 2013).
3. Anticevic, A., et al. Characterizing thalamo-cortical disturbances in schizophrenia and bipolar illness. *Cereb Cortex* 24, 3116-3130 (2014).
4. Insel, T., et al. Research domain criteria (RDoC): toward a new classification framework for research on mental disorders. *Am J Psychiatry* 167, 748-751 (2010).
5. Yang, G. J., et al. Altered Global Signal Topography in Schizophrenia. *Cereb Cortex* (2016).
6. Shen, W. W. A history of antipsychotic drug development. *Compr Psychiatry* 40, 407-414 (1999).
7. Tamminga, C. A., et al. Clinical phenotypes of psychosis in the Bipolar-Schizophrenia Network on Intermediate Phenotypes (B-SNIP). *Am J Psychiatry* 170, 1263-1274 (2013).
8. Anticevic, A., et al. Global Prefrontal and Fronto-amygdala Dysconnectivity in Bipolar I Disorder with Psychosis History. *Biological Psychiatry* 73, 565-573 (2012).
9. Anticevic, A., et al. Global resting-state fMRI analysis identifies frontal cortex, striatal, and cerebellar dysconnectivity in obsessive-compulsive disorder. *Biol. Psychiatry* 75, 595-605 (2013).
10. Cole, M. W., Anticevic, A., Repovs, G. & Barch, D. M. Variable global dysconnectivity and individual differences in schizophrenia. *Biological Psychiatry* 70, 43-50 (2011).
11. Yeo, B. T., et al. The organization of the human cerebral cortex estimated by intrinsic functional connectivity. *J Neurophysiol* 106, 1125-1165 (2011).
12. Glasser, M. F., et al. A multi-modal parcellation of human cerebral cortex. *Nature* 536, 171-178 (2016).
13. Hawrylycz, M. J., et al. An anatomically comprehensive atlas of the adult human brain transcriptome. *Nature* 489, 391-399 (2012).
14. Burt, J. D., M; Eckner, W J; Navejar, N M; Ji, J L; Martin, W J; Bernacchia, A; Anticevic, A; Murray, JD. Hierarchy of transcriptomic specialization across human cortex captured by myelin map topography. (2017).

What is claimed is:

1. A method for determining a therapeutic for treating a patient with a psychiatric disorder or a neurological disorder, the method comprising:
   receiving, from a user interface associated with a computing device, behavioral data of the patient corresponding to at least one of a psychiatric symptom, a neurological symptom, or a cognitive status of the patient;
   processing, by at least one processor of the computing device, the behavioral data of the patient into behavioral features;
   receiving, by the at least one processor, neural data of the patient corresponding to a neural status of the patient;
   processing, by the at least one processor, the neural data into a neural feature map which comprises two-dimensional surfaces and subcortical volumetric structures, wherein the two-dimensional surfaces and the subcortical volumetric structures comprise one or more numerical values assigned to specific brain locations represented by the two-dimensional surfaces and the subcortical volumetric structures;
   retrieving, by the at least one processor, a multi-dimensional neuro-behavioral geometry which is derived by mapping behavioral features and neural features for a plurality of individuals based on a statistical analysis of neural data and behavioral data of the plurality of individuals;
   determining, by the at least one processor, one or more neuro-behavioral dimensions from the multi-dimensional neuro-behavioral geometry, the one or more neuro-behavioral dimensions having one or more highest degrees of similarities, respectively, with at least one of the behavioral features or the neural features, wherein each of the one or more neuro-behavioral dimensions comprises a group-level neural feature map and group-level behavioral features computed from the plurality of individuals;
   generating, by the at least one processor, for each of the one or more neuro-behavioral dimensions, a neural composite score based on at least one of:
      the neural feature map for the patient relative to the group-level neural feature map for the one or more neuro-behavioral dimensions, the generating the neural composite score including computing a statistical association of the one or more numerical values assigned across at least one of two-dimensional cortical surface-based areas or subcortical volumetric brain structures, wherein each neural composite score represents a statistical likelihood that the patient exhibits the at least one of the psychiatric symptom, the neurological symptom, or the cognitive status that are associated with the group-level behavioral features from the one or more neuro-behavioral dimensions,
      a predicted neural feature map for the patient, wherein the predicted neural feature map is computed from a statistical model using the behavioral features for the patient, or
      both the neural feature map and the predicted neural feature map for the patient;
   determining, by the at least one processor, the therapeutic for treating the patient based on the neural composite score for the one or more neuro-behavioral dimensions; and
   treating the patient with the therapeutic.

2. The method of claim 1, wherein the generating the neural composite score derived from the predicted neural feature map for the patient further comprises:
retrieving, by the at least one processor, the behavioral data for the patient;
retrieving, by the at least one processor, the statistical model for predicting the predicted neural feature map from the behavioral data for the patient, wherein the statistical model is computed using the neural data and the behavioral data from the plurality of individuals; and
computing, by the at least one processor, the predicted neural feature map for the patient using the behavioral data for the patient and the statistical model.

3. The method of claim 1, wherein the neural feature map for the patient comprises an assignment of the one or more numerical values to the at least one of the two-dimensional cortical surface-based areas or subcortical volumetric structures brain structures from a given assessment or analysis, from the neural data of a particular modality.

4. The method of claim 1, wherein at least one of the neural feature map, the group-level neural feature map, or the predicted neural feature map comprises a representation of at least one of cerebral cortices or cerebellar cortices as the two-dimensional surfaces and a representation of subcortical neural data as appropriate volumetric structures.

5. The method of claim 1, wherein determining the therapeutic for treating the patient based on the respective neural composite score for each of the one or more neuro-behavioral dimensions further comprises:
determining, by the at least one processor, whether each of the respective neural composite score for the patient exceeds a respective predetermined threshold, the exceeding indicating that the patient is likely to respond to a therapeutic associated with the one or more neuro-behavioral dimensions;
retrieving, by the at least one processor, each of the group-level neural feature maps for the one or more neuro-behavioral dimensions for which the respective neural composite score exceeds the respective predetermined threshold;
retrieving, by the at least one processor, one or more neural therapeutic feature maps;
determining, by the at least one processor, a quantitative correspondence of similarity of each of the group-level neural feature map for the one or more neuro-behavioral dimensions with one or more neural therapeutic feature maps;
identifying, by the at least one processor, one or more neural therapeutic targets, wherein each of the one or more neural therapeutic targets correspond to the one or more neural therapeutic feature maps for which the quantitative correspondence of similarity with the group-level neural feature maps exceeds the respective predetermined threshold; and
determining, by the at least one processor, the therapeutic associated with the one or more neural therapeutic targets for treatment of the patient.

6. The method of claim 5, wherein each of the one or more neural therapeutic feature maps comprises a pharmacological map associated with one or more receptor targets or a gene expression map associated with one or more gene expression targets.

7. The method of claim 1, further comprising displaying, on the user interface associated with the computing device, at least one of:
a numerical and graphical representation of the one or more group-level behavioral features or the group-level neural feature map comprising the one or more neuro-behavioral dimensions of the multi-dimensional neuro-behavioral geometry,
at least one of a numerical and graphical representation of the one or more behavioral features or the neural feature map,
at least one of the neural composite score or a predicted neural composite score for the patient,
one or more neural therapeutic feature maps,
one or more neural therapeutic targets, and
the therapeutic associated with the one or more neural therapeutic targets for treatment of the patient.

8. A method for prognosticating a treatment for a patient based on neuro-behavioral mapping, and using at least one processor, the method comprising:
receiving, from a user interface associated with a computing device, behavioral data of the patient corresponding to at least one of a psychiatric symptom, a neurological symptom, or a cognitive status of the patient;
processing, by the at least one processor, the behavioral data of the patient into behavioral features;
receiving, by the at least one processor, neural data of the patient corresponding to a neural status of the patient;
processing, by the at least one processor, the neural data into a neural feature map, wherein the neural feature map comprises two-dimensional surfaces and subcortical volumetric structures, wherein the two-dimensional surfaces and the subcortical volumetric structures comprise one or more numerical values assigned to specific brain locations represented by the two-dimensional surfaces and the subcortical volumetric structures;
retrieving, by the at least one processor, a multi-dimensional neuro-behavioral geometry, wherein the multi-dimensional neuro-behavioral geometry is derived by mapping behavioral features and neural features for a plurality of individuals based on a statistical analysis of neural data and behavioral data of the plurality of individuals;
determining, by the at least one processor, one or more neuro-behavioral dimensions from the multi-dimensional neuro-behavioral geometry, wherein the one or more neuro-behavioral dimensions has a highest degree of similarity with the behavioral and/or neural features of the patient, wherein each of the one or more neuro-behavioral dimensions comprises a group-level neural feature map and group-level behavioral features computed from the plurality of individuals;
generating, by the at least one processor, for each of the one or more neuro-behavioral dimensions, a neural composite score based on at least one of:
the neural feature map for the patient relative to the group-level neural feature map for the one or more neuro-behavioral dimensions, the generating the neural composite score including computing a statistical association of the one or more numerical values assigned across at least one of multiple two-dimensional cortical surface-based areas or subcortical volumetric brain structures, wherein each neural composite score represents a statistical likelihood that the patient exhibits the at least one of the psychiatric symptom, the neurological symptom, or the cognitive status that are associated with the group-level behavioral features from the one or more neuro-behavioral dimensions, a predicted neural feature map for the patient, wherein the predicted neural feature map is computed from a statistical model using the behavioral features for the patient, or both the neural feature map and the predicted neural feature map for the patient;

determining, by the at least one processor, at least one neural therapeutic target for a specific brain location with a quantitative score indicating correspondence with the neural composite score above a predetermined threshold that the patient will likely respond to; and prognosticating, by the at least one processor, a therapeutic associated with the at least one neural therapeutic target for a current treatment of the patient based on at least one of the behavioral data or the neural data of the patient is presenting.

9. The method of claim 8, wherein the generating the neural composite score further comprises:

retrieving, by the at least one processor, the behavioral data for the patient;

retrieving, by the at least one processor, a statistical model for predicting a neural feature map from the behavioral data for the patient wherein the statistical model is computed using neural and behavioral data from the plurality of individuals; and computing, by the at least one processor of the computing device, the predicted neural feature map for the patient using the behavioral data for the patient and the statistical model.

10. The method of claim 8, wherein the neural feature map for the patient comprises an assignment of the one or more numerical values to the at least one of the multiple two-dimensional cortical surface-based areas or subcortical volumetric brain structures from a given assessment or analysis, from the neural data of a particular modality.

11. The method of claim 8, wherein the neural feature map for the patient or the predicted neural feature map for the patient or the group-level neural feature map for the plurality of individuals comprises a representation of at least one of cerebral cortices or cerebellar cortices as the two-dimensional surfaces and a representation of subcortical neural data as appropriate volumetric structures.

12. The method of claim 8, further comprising:

determining, by the at least one processor, whether each of the respective neural composite score for the patient exceeds a respective predetermined threshold, the exceeding indicating that the patient is likely to respond to a therapeutic associated with the one or more neuro-behavioral dimensions;

retrieving, by the at least one processor, each of the group-level neural feature maps for the one or more neuro-behavioral dimensions for which the respective neural composite score exceeds the respective predetermined threshold;

retrieving, by the at least one processor, one or more neural therapeutic feature maps;

determining, by the at least one processor, a quantitative correspondence of similarity of the group-level neural feature maps for the one or more neuro-behavioral dimensions with the one or more neural therapeutic feature maps;

determining, by the at least one processor, a quantitative correspondence of similarity of each of the group-level neural feature maps for the one or more neuro-behavioral dimensions with the one or more neural therapeutic feature maps;

identifying, by the at least one processor, one or more neural therapeutic targets, wherein each of the one or more neural therapeutic targets corresponds to the one or more neural therapeutic feature maps for which the quantitative correspondence of similarity with the group-level neural feature map(s) exceeds the predetermined threshold; and determining, by the at least one processor, the therapeutic associated with the one or more neural therapeutic targets for treatment of the patient, wherein each of the one or more neural therapeutic feature maps comprises a pharmacological map associated with one or more receptor targets or a gene expression map associated with one or more gene expression targets.

13. The method of claim 8, further comprising:

displaying, on the user interface associated with the computing device, at least one of:

a numerical and graphical representation of the group-level behavioral features or the group-level neural feature map comprising the one or more neuro-behavioral dimensions of the multi-dimensional neuro-behavioral geometry, at least one of a numerical and graphical representation of the behavioral features or the neural feature map, at least one of the neural composite score or a predicted neural composite score for the patient, one or more neural therapeutic feature maps, one or more neural therapeutic targets, and the therapeutic associated with the one or more neural therapeutic target for treatment of the patient.

* * * * *